US010138489B2

(12) United States Patent
Roessler et al.

(10) Patent No.: US 10,138,489 B2
(45) Date of Patent: Nov. 27, 2018

(54) CYANOBACTERIAL STRAINS CAPABLE OF UTILIZING PHOSPHITE

(71) Applicant: Algenol Biotech LLC, Fort Myers, FL (US)

(72) Inventors: Paul Gordon Roessler, San Diego, CA (US); Charles Ryan Budinoff, Fort Myers, FL (US); Songhua Zhu, Fort Myers, FL (US); Kui Wang, Fort Myers, FL (US); Heike Enke, Berlin (DE); Christian Weissert, Berlin (DE); Frank Jochem, West Palm Beach, FL (US); Ming-De Deng, Manitowoc, WI (US)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 15/782,404

(22) Filed: Oct. 12, 2017

(65) Prior Publication Data

US 2018/0112225 A1 Apr. 26, 2018

Related U.S. Application Data

(60) Provisional application No. 62/410,577, filed on Oct. 20, 2016.

(51) Int. Cl.

| | |
|---|---|
| ***C12N 1/20*** | (2006.01) |
| ***C12N 15/52*** | (2006.01) |
| ***C07K 14/195*** | (2006.01) |
| ***C12N 15/63*** | (2006.01) |
| ***C12N 15/74*** | (2006.01) |
| ***C12N 15/67*** | (2006.01) |
| ***C12R 1/01*** | (2006.01) |
| ***C12P 1/04*** | (2006.01) |
| ***C12P 7/06*** | (2006.01) |

(52) U.S. Cl.

CPC ............. *C12N 15/635* (2013.01); *C12N 1/20* (2013.01); *C12N 15/52* (2013.01); *C12N 15/67* (2013.01); *C12N 15/74* (2013.01); *C12P 1/04* (2013.01); *C12P 7/065* (2013.01); *C12R 1/01* (2013.01); *C12Y 101/01001* (2013.01); *C12Y 120/01001* (2013.01); *C12Y 401/01001* (2013.01); *C12N 2320/50* (2013.01); *C12N 2330/51* (2013.01)

(58) Field of Classification Search

CPC ........ C12N 15/52; C12N 9/0004; C12N 1/20; C07K 14/195

See application file for complete search history.

(56) References Cited

U.S. PATENT DOCUMENTS

| | | | |
|---|---|---|---|
| 5,707,418 | A | 1/1998 | Hsu |
| 5,997,910 | A | 12/1999 | Taylor |
| 6,306,639 | B1 | 10/2001 | Woods et al. |
| 6,338,860 | B1 | 1/2002 | Taylor |
| 6,509,041 | B2 | 1/2003 | Taylor |
| 6,541,421 | B1 | 4/2003 | Forsyth et al. |
| 6,689,392 | B2 | 2/2004 | Lifshitz |
| 6,699,696 | B2 | 3/2004 | Woods et al. |
| 6,720,313 | B1 | 4/2004 | Maynard |
| 7,160,349 | B2 | 1/2007 | Lovatt |
| 7,402,419 | B2 | 7/2008 | Zhao et al. |
| 7,770,322 | B2 | 8/2010 | Huntley |
| 7,794,969 | B1 | 9/2010 | Reppas et al. |
| RE41,789 | E | 10/2010 | Lovatt |
| 7,968,321 | B1 | 6/2011 | Green et al. |
| 7,981,647 | B2 | 7/2011 | Berry et al. |
| 8,048,666 | B1 | 11/2011 | Green et al. |
| 8,183,027 | B2 | 5/2012 | Reppas et al. |
| 8,216,816 | B2 | 7/2012 | Green et al. |
| 8,216,972 | B1 | 7/2012 | Fabry et al. |
| 8,268,601 | B2 | 9/2012 | Huntley |
| 8,304,232 | B2 | 11/2012 | Morgan et al. |
| 8,404,466 | B2 | 3/2013 | Baier et al. |
| 8,465,954 | B2 | 6/2013 | Green et al. |
| 8,709,808 | B2 | 4/2014 | Cuello et al. |
| 8,753,840 | B2 | 6/2014 | Vermaas |
| 8,846,369 | B2 | 9/2014 | Piven et al. |
| 8,986,964 | B2 | 3/2015 | Green et al. |
| 9,127,297 | B2 | 9/2015 | Dühring et al. |
| 9,157,101 | B2 | 10/2015 | Piven et al. |
| 9,163,264 | B2 | 10/2015 | Green et al. |
| 9,315,820 | B2 | 4/2016 | Dühring et al. |
| 9,315,832 | B2 | 4/2016 | Piven et al. |
| 9,493,794 | B2 | 11/2016 | Dühring et al. |
| 9,493,795 | B2 | 11/2016 | Dühring et al. |
| 9,499,822 | B2 | 11/2016 | Kuroda et al. |
| 9,551,014 | B2 | 1/2017 | Dühring et al. |

(Continued)

FOREIGN PATENT DOCUMENTS

| | | |
|---|---|---|
| EP | 2285948 B1 | 1/2014 |
| WO | WO/2008/106803 | 9/2008 |

(Continued)

OTHER PUBLICATIONS

Deng, M.D. et al. (1999), "Ethanol Synthesis by Genetic Engineering in Cyanobacteria," Applied and Environmental Microbiology, 65:523-52.
Blanch, H.W. (2012), "Bioprocessing for Biofuels," Current Opinion in Biotechnology, 23:390-395.
Wang, B. (2012), "Application of synthetic biology in cyanobacteria and algae," Frontiers in Microbiology, 3 (article 344): 1-15.
Shih, PM. (2013), "Improving the coverage of the cyanobacterial phylum using diversity-driven genome sequencing," Proceedings of the National Academy of Sciences, 110:1053-1058.
Rippka, R. (1979),"Generic assignments, strain histories and properties of pure cultures of cyanobacteria," Journal of General Microbiology, 111:1-61.

(Continued)

*Primary Examiner* — Maryam Monshipouri

(57) ABSTRACT

The invention provides genetically modified cyanobacterial cells that are capable of utilizing phosphite as a primary phosphorus source, and can out-compete contaminant organisms for certain forms of phosphorus more effectively.

22 Claims, 30 Drawing Sheets

Specification includes a Sequence Listing.

(56) References Cited

U.S. PATENT DOCUMENTS

| | | | | |
|---|---|---|---|---|
| 9,650,642 | B2 | 5/2017 | Woods et al. | |
| 9,765,364 | B2 | 9/2017 | Dühring et al. | |
| 2004/0091985 | A1 | 5/2004 | Metcalf et al. | |
| 2010/0055702 | A1 * | 3/2010 | Battle | C12Q 1/689 435/6.13 |
| 2010/0210602 | A1 * | 8/2010 | Zhang | A61K 31/00 514/152 |
| 2010/0297736 | A1 | 11/2010 | Duhring et al. | |
| 2011/0231958 | A1 | 9/2011 | Herrera-Estrella et al. | |
| 2012/0295303 | A1 | 11/2012 | Herrera-Estrella et al. | |
| 2013/0075279 | A1 | 3/2013 | Buck et al. | |
| 2013/0143284 | A1 | 6/2013 | Roberts et al. | |
| 2014/0113342 | A1 | 4/2014 | Ziegler et al. | |
| 2014/0154762 | A1 | 6/2014 | Duehring et al. | |
| 2015/0125934 | A1 * | 5/2015 | Kuroda | C12N 1/14 435/252.33 |
| 2015/0211028 | A1 | 7/2015 | Chin et al. | |
| 2015/0232884 | A1 | 8/2015 | Duehring et al. | |
| 2016/0115492 | A1 | 4/2016 | South et al. | |
| 2016/0215274 | A1 | 7/2016 | Shaw et al. | |
| 2017/0096691 | A1 | 4/2017 | Greenhagen et al. | |
| 2017/0175148 | A1 | 6/2017 | Kramer et al. | |

FOREIGN PATENT DOCUMENTS

| | | |
|---|---|---|
| WO | WO/2009/111513 | 9/2009 |
| WO | WO/2010/044960 | 4/2010 |
| WO | WO/2011/017565 | 2/2011 |
| WO | WO/2011/029013 | 3/2011 |
| WO | WO/2011/094457 | 8/2011 |
| WO | WO/2012/000057 | 1/2012 |
| WO | WO/2012/101459 | 8/2012 |
| WO | WO/2012/129031 | 9/2012 |
| WO | WO/2014/100799 | 6/2014 |
| WO | WO/2014/201298 | 12/2014 |
| WO | WO/2015/031441 | 3/2015 |
| WO | WO2015157431 | 10/2015 |
| WO | WO/2016/105405 | 6/2016 |
| WO | WO/2016/105483 | 6/2016 |
| WO | WO/2016/181205 | 11/2016 |

OTHER PUBLICATIONS

Helman et al. (2003), "Genes Encoding A-Type Flavoproteins are essential for Photoreduction of O2 in Cyanobacteria," Current Biology, 13:230-235.

Broun et al. (1998), "Catalytic plasticity of fatty acid modification enzymes underlying chemical diversity of plant lipids," Science, 282:1315-1317.

Chica et al. (2005), "Semi-rational approaches to engineering enzyme activity: combining the benefits of directed evolution and rational design," Curr. Opi. Biotechnol., 16:378-384.

Devos et al. (2000), "Practical limits of function prediction," Proteins: Structure, Function, and Genetics, 41:98-107.

Kisselev et al. (2002), "Polypeptide release factors in prokaryotes and eukaryotes: same function, different structure," Structure, 10:8-9.

Seffernick et al. (2001), "Melamine deaminase and Atrazine chlorohydrolase; 98 percent identical but functionally different," J. Bacteriol., 183:2405-2410.

Whisstock et al. (2003), "Prediction of protein function from protein sequence," Q. Rev. Biophysics, 36:307-340.

Wishart et al. (1995), "A single mutation converts a novel phosphotyrosine binding domain into a dual-specificity phosphatase," J. Biol. Chem., 270:26782-26785.

Witkowski et al. (1999), "Conversion of b-ketoacyl synthase to a Malonyl Decarboxylase by replacement of the active cysteine with glutamine," Biochemistry, 38:11643-11650.

Trautmann et al. (2013), GenBank accession No. AGF53389.

Neale et al. (1993), GenBank accession No. AAA27697.

Sen et al. (2007), "Developments in Directed Evolution for Improving Enzyme Functions," Appl. Biochem. Biotechnol., 143:212-223.

Kirkwood, D. (1993), "Nutrients: Practical Notes on their Determination in Seawater," HELCOM 1994; ICES/HELCOM Workshop on Quality Assurance of Chemical Analytical Procedures for the Baltic Monitoring Programme, Baltic Sea Environmental Proceedings of Oct. 5, 1993, 58:23-47.

Nakamura et al. (2002), "Complete Genome Structure of the Thermophilic Cyanobacterium Thermosynechococcus Elongatus BP-1," DNA Research, 9:123-130.

Burut-Archanai et al. (2013), "Phosphorus removal in a dosed recirculating aquaculture system using the cyanobacterium *Synechocystis* sp. PCC 6803 strain lacking the SphU regulator of the Pho regulon," Biochemical Engineering Journal, 74:69-75.

Moutin (2002), "Does competition for nanomolar phosphate supply explain the predominance of the cyanobacterium Synechococcus?" Limnol. Oceanogr., 47:1562-1567.

Thingstad et al. (1993), "Phosphorus cycling and algal-bacterial competition in Sandsfjord, western Norway," Marine Ecology Progress Series, 99:239-259.

Yu et al. (2013), "Development of *Synechocystis* sp. PCC 6803 as a Phototrophic Cell Factory," Marine Drugs, 11:2894-2916.

Currie et al. (1984), "A comparison of the abilities of freshwater algae and bacteria to acquire and retain phosphorus," Limnol. Oceanogr., 29:298-310.

Drakare (2002), "Competition between Picoplanktonic Cyanobacteria and Heterotrophic Bacteria along Crossed Gradients of Glucose and Phosphate," Microbial Ecology, 44:327-335.

Fuszard et al. (2013), "The quantitative proteomic response of *Synechocystis* sp. PCC6803 to phosphate acclimation," Aquatic Biosystems, 9:5 (12 pages).

Morohoshi et al. (2002), "Accumulation of Inorganic Polyphosphate in phoU Mutants of *Escherichia coli* and *Synechocystis* sp. Strain PCC6803," Applied and Environmental Microbiology, 68:4107-4110.

Leymonie, J.P., (2007) Phosphites and phosphates: when growers and distributors alike could get confused, Products and trends, New AG International, Kingston upon Thames, UK. (7 pages).

Adams et al. (2008), "Phosphorus Deprivation Responses and Phosphonate Utilization in a Thermophilic *Synechococcus* sp. from Microbial Mats," Jour. Bacteriol., 190:8171-8184.

Costas et al. (2001), "Purification and Characterization of a Novel Phosphorus-oxidizing Enzyme from Pseudomonas stutzeri WM88," Jour. Biol. Chem. 276:17429-17436.

Shaw et al. (2016), "Metabolic engineering of microbial competitive advantage for industrial fermentation processes," Science, 353:583-586.

Metcalf et al. (1998), "Molecular Genetic Analysis of Phosphite and Hypophosphite Oxidation by Pseudomonas stutzeri WM88," Jour. Bacteriol., 180:5547-5558.

Lopez-Arredondo et al. (2012), "Engineering phosphorus metabolism i plants to produce a dual fertilization and weed control system," Nature Biotechnology 30:889-893.

Loera-Quezada et al. (2015), "Phosphite cannot be used as a phosphorus source but is non-toxic for microalgae," Plant Science 231:124-130.

Loera-Quezada et al. (2016), "A novel genetic engineering platform for the effective management of biological contaminants for the production of microalgae," Plant Biotechnol. Jour., pp. 1-11.

Liu et al. (2012), "Cloning, Expression, and Characterization of a Wide-pH-Range Stable Phosphite Dehydrogenase from *Pseudomonas* sp. K in *Escherichia coli,*" Appl. Biochem. Biotechnol. 166:1301-1313.

Nahampun et al. (2016), "Assessment of ptxD gene as an alternative selectable marker for Agrobacterium-mediated maize transformation," Plant Cell Rep. 35:1121-1132.

Polyviou et al. (2015), "Phosphite utilization by the globally important marine diazotroph Trichodesmium," Envir. Microbiol. Reports, 7:824-830.

(56) References Cited

OTHER PUBLICATIONS

Simeonova et al. (2010), "Identification and Heterologous Expression of Genes Involved in Anaerobic Dissimilatory Phosphite Oxidation by Desulfotignum phosphitoxidans," Jour. Bacteriol., 192:5237-5244.

* cited by examiner

| Strain ID | Plasmid | Genotype | Host strain | Promoter Pt operon | Pt-Dehydro-genase | Pt Trans-porter | EtOH cassette | SEQ ID NO: | FIG No. | Note |
|---|---|---|---|---|---|---|---|---|---|---|
| AB0250 | #1904 | pAB1-6.8::PnirA*2-PDC(AB1opt1)-TdsrA-PcpcB-ADH111-TrbcS | AB1 | — | — | — | PnirA (#1904) | — | Not shown | Control |
| AB0012 | #1938 | Porf0316- pdc(AB1opt1)-TdsrA-PcpcB-adh111 (AB1opt)-TrbcS | AB1 | ..... | ..... | ..... | Porf0316 (#1938) | ..... | Not shown | Control- ethanologenic host cell |
| AB0493 | #1962 | pAB1_6.8::Porf221-ptxABCD2104 | AB1 wt | Porf221 | $ptxD_{2104}$ | $ptxABC_{2104}$ | no | 1 | 6 | copper inducible expression of Pt genes in non ethanologenic AB1 wt background |
| AB0524 | pAB1617 | pAB1_6.8::PnirA*2-ptxDR4506(AB1opt)-His6-IScpcBA-ptxABC2104-Toop | wt | PnirA*2 | $ptxD_{R4506}$-His | $ptxABC_{2104}$ | no | 2 | 7 | nitrate inducible expression of Pt genes in non ethanologenic AB1 wt background |
| AB0701 | pAB611 | pAB1_6.8::Porf0316-pdc(AB1opt1)-TdsrA-PcpcB-adh111(AB1opt)-TrbcS-PpstS_ptxDR4506His_IScpcBA_ptxABC2104 | wt | PpstS | $ptxD_{R4506}$-His | $ptxABC_{2104}$ | Porf0316 (#1938) | 3 | 8 | P starvation inducible expression of Pt genes<br>+ Cu-induc. EtOH cassette in AB1 wt background |
| AB0762 | cc215 | pAB1_6.8::PnirA*2-PDC(AB1opt1)-TdsrA-PcpcB-ADH111(AB1opt)-TrbcS-Toop-Porf00615-ptxA2104(AB1opt)-IScpcBA*1-ptxB2104(AB1opt)-ISpsaAB-ptxC2104(AB1opt)-TB0011-PpsaA-ptxDR4506(AB1opt)-His6-TpsaB | AB1 wt | Porf0615/ PpsaA | $ptxD_{R4506}$-His | $ptxABC_{2104}$(opt) | PnirA (#1904) | 6 | 9 | constitutive expression of Pt genes<br>+ nitrate induc. EtOH cassette in AB1 wt background |
| AB0764 | cc220 | pAB1_6.8::PnirA*2-PDC(AB1opt1)-TdsrA-PcpcB-ADH111(AB1opt)-TrbcS-Porf0316- ptxDR4506(AB1opt)-His6-IScpcBA-ptdCDp(AB1opt)-Toop-Porf0221-ptxABC2104-TB0011 | AB1 wt | Porf0316/ Porf0221 | $ptxD_{R4506}$-His | $ptdC_{DP}$ $ptxABC_{2104}$ | PnirA (#1904) | 7 | 10 | copper inducible expression of Pt genes with 2 Pt transporters + nitrate induc. EtOH cassette in AB1 wt |
| AB0765 | cc222 | pAB1_6.8::Porf0316-PDC(AB1opt1)-TdsrA-PcpcB-ADH111(AB1opt)-TrbcS-PnirA*2-ptxDR4506(AB1opt)-His6-IScpcBA-ptxABC2104-Toop | wt | PnirA*2 | $ptxD_{R4506}$-His | $ptxABC_{2104}$ | Porf0316 (#1938) | 8 | 11 | nitrate inducible expression of Pt genes<br>+ copper induc. EtOH cassette in AB1 wt background |
| AB0766 | cc233 | pAB1_6.8::PnirA*2-PDC(AB1opt1)-TdsrA-PcpcB-ADH111(AB1opt)-TrbcS-Porf0316-ptxDR4506(AB1opt)-His6-IScpcBA-ptxA2104(AB1opt)-IScpcBA*1-ptxB2104(AB1opt)-ISpsaAB-ptxC2104(AB1opt)-TB0011 | AB1 wt | Porf0316 | $ptxD_{R4506}$-His | $ptxABC_{2104}$(opt) | PnirA (#1904) | 9 | 12 | copper inducible expression of Pt genes<br>+ nitrate induc. EtOH cassette in AB1 wt background |
| AB0040 | | ΔAB1_orf0666 | AB0040 (Δorf0666) | — | — | — | — | — | 13 | ΔphoU (orf0666 knock-out) strain |
| AB0793 | cc233 | ΔAB1_orf0666; pAB1-6.8::PnirA*2-PDC(AB1opt1)-TdsrA-PcpcB-ADH111(AB1opt)-TrbcS-Porf0316-ptxDR4506(AB1opt)-His6-IScpcBA-ptxA2104(AB1opt)-IScpcBA*1-ptxB2104(AB1opt)-ISpsaAB-ptxC2104(AB1opt)-TB0011 | AB0040 (Δorf0666) | Porf0316 | $ptxD_{R4506}$-His | $ptxABC_{2104}$(opt) | PnirA (#1904) | — | — | copper inducible expression of Pt genes<br>+ nitrate induc. EtOH cassette in ΔphoU background |
| AB0973 | cc215 | pAB1-6.8::PnirA*2-PDC(AB1opt1)-TdsrA-PcpcB-ADH111(AB1opt)-TrbcS-Porf00615-ptxA2104(AB1opt)-IScpcBA*1-ptxB2104(AB1opt)-ISpsaAB-ptxC2104(AB1opt)-TB0011-PpsaA-ptxDR4506(AB1opt)-His6-TpsaB | AB0040 (Δorf0666) | Porf0615, PpsaA | $ptxD_{R4506}$-His | — | PnirA (#1904) | — | — | Constitutive expression of ptxABC; PpsaA-promoter for PtxD + nitrate induc. EtOH cassette in ΔphoU background |

FIG. 5

SEQUENCE LISTING

```
<160> NUMBER OF SEQ ID NOS: 61

<210> SEQ ID NO 1
<211> LENGTH: 14260
<212> TYPE: DNA
<213> ORGANISM: Artificial sequence
<220> FEATURE:
<223> OTHER INFORMATION: Synthetic plasmid construct derived from p6.8
      endogenous plasmid from Cyanobacterium sp. PTA-13311, plus
      copper-inducible ptxA,B,C, and D from Cyanothece sp. ATCC 51142.

<400> SEQUENCE: 1

tcgacatatc tcatccttag cttctactta taccttcagc atagttaaaa atcatccctt     60

tattgatggt aataaaagaa caggttttat tagtggagta accttttttaa tgctcaatgg   120

ttctcacttt actgcttctg aagtggaagt agtacatatc atccaaacct tagctagtgg    180

cagaattacc gaggaagaat tacaacaatg gttcgtaagg aaaagtaagc agatgaataa    240

ttaaagcatc atttcatcct catttcatat tctcctgtca ccatggtatg gaagattagg    300

taaaagcatg ctttttctta ataaccttag tgtcacctat aaagatggaa ccgtggcctt    360

agaaaatatt tctcttgaat tgattccagg agaatttacg gtacttttag gggcttctgg    420

tgcaggaaaa tcaacccttt tacgttgtat caattttcta acagttccta ctaagggtga    480

agttattgtg gaggggttag gaaccctaaa taacccgaaa atcttaagaa aacatcgcca    540

aaaaacgggc atgatttttc aacaacatca attaattcct cgacaaactg cccttaaaaa    600

tgttttagtt ggtcgtttag cctatcactc taccttaaga agttttttcc ctttgcctaa    660

aattgatcaa atgattgctt tagattgttt ggacagagtt ggcctattaa ataaagcttt    720

aactcctgtt aaacaactaa gtggaggaca acaacaacgg gtaggaatag ccagagcttt    780

agctcaaaaa cccagatttc tcttagcaga tgaacctgtt gctagtttag atcctggtag    840
```

-continued

```
ttctcataag atattaacta atctcaaaaa aatttgtcaa gaagatggta ttggggcagt    900
ggttagttta catcaaatag atttcgcttt agactatggc gatcgcatta ttggccttgc    960
agatggaaac atccttttg atagtcaccc gtcagaaata caatcatacc agttagaaaa   1020
aatttatcac aattcttctt tgattaaggc aggttaattg ttatctaaat cacacttaaa   1080
aaatcattaa aatcttgctt ttttcaagaa aatcattata atcaacagta aaattatttg   1140
actcaaaatt ggtatgatca gtttcatctt taaaaaatcc ttaacccctg ttgtttcttt   1200
taccctatta actctaattg gttgtagtac accgaatagt caaacatcca ataataaccc   1260
tgaaaatagc aaagcagaca caaaagctaa ccctaaaaaa ttagtagttg ctttgttacc   1320
cgatgaatca gtatctaccg taattcaaaa taataagggg ttagaaagct acttagaaga   1380
ccgactgaat aaagatgttg aattgtttgt cagtaccgat tattcttcta tgatcgaagc   1440
agcgagtaat ggaagattag acttagccta ttttggtcct ttgtcgtatg ttttggccaa   1500
aactaaaagt aatatcgaag cctttgcagc gttagaaaaa gatggagaag ccacctataa   1560
atctgtcatt attggtaatg cagaagcagg aattgattcc tatgacaaaa tcgaaggaaa   1620
aactatggct tatggagatc aagcctcgac ctctagtcat ttaattccta agtcaatgtt   1680
aatggaaaaa ggcttaaaag cagaagaaaa ttatcaagaa gtatttgtcg gttctcatga   1740
tgctgtagct gtagctgttg ccaatggaaa agcccaagca gggggcttaa gtaaacccat   1800
ttataccgct ttaattaata agggaaccat tgatgaaaat aaagtcattt taatagaaga   1860
atctaaacca tttccccaat atccttggac gatgcgatct gacttagaac ctcaattaaa   1920
acagcaaatt aagcaagctt ttctagaact agaagataag gcagttttag aaccatttaa   1980
agcagaaggg tttcaatcag tagaagacaa ggattataat gttgtccgag acttaggaaa   2040
aatcctcaat cttgattttg ctaaacttaa ttaatctgag ggtttagcta ctgtaaagat   2100
caattattca tttagggata accatcttaa actctcaagt gagatttttt cttttactaa   2160
acaaagaatc aaatcaaagt aaacataaag ttataaggtt atccctaatt tttggtaatc   2220
aaatattgga aaaatgacaa tcaatcaaga taaatattct aatctgttgc gccaatacaa   2280
gattctttgg tatcgttcac taataaacat cattattttg ctaataataa ttattattag   2340
ttttgctgta gttggtttat tagatggaaa acgcttatct gaaggaattc ctgacctatt   2400
agaaatggta gcacaaatgc tgcctcccga ttttactcgt gcttctgatt ggattaaacc   2460
actaattgat accttaggaa tgagtattgc aggaacagga atggctgtta tttttctct   2520
gcctattact ttcggggcag cacaaaatac cagtccccat cctttcgttt attttgtatc   2580
aagaattatt ttaaatatag caagagctat tcctgaatta cttctaggaa ttatctttgt   2640
tgccgctgtt gggtttggcg cacttcctgg ggtattagca ttgggatttc attctattgg   2700
tatggtaggt aaattttttg ctgagtccat agaacataca gacaacgcac ctattgaagc   2760
agcaaaagca gtcggagcaa atcatttaca aatcatttat catagtattt taccccaagt   2820
tttaccacaa atcgccgatg ttacatttta tcgttgggag tacaatttta gagcttctct   2880
agtattaggc gcagtgggag ccggtggcat tggatttgaa attattgggg cattacgttt   2940
actcaaatat caggaagttt ctgccctttt gttagttgtt ttagttatgg taacattagt   3000
agatagttta ggtaactttt taagaaaaaa attcatttaa aataatcgac tatgaatcaa   3060
aaacctaaag ttgtgattac ccattgggtt catccagaaa tcattgacta tttaactcca   3120
cattgtgagc ttattcttaa tcaaacaaaa gaaaccttaa cccgtgaaga agttattaat   3180
```

-continued

```
agaagcaaag atgctcaagg tttaatggtt tttatgccag attatattga tgtaaatttt   3240
ttagaagcct gtcctcaatt aaaagtaatt tcaggagcct taagaggcta tgataatttt   3300
gatgtagaag cttgcacaaa gcgaaatatt tggtttacta ttgttcctga tttattagct   3360
gcacctacag cagaattaac cataggatta ctactaatat tagcccgtag aatggtagaa   3420
ggcgatcgcc taattcgttc gggtaatttt cagggttgga aacctcaatt atacagtaca   3480
ggattattaa ataagaccct cggaattatt ggtatgggca agttaggaaa agccttgaca   3540
aaacggttaa tgggctttga tatgaccctg ttatatcatg ataaaattac tctaacaagc   3600
caacaagaaa gagattggaa aattaccaaa acctctctag aagaattatt aacaaaaagt   3660
gattatgttg tgttaatggt tcccttagtt cctgatacct atcatttaat taatgagaat   3720
agtttaaaaa tgatgaaacc taatagtttt ttaattaatc cttgtcgggg ttccatagta   3780
gatgaaaccg ccgtagctac tgccattaaa tcaggacatt tagccgggta tgctgctgat   3840
gtttttgaaa tggaagattg ggcgatcgcc aaccgtcctc aaagcattaa tcaaacctta   3900
ttaactgata taaaccatac ttttttaca ccccatttag gctcagccgt taatgaggtt   3960
cgtcgtgata ttgccctaga agcagccaaa aatattatcg aagttctctc agaaaacaga   4020
ccacaaggtg ctgtaaatgg tatcgtatag aaaaaacttg atttttaata agtatttaga   4080
ttataatctc taaaccaaaa tttacttatc ctttttaacc cttactaaga tgatgtcaaa   4140
atcatggaaa aatatattaa taattagttc aattgtattg gctgacgtta tcttactatc   4200
gactaaccta accctagctc aatattcctc ccgttctcag tcttattgcg aaagctacgc   4260
cagagacttt gccgatcgct acgcccaaag tggatttttc cgaggaggag caagaggggc   4320
agccagtgga gcagccatag gagctattat tgatggggga agaggagccg gtacaggggc   4380
agccattggc tctgtagtag gtattatagg tggtagtgcg cgtcgtgcct cggatcatga   4440
tctgcaatct tgctgaaaaa ctcgagccat ccggaagatc tggcggccgc tctccctata   4500
gtgagtcgta ttacgccgga tggatatggt gttcaggcac aagtgttaaa gcagttgatt   4560
ttattcacta tgatgaaaaa aacaatgaat ggaacctgct ccaagttaaa aatagagata   4620
ataccgaaaa ctcatcgagt agtaagatta gagataatac aacaataaaa aaatggttta   4680
gaacttactc acagcgtgat gctactaatt gggacaattt tccagatgaa gtatcatcta   4740
agaatttaaa tgaagaagac ttcagagctt ttgttaaaaa ttatttggca aaaataaatat  4800
aattcggctg caggatcatc ttgctgaaaa actcgagcgc tcgttccgca aagcggtacg   4860
gagttagtta ggggctaatg ggcattctcc cgtacaggaa agagttagaa gttattaatt   4920
atcaacaatt ctcctttgcc tagtgcatcg ttaccttttt aattaaaaca taaggaaaac   4980
taataatcgt aataatttaa cctcaaagtg taaagaaatg tgaaattctg acttttataa   5040
cgttaaagag ggaaaaatta gcagtttaaa atacctagag aatagtctgg ggtaagcata   5100
gagaattaga ttagttaagt taatcaaatt cagaaaaaat aataatcgta aatagttaat   5160
ctgggtgtat agaaaatgat ccccttcatg ataagattta aactcgaaaa gcaaaagcca   5220
aaaaactaac ttccattaaa agaagttgtt acatataacg ctataaagaa aatttatata   5280
tttggaggat accaaccatg tctcatattc aacgtgaaac tagttgttct cgccctcgtt   5340
taaattctaa tatggatgcc gatttatatg gttataaatg ggctcgtgat aatgttggtc   5400
aatctggtgc tactatttat cgtttatatg gtaaacctga tgctcctgaa ttattcttga   5460
aacatggtaa aggttctgtt gctaatgatg ttactgatga aatggttcgt ttaaactggt   5520
tgactgaatt tatgccttta cctactatta aacattttat tcgtactccc gatgatgctt   5580
```

-continued

```
ggttattaac tactgctatt cctggtaaaa ctgcttttca agttttagaa gaatatcctg   5640
attctggtga aaatattgtt gatgctttag ctgttttttt acgtcgttta cattctattc   5700
ccgtttgtaa ttgtcctttt aattctgatc gtgtttttcg tttagctcaa gctcaatctc   5760
gtatgaataa tggtttagtt gatgcttctg attttgatga tgaacgtaat ggttggcctg   5820
ttgaacaagt ttggaaagaa atgcacaaat tgttaccttt ttctcctgat tctgttgtta   5880
ctcatggtga tttttcttta gataatttga tctttgatga aggtaaattg attggttgta   5940
ttgatgttgg tcgtgttggt attgctgatc gttatcaaga tttagctatt ttatggaatt   6000
gtttaggtga attttctcct tctttacaga aacgtttatt tcagaaatat ggtattgata   6060
atcctgatat gaacaagtta caatttcatt taatgttgga cgagttcttt taagaattaa   6120
ttcatgacca aaatccctta acgtgagttt tcgttccact gagcgtcaga ccccgtagaa   6180
aagatcaaag gatcttcttg agatcctttt tttctgcgcg taatctgctg ctatttaaat   6240
tacgtacacg tgttattact ttgttaacga caattgtctt aattaactgg gcctcatggg   6300
ccttccgctc actgcccgct ttccagtcgg gaaacctgtc gtgccagctc tgcagatgac   6360
ggtgaaaacc tctgacacat gcagctcccg gagacggtca cagcttgtct gtaagcggat   6420
gccgggagca gacaagcccg tcagggcgcg tcagcgggtg ttggcgggtg tcggggcgca   6480
gccatgaccc agtcacgtag cgatagcgga gtgtatactg gcttaactat gcggcatcag   6540
agcagattgt actgagagtg caccatatgc ggtgtgaaat accgcacaga tgcgtaagga   6600
gaaaataccg catcaggcgc tcttccgctt cctcgctcac tgactcgctg cgctcggtcg   6660
ttcggctgcg gcgagcggta tcagctcact caaaggcggt aatacggtta tccacagaat   6720
caggggataa cgcaggaaag aacatgtgag caaaaggcca gcaaaaggcc aggaaccgta   6780
aaaaggccgc gttgctggcg tttttccata ggctccgccc ccctgacgag catcacaaaa   6840
atcgacgctc aagtcagagg tggcgaaacc cgacaggact ataaagatac caggcgtttc   6900
cccctggaag ctccctcgtg cgctctcctg ttccgaccct gccgcttacc ggatacctgt   6960
ccgcctttct cccttcggga agcgtggcgc tttctcatag ctcacgctgt aggtatctca   7020
gttcggtgta ggtcgttcgc tccaagctgg gctgtgtgca cgaacccccc gttcagcccg   7080
accgctgcgc cttatccggt aactatcgtc ttgagtccaa cccggtaaga cacgacttat   7140
cgccactggc agcagccact ggtaacagga ttagcagagc gaggtatgta ggcggtgcta   7200
cagagttctt gaagtggtgg cctaactacg gctacactag aaggacagta tttggtatct   7260
gcgctctgct gaagccagtt accttcggaa aaagagttgg tagctcttga tccggcaaac   7320
aaaccaccgc tggtagcggt ggtttttttg tttgcaagca gcagattacg cgcagaaaaa   7380
aaggatctca agaagatcct ttgatctttt ctactgcaga agcttgttag acaccctgtc   7440
atgtatttta tattatttat ttcaccatac ggattaagtg aaacctaatg aaaatagtac   7500
tttcggagct ttaactttaa tgaaggtatg ttttttttata gacatcgatg tctggtttaa   7560
caataggaaa aagtagctaa aactcccatg aattaaagaa ataacaaggt gtctaacaac   7620
ctgttattaa gaatgttaga aaagacttaa catttgtgtt gagtttttat agacattggt   7680
gtctagacat acggtagata aggtttgctc aaaaataaaa taaaaaaaga ttggactaaa   7740
aaacatttaa tttagtacaa tttaattagt tattttttcg tctcaaattt tgctttgttg   7800
agcagaaatt tagataaaaa aatccccgtg atcagattac aatgtcgttc attgtacgat   7860
gtgtcgaaaa atctttacga cactctaaac tgaccacacg ggggaaaaag aaaactgaac   7920
```

-continued

```
taataacatc atgatactcg gaaaacctag caattctcaa cccctaaaca aaagaaactt   7980
ccaaaaccct gaccatataa aggagtggca acaatcagca atcagtcaag atttgatagc   8040
agaaaatctt gtatcggttg ctaatggttt tgatgtacta tttatcggca ataaataccg   8100
aactaacacg ggtgttctgt cacggcacat attaaactcc tattctcatt tagaagatgg   8160
tggttcgtat ggtagaacat ttgacccatt taccaataaa gaaatgcagt gggttcaatt   8220
taaaccgaat agaccaagaa aaggttctac tggtaaggta atcaaatatg aatcgccaaa   8280
aggtgaacct acaagagttc taatgccgtt tgtgcctatg aaaatatggc aacggattag   8340
cgataagttc ggagtaccga ttaatccgaa aaaagatact cacttttggg aatgggtaaa   8400
gaataatcca tcgataccga ttgccattac agaaggaaat aaaaaagcta attgcctatt   8460
atcctatggc tatcctgcta ttgcctttgt aggcatttgg aacggattag agaaaataaa   8520
tgatttctcg aaggaaaagc agttaaaaga ggatttgaaa tggttgttat ccaacggcaa   8580
ccgaaatatt aatatcatct ttgaccaaga ccagaaacaa aaaactgtaa ttaatgtaaa   8640
caaagctatt ttcgctttat cttctctaat aagtagaaat ggtcataaag ttaatattgt   8700
gcaatggttg ccgtcaaaag gtaaaggaat agatgattat ttggtagctt taccttttga   8760
gaaaagagaa aatcatttag acaacttaat taaaattgca ccatcattta atttttggtc   8820
aactaaatac ttattcaagt gtcgtaaacc agatttaacc gtaaattgcc gttatttgag   8880
cgatgcagta aaagaattac ctcaagagga tatagcatta atagcacctc acggcacggg   8940
taaaacttca ttagtagcta ctcacgttaa gaatcggagt tatcacggaa ggaaaactat   9000
ttcattggtg catcttgaaa gtttagccaa agctaatggc aacgcacttg gattatatta   9060
ccgaaccgaa aataatattg aaaagcaata tcttggattt agcttatgtg tagatagttg   9120
ccgtgataag attaacggca ttacaactga tattatttca ggtcaagatt attgcctttt   9180
cattgatgaa attgaccaag taattccaca catccttaac agtgaaactg aagtaagtaa   9240
gtatagatgc accatcattg acactttttc tgaactggtg agaaatgctg aacaggtcat   9300
tattgctgat gctgatttat ccgatgtgac gattgaccta atagaaaaca tcagaggtaa   9360
aaaactatat gtaatcaaga atgaatatca gtatcaggga atgactttta acgccgttgg   9420
ttcaccatta gaaatgatgg caatgatggg aaaatcggtg tcagaaggca agaaattatt   9480
tattaacacc acatcccaaa aggcaaaaag taagtacggc acaatcgctc ttgagtctta   9540
tatttttggt ctaaataaag aagcaaagat attaagaata gactctgaaa ccactaaaaa   9600
ccctgaacat ccagcctata aaatcattga ccaagactta aataatatcc tcaaagatta   9660
tgattatgtc attgcctcac cttgccttca aacaggtgtc agtattacct taaaagggca   9720
ttttgaccag caatttaact tttccagtgg aaacattaca cctcattgct ttttacagca   9780
aatgtggcgg ttgagggatg cagaaattga aagattctat tatgtgccga actcatctaa   9840
cctcaatctc attgggaata agtcaagttc accatcagac cttctaaaga gcaataacaa   9900
gatggcaacg gcaacggtta accttttggg tagaatcgac tccgaatatt ccctagagta   9960
tgaatcgcac ggcatttggc ttgagacgtg ggcaaaatta tcagcacggc ataacagttc  10020
aatgcgttgt tactctgaaa ttcttaccta tctaattacg tctcaagggc ataaattaaa  10080
tatcaacatt ccctcacctc ttgcagatat taagaagcta aatgatgagg taagtagtaa  10140
cagggaaaag gtaaaaaatg agagatactc tcagaggtta aactcaccag atattaacga  10200
tgcagaagct accatactcg aatctaaaga gcaaaaaatc ggattgactc tcaatgagag  10260
atgcacccta gaaaagcata aagttaagaa gcggtatggg aatgtaaaga tggatattct  10320
```

-continued

```
cacctttgat gatgatggac tataccccaa actcagacta ttttattacc tcaccatcgg  10380
taaacctcat ctcaaggcta atgacagaaa agctattgcc aaaatgggca atgacaataa  10440
aggcaagatt ctatcaaaag acttagttaa taaaacttac tccgctcgtg tgaaggtctt  10500
agagattctt aaactaactg actttatcga caatcttaga gatgaactct taataactcc  10560
caataatcca gctatcaccg attttaataa tcttctgcta agagctaaga aggatttaag  10620
agtattagga gtcaacatcg gaaaatatcc aatggccaac attaatgccg tacttactct  10680
cattggtcac aaactttctg taatgagaga tgagttcgga aaagagaaaa ggataaaagt  10740
agatggtaaa tcataccgat gttatcaact tgaaacatta ccagatttta ccaatgatac  10800
tcttgactac tggttagaaa atgatagcca aaaagaagta acagcaacag aaaattactc  10860
cgaaaatttt aacccttcaa atagctacaa tccagacagt aagacacttt cagagggtgc  10920
aaatttccta tatataaata aagaagaatt gcatccaaat aaattgcacc tagaaataaa  10980
agaaggtgct gaacttttt tattcggggt aaaggtgatt gtgaaaggaa tcttggacgg  11040
ggcagtaact atattctcta tgggtcaaga atacgattta tccctcaatg aactagaggg  11100
gatgttaaca tcatgaactt tacaagaatc tttttaaagg gcgatcgcac catgttaaat  11160
gatggtacat ttgttcagat atttgatatt taccatgacc acgcattggg agtgaccctt  11220
gaccttaaga cagaaaaaat tatttccgat gatgttaggg taattactgt caaagactta  11280
ttgttcgatg gcacttataa aggggtaaaa tcttttatgc ccgataatgc ccgataatgc  11340
ccgattgatg ctacaaaatc ccataatcat aagcgataat cccctaatag cttgtaattc  11400
ttgaaccgta gcgattttag agtattccaa aaagaagaaa taaacaccgc aaaatgtcgt  11460
atttcacata tataaaccaa ggtttttgc cctaaaatct ttatgtttgt agtgtgatgt  11520
tgggtcaaaa tggtcagaaa agttgcaagg tttttatgga tgcttacgcg cgcgaggggt  11580
aagcatcccc aaatagttac tttatcctag tccatgccca tttattgccg tcccgttcgg  11640
ctttaaaaaa gtgccaaaac tcacaaggtg caataaaaag ttctgtacct ttcgcaaccc  11700
tagataatct ttcaacagtt actttttttc ctattatctc ggtacaaagt ttggctagtt  11760
tctcttttcc ctctttttca atcaagcctt cttgtatgcc caactcattg attaatctct  11820
ctatttttac cattatttcc cgttcaggta gtttatcccc taaatcttca tcggggggca  11880
atgtagggca ttctgaaggg gctttttctt ctgtctggac attatctaat attgaagtaa  11940
ccaaactatc ttcagttttt tctattccta ttaattcata ttcggttact gtatccgtat  12000
caatatccga ataactatct ttatccgtat tagctattcg gttaagttta tccgttaact  12060
cagaaacaag actatatagc ggttttagct tttcttctat cctgttatct aatacggata  12120
agtttatacg gttatcatta tccgtattag tatcattggg ctttttttggt agttctaccc  12180
cctcataaac cgcttttatt cccaattcca acagactgat aacagtatcc tttataatgg  12240
gtttttgct gatatggtga acttttgccc cttccatcat tgcgatactt tctatctcac  12300
tcatcaactt atcgcttaag tgaatctcgt atctgtttaa tcccttactg gttttattca  12360
tatccgttta ctttattcgg ttaacaattc tattttatac gaataaaata ttatacggtt  12420
aactttatac gtttaactat tttatctata cggataacag taataagtta ttcgtattag  12480
ttatacgttt acttttatcc aaataaaatt agtgcattta aactaaaaga atgattttat  12540
cggagttgat agcattggat taacctaaag atgtttataa gctatatctg ataagtattt  12600
aaggttattt tgttattctg tttattgaca ttatcagaat aaaagaatag aatataattg  12660
```

-continued

```
ttgagagata agaggtttaa gtgattatgg ttaagaagtt agttggttat gtcagggtca  12720

gtagtgaatc gcaagaggat aacactagct tacagaatca gatagagaga attgaagcat  12780

attgtatggc ttttggttat gagttggtaa aaatattcaa agaggttgcc actggtacaa  12840

aagcagatat tgaaacccgt cctattttta atgaagctat agaatacttg aaacaggata  12900

atgctaatgg aattattgcc ttgaagctag accgaatcgc acggaatgct ttagatgtat  12960

tgcgtttggt tcgtgaaacc ttagaaccac aaaataaaat gttagtgtta ctagatattc  13020

aggtagatac ttcgacacct tcaggaaaaa tgattttaac tgtaatgagt gccgttgctg  13080

aactcgaaag agacatgatc tatgatcgca ctcagggggg tagaaagact aaagcccaaa  13140

agggcgggta tgcctacggg aaacctaaat ttggctataa gactgaagaa aaggaactaa  13200

aagaagattc agcacaacag gaaactatta aactaattaa gagacaccgt aggtcaggga  13260

aaagctacca gaaaatagct gattatctca atgcccaaag tattcccact aaacaaggta  13320

agaaatggag ttctagcgtc gtctatcgaa tctgtcagga aaaagctggt taagtctgtt  13380

tatagatatt tagaatttat tgaataaaaa tagtatgaac aataaatatt tatggactaa  13440

ccacgctcgg aaacgtttaa ctgaacgatg ggaaataaaa gaatcatggg ttattgatac  13500

catcgaaaat cctgaacgtt cagaatttat tgttgatgag tcaggggaaa aatatcatta  13560

ctataaaaga atagctaagt ttaagaatag agtgttagaa gtgataactt ctgccaactc  13620

aacacccaca agaataataa ccttttactt taaccgtaac atgaggaaaa atttatgatt  13680

gttacttacg ataatgaagt tgacgcaatt tattttaagt taacggaaaa taaaattgat  13740

agcaccgaac ctcaaacaga caggattatc attgattacg atgaaagtaa taatattgtt  13800

ggcattgagg tattagattt taattatctt gtcaagaaag gtttaaccgt tgctgattta  13860

cctttttctg aagatgaaag attaacagct tctcaatatt ttaattttcc tgttgctatc  13920

taatccagaa ggggcaataa tccccttctt tcatcgagtt agacttaata tcacaaaagt  13980

cattttcatt ttaccgtttc ttttccacag cgtccgtacg cccctcgtta aatctcaaaa  14040

ccgacaattt atgatgttta taaaaagtta ctcactttaa taagtattta tactcattaa  14100

agggttattc ttttttgta gcctgatagg ttgggaagga atatttcaga ttatcagatt  14160

tgttgaatat ttttcgtcag atacgcaaac cttacaaaca taattaacaa ctgaaactat  14220

tgatatgtct aggttttagc tctatcacag gttggatctg                        14260
```

<210> SEQ ID NO 2
<211> LENGTH: 13653
<212> TYPE: DNA
<213> ORGANISM: Artificial sequence
<220> FEATURE:
<223> OTHER INFORMATION: Synthetic plasmid construct derived from p6.8 endogenous plasmid from Cyanobacterium sp. PTA-13311, plus copper-inducible ptxA,B,C from Cyanothece sp. ATCC 51142, and ptxD from Ralstonia sp. 4506.

<400> SEQUENCE: 2

```
acaattaata acttcttcct gtacgggcga atggccattt gctcctaact aactccgtac     60

tgctttgcgg aacgagcgta gcgaactctc cgaattacta agccttcatc cctgatagat    120

gcaaaaaacg aattaaaatt atgtgtaaaa agaaaatgtg tctttattta gtagtcaaag    180

ttacaaaata ttaagaatca aattaataat gtattgggca gttaagtata taagtcttta    240

aatatttatt tgtattcaat atattaagga ggatcagcct tatgaattca atgaaaccta    300

aagtagtatt aactcattgg gtacaccccg aaataataga attattaagt gctagtgcag    360
```

-continued

```
atgtgattcc caatacaaca agagaaactt tacctcgtag tgaagtaatt gccagagcca    420
aagatgctga tgctttaatg gcctttatgc ctgattctat tgattctgca tttttagagg    480
aatgtcctaa attaagagtg atcggtgccg ctttaaaagg ttatgataat tttgatgtaa    540
acgcctgtac aagacacggt gtttggttaa ccatcgtacc tgatttatta actattccta    600
ccgccgaatt aacaattgga ttattattag gtttaactag acacatgtta gaaggtgatc    660
gtcagatacg ttctggacat tttcaaggat ggagacctac tttatatggt tctggattaa    720
ccggtaaaac tttaggaatt ataggtatgg gtgctgtagg acgtgctatt gctcaaagat    780
tagcaggatt tgaaatgaat ttattatatt gtgatcctat acctttaaat gcagaacaag    840
aaaaagcatg gcatgtacaa agagttactt tagacgaatt attagagaaa tgtgattacg    900
ttgttcctat ggtgcccatg gcagcagaga cattacattt aattgatgcc accgccttag    960
caaaaatgaa aacaggatct tatttaatca atgcttgtag aggttctgtt gtggacgaga   1020
atgccgttat agctgcttta gctagtggta aattagcagg atatgctgcc gacgtatttg   1080
agatggaaga gtggataaga gcagacagac ctcaagctat tcccaaagcc ttattagata   1140
acaccgcaca aaccttttt acacctcatt taggtagtgc tgtaaaagaa gtacgtttag   1200
aaattgaaag acaagctgca atgaatatta tacaggcttt agcaggtgaa aaacctatgg   1260
gtgcaattaa tcaaccctat cctggtgtaa aagctgctgg atcctacgta caccatcatc   1320
accatcacta gttataatga gctctttaaa ccaagattag aaaatccatt tcattaacgt   1380
aaaccaacat aattaggaga aattaattac aatgcatatt tttcttaata accttagtgt   1440
cacctataaa gatggaaccg tggccttaga aaatatttct cttgaattga ttccaggaga   1500
atttacggta cttttagggg cttctggtgc aggaaaatca accctttac gttgtatcaa   1560
ttttctaaca gttcctacta agggtgaagt tattgtggag gggttaggaa ccctaaataa   1620
cccgaaaatc ttaagaaaac atcgccaaaa aacgggcatg atttttcaac aacatcaatt   1680
aattcctcga caaactgccc ttaaaaatgt tttagttggt cgtttagcct atcactctac   1740
cttaagaagt tttttccctt tgcctaaaat tgatcaaatg attgctttag attgtttgga   1800
cagagttggc ctattaaata aagctttaac tcctgttaaa caactaagtg gaggacaaca   1860
acaacgggta ggaatagcca gagctttagc tcaaaaaccc agatttctct tagcagatga   1920
acctgttgct agtttagatc ctggtagttc tcataagata ttaactaatc tcaaaaaaat   1980
ttgtcaagaa gatggtattg gggcagtggt tagtttacat caaatagatt tcgctttaga   2040
ctatggcgat cgcattattg gccttgcaga tggaaacatc ctttttgata gtcacccgtc   2100
agaaatacaa tcataccagt tagaaaaaat ttatcacaat tcttctttga ttaaggcagg   2160
ttaattgtta tctaaatcac acttaaaaaa tcattaaaat cttgcttttt tcaagaaaat   2220
cattataatc aacagtaaaa ttatttgact caaaattggt atgatcagtt tcatctttaa   2280
aaaatcctta acccctgttg tttcttttac cctattaact ctaattggtt gtagtacacc   2340
gaatagtcaa acatccaata ataaccctga aaatagcaaa gcagacacaa aagctaaccc   2400
taaaaaatta gtagttgctt tgttacccga tgaatcagta tctaccgtaa ttcaaaataa   2460
taaggggtta gaaagctact tagaagaccg actgaataaa gatgttgaat tgtttgtcag   2520
taccgattat tcttctatga tcgaagcagc gagtaatgga agattagact tagcctattt   2580
tggtcctttg tcgtatgttt tggccaaaac taaaagtaat atcgaagcct ttgcagcgtt   2640
agaaaaagat ggagaagcca cctataaatc tgtcattatt ggtaatgcag aagcaggaat   2700
tgattcctat gacaaaatcg aaggaaaaac tatggcttat ggagatcaag cctcgacctc   2760
```

-continued

```
tagtcattta attcctaagt caatgttaat ggaaaaaggc ttaaaagcag aagaaaatta   2820
tcaagaagta tttgtcggtt ctcatgatgc tgtagctgta gctgttgcca atggaaaagc   2880
ccaagcaggg ggcttaagta aacccattta taccgcttta attaataagg gaaccattga   2940
tgaaaataaa gtcattttaa tagaagaatc taaaccattt ccccaatatc cttggacgat   3000
gcgatctgac ttagaacctc aattaaaaca gcaaattaag caagcttttc tagaactaga   3060
agataaggca gttttagaac catttaaagc agaagggttt caatcagtag aagacaagga   3120
ttataatgtt gtccgagact taggaaaaat cctcaatctt gattttgcta aacttaatta   3180
atctgagggt ttagctactg taaagatcaa ttattcattt agggataacc atcttaaact   3240
ctcaagtgag atttttctt ttactaaaca aagaatcaaa tcaaagtaaa cataaagtta   3300
taaggttatc cctaattttt ggtaatcaaa tattggaaaa atgacaatca atcaagataa   3360
atattctaat ctgttgcgcc aatacaagat tctttggtat cgttcactaa taaacatcat   3420
tattttgcta ataataatta ttattagttt tgctgtagtt ggtttattag atggaaaacg   3480
cttatctgaa ggaattcctg acctattaga aatggtagca caaatgctgc ctcccgattt   3540
tactcgtgct tctgattgga ttaaaccact aattgatacc ttaggaatga gtattgcagg   3600
aacaggaatg gctgttattt tttctctgcc tattactttc ggggcagcac aaaataccag   3660
tccccatcct ttcgtttatt ttgtatcaag aattatttta aatatagcaa gagctattcc   3720
tgaattactt ctaggaatta tctttgttgc cgctgttggg tttggcgcac ttcctggggt   3780
attagcattg ggatttcatt ctattggtat ggtaggtaaa ttttttgctg agtccataga   3840
acatacagac aacgcaccta ttgaagcagc aaaagcagtc ggagcaaatc atttacaaat   3900
catttatcat agtattttac cccaagtttt accacaaatc gccgatgtta cattttatcg   3960
ttgggagtac aattttagag cttctctagt attaggcgca gtgggagccg gtggcattgg   4020
atttgaaatt attggggcat tacgtttact caaatatcag gaagtttctg ccctttttgtt   4080
agttgtttta gttatggtaa cattagtaga tagtttaggt aactttttaa gaaaaaaatt   4140
catttaaaga tcttagttac cgtggaacgc tcggttgccg ccgggcgttt tttattcctg   4200
caggatcatc ttgctgaaaa actcgagcgc tcgttccgca aagcggtacg gagttagtta   4260
ggggctaatg ggcattctcc cgtacaggaa agagttagaa gttattaatt atcaacaatt   4320
ctcctttgcc tagtgcatcg ttaccttttt aattaaaaca taaggaaaac taataatcgt   4380
aataatttaa cctcaaagtg taaagaaatg tgaaattctg acttttataa cgttaaagag   4440
ggaaaaatta gcagtttaaa atacctagag aatagtctgg ggtaagcata gagaattaga   4500
ttagttaagt taatcaaatt cagaaaaaat aataatcgta aatagttaat ctgggtgtat   4560
agaaaatgat ccccttcatg ataagattta aactcgaaaa gcaaaagcca aaaaactaac   4620
ttccattaaa agaagttgtt acatataacg ctataaagaa aatttatata tttggaggat   4680
accaaccatg tctcatattc aacgtgaaac tagttgttct cgccctcgtt taaattctaa   4740
tatggatgcc gatttatatg gttataaatg ggctcgtgat aatgttggtc aatctggtgc   4800
tactatttat cgtttatatg gtaaacctga tgctcctgaa ttattcttga aacatggtaa   4860
aggttctgtt gctaatgatg ttactgatga aatggttcgt ttaaactggt tgactgaatt   4920
tatgccttta cctactatta aacattttat tcgtactccc gatgatgctt ggttattaac   4980
tactgctatt cctggtaaaa ctgcttttca agttttagaa gaatatcctg attctggtga   5040
aaatattgtt gatgctttag ctgttttttt acgtcgttta cattctattc ccgtttgtaa   5100
```

-continued

```
ttgtcctttt aattctgatc gtgtttttcg tttagctcaa gctcaatctc gtatgaataa   5160
tggtttagtt gatgcttctg attttgatga tgaacgtaat ggttggcctg ttgaacaagt   5220
ttggaaagaa atgcacaaat tgttaccttt ttctcctgat tctgttgtta ctcatggtga   5280
tttttcttta gataatttga tctttgatga aggtaaattg attggttgta ttgatgttgg   5340
tcgtgttggt attgctgatc gttatcaaga tttagctatt ttatggaatt gtttaggtga   5400
attttctcct tctttacaga aacgtttatt tcagaaatat ggtattgata atcctgatat   5460
gaacaagtta caatttcatt taatgttgga cgagttcttt taagaattaa ttcatgacca   5520
aaatccctta acgtgagttt tcgttccact gagcgtcaga ccccgtagaa aagatcaaag   5580
gatcttcttg agatcctttt tttctgcgcg taatctgctg ctatttaaat tacgtacacg   5640
tgttattact ttgttaacga caattgtctt aattaactgg gcctcatggg ccttccgctc   5700
actgcccgct ttccagtcgg gaaacctgtc gtgccagctc tgcagatgac ggtgaaaacc   5760
tctgacacat gcagctcccg gagacggtca cagcttgtct gtaagcggat gccgggagca   5820
gacaagcccg tcagggcgcg tcagcgggtg ttggcgggtg tcggggcgca gccatgaccc   5880
agtcacgtag cgatagcgga gtgtatactg gcttaactat gcggcatcag agcagattgt   5940
actgagagtg caccatatgc ggtgtgaaat accgcacaga tgcgtaagga gaaaataccg   6000
catcaggcgc tcttccgctt cctcgctcac tgactcgctg cgctcggtcg ttcggctgcg   6060
gcgagcggta tcagctcact caaaggcggt aatacggtta tccacagaat caggggataa   6120
cgcaggaaag aacatgtgag caaaaggcca gcaaaaggcc aggaaccgta aaaaggccgc   6180
gttgctggcg tttttccata ggctccgccc ccctgacgag catcacaaaa atcgacgctc   6240
aagtcagagg tggcgaaacc cgacaggact ataaagatac caggcgtttc cccctggaag   6300
ctccctcgtg cgctctcctg ttccgaccct gccgcttacc ggatacctgt ccgcctttct   6360
cccttcggga agcgtggcgc tttctcatag ctcacgctgt aggtatctca gttcggtgta   6420
ggtcgttcgc tccaagctgg gctgtgtgca cgaacccccc gttcagcccg accgctgcgc   6480
cttatccggt aactatcgtc ttgagtccaa cccggtaaga cacgacttat cgccactggc   6540
agcagccact ggtaacagga ttagcagagc gaggtatgta ggcggtgcta cagagttctt   6600
gaagtggtgg cctaactacg gctacactag aaggacagta tttggtatct gcgctctgct   6660
gaagccagtt accttcggaa aaagagttgg tagctcttga tccggcaaac aaaccaccgc   6720
tggtagcggt ggtttttttg tttgcaagca gcagattacg cgcagaaaaa aaggatctca   6780
agaagatcct ttgatctttt ctactgcaga agcttgttag acaccctgtc atgtatttta   6840
tattatttat ttcaccatac ggattaagtg aaacctaatg aaaatagtac tttcggagct   6900
ttaactttaa tgaaggtatg ttttttttata gacatcgatg tctggtttaa caataggaaa   6960
aagtagctaa aactcccatg aattaaagaa ataacaaggt gtctaacaac ctgttattaa   7020
gaatgttaga aaagacttaa catttgtgtt gagtttttat agacattggt gtctagacat   7080
acggtagata aggtttgctc aaaaataaaa taaaaaaaga ttggactaaa aaacatttaa   7140
tttagtacaa tttaattagt tattttttcg tctcaaattt tgctttgttg agcagaaatt   7200
tagataaaaa aatccccgtg atcagattac aatgtcgttc attgtacgat gtgtcgaaaa   7260
atctttacga cactctaaac tgaccacacg gggggaaaaag aaaactgaac taataacatc   7320
atgatactcg gaaaacctag caattctcaa cccctaaaca aaagaaactt ccaaaaccct   7380
gaccatataa aggagtggca acaatcagca atcagtcaag atttgatagc agaaaatctt   7440
gtatcggttg ctaatggttt tgatgtacta tttatcggca ataaataccg aactaacacg   7500
```

-continued

```
ggtgttctgt cacggcacat attaaactcc tattctcatt tagaagatgg tggttcgtat   7560
ggtagaacat ttgacccatt taccaataaa gaaatgcagt gggttcaatt taaaccgaat   7620
agaccaagaa aaggttctac tggtaaggta atcaaatatg aatcgccaaa aggtgaacct   7680
acaagagttc taatgccgtt tgtgcctatg aaaatatggc aacggattag cgataagttc   7740
ggagtaccga ttaatccgaa aaaagatact cacttttggg aatgggtaaa gaataatcca   7800
tcgataccga ttgccattac agaaggaaat aaaaaagcta attgcctatt atcctatggc   7860
tatcctgcta ttgcctttgt aggcatttgg aacggattag agaaaataaa tgatttctcg   7920
aaggaaaagc agttaaaaga ggatttgaaa tggttgttat ccaacggcaa ccgaaatatt   7980
aatatcatct ttgaccaaga ccagaaacaa aaaactgtaa ttaatgtaaa caaagctatt   8040
ttcgctttat cttctctaat aagtagaaat ggtcataaag ttaatattgt gcaatggttg   8100
ccgtcaaaag gtaaaggaat agatgattat ttggtagctt taccttttga gaaaagagaa   8160
aatcatttag acaacttaat taaaattgca ccatcattta atttttggtc aactaaatac   8220
ttattcaagt gtcgtaaacc agatttaacc gtaaattgcc gttatttgag cgatgcagta   8280
aaagaattac ctcaagagga tatagcatta atagcacctc acggcacggg taaaacttca   8340
ttagtagcta ctcacgttaa gaatcggagt tatcacggaa ggaaaactat ttcattggtg   8400
catcttgaaa gtttagccaa agctaatggc aacgcacttg gattatatta ccgaaccgaa   8460
aataatattg aaaagcaata tcttggattt agcttatgtg tagatagttg ccgtgataag   8520
attaacggca ttacaactga tattatttca ggtcaagatt attgcctttt cattgatgaa   8580
attgaccaag taattccaca catccttaac agtgaaactg aagtaagtaa gtatagatgc   8640
accatcattg acactttttc tgaactggtg agaaatgctg aacaggtcat tattgctgat   8700
gctgatttat ccgatgtgac gattgaccta atagaaaaca tcagaggtaa aaaactatat   8760
gtaatcaaga atgaatatca gtatcaggga atgactttta acgccgttgg ttcaccatta   8820
gaaatgatgg caatgatggg aaaatcggtg tcagaaggca agaaattatt tattaacacc   8880
acatcccaaa aggcaaaaag taagtacggc acaatcgctc ttgagtctta tatttttggt   8940
ctaaataaag aagcaaagat attaagaata gactctgaaa ccactaaaaa ccctgaacat   9000
ccagcctata aaatcattga ccaagactta aataatatcc tcaaagatta tgattatgtc   9060
attgcctcac cttgccttca aacaggtgtc agtattacct taaaagggca ttttgaccag   9120
caatttaact tttccagtgg aaacattaca cctcattgct ttttacagca aatgtggcgg   9180
ttgagggatg cagaaattga aagattctat tatgtgccga actcatctaa cctcaatctc   9240
attgggaata agtcaagttc accatcagac cttctaaaga gcaataacaa gatggcaacg   9300
gcaacggtta accttttggg tagaatcgac tccgaatatt ccctagagta tgaatcgcac   9360
ggcatttggc ttgagacgtg ggcaaaatta tcagcacggc ataacagttc aatgcgttgt   9420
tactctgaaa ttcttaccta tctaattacg tctcaagggc ataaattaaa tatcaacatt   9480
ccctcacctc ttgcagatat taagaagcta aatgatgagg taagtagtaa cagggaaaag   9540
gtaaaaaatg agagatactc tcagaggtta aactcaccag atattaacga tgcagaagct   9600
accatactcg aatctaaaga gcaaaaaatc ggattgactc tcaatgagag atgcacccta   9660
gaaaagcata aagttaagaa gcggtatggg aatgtaaaga tggatattct cacctttgat   9720
gatgatggac tataccccaa actcagacta ttttattacc tcaccatcgg taaacctcat   9780
ctcaaggcta atgacagaaa agctattgcc aaaatgggca atgacaataa aggcaagatt   9840
```

-continued

```
ctatcaaaag acttagttaa taaaacttac tccgctcgtg tgaaggtctt agagattctt   9900

aaactaactg actttatcga caatcttaga gatgaactct taataactcc caataatcca   9960

gctatcaccg attttaataa tcttctgcta agagctaaga aggatttaag agtattagga  10020

gtcaacatcg gaaaatatcc aatggccaac attaatgccg tacttactct cattggtcac  10080

aaactttctg taatgagaga tgagttcgga aaagagaaaa ggataaaagt agatggtaaa  10140

tcataccgat gttatcaact tgaaacatta ccagatttta ccaatgatac tcttgactac  10200

tggttagaaa atgatagcca aaaagaagta acagcaacag aaaattactc cgaaaatttt  10260

aacccttcaa atagctacaa tccagacagt aagacacttt cagagggtgc aaatttccta  10320

tatataaata aagaagaatt gcatccaaat aaattgcacc tagaaataaa agaaggtgct  10380

gaactttttt tattcggggt aaaggtgatt gtgaaaggaa tcttggacgg ggcagtaact  10440

atattctcta tgggtcaaga atacgattta tccctcaatg aactagaggg gatgttaaca  10500

tcatgaactt tacaagaatc tttttaaagg gcgatcgcac catgttaaat gatggtacat  10560

ttgttcagat atttgatatt taccatgacc acgcattggg agtgaccctt gaccttaaga  10620

cagaaaaaat tatttccgat gatgttaggg taattactgt caaagactta ttgttcgatg  10680

gcacttataa aggggtaaaa tcttttatgc ccgataatgc ccgataatgc ccgattgatg  10740

ctacaaaatc ccataatcat aagcgataat cccctaatag cttgtaattc ttgaaccgta  10800

gcgattttag agtattccaa aaagaagaaa taaacaccgc aaaatgtcgt atttcacata  10860

tataaaccaa ggtttttgc cctaaaatct ttatgtttgt agtgtgatgt tgggtcaaaa  10920

tggtcagaaa agttgcaagg tttttatgga tgcttacgcg cgcgaggggt aagcatcccc  10980

aaatagttac tttatcctag tccatgccca tttattgccg tcccgttcgg ctttaaaaaa  11040

gtgccaaaac tcacaaggtg caataaaaag ttctgtacct ttcgcaaccc tagataatct  11100

ttcaacagtt actttttttc ctattatctc ggtacaaagt ttggctagtt tctcttttcc  11160

ctctttttca atcaagcctt cttgtatgcc caactcattg attaatctct ctatttttac  11220

cattatttcc cgttcaggta gtttatcccc taaatcttca tcggggggca atgtagggca  11280

ttctgaaggg gctttttctt ctgtctggac attatctaat attgaagtaa ccaaactatc  11340

ttcagttttt tctattccta ttaattcata ttcggttact gtatccgtat caatatccga  11400

ataactatct ttatccgtat tagctattcg gttaagttta tccgttaact cagaaacaag  11460

actatatagc ggttttagct tttcttctat cctgttatct aatacggata agtttatacg  11520

gttatcatta tccgtattag tatcattggg ctttttggt agttctaccc cctcataaac  11580

cgcttttatt cccaattcca acagactgat aacagtatcc tttataatgg gtttttgct  11640

gatatggtga acttttgccc cttccatcat tgcgatactt tctatctcac tcatcaactt  11700

atcgcttaag tgaatctcgt atctgtttaa tcccttactg gttttattca tatccgttta  11760

ctttattcgg ttaacaattc tattttatac gaataaaata ttatacggtt aactttatac  11820

gtttaactat tttatctata cggataacag taataagtta ttcgtattag ttatacgttt  11880

acttttatcc aaataaaatt agtgcattta aactaaaaga atgattttat cggagttgat  11940

agcattggat taacctaaag atgtttataa gctatatctg ataagtattt aaggttattt  12000

tgttattctg tttattgaca ttatcagaat aaaagaatag aatataattg ttgagagata  12060

agaggtttaa gtgattatgg ttaagaagtt agttggttat gtcagggtca gtagtgaatc  12120

gcaagaggat aacactagct tacagaatca gatagagaga attgaagcat attgtatggc  12180

ttttggttat gagttggtaa aaatattcaa agaggttgcc actggtacaa aagcagatat  12240
```

tgaaacccgt cctattttta atgaagctat agaatacttg aaacaggata atgctaatgg 12300
aattattgcc ttgaagctag accgaatcgc acggaatgct ttagatgtat tgcgtttggt 12360
tcgtgaaacc ttagaaccac aaaataaaat gttagtgtta ctagatattc aggtagatac 12420
ttcgacacct tcaggaaaaa tgattttaac tgtaatgagt gccgttgctg aactcgaaag 12480
agacatgatc tatgatcgca ctcagggggg tagaaagact aaagcccaaa agggcgggta 12540
tgcctacggg aaacctaaat ttggctataa gactgaagaa aaggaactaa aagaagattc 12600
agcacaacag gaaactatta aactaattaa gagacaccgt aggtcaggga aaagctacca 12660
gaaaatagct gattatctca atgcccaaag tattccccact aaacaaggta agaaatggag 12720
ttctagcgtc gtctatcgaa tctgtcagga aaaagctggt taagtctgtt tatagatatt 12780
tagaatttat tgaataaaaa tagtatgaac aataaatatt tatggactaa ccacgctcgg 12840
aaacgtttaa ctgaacgatg ggaaataaaa gaatcatggg ttattgatac catcgaaaat 12900
cctgaacgtt cagaatttat tgttgatgag tcaggggaaa aatatcatta ctataaaaga 12960
atagctaagt ttaagaatag agtgttagaa gtgataactt ctgccaactc aacacccaca 13020
agaataataa ccttttactt taaccgtaac atgaggaaaa atttatgatt gttacttacg 13080
ataatgaagt tgacgcaatt tattttaagt taacggaaaa taaaattgat agcaccgaac 13140
ctcaaacaga caggattatc attgattacg atgaaagtaa taatattgtt ggcattgagg 13200
tattagattt taattatctt gtcaagaaag gtttaaccgt tgctgattta cctttttctg 13260
aagatgaaag attaacagct tctcaatatt ttaattttcc tgttgctatc taatccagaa 13320
ggggcaataa tccccttctt tcatcgagtt agacttaata tcacaaaagt cattttcatt 13380
ttaccgtttc ttttccacag cgtccgtacg cccctcgtta aatctcaaaa ccgacaattt 13440
atgatgttta taaaaagtta ctcactttaa taagtattta tactcattaa agggttattc 13500 ttttttgta gcctgatagg ttgggaagga atatttcaga ttatcagatt tgttgaatat 13560
ttttcgtcag atacgcaaac cttacaaaca taattaacaa ctgaaactat tgatatgtct 13620
aggttttagc tctatcacag gttggatctg tcg 13653

<210> SEQ ID NO 3
<211> LENGTH: 17623
<212> TYPE: DNA
<213> ORGANISM: Artificial sequence
<220> FEATURE:
<223> OTHER INFORMATION: Synthetic plasmid construct derived from p6.8 endogenous plasmid from Cyanobacterium sp. PTA-13311, plus ptxA,B,C, from Cyanothece sp. ATCC-51142, ptxD from Ralstonia sp. 4506, plus copper-inducible ethanologenic genes pdc and adh.

<400> SEQUENCE: 3
tcgactggtc aagttactat atgtttagaa acaacaaaaa aagaagtcat tataaaaata 60
attgatacag gaattggcat taataaagaa gaacaaaaat taatttttaa tcgtttttat 120
cgaatcaata aagcaagaaa tagagagaaa ggcagttgcg gattaggttt agctattgca 180
aatgcgatcg cgcttaatca tggtggtaga ataattttag aaagtcaaga aaatcaaggc 240
agtattttta ccgtttattt accgaaaatc atttcatcct aatttcatat tcttttgaca 300
gaatcaaagg taaagataaa aagagagaaa cagtcatgaa ttcttatacc gtgggtactt 360
atttagccga acgcttagtg caaattggtt taaaacatca ttttgccgtg gctggggact 420
ataatttagt gttattggat aacttattat taaataaaaa catggaacaa gtgtattgtt 480
gtaatgaatt aaattgtggt ttttctgctg aaggttatgc tagagctaaa ggtgcagctg 540

-continued

```
ctgctgttgt tacttattct gtgggtgctt tatctgcttt tgatgctatt ggtggtgctt    600
atgccgaaaa tttacccgtg attttaattt ctggtgcccc taataataat gatcatgccg    660
ctggacatgt tttacatcat gccttaggta aaaccgatta tcattatcaa ttagaaatgg    720
ccaaaaatat tactgctgct gccgaagcta tttatactcc tgaagaagcc cctgccaaaa    780
ttgatcatgt gattaaaacc gccttacgcg aaaaaaaacc cgtgtattta gaaattgcct    840
gtaatattgc ttctatgcct tgtgctgctc ctgggcctgc ttctgcttta tttaatgatg    900
aagcctctga tgaagctagt ttaaatgctg ccgtggaaga aaccttaaaa tttattgcca    960
atcgcgataa agttgccgtg ttagttggtt ctaaattaag agctgctggt gctgaagaag   1020
ctgctgttaa atttgctgat gctttaggtg gtgcagttgc tactatggct gctgccaaat   1080
ctttttttcc cgaagaaaat ccccattata ttggaactag ttggggagaa gtttcttatc   1140
ctggtgtgga aaaaactatg aaagaagccg acgctgttat tgctttagcc cctgtgttta   1200
atgattattc taccactggt tggactgata ttcccgatcc caaaaaatta gttttagccg   1260
aacctcgttc tgttgttgtt aatggtgttc gctttccctc tgtgcattta aaagattatt   1320
taacccgctt agcccaaaaa gtttctaaaa aaactggtgc cttagatttt tttaaatctt   1380
taaatgcggg tgaattaaaa aaagctgctc ctgctgatcc ttctgctcct ttagttaatg   1440
ctgaaattgc ccgtcaagtt gaagccttat taacccctaa tactaccgtt attgccgaaa   1500
ctggtgattc ttggtttaat gcccaacgca tgaaattacc taatggtgcc cgtgttgaat   1560
atgaaatgca atggggtcat attggttggt ctgtacctgc tgcttttggt tatgctgttg   1620
gtgctcctga acgtcgtaat attttaatgg tgggtgatgg ttcttttcaa ttaactgccc   1680
aagaagttgc ccaaatggtt cgcttaaaat tacccgttat tatttttta ataaataatt   1740
atggttatac cattgaagtg atgattcatg atgggccata taataatatt aaaaattggg   1800
attatgcggg tttaatggaa gtgtttaatg gtaatggtgg ttatgattct ggtgctggta   1860
aaggtttaaa agccaaaact ggtggtgaat tagctgaagc tattaaagtt gccttagcca   1920
atactgatgg gccaacctta attgaatgtt ttattggtcg cgaagattgt accgaagaat   1980
tagttaaatg gggtaaacgt gttgctgctg ctaattctcg caaacccgtg aataaattat   2040
tgtaaggatc cagcaaggtt tcatcccgac cccctcaggg tcgggatttt tttattgtga   2100
gctcaacttt agatattcgt agttggcaat gtcgtaaatg cggaacaata catggaaaac   2160
atatagattt gtaatgagaa aaagtgtaaa caaatattaa gaaaaagatc agaaaaattt   2220
aacaacacgt aataaaaaaa tgcgtcacta cgggttataa atttacatga aaggttaaaa   2280
cacttttctg agacgatttt gataaaaaag ttgtcaaaaa attaagtttc tttacaaatg   2340
cttaacaaaa acttggtttt aagcacaaaa taagagagac taatttgcag aagttttaca   2400
aggaaatctt gaagaaaaag atctaagtaa aacgactctg tttaaccaaa atttaacaaa   2460
tttaacaaaa caaactaaat ctattaggag attaactaca tatgagtgaa actaaattta   2520
aagcctatgc cgtaatgaat cctggtgaaa aattacaacc ctgggaatat gaacctgctc   2580
ctttacaggt agatgaaatt gaagtaagag ttactcacaa tggtttatgt cacactgact   2640
tacacatgag agataatgac tggaatgtta gtgagttccc cttagtagca ggtcatgaag   2700
ttgttggtga agtaaccgct gttggtgaaa aagtaaccag tcgtaaaaaa ggtgatagag   2760
ttggtgtagg ttggattcgt aattcttgtc gcgcttgtga ccattgttta caaggagaag   2820
agaacatttg tagagagggt tatactggtt taattgttgg tcatcacggt ggatttgctg   2880
```

-continued

```
atcgtgtacg tgtacctgct gacttcactt ataaaattcc tgatgcttta gatagtgcat   2940
ctgctgctcc tttattatgt gccggtatta ccgtttacac tcctttaaga acctacatta   3000
aacatcccgg tatgaaagta ggtgttatgg gtattggagg attaggacat ttagctatta   3060
aatttgctcg tgcaatggga gcagaagtta ctgcctttag taccagtcct aataaagaag   3120
cccaagccaa agaatttggt gctcatcatt tccaacaatg gggtactgct gaagaaatga   3180
aagctgttgc cggtaatttt gatttagttt tatctaccat ctctgctgaa actgactggg   3240
atgctgcctt ctctttatta gcaaataacg gtgttttatg tttcgtaggt attcccgtta   3300
gttctttaaa tgttccttta attcctttaa ttttcggaca aaaatctgtt gtaggttctg   3360
tagttggagg aagaagattc atggcagaaa tgttagagtt cgccgctgta aatcagatta   3420
aacctatgat cgaaactatg cccttatctc aagtaaatga agctatggat aaagttgccg   3480
ccaataaagc cagatataga attgtattat tatctgaata actagatcta cttctaaact   3540
gaaacaaatt tgagggtagg cttcattgtc tgcccttatt tttttattta ggaaaagtga   3600
acagactaaa gagtgttggc tctattgctt tgagtatgta aattaggcgt tgctgaatta   3660
aggtatgatt tttgacccct gcaggtttaa atgctgtcaa ggttagcaaa taatatctaa   3720
tatttatcaa ttgaatatat taaattgtta atattaagtg aaaatatttt aaaattctaa   3780
gaaaaataaa ttaaattaag ctacatttat caaataatta ttagtattta ttaattgata   3840
tttattgaca ataatataca taaaatacaa aaaataagcc aaatcttaaa aattattaaa   3900
tataaaaaaa aactttgctt attactaaga tgttttatta caggtgctac acaaaaaaaa   3960
agtcttttac tattctaatg acagtataaa aaaagtgcta agtctttgtc agaaaagatt   4020
ttatcgattt caactaataa ctttcatact taatttatcc atttaataaa aaataagatt   4080
tctaaatgat ttatcgctat ttataatatt tttaaatcat ggtcaagaat atattttttg   4140
atgatttccc aactatttct taaccttttc tttaccacag gataggaata gtcatattat   4200
gatgagagac taaataaaga ctaagtaaaa atacactcat aaacaacaac aaaaatgaat   4260
tcaatgaaac ctaaagtagt attaactcat tgggtacacc ccgaaataat agaattatta   4320
agtgctagtg cagatgtgat tcccaataca acaagagaaa ctttacctcg tagtgaagta   4380
attgccagag ccaaagatgc tgatgcttta atggccttta tgcctgattc tattgattct   4440
gcatttttag aggaatgtcc taaattaaga gtgatcggtg ccgctttaaa aggttatgat   4500
aattttgatg taaacgcctg tacaagacac ggtgtttggt taaccatcgt acctgattta   4560
ttaactattc ctaccgccga attaacaatt ggattattat taggtttaac tagacacatg   4620
ttagaaggtg atcgtcagat acgttctgga cattttcaag gatggagacc tactttatat   4680
ggttctggat taaccggtaa aactttagga attataggta tgggtgctgt aggacgtgct   4740
attgctcaaa gattagcagg atttgaaatg aatttattat attgtgatcc tataccttta   4800
aatgcagaac aagaaaaagc atggcatgta caaagagtta ctttagacga attattagag   4860
aaatgtgatt acgttgttcc tatggtgccc atggcagcag agacattaca tttaattgat   4920
gccaccgcct tagcaaaaat gaaaacagga tcttatttaa tcaatgcttg tagaggttct   4980
gttgtggacg agaatgccgt tatagctgct ttagctagtg gtaaattagc aggatatgct   5040
gccgacgtat ttgagatgga agagtggata agagcagaca gacctcaagc tattcccaaa   5100
gccttattag ataacaccgc acaaaccttt tttacacctc atttaggtag tgctgtaaaa   5160
gaagtacgtt tagaaattga aagacaagct gcaatgaata ttatacaggc tttagcaggt   5220
gaaaaaccta tgggtgcaat taatcaaccc tatcctggtg taaaagctgc tggatcctac   5280
```

-continued

```
gtacaccatc atcaccatca ctagttataa tgagctcttt aaaccaagat tagaaaatcc   5340

atttcattaa cgtaaaccaa cataattagg agaaattaat tacaatgcat atttttctta   5400

ataaccttag tgtcacctat aaagatggaa ccgtggcctt agaaaatatt tctcttgaat   5460

tgattccagg agaatttacg gtacttttag ggcttctgg tgcaggaaaa tcaacccttt    5520

tacgttgtat caattttcta acagttccta ctaagggtga agttattgtg gaggggttag   5580

gaaccctaaa taacccgaaa atcttaagaa aacatcgcca aaaaacgggc atgatttttc   5640

aacaacatca attaattcct cgacaaactg cccttaaaaa tgttttagtt ggtcgtttag   5700

cctatcactc taccttaaga agttttttcc ctttgcctaa aattgatcaa atgattgctt   5760

tagattgttt ggacagagtt ggcctattaa ataaagcttt aactcctgtt aaacaactaa   5820

gtggaggaca acaacaacgg gtaggaatag ccagagcttt agctcaaaaa cccagatttc   5880

tcttagcaga tgaacctgtt gctagtttag atcctggtag ttctcataag atattaacta   5940

atctcaaaaa aatttgtcaa gaagatggta ttggggcagt ggttagttta catcaaatag   6000

atttcgcttt agactatggc gatcgcatta ttggccttgc agatggaaac atcctttttg   6060

atagtcaccc gtcagaaata caatcatacc agttagaaaa aatttatcac aattcttctt   6120

tgattaaggc aggttaattg ttatctaaat cacacttaaa aaatcattaa aatcttgctt   6180

ttttcaagaa aatcattata atcaacagta aaattatttg actcaaaatt ggtatgatca   6240

gtttcatctt taaaaaatcc ttaaccccctg ttgtttcttt taccctatta actctaattg  6300

gttgtagtac accgaatagt caaacatcca ataataaccc tgaaaatagc aaagcagaca   6360

caaaagctaa ccctaaaaaa ttagtagttg ctttgttacc cgatgaatca gtatctaccg   6420

taattcaaaa taataagggg ttagaaagct acttagaaga ccgactgaat aaagatgttg   6480

aattgtttgt cagtaccgat tattcttcta tgatcgaagc agcgagtaat ggaagattag   6540

acttagccta ttttggtcct ttgtcgtatg ttttggccaa aactaaaagt aatatcgaag   6600

cctttgcagc gttagaaaaa gatggagaag ccacctataa atctgtcatt attggtaatg   6660

cagaagcagg aattgattcc tatgacaaaa tcgaaggaaa aactatggct tatggagatc   6720

aagcctcgac ctctagtcat ttaattccta agtcaatgtt aatggaaaaa ggcttaaaag   6780

cagaagaaaa ttatcaagaa gtatttgtcg gttctcatga tgctgtagct gtagctgttg   6840

ccaatggaaa agcccaagca gggggcttaa gtaaacccat ttataccgct ttaattaata   6900

agggaaccat tgatgaaaat aaagtcattt taatagaaga atctaaacca tttccccaat   6960

atccttggac gatgcgatct gacttagaac ctcaattaaa acagcaaatt aagcaagctt   7020

ttctagaact agaagataag gcagttttag aaccatttaa agcagaaggg tttcaatcag   7080

tagaagacaa ggattataat gttgtccgag acttaggaaa aatcctcaat cttgattttg   7140

ctaaacttaa ttaatctgag ggtttagcta ctgtaaagat caattattca tttagggata   7200

accatcttaa actctcaagt gagatttttt cttttactaa acaaagaatc aaatcaaagt   7260

aaacataaag ttataaggtt atccctaatt tttggtaatc aaatattgga aaaatgacaa   7320

tcaatcaaga taaatattct aatctgttgc gccaatacaa gattctttgg tatcgttcac   7380

taataaacat cattattttg ctaataataa ttattattag ttttgctgta gttggtttat   7440

tagatggaaa acgcttatct gaaggaattc ctgacctatt agaaatggta gcacaaatgc   7500

tgcctcccga ttttactcgt gcttctgatt ggattaaacc actaattgat accttaggaa   7560

tgagtattgc aggaacagga atggctgtta ttttttctct gcctattact ttcggggcag   7620
```

-continued

```
cacaaaatac cagtccccat cctttcgttt attttgtatc aagaattatt ttaaatatag   7680
caagagctat tcctgaatta cttctaggaa ttatctttgt tgccgctgtt gggtttggcg   7740
cacttcctgg ggtattagca ttgggatttc attctattgg tatggtaggt aaattttttg   7800
ctgagtccat agaacataca gacaacgcac ctattgaagc agcaaaagca gtcggagcaa   7860
atcatttaca aatcatttat catagtattt taccccaagt tttaccacaa atcgccgatg   7920
ttacatttta tcgttgggag tacaatttta gagcttctct agtattaggc gcagtgggag   7980
ccggtggcat tggatttgaa attattgggg cattacgttt actcaaatat caggaagttt   8040
ctgccctttt gttagttgtt ttagttatgg taacattagt agatagttta ggtaactttt   8100
taagaaaaaa attcatttaa agatcttagt taccgtggaa cgctcggttg ccgccgggcg   8160
ttttttattc ctgcaggatc atcttgctga aaaactcgag cgctcgttcc gcaaagcggt   8220
acggagttag ttaggggcta atgggcattc tcccgtacag gaaagagtta gaagttatta   8280
attatcaaca attctccttt gcctagtgca tcgttacctt tttaattaaa acataaggaa   8340
aactaataat cgtaataatt taacctcaaa gtgtaaagaa atgtgaaatt ctgactttta   8400
taacgttaaa gagggaaaaa ttagcagttt aaaataccta gagaatagtc tggggtaagc   8460
atagagaatt agattagtta agttaatcaa attcagaaaa aataataatc gtaaatagtt   8520
aatctgggtg tatagaaaat gatccccttc atgataagat ttaaactcga aaagcaaaag   8580
ccaaaaaact aacttccatt aaaagaagtt gttacatata acgctataaa gaaaatttat   8640
atatttggag gataccaacc atgtctcata ttcaacgtga aactagttgt tctcgccctc   8700
gtttaaattc taatatggat gccgatttat atggttataa atgggctcgt gataatgttg   8760
gtcaatctgg tgctactatt tatcgtttat atggtaaacc tgatgctcct gaattattct   8820
tgaaacatgg taaaggttct gttgctaatg atgttactga tgaaatggtt cgtttaaact   8880
ggttgactga atttatgcct ttacctacta ttaaacattt tattcgtact cccgatgatg   8940
cttggttatt aactactgct attcctggta aaactgcttt tcaagtttta gaagaatatc   9000
ctgattctgg tgaaaatatt gttgatgctt tagctgtttt tttacgtcgt ttacattcta   9060
ttcccgtttg taattgtcct tttaattctg atcgtgtttt tcgtttagct caagctcaat   9120
ctcgtatgaa taatggttta gttgatgctt ctgattttga tgatgaacgt aatggttggc   9180
ctgttgaaca agtttggaaa gaaatgcaca aattgttacc tttttctcct gattctgttg   9240
ttactcatgg tgatttttct ttagataatt tgatctttga tgaaggtaaa ttgattggtt   9300
gtattgatgt tggtcgtgtt ggtattgctg atcgttatca agatttagct attttatgga   9360
attgtttagg tgaattttct ccttctttac agaaacgttt atttcagaaa tatggtattg   9420
ataatcctga tatgaacaag ttacaatttc atttaatgtt ggacgagttc ttttaagaat   9480
taattcatga ccaaaatccc ttaacgtgag ttttcgttcc actgagcgtc agaccccgta   9540
gaaaagatca aaggatcttc ttgagatcct ttttttctgc gcgtaatctg ctgctattta   9600
aattacgtac acgtgttatt actttgttaa cgacaattgt cttaattaac tgggcctcat   9660
gggccttccg ctcactgccc gctttccagt cgggaaacct gtcgtgccag ctctgcagat   9720
gacggtgaaa acctctgaca catgcagctc ccggagacgg tcacagcttg tctgtaagcg   9780
gatgccggga gcagacaagc ccgtcagggc gcgtcagcgg gtgttggcgg gtgtcggggc   9840
gcagccatga cccagtcacg tagcgatagc ggagtgtata ctggcttaac tatgcggcat   9900
cagagcagat tgtactgaga gtgcaccata tgcggtgtga aataccgcac agatgcgtaa   9960
ggagaaaata ccgcatcagg cgctcttccg cttcctcgct cactgactcg ctgcgctcgg  10020
```

-continued

```
tcgttcggct gcggcgagcg gtatcagctc actcaaaggc ggtaatacgg ttatccacag  10080
aatcagggga taacgcagga aagaacatgt gagcaaaagg ccagcaaaag gccaggaacc  10140
gtaaaaaggc cgcgttgctg gcgtttttcc ataggctccg cccccctgac gagcatcaca  10200
aaaatcgacg ctcaagtcag aggtggcgaa acccgacagg actataaaga taccaggcgt  10260
ttccccctgg aagctccctc gtgcgctctc ctgttccgac cctgccgctt accggatacc  10320
tgtccgcctt tctcccttcg ggaagcgtgg cgctttctca tagctcacgc tgtaggtatc  10380
tcagttcggt gtaggtcgtt cgctccaagc tgggctgtgt gcacgaaccc cccgttcagc  10440
ccgaccgctg cgccttatcc ggtaactatc gtcttgagtc caacccggta agacacgact  10500
tatcgccact ggcagcagcc actggtaaca ggattagcag agcgaggtat gtaggcggtg  10560
ctacagagtt cttgaagtgg tggcctaact acggctacac tagaaggaca gtatttggta  10620
tctgcgctct gctgaagcca gttaccttcg gaaaaagagt tggtagctct tgatccggca  10680
aacaaaccac cgctggtagc ggtggttttt ttgtttgcaa gcagcagatt acgcgcagaa  10740
aaaaaggatc tcaagaagat cctttgatct tttctactgc agaagcttgt tagacaccct  10800
gtcatgtatt ttatattatt tatttcacca tacggattaa gtgaaaccta atgaaaatag  10860
tactttcgga gctttaactt taatgaaggt atgttttttt atagacatcg atgtctggtt  10920
taacaatagg aaaaagtagc taaaactccc atgaattaaa gaaataacaa ggtgtctaac  10980
aacctgttat taagaatgtt agaaaagact taacatttgt gttgagtttt tatagacatt  11040
ggtgtctaga catacggtag ataaggtttg ctcaaaaata aaataaaaaa agattggact  11100
aaaaaacatt taatttagta caatttaatt agttattttt tcgtctcaaa ttttgctttg  11160
ttgagcagaa atttagataa aaaaatcccc gtgatcagat tacaatgtcg ttcattgtac  11220
gatgtgtcga aaaatcttta cgacactcta aactgaccac acgggggaaa aagaaaactg  11280
aactaataac atcatgatac tcggaaaacc tagcaattct caacccctaa acaaaagaaa  11340
cttccaaaac cctgaccata taaaggagtg gcaacaatca gcaatcagtc aagatttgat  11400
agcagaaaat cttgtatcgg ttgctaatgg ttttgatgta ctatttatcg gcaataaata  11460
ccgaactaac acgggtgttc tgtcacggca catattaaac tcctattctc atttagaaga  11520
tggtggttcg tatggtagaa catttgaccc atttaccaat aaagaaatgc agtgggttca  11580
atttaaaccg aatagaccaa gaaaaggttc tactggtaag gtaatcaaat atgaatcgcc  11640
aaaaggtgaa cctacaagag ttctaatgcc gtttgtgcct atgaaaatat ggcaacggat  11700
tagcgataag ttcggagtac cgattaatcc gaaaaaagat actcactttt gggaatgggt  11760
aaagaataat ccatcgatac cgattgccat tacagaagga aataaaaaag ctaattgcct  11820
attatcctat ggctatcctg ctattgcctt tgtaggcatt tggaacggat tagagaaaat  11880
aaatgatttc tcgaaggaaa agcagttaaa agaggatttg aaatggttgt tatccaacgg  11940
caaccgaaat attaatatca tctttgacca agaccagaaa caaaaaactg taattaatgt  12000
aaacaaagct attttcgctt tatcttctct aataagtaga aatggtcata aagttaatat  12060
tgtgcaatgg ttgccgtcaa aaggtaaagg aatagatgat tatttggtag ctttaccttt  12120
tgagaaaaga gaaaatcatt tagacaactt aattaaaatt gcaccatcat ttaatttttg  12180
gtcaactaaa tacttattca agtgtcgtaa accagattta accgtaaatt gccgttattt  12240
gagcgatgca gtaaaagaat tacctcaaga ggatatagca ttaatagcac ctcacggcac  12300
gggtaaaact tcattagtag ctactcacgt taagaatcgg agttatcacg gaaggaaaac  12360
```

-continued

```
tatttcattg gtgcatcttg aaagtttagc caaagctaat ggcaacgcac ttggattata  12420
ttaccgaacc gaaaataata ttgaaaagca atatcttgga tttagcttat gtgtagatag  12480
ttgccgtgat aagattaacg gcattacaac tgatattatt tcaggtcaag attattgcct  12540
tttcattgat gaaattgacc aagtaattcc acacatcctt aacagtgaaa ctgaagtaag  12600
taagtataga tgcaccatca ttgacacttt ttctgaactg gtgagaaatg ctgaacaggt  12660
cattattgct gatgctgatt tatccgatgt gacgattgac ctaatagaaa acatcagagg  12720
taaaaaacta tatgtaatca agaatgaata tcagtatcag ggaatgactt ttaacgccgt  12780
tggttcacca ttagaaatga tggcaatgat gggaaaatcg gtgtcagaag gcaagaaatt  12840
atttattaac accacatccc aaaaggcaaa aagtaagtac ggcacaatcg ctcttgagtc  12900
ttatattttt ggtctaaata aagaagcaaa gatattaaga atagactctg aaaccactaa  12960
aaaccctgaa catccagcct ataaaatcat tgaccaagac ttaaataata tcctcaaaga  13020
ttatgattat gtcattgcct caccttgcct tcaaacaggt gtcagtatta ccttaaaagg  13080
gcattttgac cagcaattta acttttccag tggaaacatt acacctcatt gctttttaca  13140
gcaaatgtgg cggttgaggg atgcagaaat tgaaagattc tattatgtgc cgaactcatc  13200
taacctcaat ctcattggga ataagtcaag ttcaccatca gaccttctaa agagcaataa  13260
caagatggca acggcaacgg ttaacctttt gggtagaatc gactccgaat attccctaga  13320
gtatgaatcg cacggcattt ggcttgagac gtgggcaaaa ttatcagcac ggcataacag  13380
ttcaatgcgt tgttactctg aaattcttac ctatctaatt acgtctcaag ggcataaatt  13440
aaatatcaac attccctcac ctcttgcaga tattaagaag ctaaatgatg aggtaagtag  13500
taacagggaa aaggtaaaaa atgagagata ctctcagagg ttaaactcac cagatattaa  13560
cgatgcagaa gctaccatac tcgaatctaa agagcaaaaa atcggattga ctctcaatga  13620
gagatgcacc ctagaaaagc ataaagttaa gaagcggtat gggaatgtaa agatggatat  13680
tctcaccttt gatgatgatg gactataccc caaactcaga ctattttatt acctcaccat  13740
cggtaaacct catctcaagg ctaatgacag aaaagctatt gccaaaatgg gcaatgacaa  13800
taaaggcaag attctatcaa aagacttagt taataaaact tactccgctc gtgtgaaggt  13860
cttagagatt cttaaactaa ctgactttat cgacaatctt agagatgaac tcttaataac  13920
tcccaataat ccagctatca ccgattttaa taatcttctg ctaagagcta agaaggattt  13980
aagagtatta ggagtcaaca tcggaaaata tccaatggcc aacattaatg ccgtacttac  14040
tctcattggt cacaaacttt ctgtaatgag agatgagttc ggaaaagaga aaaggataaa  14100
agtagatggt aaatcatacc gatgttatca acttgaaaca ttaccagatt ttaccaatga  14160
tactcttgac tactggttag aaaatgatag ccaaaaagaa gtaacagcaa cagaaaatta  14220
ctccgaaaat tttaaccctt caaatagcta caatccagac agtaagacac tttcagaggg  14280
tgcaaatttc ctatatataa ataaagaaga attgcatcca aataaattgc acctagaaat  14340
aaaagaaggt gctgaacttt ttttattcgg ggtaaaggtg attgtgaaag gaatcttgga  14400
cggggcagta actatattct ctatgggtca agaatacgat ttatccctca atgaactaga  14460
ggggatgtta acatcatgaa ctttacaaga atctttttaa agggcgatcg caccatgtta  14520
aatgatggta catttgttca gatatttgat atttaccatg accacgcatt gggagtgacc  14580
cttgacctta agacagaaaa aattatttcc gatgatgtta gggtaattac tgtcaaagac  14640
ttattgttcg atggcactta taaaggggta aaatctttta tgcccgataa tgcccgataa  14700
tgcccgattg atgctacaaa atcccataat cataagcgat aatcccctaa tagcttgtaa  14760
```

ttcttgaacc gtagcgattt tagagtattc caaaaagaag aaataaacac cgcaaaatgt 14820
cgtatttcac atatataaac caaggttttt tgccctaaaa tctttatgtt tgtagtgtga 14880
tgttgggtca aaatggtcag aaaagttgca aggtttttat ggatgcttac gcgcgcgagg 14940
ggtaagcatc cccaaatagt tactttatcc tagtccatgc ccatttattg ccgtcccgtt 15000
cggctttaaa aaagtgccaa aactcacaag gtgcaataaa aagttctgta cctttcgcaa 15060
ccctagataa tctttcaaca gttacttttt ttcctattat ctcggtacaa agtttggcta 15120
gtttctcttt tccctctttt tcaatcaagc cttcttgtat gcccaactca ttgattaatc 15180
tctctatttt taccattatt tcccgttcag gtagtttatc ccctaaatct tcatcggggg 15240
gcaatgtagg gcattctgaa ggggcttttt cttctgtctg gacattatct aatattgaag 15300
taaccaaact atcttcagtt ttttctattc ctattaattc atattcggtt actgtatccg 15360
tatcaatatc cgaataacta tctttatccg tattagctat tcggttaagt ttatccgtta 15420
actcagaaac aagactatat agcggtttta gcttttcttc tatcctgtta tctaatacgg 15480
ataagtttat acggttatca ttatccgtat tagtatcatt gggctttttt ggtagttcta 15540
ccccctcata aaccgctttt attcccaatt ccaacagact gataacagta tcctttataa 15600
tgggtttttt gctgatatgg tgaacttttg ccccttccat cattgcgata ctttctatct 15660
cactcatcaa cttatcgctt aagtgaatct cgtatctgtt taatccctta ctggttttat 15720
tcatatccgt ttactttatt cggttaacaa ttctatttta tacgaataaa atattatacg 15780
gttaacttta tacgtttaac tattttatct atacggataa cagtaataag ttattcgtat 15840
tagttatacg tttactttta tccaaataaa attagtgcat ttaaactaaa agaatgattt 15900
tatcggagtt gatagcattg gattaaccta aagatgttta taagctatat ctgataagta 15960
tttaaggtta ttttgttatt ctgtttattg acattatcag aataaaagaa tagaatataa 16020
ttgttgagag ataagaggtt taagtgatta tggttaagaa gttagttggt tatgtcaggg 16080
tcagtagtga atcgcaagag gataacacta gcttacagaa tcagatagag agaattgaag 16140
catattgtat ggcttttggt tatgagttgg taaaaatatt caaagaggtt gccactggta 16200
caaaagcaga tattgaaacc cgtcctattt ttaatgaagc tatagaatac ttgaaacagg 16260
ataatgctaa tggaattatt gccttgaagc tagaccgaat cgcacggaat gctttagatg 16320
tattgcgttt ggttcgtgaa accttagaac cacaaaataa aatgttagtg ttactagata 16380
ttcaggtaga tacttcgaca ccttcaggaa aaatgatttt aactgtaatg agtgccgttg 16440
ctgaactcga aagagacatg atctatgatc gcactcaggg gggtagaaag actaaagccc 16500
aaaagggcgg gtatgcctac gggaaaccta aatttggcta taagactgaa gaaaaggaac 16560
taaaagaaga ttcagcacaa caggaaacta ttaaactaat taagagacac cgtaggtcag 16620
ggaaaagcta ccagaaaata gctgattatc tcaatgccca aagtattccc actaaacaag 16680
gtaagaaatg gagttctagc gtcgtctatc gaatctgtca ggaaaaagct ggttaagtct 16740
gtttatagat atttagaatt tattgaataa aaatagtatg aacaataaat atttatggac 16800
taaccacgct cggaaacgtt taactgaacg atgggaaata aaagaatcat gggttattga 16860
taccatcgaa aatcctgaac gttcagaatt tattgttgat gagtcagggg aaaaatatca 16920
ttactataaa agaatagcta agtttaagaa tagagtgtta gaagtgataa cttctgccaa 16980
ctcaacaccc acaagaataa taacctttta ctttaaccgt aacatgagga aaaatttatg 17040
attgttactt acgataatga agttgacgca atttatttta agttaacgga aaataaaatt 17100

-continued

```
gatagcaccg aacctcaaac agacaggatt atcattgatt acgatgaaag taataatatt  17160

gttggcattg aggtattaga ttttaattat cttgtcaaga aaggtttaac cgttgctgat  17220

ttaccttttt ctgaagatga aagattaaca gcttctcaat attttaattt tcctgttgct  17280

atctaatcca gaaggggcaa taatcccctt ctttcatcga gttagactta atatcacaaa  17340

agtcattttc attttaccgt ttcttttcca cagcgtccgt acgcccctcg ttaaatctca  17400

aaaccgacaa tttatgatgt ttataaaaag ttactcactt taataagtat ttatactcat  17460

taaagggtta ttcttttttt gtagcctgat aggttgggaa ggaatatttc agattatcag  17520

atttgttgaa tatttttcgt cagatacgca aaccttacaa acataattaa caactgaaac  17580

tattgatatg tctaggtttt agctctatca caggttggat ctg                    17623


<210> SEQ ID NO 4
<211> LENGTH: 24
<212> TYPE: DNA
<213> ORGANISM: artificial sequence
<220> FEATURE:
<223> OTHER INFORMATION: Synthetic PCR primer sequence

<400> SEQUENCE: 4

tgctttagct agtggtaaat tagc                                            24


<210> SEQ ID NO 5
<211> LENGTH: 23
<212> TYPE: DNA
<213> ORGANISM: artificial sequence
<220> FEATURE:
<223> OTHER INFORMATION: Synthetic PCR primer sequence

<400> SEQUENCE: 5

ctaaccactg ccccaatacc atc                                             23


<210> SEQ ID NO 6
<211> LENGTH: 17295
<212> TYPE: DNA
<213> ORGANISM: Artificial Sequence
<220> FEATURE:
<223> OTHER INFORMATION: Synthetic plasmid construct derived from p6.8
      endogenous plasmid from Cyanobacterium sp. PTA-13311, plus
      ptxA,B,C, from Cyanothece sp. ATCC-51142, ptxD from Ralstonia sp.
      4506, plus nitrate-inducible ethanologenic genes pdc and adh.

<400> SEQUENCE: 6

acaattaata acttcttcct gtacgggcga atggccattt gctcctaact aactccgtac     60

tgctttgcgg aacgagcgta gcgaactctc cgaattacta agccttcatc cctgatagat    120

gcaaaaaacg aattaaaatt atgtgtaaaa agaaaatgtg tctttattta gtagtcaaag    180

ttacaaaata ttaagaatca aattaataat gtattgggca gttaagtata taagtcttta    240

aatatttatt tgtattcaat atattaagga ggatcagcct tatgaattct tataccgtgg    300

gtacttattt agccgaacgc ttagtgcaaa ttggtttaaa acatcatttt gccgtggctg    360

gggactataa tttagtgtta ttggataact tattattaaa taaaaacatg gaacaagtgt    420

attgttgtaa tgaattaaat tgtggttttt ctgctgaagg ttatgctaga gctaaaggtg    480

cagctgctgc tgttgttact tattctgtgg gtgctttatc tgcttttgat gctattggtg    540

gtgcttatgc cgaaaattta cccgtgattt taatttctgg tgcccctaat aataatgatc    600

atgccgctgg acatgtttta catcatgcct taggtaaaac cgattatcat tatcaattag    660

aaatggccaa aaatattact gctgctgccg aagctattta tactcctgaa gaagcccctg    720
```

-continued ccaaaattga tcatgtgatt aaaaccgcct tacgcgaaaa aaaacccgtg tatttagaaa 780
ttgcctgtaa tattgcttct atgccttgtg ctgctcctgg gcctgcttct gctttattta 840
atgatgaagc ctctgatgaa gctagtttaa atgctgccgt ggaagaaacc ttaaaattta 900
ttgccaatcg cgataaagtt gccgtgttag ttggttctaa attaagagct gctggtgctg 960
aagaagctgc tgttaaattt gctgatgctt taggtggtgc agttgctact atggctgctg 1020
ccaaatcttt ttttcccgaa gaaaatcccc attatattgg aactagttgg ggagaagttt 1080
cttatcctgg tgtggaaaaa actatgaaag aagccgacgc tgttattgct ttagcccctg 1140
tgtttaatga ttattctacc actggttgga ctgatattcc cgatcccaaa aaattagttt 1200
tagccgaacc tcgttctgtt gttgttaatg gtgttcgctt tccctctgtg catttaaaag 1260
attatttaac ccgcttagcc caaaaagttt ctaaaaaaac tggtgcctta gatttttta 1320
aatctttaaa tgcgggtgaa ttaaaaaaag ctgctcctgc tgatccttct gctcctttag 1380
ttaatgctga aattgcccgt caagttgaag ccttattaac ccctaatact accgttattg 1440
ccgaaactgg tgattcttgg tttaatgccc aacgcatgaa attacctaat ggtgcccgtg 1500
ttgaatatga aatgcaatgg ggtcatattg gttggtctgt acctgctgct tttggttatg 1560
ctgttggtgc tcctgaacgt cgtaatattt taatggtggg tgatggttct tttcaattaa 1620
ctgcccaaga agttgcccaa atggttcgct taaaattacc cgttattatt tttttaataa 1680
ataattatgg ttataccatt gaagtgatga ttcatgatgg gccatataat aatattaaaa 1740
attgggatta tgcgggttta atggaagtgt ttaatggtaa tggtggttat gattctggtg 1800
ctggtaaagg tttaaaagcc aaaactggtg gtgaattagc tgaagctatt aaagttgcct 1860
tagccaatac tgatgggcca accttaattg aatgttttat tggtcgcgaa gattgtaccg 1920
aagaattagt taaatggggt aaacgtgttg ctgctgctaa ttctcgcaaa cccgtgaata 1980
aattattgta aggatccagc aaggtttcat cccgaccccc tcagggtcgg gatttttta 2040
ttgtgagctc aactttagat attcgtagtt ggcaatgtcg taaatgcgga acaatacatg 2100
gaaaacatat agatttgtaa tgagaaaaag tgtaaacaaa tattaagaaa aagatcagaa 2160
aaatttaaca acacgtaata aaaaaatgcg tcactacggg ttataaattt acatgaaagg 2220
ttaaaacact tttctgagac gattttgata aaaaagttgt caaaaaatta agtttcttta 2280
caaatgctta acaaaaactt ggttttaagc acaaaataag agagactaat ttgcagaagt 2340
tttacaagga aatcttgaag aaaaagatct aagtaaaacg actctgttta accaaaattt 2400
aacaaattta acaaaacaaa ctaaatctat taggagatta actacatatg agtgaaacta 2460
aatttaaagc ctatgccgta atgaatcctg gtgaaaaatt acaaccctgg gaatatgaac 2520
ctgctccttt acaggtagat gaaattgaag taagagttac tcacaatggt ttatgtcaca 2580
ctgacttaca catgagagat aatgactgga atgttagtga gttcccctta gtagcaggtc 2640
atgaagttgt tggtgaagta accgctgttg gtgaaaaagt aaccagtcgt aaaaaaggtg 2700
atagagttgg tgtaggttgg attcgtaatt cttgtcgcgc ttgtgaccat tgtttacaag 2760
gagaagagaa catttgtaga gagggttata ctggtttaat tgttggtcat cacggtggat 2820
ttgctgatcg tgtacgtgta cctgctgact tcacttataa aattcctgat gctttagata 2880
gtgcatctgc tgctccttta ttatgtgccg gtattaccgt ttacactcct ttaagaacct 2940
acattaaaca tcccggtatg aaagtaggtg ttatgggtat tggaggatta ggacatttag 3000
ctattaaatt tgctcgtgca atgggagcag aagttactgc ctttagtacc agtcctaata 3060
aagaagccca agccaaagaa tttggtgctc atcatttcca acaatggggt actgctgaag 3120

-continued

```
aaatgaaagc tgttgccggt aattttgatt tagttttatc taccatctct gctgaaactg   3180
actgggatgc tgccttctct ttattagcaa ataacggtgt tttatgtttc gtaggtattc   3240
ccgttagttc tttaaatgtt cctttaattc ctttaatttt cggacaaaaa tctgttgtag   3300
gttctgtagt tggaggaaga agattcatgg cagaaatgtt agagttcgcc gctgtaaatc   3360
agattaaacc tatgatcgaa actatgccct tatctcaagt aaatgaagct atggataaag   3420
ttgccgccaa taaagccaga tatagaattg tattattatc tgaataacta gatctacttc   3480
taaactgaaa caaatttgag ggtaggcttc attgtctgcc cttatttttt tatttaggaa   3540
aagtgaacag actaaagagt gttggctcta ttgctttgag tatgtaaatt aggcgttgct   3600
gaattaaggt atgatttttg acccctgcag gatcatcttg ctgaaaaact cgagcgctcg   3660
ttccgcaaag cggtacggag ttagttaggg gctaatgggc attctcccgt acaggaaaga   3720
gttagaagtt attaattatc aacaattctc ctttgcctag tgcatcgtta ccttttttaat   3780
taaaacataa ggaaaactaa taatcgtaat aatttaacct caaagtgtaa agaaatgtga   3840
aattctgact tttataacgt taaagaggga aaaattagca gtttaaaata cctagagaat   3900
agtctggggt aagcatagag aattagatta gttaagttaa tcaaattcag aaaaaataat   3960
aatcgtaaat agttaatctg ggtgtataga aaatgatccc cttcatgata agatttaaac   4020
tcgaaaagca aaagccaaaa aactaacttc cattaaaaga agttgttaca tataacgcta   4080
taaagaaaat ttatatattt ggaggatacc aaccatgtct catattcaac gtgaaactag   4140
ttgttctcgc cctcgtttaa attctaatat ggatgccgat ttatatggtt ataaatgggc   4200
tcgtgataat gttggtcaat ctggtgctac tatttatcgt ttatatggta aacctgatgc   4260
tcctgaatta ttcttgaaac atggtaaagg ttctgttgct aatgatgtta ctgatgaaat   4320
ggttcgttta aactggttga ctgaatttat gcctttacct actattaaac attttattcg   4380
tactcccgat gatgcttggt tattaactac tgctattcct ggtaaaactg cttttcaagt   4440
tttagaagaa tatcctgatt ctggtgaaaa tattgttgat gctttagctg ttttttttacg   4500
tcgtttacat tctattcccg tttgtaattg tccttttaat tctgatcgtg tttttcgttt   4560
agctcaagct caatctcgta tgaataatgg tttagttgat gcttctgatt ttgatgatga   4620
acgtaatggt tggcctgttg aacaagtttg gaaagaaatg cacaaattgt taccttttttc   4680
tcctgattct gttgttactc atggtgattt ttctttagat aatttgatct ttgatgaagg   4740
taaattgatt ggttgtattg atgttggtcg tgttggtatt gctgatcgtt atcaagattt   4800
agctatttta tggaattgtt taggtgaatt ttctccttct ttacagaaac gtttatttca   4860
gaaatatggt attgataatc ctgatatgaa caagttacaa tttcatttaa tgttggacga   4920
gttcttttaa gaattaattc atgaccaaaa tcccttaacg tgagttttcg ttccactgag   4980
cgtcagaccc cgtagaaaag atcaaaggat cttcttgaga tcctttttttt ctgcgcgtaa   5040
tctgctgcta tttaaattac gtacacgtgt tattactttg ttaacgacaa ttgtcttaat   5100
taactgggcc tcatgggcct tccgctcact gcccgctttc cagtcgggaa acctgtcgtg   5160
ccagctctgc agatgacggt gaaaacctct gacacatgca gctcccggag acggtcacag   5220
cttgtctgta agcggatgcc gggagcagac aagcccgtca gggcgcgtca gcgggtgttg   5280
gcgggtgtcg gggcgcagcc atgacccagt cacgtagcga tagcggagtg tatactggct   5340
taactatgcg gcatcagagc agattgtact gagagtgcac catatgcggt gtgaaatacc   5400
gcacagatgc gtaaggagaa aataccgcat caggcgctct tccgcttcct cgctcactga   5460
```

```
ctcgctgcgc tcggtcgttc ggctgcggcg agcggtatca gctcactcaa aggcggtaat   5520
acggttatcc acagaatcag gggataacgc aggaaagaac atgtgagcaa aaggccagca   5580
aaaggccagg aaccgtaaaa aggccgcgtt gctggcgttt ttccataggc tccgcccccc   5640
tgacgagcat cacaaaaatc gacgctcaag tcagaggtgg cgaaacccga caggactata   5700
aagataccag gcgtttcccc ctggaagctc cctcgtgcgc tctcctgttc cgaccctgcc   5760
gcttaccgga tacctgtccg cctttctccc ttcgggaagc gtggcgcttt ctcatagctc   5820
acgctgtagg tatctcagtt cggtgtaggt cgttcgctcc aagctgggct gtgtgcacga   5880
accccccgtt cagcccgacc gctgcgcctt atccggtaac tatcgtcttg agtccaaccc   5940
ggtaagacac gacttatcgc cactggcagc agccactggt aacaggatta gcagagcgag   6000
gtatgtaggc ggtgctacag agttcttgaa gtggtggcct aactacggct acactagaag   6060
gacagtattt ggtatctgcg ctctgctgaa gccagttacc ttcggaaaaa gagttggtag   6120
ctcttgatcc ggcaaacaaa ccaccgctgg tagcggtggt ttttttgttt gcaagcagca   6180
gattacgcgc agaaaaaaag gatctcaaga agatcctttg atcttttcta ctgcagaagc   6240
ttgttagaca ccctgtcatg tattttatat tatttatttc accatacgga ttaagtgaaa   6300
cctaatgaaa atagtacttt cggagcttta actttaatga aggtatgttt ttttatagac   6360
atcgatgtct ggtttaacaa taggaaaaag tagctaaaac tcccatgaat taaagaaata   6420
acaaggtgtc taacaacctg ttattaagaa tgttagaaaa gacttaacat ttgtgttgag   6480
tttttataga cattggtgtc tagacatacg gtagataagg tttgctcaaa aataaaataa   6540
aaaaagattg gactaaaaaa catttaattt agtacaattt aattagttat tttttcgtct   6600
caaattttgc tttgttgagc agaaatttag ataaaaaaat ccccgtgatc agattacaat   6660
gtcgttcatt gtacgatgtg tcgaaaaatc tttacgacac tctaaactga ccacacgggg   6720
gaaaaagaaa actgaactaa taacatcatg atactcggaa aacctagcaa ttctcaaccc   6780
ctaaacaaaa gaaacttcca aaaccctgac catataaagg agtggcaaca atcagcaatc   6840
agtcaagatt tgatagcaga aaatcttgta tcggttgcta atggttttga tgtactattt   6900
atcggcaata aataccgaac taacacgggt gttctgtcac ggcacatatt aaactcctat   6960
tctcatttag aagatggtgg ttcgtatggt agaacatttg acccatttac caataaagaa   7020
atgcagtggg ttcaatttaa accgaataga ccaagaaaag gttctactgg taaggtaatc   7080
aaatatgaat cgccaaaagg tgaacctaca agagttctaa tgccgtttgt gcctatgaaa   7140
atatggcaac ggattagcga taagttcgga gtaccgatta atccgaaaaa agatactcac   7200
ttttgggaat gggtaaagaa taatccatcg ataccgattg ccattacaga aggaaataaa   7260
aaagctaatt gcctattatc ctatggctat cctgctattg cctttgtagg catttggaac   7320
ggattagaga aaataaatga tttctcgaag gaaaagcagt taaaagagga tttgaaatgg   7380
ttgttatcca acggcaaccg aaatattaat atcatctttg accaagacca gaaacaaaaa   7440
actgtaatta atgtaaacaa agctattttc gctttatctt ctctaataag tagaaatggt   7500
cataaagtta atattgtgca atggttgccg tcaaaaggta aaggaataga tgattatttg   7560
gtagctttac cttttgagaa aagagaaaat catttagaca acttaattaa aattgcacca   7620
tcatttaatt tttggtcaac taaatactta ttcaagtgtc gtaaaccaga tttaaccgta   7680
aattgccgtt atttgagcga tgcagtaaaa gaattacctc aagaggatat agcattaata   7740
gcacctcacg gcacgggtaa aacttcatta gtagctactc acgttaagaa tcggagttat   7800
cacggaagga aaactatttc attggtgcat cttgaaagtt tagccaaagc taatggcaac   7860
```

```
gcacttggat tatattaccg aaccgaaaat aatattgaaa agcaatatct tggatttagc   7920
ttatgtgtag atagttgccg tgataagatt aacggcatta caactgatat tatttcaggt   7980
caagattatt gccttttcat tgatgaaatt gaccaagtaa ttccacacat ccttaacagt   8040
gaaactgaag taagtaagta tagatgcacc atcattgaca ctttttctga actggtgaga   8100
aatgctgaac aggtcattat tgctgatgct gatttatccg atgtgacgat tgacctaata   8160
gaaaacatca gaggtaaaaa actatatgta atcaagaatg aatatcagta tcagggaatg   8220
acttttaacg ccgttggttc accattagaa atgatggcaa tgatgggaaa atcggtgtca   8280
gaaggcaaga aattatttat taacaccaca tcccaaaagg caaaaagtaa gtacggcaca   8340
atcgctcttg agtcttatat ttttggtcta aataaagaag caaagatatt aagaatagac   8400
tctgaaacca ctaaaaaccc tgaacatcca gcctataaaa tcattgacca agacttaaat   8460
aatatcctca aagattatga ttatgtcatt gcctcacctt gccttcaaac aggtgtcagt   8520
attaccttaa aagggcattt tgaccagcaa tttaactttt ccagtggaaa cattacacct   8580
cattgctttt tacagcaaat gtggcggttg agggatgcag aaattgaaag attctattat   8640
gtgccgaact catctaacct caatctcatt gggaataagt caagttcacc atcagacctt   8700
ctaaagagca ataacaagat ggcaacggca acggttaacc ttttgggtag aatcgactcc   8760
gaatattccc tagagtatga atcgcacggc atttggcttg agacgtgggc aaaattatca   8820
gcacggcata acagttcaat gcgttgttac tctgaaattc ttacctatct aattacgtct   8880
caagggcata aattaaatat caacattccc tcacctcttg cagatattaa gaagctaaat   8940
gatgaggtaa gtagtaacag ggaaaaggta aaaaatgaga gatactctca gaggttaaac   9000
tcaccagata ttaacgatgc agaagctacc atactcgaat ctaaagagca aaaaatcgga   9060
ttgactctca atgagagatg caccctagaa aagcataaag ttaagaagcg gtatgggaat   9120
gtaaagatgg atattctcac ctttgatgat gatggactat accccaaact cagactattt   9180
tattacctca ccatcggtaa acctcatctc aaggctaatg acagaaaagc tattgccaaa   9240
atgggcaatg acaataaagg caagattcta tcaaaagact tagttaataa aacttactcc   9300
gctcgtgtga aggtcttaga gattcttaaa ctaactgact ttatcgacaa tcttagagat   9360
gaactcttaa taactcccaa taatccagct atcaccgatt ttaataatct tctgctaaga   9420
gctaagaagg atttaagagt attaggagtc aacatcggaa aatatccaat ggccaacatt   9480
aatgccgtac ttactctcat tggtcacaaa ctttctgtaa tgagagatga gttcggaaaa   9540
gagaaaagga taaaagtaga tggtaaatca taccgatgtt atcaacttga aacattacca   9600
gattttacca atgatactct tgactactgg ttagaaaatg atagccaaaa agaagtaaca   9660
gcaacagaaa attactccga aaattttaac ccttcaaata gctacaatcc agacagtaag   9720
acactttcag agggtgcaaa tttcctatat ataaataaag aagaattgca tccaaataaa   9780
ttgcacctag aaataaaaga aggtgctgaa cttttttttat tcggggtaaa ggtgattgtg   9840
aaaggaatct tggacggggc agtaactata ttctctatgg gtcaagaata cgatttatcc   9900
ctcaatgaac tagaggggat gttaacatca tgaactttac aagaatcttt ttaaagggcg   9960
atcgcaccat gttaaatgat ggtacatttg ttcagatatt tgatatttac catgaccacg  10020
cattgggagt gacccttgac cttaagacag aaaaaattat ttccgatgat gttagggtaa  10080
ttactgtcaa agacttattg ttcgatggca cttataaagg ggtaaaatct tttatgcccg  10140
ataatgcccg ataatgcccg attgatgcta caaaatccca taatcataag cgataatccc  10200
```

-continued

```
ctaatagctt gtaattcttg aaccgtagcg attttagagt attccaaaaa gaagaaataa  10260
acaccgcaaa atgtcgtatt tcacatatat aaaccaaggt tttttgccct aaaatcttta  10320
tgtttgtagt gtgatgttgg gtcaaaatgg tcagaaaagt tgcaaggttt ttatggatgc  10380
ttacgcgcgc gaggggtaag catccccaaa tagttacttt atcctagtcc atgcccattt  10440
attgccgtcc cgttcggctt taaaaaagtg ccaaaactca caaggtgcaa taaaaagttc  10500
tgtacctttc gcaaccctag ataatctttc aacagttact ttttttccta ttatctcggt  10560
acaaagtttg gctagtttct cttttccctc tttttcaatc aagccttctt gtatgcccaa  10620
ctcattgatt aatctctcta tttttaccat tatttcccgt tcaggtagtt tatcccctaa  10680
atcttcatcg gggggcaatg tagggcattc tgaaggggct ttttcttctg tctggacatt  10740
atctaatatt gaagtaacca aactatcttc agttttttct attcctatta attcatattc  10800
ggttactgta tccgtatcaa tatccgaata actatcttta tccgtattag ctattcggtt  10860
aagtttatcc gttaactcag aaacaagact atatagcggt tttagctttt cttctatcct  10920
gttatctaat acggataagt ttatacggtt atcattatcc gtattagtat cattgggctt  10980
ttttggtagt tctacccct cataaaccgc ttttattccc aattccaaca gactgataac  11040
agtatccttt ataatgggtt ttttgctgat atggtgaact tttgcccctt ccatcattgc  11100
gatactttct atctcactca tcaacttatc gcttaagtga atctcgtatc tgtttaatcc  11160
cttactggtt ttattcatat ccgtttactt tattcggtta acaattctat tttatacgaa  11220
taaaatatta tacggttaac tttatacgtt taactatttt atctatacgg ataacagtaa  11280
taagttattc gtattagtta tacgtttact tttatccaaa taaaattagt gcatttaaac  11340
taaaagaatg attttatcgg agttgatagc attggattaa cctaaagatg tttataagct  11400
atatctgata agtatttaag gttattttgt tattctgttt attgacatta tcagaataaa  11460
agaatagaat ataattgttg agagataaga ggtttaagtg attatggtta agaagttagt  11520
tggttatgtc agggtcagta gtgaatcgca agaggataac actagcttac agaatcagat  11580
agagagaatt gaagcatatt gtatggcttt tggttatgag ttggtaaaaa tattcaaaga  11640
ggttgccact ggtacaaaag cagatattga aacccgtcct atttttaatg aagctataga  11700
atacttgaaa caggataatg ctaatggaat tattgccttg aagctagacc gaatcgcacg  11760
gaatgcttta gatgtattgc gtttggttcg tgaaacctta gaaccacaaa ataaaatgtt  11820
agtgttacta gatattcagg tagatacttc gacaccttca ggaaaaatga ttttaactgt  11880
aatgagtgcc gttgctgaac tcgaaagaga catgatctat gatcgcactc agggggggtag  11940
aaagactaaa gcccaaaagg gcgggtatgc ctacgggaaa cctaaatttg gctataagac  12000
tgaagaaaag gaactaaaag aagattcagc acaacaggaa actattaaac taattaagag  12060
acaccgtagg tcagggaaaa gctaccagaa aatagctgat tatctcaatg cccaaagtat  12120
tcccactaaa caaggtaaga aatggagttc tagcgtcgtc tatcgaatct gtcaggaaaa  12180
agctggttaa gtctgtttat agatatttag aatttattga ataaaaatag tatgaacaat  12240
aaatatttat ggactaacca cgctcggaaa cgtttaactg aacgatggga aataaaagaa  12300
tcatgggtta ttgataccat cgaaaatcct gaacgttcag aatttattgt tgatgagtca  12360
ggggaaaaat atcattacta taaaagaata gctaagttta agaatagagt gttagaagtg  12420
ataacttctg ccaactcaac acccacaaga ataataacct tttactttaa ccgtaacatg  12480
aggaaaaatt tatgattgtt acttacgata atgaagttga cgcaatttat tttaagttaa  12540
cggaaaataa aattgatagc accgaacctc aaacagacag gattatcatt gattacgatg  12600
```

```
aaagtaataa tattgttggc attgaggtat tagattttaa ttatcttgtc aagaaaggtt  12660
taaccgttgc tgatttacct ttttctgaag atgaaagatt aacagcttct caatatttta  12720
attttcctgt tgctatctaa tccagaaggg gcaataatcc ccttctttca tcgagttaga  12780
cttaatatca caaaagtcat tttcatttta ccgtttcttt tccacagcgt ccgtacgaaa  12840
cgaaaacccc ccaccaagta ggtagagggt tgaatctagt gatggtgatg atggtgtacg  12900
taggatccag cagcttttac accaggatag ggttgattaa ttgcacccat aggtttttca  12960
cctgctaaag cctgtataat attcattgca gcttgtcttt caatttctaa acgtacttct  13020
tttacagcac tacctaaatg aggtgtaaaa aaggtttgtg cggtgttatc taataaggct  13080
ttgggaatag cttgaggtct gtctgctctt atccactctt ccatctcaaa tacgtcggca  13140
gcatatcctg ctaatttacc actagctaaa gcagctataa cggcattctc gtccacaaca  13200
gaacctctac aagcattgat taaataagat cctgttttca tttttgctaa ggcggtggca  13260
tcaattaaat gtaatgtctc tgctgccatg ggcaccatag gaacaacgta atcacatttc  13320
tctaataatt cgtctaaagt aactctttgt acatgccatg ctttttcttg ttctgcattt  13380
aaaggtatag gatcacaata taataaattc atttcaaatc ctgctaatct ttgagcaata  13440
gcacgtccta cagcacccat acctataatt cctaaagttt taccggttaa tccagaacca  13500
tataaagtag gtctccatcc ttgaaaatgt ccagaacgta tctgacgatc accttctaac  13560
atgtgtctag ttaaacctaa taataatcca attgttaatt cggcggtagg aatagttaat  13620
aaatcaggta cgatggttaa ccaaacaccg tgtcttgtac aggcgtttac atcaaaatta  13680
tcataacctt ttaaagcggc accgatcact cttaatttag gacattcctc taaaaatgca  13740
gaatcaatag aatcaggcat aaaggccatt aaagcatcag catctttggc tctggcaatt  13800
acttcactac gaggtaaagt ttctcttgtt gtattgggaa tcacatctgc actagcactt  13860
aataattcta ttatttcggg gtgtacccaa tgagttaata ctactttagg tttcattgaa  13920
ttcatgaggg attcctctct cgacaaatac ttaaactact acattactga agatgataag  13980
ggctatttgt caccattgtg gttcttgctt aacaatattt aaaatttgtt taacattccc  14040
tcagataagg ctttggtttt taatcctttc tcatttaagt caagattttg ttacttttct  14100
ttataaaatc tatcaatgtt ttagttatgc tcttttaagg ggataaaaag ttaaaggaca  14160
cagattaatc tttaatattc atgggcgttt ctatcttttt tcttaacttt tgattagttg  14220
atgtagataa gacgtcagag aatataaaaa gccagattat taatccggct tttttattat  14280
ttttaaataa atttttttct aagaaaattg cctaatgaat caactaaagt aaccattact  14340
aatacgacaa gcaataaggc actaacttct tgatatttca ataatctcaa agcaccaata  14400
atttcaaacc caataccacc tgcgccaaca gcacctaata ctaaagaagc tctaaaatta  14460
tattcccaac ggtaaaaagt tacatccgca atttggggaa gcacttgggg taagatggaa  14520
tgatatataa tttgaaggtg gttagcaccg accgctttag cagcttctat tggagcattg  14580
tctgtatgtt caatagactc cgcaaagaat tttcctacca ttccaatact atgaaaacct  14640
aaggctaata ctccaggtaa tgcaccaaaa cctactgcag caacaaatat aatccctaaa  14700
agcaattcag gaatcgctct agcaatattt aaaatgattc ttgatacaaa atagacaaaa  14760
ggatgaggag aagtgttttg tgcggcccca aaagttatgg gcaatgaaaa aattacggcc  14820
atgccagttc cagctatgga catgcccaaa gtatcaatta aaggtttgat ccagtcagac  14880
gctctggtaa agtcaggagg caacatttgt gcgaccattt ctaaaaggtc tggaatgcct  14940
```

```
tcggataagc gtttaccatc taacaaacca actactgcaa atgaaataat aataataatc  15000
aataaaataa taatattaat taaagaacga taccataaaa ttttatattg tcttaaaaga  15060
ttactatatt tatcctgatt aatggtcatg cttttttttag gaattctcct gttacacaat  15120
cagagtcaac gtttaaaata cgctggtcaa ttttggattt tatcttgcct agccctcgga  15180
attaaatttc tttaaaagaa actaggcaag gaattaaatt gatttttaaa tgttagttaa  15240
tagtgaagaa tctaagataa atatagactt tcaactatta acaattattg ttagtaaaaa  15300
cggctttatc tgttatttta taacttattt tgccgtagat tttcccacta aattagtgaa  15360
agtttacatt cttaatttaa cttcgcaaaa tctaagttta aaatttttcc aagatcgcgg  15420
acaacattat aatctttatc ttccacactc tgaaatcctt ctgctttaaa aggttctaat  15480
acagctttgt cttccaactc taaaaatgct tgtttgatct gttgtttaag ctgtggctca  15540
agatcacttc tcatggtcca aggatattga ggaaaaggct tactttcttc gatcaaaata  15600
accttgtttt catctattgt tcccttattg attaaagcag tgtagatggg tttacttaat  15660
ccacctgctt gagcttttcc attagccacg gcgaccgcaa cagcatcatg actcccaaca  15720
aaaacttctt gataattttc ttctgcttta agtcctttct ccataagcat tgatttagga  15780
atcaaatgag aagaggtact agcttgatca ccataagcca tagtttttcc ttcaatttta  15840
tcataactgt caatgcccgc ttcggcattc ccaataatta cagatttata agtagcttcg  15900
ccatcttttt ctaaggcagc aaatgcttcg atgtttgatt tagttttcgc taacacataa  15960
cttaagggcc caaagtacgc taaatctaat cgtccattgg aagctgcttc aatcatacta  16020
gaataatctg tactaacaaa caattcaacg tctttattta aacgatcctc caaataggat  16080
tctaatcctt tattattctg aatgactgta ctaacacttt catctggtaa taaagcgact  16140
actaactttt tagggtttgc tttggtgtcc gcttttgagt tctcaggatt gttattactg  16200
gtttgactat tgggggtaga acagccgata agtgttaata aagtaaaaga cacaacaggt  16260
gttaatgatt ttttaaatat aaaagaaatc attgtgctga tcctcctaat tatgttggtt  16320
tacgttaatg aaatggattt tctaatcttg gtttaaacta tccagctttg attaaactgg  16380
aattatgata gatcttttct aattgataac tttggatttc actgggatga ctatcaaaaa  16440
ggatgttccc atctgccaat ccaataattc ggtcgccata atctaaagca aagtcaatct  16500
gatgcaaact aactacagca cctattccat cttcttgaca aatttttttta agattagtta  16560
agattttatg ggaactgccg ggatctaatg atgccacagg ttcgtccgct aaaagaaatc  16620
tgggtttctg agctaatgca cgcgctatac ctactctctg ttgttgaccc ccacttaatt  16680
gtttcacagg ggttaaagcc ttatttaata aacccactct atctaaacag tctaaagcga  16740
tcatctgatc aatttttggt aaaggaaaaa aagatcttaa agtagaatga taagctaaac  16800
gtccaactaa gacattttta agtgctgttt gtctgggtat taattgatgt tgttgaaaaa  16860
tcattcctgt tttttgtctg tgcttacgaa gaatttttgg attattcaaa gttcctaaac  16920
cctcaactat aacttcccct ttggtaggaa cggttaaaaa atttatacat ctcaataagg  16980
tagatttacc agctccacta gctcccaata aaacggtaaa ctctccgggg atcaattcta  17040
aagaaatatt ttccaaagct acggtcccat ctttataggt tacacttaaa ttgtttaaaa  17100
aaatcatatt ttatttttct tactcttaat tattcttagt ctagcgtgaa gtacgccttt  17160
tagcgatgtt tcgattcgat ataaactttt tagaggtgtt agggtgtcgg taattgagta  17220
ttagttaaag acggcataat tgcatataat tacttaggag aacgctcggt tgccgccggg  17280
cgtttttttat tgtcg                                                  17295
```

<210> SEQ ID NO 7
<211> LENGTH: 18769
<212> TYPE: DNA
<213> ORGANISM: Artificial Sequence
<220> FEATURE:
<223> OTHER INFORMATION: Synthetic plasmid construct derived from p6.8 endogenous plasmid from Cyanobacterium sp. PTA-13311, plus ptxA,B,C, from Cyanothece sp. ATCC-51142, ptxD from Ralstonia sp. 4506, and ptdCDp, plus copper-inducible ethanologenic genes pdc and adh.

<400> SEQUENCE: 7

```
acaattaata acttcttcct gtacgggcga atggccattt gctcctaact aactccgtac     60
tgctttgcgg aacgagcgta gcgaactctc cgaattacta agccttcatc cctgatagat    120
gcaaaaaacg aattaaaatt atgtgtaaaa agaaaatgtg tctttattta gtagtcaaag    180
ttacaaaata ttaagaatca aattaataat gtattgggca gttaagtata taagtcttta    240
aatatttatt tgtattcaat atattaagga ggatcagcct tatgaattct tataccgtgg    300
gtacttattt agccgaacgc ttagtgcaaa ttggtttaaa acatcatttt gccgtggctg    360
gggactataa tttagtgtta ttggataact tattattaaa taaaaacatg gaacaagtgt    420
attgttgtaa tgaattaaat tgtggttttt ctgctgaagg ttatgctaga gctaaaggtg    480
cagctgctgc tgttgttact tattctgtgg gtgctttatc tgcttttgat gctattggtg    540
gtgcttatgc cgaaaattta cccgtgattt taatttctgg tgcccctaat aataatgatc    600
atgccgctgg acatgtttta catcatgcct taggtaaaac cgattatcat tatcaattag    660
aaatggccaa aaatattact gctgctgccg aagctattta tactcctgaa gaagcccctg    720
ccaaaattga tcatgtgatt aaaaccgcct tacgcgaaaa aaaacccgtg tatttagaaa    780
ttgcctgtaa tattgcttct atgccttgtg ctgctcctgg gcctgcttct gctttattta    840
atgatgaagc ctctgatgaa gctagtttaa atgctgccgt ggaagaaacc ttaaaattta    900
ttgccaatcg cgataaagtt gccgtgttag ttggttctaa attaagagct gctggtgctg    960
aagaagctgc tgttaaattt gctgatgctt taggtggtgc agttgctact atggctgctg   1020
ccaaatcttt ttttcccgaa gaaaatcccc attatattgg aactagttgg ggagaagttt   1080
cttatcctgg tgtggaaaaa actatgaaag aagccgacgc tgttattgct ttagcccctg   1140
tgtttaatga ttattctacc actggttgga ctgatattcc cgatcccaaa aaattagttt   1200
tagccgaacc tcgttctgtt gttgttaatg gtgttcgctt tccctctgtg catttaaaag   1260
attatttaac ccgcttagcc caaaaagttt ctaaaaaaac tggtgcctta gatttttta   1320
aatctttaaa tgcgggtgaa ttaaaaaaag ctgctcctgc tgatccttct gctcctttag   1380
ttaatgctga aattgcccgt caagttgaag ccttattaac ccctaatact accgttattg   1440
ccgaaactgg tgattcttgg tttaatgccc aacgcatgaa attacctaat ggtgcccgtg   1500
ttgaatatga aatgcaatgg ggtcatattg gttggtctgt acctgctgct tttggttatg   1560
ctgttggtgc tcctgaacgt cgtaatattt taatggtggg tgatggttct tttcaattaa   1620
ctgcccaaga agttgcccaa atggttcgct taaaattacc cgttattatt tttttaataa   1680
ataattatgg ttataccatt gaagtgatga ttcatgatgg gccatataat aatattaaaa   1740
attgggatta tgcgggttta atggaagtgt ttaatggtaa tggtggttat gattctggtg   1800
ctggtaaagg tttaaaagcc aaaactggtg gtgaattagc tgaagctatt aaagttgcct   1860
tagccaatac tgatgggcca accttaattg aatgttttat tggtcgcgaa gattgtaccg   1920
```

-continued

```
aagaattagt taaatggggt aaacgtgttg ctgctgctaa ttctcgcaaa cccgtgaata   1980
aattattgta aggatccagc aaggtttcat cccgaccccc tcagggtcgg gattttttta   2040
ttgtgagctc aactttagat attcgtagtt ggcaatgtcg taaatgcgga acaatacatg   2100
gaaaacatat agatttgtaa tgagaaaaag tgtaaacaaa tattaagaaa aagatcagaa   2160
aaatttaaca acacgtaata aaaaaatgcg tcactacggg ttataaattt acatgaaagg   2220
ttaaaacact tttctgagac gattttgata aaaaagttgt caaaaaatta agtttcttta   2280
caaatgctta acaaaaactt ggttttaagc acaaaataag agagactaat ttgcagaagt   2340
tttacaagga aatcttgaag aaaaagatct aagtaaaacg actctgttta accaaaattt   2400
aacaaattta acaaaacaaa ctaaatctat taggagatta actacatatg agtgaaacta   2460
aatttaaagc ctatgccgta atgaatcctg gtgaaaaatt acaaccctgg gaatatgaac   2520
ctgctccttt acaggtagat gaaattgaag taagagttac tcacaatggt ttatgtcaca   2580
ctgacttaca catgagagat aatgactgga atgttagtga gttcccctta gtagcaggtc   2640
atgaagttgt tggtgaagta accgctgttg gtgaaaaagt aaccagtcgt aaaaaaggtg   2700
atagagttgg tgtaggttgg attcgtaatt cttgtcgcgc ttgtgaccat tgtttacaag   2760
gagaagagaa catttgtaga gagggttata ctggtttaat tgttggtcat cacggtggat   2820
ttgctgatcg tgtacgtgta cctgctgact tcacttataa aattcctgat gctttagata   2880
gtgcatctgc tgctccttta ttatgtgccg gtattaccgt ttacactcct ttaagaacct   2940
acattaaaca tcccggtatg aaagtaggtg ttatgggtat tggaggatta ggacatttag   3000
ctattaaatt tgctcgtgca atgggagcag aagttactgc ctttagtacc agtcctaata   3060
aagaagccca agccaaagaa tttggtgctc atcatttcca acaatggggt actgctgaag   3120
aaatgaaagc tgttgccggt aattttgatt tagttttatc taccatctct gctgaaactg   3180
actgggatgc tgccttctct ttattagcaa ataacggtgt tttatgtttc gtaggtattc   3240
ccgttagttc tttaaatgtt cctttaattc ctttaatttt cggacaaaaa tctgttgtag   3300
gttctgtagt tggaggaaga agattcatgg cagaaatgtt agagttcgcc gctgtaaatc   3360
agattaaacc tatgatcgaa actatgccct tatctcaagt aaatgaagct atggataaag   3420
ttgccgccaa taaagccaga tatagaattg tattattatc tgaataacta gatctacttc   3480
taaactgaaa caaatttgag ggtaggcttc attgtctgcc cttatttttt tatttaggaa   3540
aagtgaacag actaaagagt gttggctcta ttgctttgag tatgtaaatt aggcgttgct   3600
gaattaaggt atgatttttg acccctgcag gatcatcttg ctgaaaaact cgagcgctcg   3660
ttccgcaaag cggtacggag ttagttaggg gctaatgggc attctcccgt acaggaaaga   3720
gttagaagtt attaattatc aacaattctc ctttgcctag tgcatcgtta ccttttttaat   3780
taaaacataa ggaaaactaa taatcgtaat aatttaacct caaagtgtaa agaaatgtga   3840
aattctgact tttataacgt taaagaggga aaaattagca gtttaaaata cctagagaat   3900
agtctggggt aagcatagag aattagatta gttaagttaa tcaaattcag aaaaaataat   3960
aatcgtaaat agttaatctg ggtgtataga aaatgatccc cttcatgata agatttaaac   4020
tcgaaaagca aaagccaaaa aactaacttc cattaaaaga agttgttaca tataacgcta   4080
taaagaaaat ttatatattt ggaggatacc aaccatgtct catattcaac gtgaaactag   4140
ttgttctcgc cctcgtttaa attctaatat ggatgccgat ttatatggtt ataaatgggc   4200
tcgtgataat gttggtcaat ctggtgctac tatttatcgt ttatatggta aacctgatgc   4260
tcctgaatta ttcttgaaac atggtaaagg ttctgttgct aatgatgtta ctgatgaaat   4320
```

```
ggttcgttta aactggttga ctgaatttat gcctttacct actattaaac attttattcg   4380
tactcccgat gatgcttggt tattaactac tgctattcct ggtaaaactg cttttcaagt   4440
tttagaagaa tatcctgatt ctggtgaaaa tattgttgat gctttagctg ttttttacg   4500
tcgtttacat tctattcccg tttgtaattg tccttttaat tctgatcgtg tttttcgttt   4560
agctcaagct caatctcgta tgaataatgg tttagttgat gcttctgatt ttgatgatga   4620
acgtaatggt tggcctgttg aacaagtttg gaaagaaatg cacaaattgt taccttttc   4680
tcctgattct gttgttactc atggtgattt ttctttagat aatttgatct ttgatgaagg   4740
taaattgatt ggttgtattg atgttggtcg tgttggtatt gctgatcgtt atcaagattt   4800
agctatttta tggaattgtt taggtgaatt ttctccttct ttacagaaac gtttatttca   4860
gaaatatggt attgataatc ctgatatgaa caagttacaa tttcatttaa tgttggacga   4920
gttcttttaa gaattaattc atgaccaaaa tcccttaacg tgagttttcg ttccactgag   4980
cgtcagaccc cgtagaaaag atcaaaggat cttcttgaga tcctttttt ctgcgcgtaa   5040
tctgctgcta tttaaattac gtacacgtgt tattactttg ttaacgacaa ttgtcttaat   5100
taactgggcc tcatgggcct tccgctcact gcccgctttc cagtcgggaa acctgtcgtg   5160
ccagctctgc agatgacggt gaaaacctct gacacatgca gctcccggag acggtcacag   5220
cttgtctgta agcggatgcc gggagcagac aagcccgtca gggcgcgtca gcgggtgttg   5280
gcgggtgtcg gggcgcagcc atgacccagt cacgtagcga tagcggagtg tatactggct   5340
taactatgcg gcatcagagc agattgtact gagagtgcac catatgcggt gtgaaatacc   5400
gcacagatgc gtaaggagaa aataccgcat caggcgctct tccgcttcct cgctcactga   5460
ctcgctgcgc tcggtcgttc ggctgcggcg agcggtatca gctcactcaa aggcggtaat   5520
acggttatcc acagaatcag gggataacgc aggaaagaac atgtgagcaa aaggccagca   5580
aaaggccagg aaccgtaaaa aggccgcgtt gctggcgttt ttccataggc tccgcccccc   5640
tgacgagcat cacaaaaatc gacgctcaag tcagaggtgg cgaaacccga caggactata   5700
aagataccag gcgtttcccc ctggaagctc cctcgtgcgc tctcctgttc cgaccctgcc   5760
gcttaccgga tacctgtccg cctttctccc ttcgggaagc gtggcgcttt ctcatagctc   5820
acgctgtagg tatctcagtt cggtgtaggt cgttcgctcc aagctgggct gtgtgcacga   5880
accccccgtt cagcccgacc gctgcgcctt atccggtaac tatcgtcttg agtccaaccc   5940
ggtaagacac gacttatcgc cactggcagc agccactggt aacaggatta gcagagcgag   6000
gtatgtaggc ggtgctacag agttcttgaa gtggtggcct aactacggct acactagaag   6060
gacagtattt ggtatctgcg ctctgctgaa gccagttacc ttcggaaaaa gagttggtag   6120
ctcttgatcc ggcaaacaaa ccaccgctgg tagcggtggt ttttttgttt gcaagcagca   6180
gattacgcgc agaaaaaaag gatctcaaga agatcctttg atcttttcta ctgcagaagc   6240
ttgttagaca ccctgtcatg tattttatat tatttatttc accatacgga ttaagtgaaa   6300
cctaatgaaa atagtacttt cggagcttta actttaatga aggtatgttt ttttatagac   6360
atcgatgtct ggtttaacaa taggaaaaag tagctaaaac tcccatgaat taaagaaata   6420
acaaggtgtc taacaacctg ttattaagaa tgttagaaaa gacttaacat ttgtgttgag   6480
tttttataga cattggtgtc tagacatacg gtagataagg tttgctcaaa aataaaataa   6540
aaaaagattg gactaaaaaa catttaattt agtacaattt aattagttat tttttcgtct   6600
caaattttgc tttgttgagc agaaatttag ataaaaaaat ccccgtgatc agattacaat   6660
```

-continued

```
gtcgttcatt gtacgatgtg tcgaaaaatc tttacgacac tctaaactga ccacacgggg   6720
gaaaaagaaa actgaactaa taacatcatg atactcggaa aacctagcaa ttctcaaccc   6780
ctaaacaaaa gaaacttcca aaaccctgac catataaagg agtggcaaca atcagcaatc   6840
agtcaagatt tgatagcaga aaatcttgta tcggttgcta atggttttga tgtactattt   6900
atcggcaata aataccgaac taacacgggt gttctgtcac ggcacatatt aaactcctat   6960
tctcatttag aagatggtgg ttcgtatggt agaacatttg acccatttac caataaagaa   7020
atgcagtggg ttcaatttaa accgaataga ccaagaaaag gttctactgg taaggtaatc   7080
aaatatgaat cgccaaaagg tgaacctaca agagttctaa tgccgtttgt gcctatgaaa   7140
atatggcaac ggattagcga taagttcgga gtaccgatta atccgaaaaa agatactcac   7200
ttttgggaat gggtaaagaa taatccatcg ataccgattg ccattacaga aggaaataaa   7260
aaagctaatt gcctattatc ctatggctat cctgctattg cctttgtagg catttggaac   7320
ggattagaga aaataaatga tttctcgaag gaaaagcagt taaaagagga tttgaaatgg   7380
ttgttatcca acggcaaccg aaatattaat atcatctttg accaagacca gaaacaaaaa   7440
actgtaatta atgtaaacaa agctattttc gctttatctt ctctaataag tagaaatggt   7500
cataaagtta atattgtgca atggttgccg tcaaaaggta aaggaataga tgattatttg   7560
gtagctttac cttttgagaa aagagaaaat catttagaca acttaattaa aattgcacca   7620
tcatttaatt tttggtcaac taaatactta ttcaagtgtc gtaaaccaga tttaaccgta   7680
aattgccgtt atttgagcga tgcagtaaaa gaattacctc aagaggatat agcattaata   7740
gcacctcacg gcacgggtaa aacttcatta gtagctactc acgttaagaa tcggagttat   7800
cacggaagga aactatttc attggtgcat cttgaaagtt tagccaaagc taatggcaac   7860
gcacttggat tatattaccg aaccgaaaat aatattgaaa agcaatatct tggatttagc   7920
ttatgtgtag atagttgccg tgataagatt aacggcatta caactgatat tatttcaggt   7980
caagattatt gccttttcat tgatgaaatt gaccaagtaa ttccacacat ccttaacagt   8040
gaaactgaag taagtaagta tagatgcacc atcattgaca ctttttctga actggtgaga   8100
aatgctgaac aggtcattat tgctgatgct gatttatccg atgtgacgat tgacctaata   8160
gaaaacatca gaggtaaaaa actatatgta atcaagaatg aatatcagta tcagggaatg   8220
acttttaacg ccgttggttc accattagaa atgatggcaa tgatgggaaa atcggtgtca   8280
gaaggcaaga aattatttat taacaccaca tcccaaaagg caaaaagtaa gtacggcaca   8340
atcgctcttg agtcttatat ttttggtcta aataaagaag caaagatatt aagaatagac   8400
tctgaaacca ctaaaaaccc tgaacatcca gcctataaaa tcattgacca agacttaaat   8460
aatatcctca aagattatga ttatgtcatt gcctcacctt gccttcaaac aggtgtcagt   8520
attaccttaa aagggcattt tgaccagcaa tttaactttt ccagtggaaa cattacacct   8580
cattgctttt tacagcaaat gtggcggttg agggatgcag aaattgaaag attctattat   8640
gtgccgaact catctaacct caatctcatt gggaataagt caagttcacc atcagacctt   8700
ctaaagagca ataacaagat ggcaacggca acggttaacc ttttgggtag aatcgactcc   8760
gaatattccc tagagtatga atcgcacggc atttggcttg agacgtgggc aaaattatca   8820
gcacggcata acagttcaat gcgttgttac tctgaaattc ttacctatct aattacgtct   8880
caagggcata aattaaatat caacattccc tcacctcttg cagatattaa gaagctaaat   8940
gatgaggtaa gtagtaacag ggaaaaggta aaaaatgaga gatactctca gaggttaaac   9000
tcaccagata ttaacgatgc agaagctacc atactcgaat ctaaagagca aaaaatcgga   9060
```

-continued ttgactctca atgagagatg caccctagaa aagcataaag ttaagaagcg gtatgggaat 9120
gtaaagatgg atattctcac ctttgatgat gatggactat accccaaact cagactattt 9180
tattacctca ccatcggtaa acctcatctc aaggctaatg acagaaaagc tattgccaaa 9240
atgggcaatg acaataaagg caagattcta tcaaaagact tagttaataa aacttactcc 9300
gctcgtgtga aggtcttaga gattcttaaa ctaactgact ttatcgacaa tcttagagat 9360
gaactcttaa taactcccaa taatccagct atcaccgatt ttaataatct tctgctaaga 9420
gctaagaagg atttaagagt attaggagtc aacatcggaa aatatccaat ggccaacatt 9480
aatgccgtac ttactctcat tggtcacaaa ctttctgtaa tgagagatga gttcggaaaa 9540
gagaaaagga taaaagtaga tggtaaatca taccgatgtt atcaacttga aacattacca 9600
gattttacca atgatactct tgactactgg ttagaaaatg atagccaaaa agaagtaaca 9660
gcaacagaaa attactccga aaattttaac ccttcaaata gctacaatcc agacagtaag 9720
acactttcag agggtgcaaa tttcctatat ataaataaag aagaattgca tccaaataaa 9780
ttgcacctag aaataaaaga aggtgctgaa ctttttttat tcggggtaaa ggtgattgtg 9840
aaaggaatct tggacggggc agtaactata ttctctatgg gtcaagaata cgatttatcc 9900
ctcaatgaac tagaggggat gttaacatca tgaactttac aagaatcttt ttaaagggcg 9960
atcgcaccat gttaaatgat ggtacatttg ttcagatatt tgatatttac catgaccacg 10020
cattgggagt gacccttgac cttaagacag aaaaaattat ttccgatgat gttagggtaa 10080
ttactgtcaa agacttattg ttcgatggca cttataaagg ggtaaaatct tttatgcccg 10140
ataatgcccg ataatgcccg attgatgcta caaaatccca taatcataag cgataatccc 10200
ctaatagctt gtaattcttg aaccgtagcg attttagagt attccaaaaa gaagaaataa 10260
acaccgcaaa atgtcgtatt tcacatatat aaaccaaggt tttttgccct aaaatcttta 10320
tgtttgtagt gtgatgttgg gtcaaaatgg tcagaaaagt tgcaaggttt ttatggatgc 10380
ttacgcgcgc gaggggtaag catccccaaa tagttacttt atcctagtcc atgcccattt 10440
attgccgtcc cgttcggctt taaaaaagtg ccaaaactca caaggtgcaa taaaaagttc 10500
tgtacctttc gcaaccctag ataatctttc aacagttact ttttttccta ttatctcggt 10560
acaaagtttg gctagtttct cttttccctc tttttcaatc aagccttctt gtatgcccaa 10620
ctcattgatt aatctctcta tttttaccat tatttcccgt tcaggtagtt tatcccctaa 10680
atcttcatcg gggggcaatg tagggcattc tgaaggggct ttttcttctg tctggacatt 10740
atctaatatt gaagtaacca aactatcttc agtttttttct attcctatta attcatattc 10800
ggttactgta tccgtatcaa tatccgaata actatcttta tccgtattag ctattcggtt 10860
aagtttatcc gttaactcag aaacaagact atatagcggt tttagctttt cttctatcct 10920
gttatctaat acggataagt ttatacggtt atcattatcc gtattagtat cattgggctt 10980
ttttggtagt tctacccccct cataaaccgc ttttattccc aattccaaca gactgataac 11040
agtatccttt ataatgggtt ttttgctgat atggtgaact tttgcccctt ccatcattgc 11100
gatactttct atctcactca tcaacttatc gcttaagtga atctcgtatc tgtttaatcc 11160
cttactggtt ttattcatat ccgtttactt tattcggtta acaattctat tttatacgaa 11220
taaaatatta tacggttaac tttatacgtt taactatttt atctatacgg ataacagtaa 11280
taagttattc gtattagtta tacgtttact tttatccaaa taaaattagt gcatttaaac 11340
taaaagaatg attttatcgg agttgatagc attggattaa cctaaagatg tttataagct 11400

-continued atatctgata agtatttaag gttattttgt tattctgttt attgacatta tcagaataaa 11460
agaatagaat ataattgttg agagataaga ggtttaagtg attatggtta agaagttagt 11520
tggttatgtc agggtcagta gtgaatcgca agaggataac actagcttac agaatcagat 11580
agagagaatt gaagcatatt gtatggcttt tggttatgag ttggtaaaaa tattcaaaga 11640
ggttgccact ggtacaaaag cagatattga aacccgtcct atttttaatg aagctataga 11700
atacttgaaa caggataatg ctaatggaat tattgccttg aagctagacc gaatcgcacg 11760
gaatgcttta gatgtattgc gtttggttcg tgaaacctta gaaccacaaa ataaaatgtt 11820
agtgttacta gatattcagg tagatacttc gacaccttca ggaaaaatga ttttaactgt 11880
aatgagtgcc gttgctgaac tcgaaagaga catgatctat gatcgcactc agggggtag 11940 aaagactaaa gcccaaaagg gcgggtatgc ctacgggaaa cctaaatttg gctataagac 12000
tgaagaaaag gaactaaaag aagattcagc acaacaggaa actattaaac taattaagag 12060
acaccgtagg tcagggaaaa gctaccagaa aatagctgat tatctcaatg cccaaagtat 12120
tcccactaaa caaggtaaga aatggagttc tagcgtcgtc tatcgaatct gtcaggaaaa 12180
agctggttaa gtctgtttat agatatttag aatttattga ataaaaatag tatgaacaat 12240
aaatatttat ggactaacca cgctcggaaa cgtttaactg aacgatggga aataaaagaa 12300
tcatgggtta ttgataccat cgaaaatcct gaacgttcag aatttattgt tgatgagtca 12360
ggggaaaaat atcattacta taaaagaata gctaagttta agaatagagt gttagaagtg 12420
ataacttctg ccaactcaac acccacaaga ataataacct tttactttaa ccgtaacatg 12480
aggaaaaatt tatgattgtt acttacgata atgaagttga cgcaatttat tttaagttaa 12540
cggaaaataa aattgatagc accgaacctc aaacagacag gattatcatt gattacgatg 12600
aaagtaataa tattgttggc attgaggtat tagattttaa ttatcttgtc aagaaaggtt 12660
taaccgttgc tgatttacct ttttctgaag atgaaagatt aacagcttct caatatttta 12720
attttcctgt tgctatctaa tccagaaggg gcaataatcc ccttctttca tcgagttaga 12780
cttaatatca caaaagtcat tttcatttta ccgtttcttt tccacagcgt ccgtacgaga 12840
gaatataaaa agccagatta ttaatccggc tttttttatta tttttaaatg aattttttttc 12900 ttaaaaagtt acctaaacta tctactaatg ttaccataac taaaacaact aacaaaaggg 12960
cagaaacttc ctgatatttg agtaaacgta atgccccaat aatttcaaat ccaatgccac 13020
cggctcccac tgcgcctaat actagagaag ctctaaaatt gtactcccaa cgataaaatg 13080
taacatcggc gatttgtggt aaaacttggg gtaaaatact atgataaatg atttgtaaat 13140
gatttgctcc gactgctttt gctgcttcaa taggtgcgtt gtctgtatgt tctatggact 13200
cagcaaaaaa tttacctacc ataccaatag aatgaaatcc caatgctaat accccaggaa 13260
gtgcgccaaa cccaacagcg gcaacaaaga taattcctag aagtaattca ggaatagctc 13320
ttgctatatt taaaataatt cttgatacaa aataaacgaa aggatgggga ctggtatttt 13380
gtgctgcccc gaaagtaata ggcagagaaa aaataacagc cattcctgtt cctgcaatac 13440
tcattcctaa ggtatcaatt agtggtttaa tccaatcaga agcacgagta aaatcgggag 13500
gcagcatttg tgctaccatt tctaataggt caggaattcc ttcagataag cgttttccat 13560
ctaataaacc aactacagca aaactaataa taattattat tagcaaaata atgatgttta 13620
ttagtgaacg ataccaaaga atcttgtatt ggcgcaacag attagaatat ttatcttgat 13680
tgattgtcat ttttccaata tttgattacc aaaaattagg gataacctta taactttatg 13740
tttactttga tttgattctt tgtttagtaa aagaaaaaat ctcacttgag agtttaagat 13800

-continued

```
ggttatccct aaatgaataa ttgatcttta cagtagctaa accctcagat taattaagtt  13860
tagcaaaatc aagattgagg atttttccta agtctcggac aacattataa tccttgtctt  13920
ctactgattg aaacccttct gctttaaatg gttctaaaac tgccttatct tctagttcta  13980
gaaaagcttg cttaatttgc tgttttaatt gaggttctaa gtcagatcgc atcgtccaag  14040
gatattgggg aaatggttta gattcttcta ttaaaatgac tttattttca tcaatggttc  14100
ccttattaat taaagcggta taaatgggtt tacttaagcc ccctgcttgg gcttttccat  14160
tggcaacagc tacagctaca gcatcatgag aaccgacaaa tacttcttga taattttctt  14220
ctgcttttaa gcctttttcc attaacattg acttaggaat taaatgacta gaggtcgagg  14280
cttgatctcc ataagccata gtttttcctt cgattttgtc ataggaatca attcctgctt  14340
ctgcattacc aataatgaca gatttatagg tggcttctcc atctttttct aacgctgcaa  14400
aggcttcgat attactttta gttttggcca aaacatacga caaaggacca aaataggcta  14460
agtctaatct tccattactc gctgcttcga tcatagaaga ataatcggta ctgacaaaca  14520
attcaacatc tttattcagt cggtcttcta agtagctttc taacccctta ttattttgaa  14580
ttacggtaga tactgattca tcgggtaaca aagcaactac taattttta gggttagctt  14640
ttgtgtctgc tttgctattt tcagggttat tattggatgt ttgactattc ggtgtactac  14700
aaccaattag agttaatagg gtaaaagaaa caacaggggt taaggatttt ttaaagatga  14760
aactgatcat accaatttg agtcaaataa ttttactgtt gattataatg attttcttga  14820
aaaaagcaag attttaatga ttttttaagt gtgatttaga taacaattaa cctgccttaa  14880
tcaaagaaga attgtgataa attttttcta actggtatga ttgtatttct gacgggtgac  14940
tatcaaaaag gatgtttcca tctgcaaggc caataatgcg atcgccatag tctaaagcga  15000
aatctatttg atgtaaacta accactgccc caataccatc ttcttgacaa attttttga  15060
gattagttaa tatcttatga gaactaccag gatctaaact agcaacaggt tcatctgcta  15120
agagaaatct gggtttttga gctaaagctc tggctattcc tacccgttgt tgttgtcctc  15180
cacttagttg tttaacagga gttaaagctt tatttaatag gccaactctg tccaaacaat  15240
ctaaagcaat catttgatca attttaggca aagggaaaaa acttcttaag gtagagtgat  15300
aggctaaacg accaactaaa acattttaa gggcagtttg tcgaggaatt aattgatgtt  15360
gttgaaaaat catgcccgtt ttttggcgat gttttcttaa gattttcggg ttatttaggg  15420
ttcctaaccc ctccacaata acttcaccct tagtaggaac tgttagaaaa ttgatacaac  15480
gtaaaagggt tgattttcct gcaccagaag cccctaaaag taccgtaaat tctcctggaa  15540
tcaattcaag agaaatattt tctaaggcca cggttccatc tttataggtg acactaaggt  15600
tattaagaaa aagcataata aacttttcc tcatttttac ctaatcttcc ataccatggt  15660
gacaggagaa tatgaaatga ggatgaaatg atgctttaat tattcatctg cttacttttc  15720
cttacgaacc attgttgtaa ttcttcctcg gtaattctgc cactagctaa ggtttggatg  15780
atatgtacta cttccacttc agaagcagta aagtgagaac cattgagcat taaaaaggtt  15840
actccactaa taaaacctgt tcttttatta ccatcaataa agggatgatt tttaactatg  15900
ctgaaggtat aagtagaagc taaggatgag atattcaata aaaaacgccc ggcggcaacc  15960
gagcgttcca cggtaactaa gatctctact ctcttactat atttactaag atgattccta  16020
atattgcaca accagataat aaaccaaata caattcccca atttttagta gcatctaata  16080
tcataccaat aacaaaacct tgggttcctg ctcccatata attaaaaaaa tttacacttc  16140
```

-continued

```
ccactgctgt tccggccatt ctacgaccac caaaatcaca tgcagtggta aaaactaaac  16200
ccacacttcc taacacaaaa aatccaccga ttgctaataa aaagaaagat aaaggtaaac  16260
ctaaagtttt taaacctgca cttgctaaga taatcataat ggtagtaaat gctaacatgt  16320
atatggttaa aatttggtat cttttggctt taaaaaatct atcagagatc caacctgcaa  16380
ttataggtcc aactgccatt cctaagggta aggcaatagt agctatggga attttttta  16440
aattaattcc ggctgtttca gcataaatata aaggaaccca ggttaataaa ccataacgtc  16500
ccatatataa cataaaactt gcaacggcta agcaaacaaa tttccaatta ccaaataata  16560
aaccccaggc tttaaaacca gatatttgat catcacgtaa ttcttcggct ttactactaa  16620
tggtattggt cattgtttct ttatattcag gataaccggc atctttgggt ttacttcttg  16680
ctaatataaa aaataagata gttaaaggta aagtacaaaa taataaaggg tatgtaaaag  16740
cagcacgcca accataatga gcagcaacag taccagtgat taaccaaacg aataaacttg  16800
ccactcccat agaggtagca aatattccag ttgctaatcc tctttttgct ttgggatacc  16860
attgtgtaat catgttatta gtgggggcat aagcctgacc ttgaataaat ccattaaatc  16920
cccaaggaat taacataata tttatacgag ccatagaggc tacaattatg tttaatatta  16980
cagttccaat accaccaatg gtattcatta ctctggctcc ataagtgtca cctaattttc  17040
cagatattaa tgttccgaaa gcataagacc aaaataaaac agtagcacca acacctgctt  17100
gggtttttgt aatacctaaa tctttaatca tccaaggcat acacataccc caatttaatc  17160
ttcctaagta gtaaaaagaa taccaaatag acactaatat aaccactttc caaaaacgaa  17220
atctatcata actaacttgt tcactatcgg ttaatcctaa accttcgaac tcagggtatt  17280
tgtctttagc agtagcatca tgcattgtaa ttaatttctc ctaattatgt tggtttacgt  17340
taatgaaatg gattttctaa tcttggttta aagagctcat tataactagt gatggtgatg  17400
atggtgtacg taggatccag cagcttttac accaggatag ggttgattaa ttgcacccat  17460
aggtttttca cctgctaaag cctgtataat attcattgca gcttgtcttt caatttctaa  17520
acgtacttct tttacagcac tacctaaatg aggtgtaaaa aaggtttgtg cggtgttatc  17580
taataaggct ttgggaatag cttgaggtct gtctgctctt atccactctt ccatctcaaa  17640
tacgtcggca gcatatcctg ctaatttacc actagctaaa gcagctataa cggcattctc  17700
gtccacaaca gaacctctac aagcattgat taaataagat cctgttttca tttttgctaa  17760
ggcggtggca tcaattaaat gtaatgtctc tgctgccatg ggcaccatag gaacaacgta  17820
atcacatttc tctaataatt cgtctaaagt aactctttgt acatgccatg ctttttcttg  17880
ttctgcattt aaaggtatag gatcacaata taataaattc atttcaaatc ctgctaatct  17940
ttgagcaata gcacgtccta cagcacccat acctataatt cctaaagttt taccggttaa  18000
tccagaacca tataaagtag gtctccatcc ttgaaaatgt ccagaacgta tctgacgatc  18060
accttctaac atgtgtctag ttaaacctaa taataatcca attgttaatt cggcggtagg  18120
aatagttaat aaatcaggta cgatggttaa ccaaacaccg tgtcttgtac aggcgtttac  18180
atcaaaatta tcataacctt ttaaagcggc accgatcact cttaatttag gacattcctc  18240
taaaaatgca gaatcaatag aatcaggcat aaaggccatt aaagcatcag catctttggc  18300
tctggcaatt acttcactac gaggtaaagt ttctcttgtt gtattgggaa tcacatctgc  18360
actagcactt aataattcta ttatttcggg gtgtacccaa tgagttaata ctactttagg  18420
tttcattgaa ttcatgactg tttctctctt tttatcttta cctttgattc tgtcaaaaga  18480
atatgaaatt aggatgaaat gattttcggt aaataaacgg taaaaatact gccttgattt  18540
```

tcttgacttt ctaaaattat tctaccacca tgattaagcg cgatcgcatt tgcaatagct 18600
aaacctaatc cgcaactgcc tttctctcta tttcttgctt tattgattcg ataaaaacga 18660
ttaaaaatta atttttgttc ttctttatta atgccaattc ctgtatcaat tatttttata 18720
atgacttctt tttttgttgt ttctaaacat atagtaactt gaccagtcg 18769

<210> SEQ ID NO 8
<211> LENGTH: 17091
<212> TYPE: DNA
<213> ORGANISM: Artificial Sequence
<220> FEATURE:
<223> OTHER INFORMATION: Synthetic plasmid construct derived from p6.8 endogenous plasmid from Cyanobacterium sp. PTA-13311, plus ptxA,B,C, from Cyanothece sp. ATCC-51142, ptxD from Ralstonia sp. 4506, plus copper-inducible ethanologenic genes pdc and adh.

<400> SEQUENCE: 8
tcgactggtc aagttactat atgtttagaa acaacaaaaa aagaagtcat tataaaaata 60
attgatacag gaattggcat taataaagaa gaacaaaaat taatttttaa tcgtttttat 120
cgaatcaata aagcaagaaa tagagagaaa ggcagttgcg gattaggttt agctattgca 180
aatgcgatcg cgcttaatca tggtggtaga ataattttag aaagtcaaga aaatcaaggc 240
agtattttta ccgtttattt accgaaaatc atttcatcct aatttcatat tcttttgaca 300
gaatcaaagg taaagataaa aagagagaaa cagtcatgaa ttcttatacc gtgggtactt 360
atttagccga acgcttagtg caaattggtt taaaacatca ttttgccgtg gctggggact 420
ataatttagt gttattggat aacttattat taaataaaaa catggaacaa gtgtattgtt 480
gtaatgaatt aaattgtggt ttttctgctg aaggttatgc tagagctaaa ggtgcagctg 540
ctgctgttgt tacttattct gtgggtgctt tatctgcttt tgatgctatt ggtggtgctt 600
atgccgaaaa tttacccgtg attttaattt ctggtgcccc taataataat gatcatgccg 660
ctggacatgt tttacatcat gccttaggta aaaccgatta tcattatcaa ttagaaatgg 720
ccaaaaatat tactgctgct gccgaagcta tttatactcc tgaagaagcc cctgccaaaa 780
ttgatcatgt gattaaaacc gccttacgcg aaaaaaaacc cgtgtattta gaaattgcct 840
gtaatattgc ttctatgcct tgtgctgctc ctgggcctgc ttctgcttta tttaatgatg 900
aagcctctga tgaagctagt ttaaatgctg ccgtggaaga aaccttaaaa tttattgcca 960
atcgcgataa agttgccgtg ttagttggtt ctaaattaag agctgctggt gctgaagaag 1020
ctgctgttaa atttgctgat gctttaggtg gtgcagttgc tactatggct gctgccaaat 1080
ctttttttcc cgaagaaaat ccccattata ttggaactag ttggggagaa gtttcttatc 1140
ctggtgtgga aaaaactatg aaagaagccg acgctgttat tgctttagcc cctgtgttta 1200
atgattattc taccactggt tggactgata ttcccgatcc caaaaaatta gttttagccg 1260
aacctcgttc tgttgttgtt aatggtgttc gctttccctc tgtgcattta aaagattatt 1320
taacccgctt agcccaaaaa gtttctaaaa aaactggtgc cttagatttt tttaaatctt 1380
taaatgcggg tgaattaaaa aaagctgctc ctgctgatcc ttctgctcct ttagttaatg 1440
ctgaaattgc ccgtcaagtt gaagccttat taacccctaa tactaccgtt attgccgaaa 1500
ctggtgattc ttggtttaat gcccaacgca tgaaattacc taatggtgcc cgtgttgaat 1560
atgaaatgca atggggtcat attggttggt ctgtacctgc tgcttttggt tatgctgttg 1620
gtgctcctga acgtcgtaat attttaatgg tgggtgatgg ttcttttcaa ttaactgccc 1680
aagaagttgc ccaaatggtt cgcttaaaat tacccgttat tatttttta ataaataatt 1740

-continued atggttatac cattgaagtg atgattcatg atgggccata taataatatt aaaaattggg 1800
attatgcggg tttaatggaa gtgtttaatg gtaatggtgg ttatgattct ggtgctggta 1860
aaggtttaaa agccaaaact ggtggtgaat tagctgaagc tattaaagtt gccttagcca 1920
atactgatgg gccaacctta attgaatgtt ttattggtcg cgaagattgt accgaagaat 1980
tagttaaatg ggtaaacgt gttgctgctg ctaattctcg caaacccgtg aataaattat 2040
tgtaaggatc cagcaaggtt tcatcccgac cccctcaggg tcgggatttt tttattgtga 2100
gctcaacttt agatattcgt agttggcaat gtcgtaaatg cggaacaata catggaaaac 2160
atatagattt gtaatgagaa aaagtgtaaa caaatattaa gaaaaagatc agaaaaattt 2220
aacaacacgt aataaaaaaa tgcgtcacta cgggttataa atttacatga aaggttaaaa 2280
cacttttctg agacgatttt gataaaaaag ttgtcaaaaa attaagtttc tttacaaatg 2340
cttaacaaaa acttggtttt aagcacaaaa taagagagac taatttgcag aagttttaca 2400
aggaaatctt gaagaaaaag atctaagtaa aacgactctg tttaaccaaa atttaacaaa 2460
tttaacaaaa caaactaaat ctattaggag attaactaca tatgagtgaa actaaattta 2520
aagcctatgc cgtaatgaat cctggtgaaa aattacaacc ctgggaatat gaacctgctc 2580
ctttacaggt agatgaaatt gaagtaagag ttactcacaa tggtttatgt cacactgact 2640
tacacatgag agataatgac tggaatgtta gtgagttccc cttagtagca ggtcatgaag 2700
ttgttggtga agtaaccgct gttggtgaaa aagtaaccag tcgtaaaaaa ggtgatagag 2760
ttggtgtagg ttggattcgt aattcttgtc gcgcttgtga ccattgttta caaggagaag 2820
agaacatttg tagagagggt tatactggtt taattgttgg tcatcacggt ggatttgctg 2880
atcgtgtacg tgtacctgct gacttcactt ataaaattcc tgatgcttta gatagtgcat 2940
ctgctgctcc tttattatgt gccggtatta ccgtttacac tcctttaaga acctacatta 3000
aacatcccgg tatgaaagta ggtgttatgg gtattggagg attaggacat ttagctatta 3060
aatttgctcg tgcaatggga gcagaagtta ctgcctttag taccagtcct aataaagaag 3120
cccaagccaa agaatttggt gctcatcatt tccaacaatg ggtactgct gaagaaatga 3180 aagctgttgc cggtaatttt gatttagttt tatctaccat ctctgctgaa actgactggg 3240
atgctgcctt ctctttatta gcaaataacg gtgttttatg tttcgtaggt attcccgtta 3300
gttctttaaa tgttccttta attcctttaa ttttcggaca aaaatctgtt gtaggttctg 3360
tagttggagg aagaagattc atggcagaaa tgttagagtt cgccgctgta aatcagatta 3420
aacctatgat cgaaactatg cccttatctc aagtaaatga agctatggat aaagttgccg 3480
ccaataaagc cagatataga attgtattat tatctgaata actagatcta cttctaaact 3540
gaaacaaatt tgagggtagg cttcattgtc tgcccttatt tttttattta ggaaaagtga 3600
acagactaaa gagtgttggc tctattgctt tgagtatgta aattaggcgt tgctgaatta 3660
aggtatgatt tttgacccct gcaggatcat cttgctgaaa aactcgagcg ctcgttccgc 3720
aaagcggtac ggagttagtt aggggctaat gggcattctc ccgtacagga aagagttaga 3780
agttattaat tatcaacaat tctcctttgc ctagtgcatc gttacctttt taattaaaac 3840
ataaggaaaa ctaataatcg taataattta acctcaaagt gtaaagaaat gtgaaattct 3900
gacttttata acgttaaaga gggaaaaatt agcagtttaa aatacctaga gaatagtctg 3960
gggtaagcat agagaattag attagttaag ttaatcaaat tcagaaaaaa taataatcgt 4020
aaatagttaa tctgggtgta tagaaaatga tccccttcat gataagattt aaactcgaaa 4080

-continued

```
agcaaaagcc aaaaaactaa cttccattaa aagaagttgt tacatataac gctataaaga   4140
aaatttatat atttggagga taccaaccat gtctcatatt caacgtgaaa ctagttgttc   4200
tcgccctcgt ttaaattcta atatggatgc cgatttatat ggttataaat gggctcgtga   4260
taatgttggt caatctggtg ctactattta tcgtttatat ggtaaacctg atgctcctga   4320
attattcttg aaacatggta aggttctgt tgctaatgat gttactgatg aaatggttcg    4380
tttaaactgg ttgactgaat ttatgccttt acctactatt aaacatttta ttcgtactcc   4440
cgatgatgct tggttattaa ctactgctat tcctggtaaa actgcttttc aagttttaga   4500
agaatatcct gattctggtg aaaatattgt tgatgcttta gctgtttttt tacgtcgttt   4560
acattctatt cccgtttgta attgtccttt taattctgat cgtgtttttc gtttagctca   4620
agctcaatct cgtatgaata atggtttagt tgatgcttct gattttgatg atgaacgtaa   4680
tggttggcct gttgaacaag tttggaaaga aatgcacaaa ttgttacctt tttctcctga   4740
ttctgttgtt actcatggtg atttttcttt agataatttg atctttgatg aaggtaaatt   4800
gattggttgt attgatgttg gtcgtgttgg tattgctgat cgttatcaag atttagctat   4860
tttatggaat tgtttaggtg aattttctcc ttctttacag aaacgtttat ttcagaaata   4920
tggtattgat aatcctgata tgaacaagtt acaatttcat ttaatgttgg acgagttctt   4980
ttaagaatta attcatgacc aaaatccctt aacgtgagtt ttcgttccac tgagcgtcag   5040
accccgtaga aaagatcaaa ggatcttctt gagatccttt ttttctgcgc gtaatctgct   5100
gctatttaaa ttacgtacac gtgttattac tttgttaacg acaattgtct taattaactg   5160
ggcctcatgg gccttccgct cactgcccgc tttccagtcg ggaaacctgt cgtgccagct   5220
ctgcagatga cggtgaaaac ctctgacaca tgcagctccc ggagacggtc acagcttgtc   5280
tgtaagcgga tgccgggagc agacaagccc gtcagggcgc gtcagcgggt gttggcgggt   5340
gtcggggcgc agccatgacc cagtcacgta gcgatagcgg agtgtatact ggcttaacta   5400
tgcggcatca gagcagattg tactgagagt gcaccatatg cggtgtgaaa taccgcacag   5460
atgcgtaagg agaaaatacc gcatcaggcg ctcttccgct tcctcgctca ctgactcgct   5520
gcgctcggtc gttcggctgc ggcgagcggt atcagctcac tcaaaggcgg taatacggtt   5580
atccacagaa tcaggggata acgcaggaaa gaacatgtga gcaaaaggcc agcaaaaggc   5640
caggaaccgt aaaaaggccg cgttgctggc gtttttccat aggctccgcc cccctgacga   5700
gcatcacaaa aatcgacgct caagtcagag gtggcgaaac ccgacaggac tataaagata   5760
ccaggcgttt ccccctggaa gctccctcgt gcgctctcct gttccgaccc tgccgcttac   5820
cggatacctg tccgcctttc tcccttcggg aagcgtggcg ctttctcata gctcacgctg   5880
taggtatctc agttcggtgt aggtcgttcg ctccaagctg ggctgtgtgc acgaaccccc   5940
cgttcagccc gaccgctgcg ccttatccgg taactatcgt cttgagtcca acccggtaag   6000
acacgactta tcgccactgg cagcagccac tggtaacagg attagcagag cgaggtatgt   6060
aggcggtgct acagagttct tgaagtggtg gcctaactac ggctacacta gaaggacagt   6120
atttggtatc tgcgctctgc tgaagccagt taccttcgga aaaagagttg gtagctcttg   6180
atccggcaaa caaaccaccg ctggtagcgg tggttttttt gtttgcaagc agcagattac   6240
gcgcagaaaa aaaggatctc aagaagatcc tttgatcttt tctactgcag aagcttgtta   6300
gacaccctgt catgtatttt atattattta tttcaccata cggattaagt gaaacctaat   6360
gaaaatagta ctttcggagc tttaacttta atgaaggtat gtttttttat agacatcgat   6420
gtctggttta acaataggaa aaagtagcta aaactcccat gaattaaaga aataacaagg   6480
```

-continued

```
tgtctaacaa cctgttatta agaatgttag aaaagactta acatttgtgt tgagttttta   6540
tagacattgg tgtctagaca tacggtagat aaggtttgct caaaaataaa ataaaaaaag   6600
attggactaa aaaacattta atttagtaca atttaattag ttatttttc gtctcaaatt    6660
ttgctttgtt gagcagaaat ttagataaaa aaatccccgt gatcagatta caatgtcgtt   6720
cattgtacga tgtgtcgaaa aatctttacg acactctaaa ctgaccacac gggggaaaaa   6780
gaaaactgaa ctaataacat catgatactc ggaaaaccta gcaattctca acccctaaac   6840
aaaagaaact tccaaaaccc tgaccatata aaggagtggc aacaatcagc aatcagtcaa   6900
gatttgatag cagaaaatct tgtatcggtt gctaatggtt ttgatgtact atttatcggc   6960
aataaatacc gaactaacac gggtgttctg tcacggcaca tattaaactc ctattctcat   7020
ttagaagatg gtggttcgta tggtagaaca tttgacccat ttaccaataa agaaatgcag   7080
tgggttcaat ttaaaccgaa tagaccaaga aaaggttcta ctggtaaggt aatcaaatat   7140
gaatcgccaa aaggtgaacc tacaagagtt ctaatgccgt ttgtgcctat gaaaatatgg   7200
caacggatta gcgataagtt cggagtaccg attaatccga aaaaagatac tcacttttgg   7260
gaatgggtaa agaataatcc atcgataccg attgccatta cagaaggaaa taaaaaagct   7320
aattgcctat tatcctatgg ctatcctgct attgcctttg taggcatttg gaacggatta   7380
gagaaaataa atgatttctc gaaggaaaag cagttaaaag aggatttgaa atggttgtta   7440
tccaacggca accgaaatat taatatcatc tttgaccaag accagaaaca aaaaactgta   7500
attaatgtaa acaaagctat tttcgcttta tcttctctaa taagtagaaa tggtcataaa   7560
gttaatattg tgcaatggtt gccgtcaaaa ggtaaaggaa tagatgatta tttggtagct   7620
ttacctttg agaaaagaga aaatcattta gacaacttaa ttaaaattgc accatcattt    7680
aatttttggt caactaaata cttattcaag tgtcgtaaac cagatttaac cgtaaattgc   7740
cgttatttga gcgatgcagt aaaagaatta cctcaagagg atatagcatt aatagcacct   7800
cacggcacgg gtaaaacttc attagtagct actcacgtta agaatcggag ttatcacgga   7860
aggaaaacta tttcattggt gcatcttgaa agtttagcca aagctaatgg caacgcactt   7920
ggattatatt accgaaccga aaataatatt gaaaagcaat atcttggatt tagcttatgt   7980
gtagatagtt gccgtgataa gattaacggc attacaactg atattatttc aggtcaagat   8040
tattgccttt tcattgatga aattgaccaa gtaattccac acatccttaa cagtgaaact   8100
gaagtaagta agtatagatg caccatcatt gacacttttt ctgaactggt gagaaatgct   8160
gaacaggtca ttattgctga tgctgattta tccgatgtga cgattgacct aatagaaaac   8220
atcagaggta aaaaactata tgtaatcaag aatgaatatc agtatcaggg aatgactttt   8280
aacgccgttg gttcaccatt agaaatgatg gcaatgatgg gaaaatcggt gtcagaaggc   8340
aagaaattat ttattaacac cacatcccaa aaggcaaaaa gtaagtacgg cacaatcgct   8400
cttgagtctt atatttttgg tctaaataaa gaagcaaaga tattaagaat agactctgaa   8460
accactaaaa accctgaaca tccagcctat aaaatcattg accaagactt aaataatatc   8520
ctcaaagatt atgattatgt cattgcctca ccttgccttc aaacaggtgt cagtattacc   8580
ttaaaagggc attttgacca gcaatttaac ttttccagtg gaaacattac acctcattgc   8640
tttttacagc aaatgtggcg gttgagggat gcagaaattg aaagattcta ttatgtgccg   8700
aactcatcta acctcaatct cattgggaat aagtcaagtt caccatcaga ccttctaaag   8760
agcaataaca agatggcaac ggcaacggtt aacctttggg gtagaatcga ctccgaatat   8820
```

-continued

```
tccctagagt atgaatcgca cggcatttgg cttgagacgt gggcaaaatt atcagcacgg   8880
cataacagtt caatgcgttg ttactctgaa attcttacct atctaattac gtctcaaggg   8940
cataaattaa atatcaacat tccctcacct cttgcagata ttaagaagct aaatgatgag   9000
gtaagtagta acagggaaaa ggtaaaaaat gagagatact ctcagaggtt aaactcacca   9060
gatattaacg atgcagaagc taccatactc gaatctaaag agcaaaaaat cggattgact   9120
ctcaatgaga gatgcaccct agaaaagcat aaagttaaga agcggtatgg gaatgtaaag   9180
atggatattc tcacctttga tgatgatgga ctataccccca aactcagact attttattac   9240
ctcaccatcg gtaaacctca tctcaaggct aatgacagaa aagctattgc caaaatgggc   9300
aatgacaata aaggcaagat tctatcaaaa gacttagtta ataaaactta ctccgctcgt   9360
gtgaaggtct tagagattct taaactaact gactttatcg acaatcttag agatgaactc   9420
ttaataactc ccaataatcc agctatcacc gattttaata atcttctgct aagagctaag   9480
aaggatttaa gagtattagg agtcaacatc ggaaaaatatc caatggccaa cattaatgcc   9540
gtacttactc tcattggtca caaactttct gtaatgagag atgagttcgg aaaagagaaa   9600
aggataaaag tagatggtaa atcataccga tgttatcaac ttgaaacatt accagatttt   9660
accaatgata ctcttgacta ctggttagaa aatgatagcc aaaaagaagt aacagcaaca   9720
gaaaattact ccgaaaattt taacccttca aatagctaca atccagacag taagacactt   9780
tcagagggtg caaatttcct atatataaat aaagaagaat tgcatccaaa taaattgcac   9840
ctagaaataa aagaaggtgc tgaacttttt ttattcgggg taaaggtgat tgtgaaagga   9900
atcttggacg gggcagtaac tatattctct atgggtcaag aatacgattt atccctcaat   9960
gaactagagg ggatgttaac atcatgaact ttacaagaat ctttttaaag ggcgatcgca  10020
ccatgttaaa tgatggtaca tttgttcaga tatttgatat ttaccatgac cacgcattgg  10080
gagtgaccct tgaccttaag acagaaaaaa ttatttccga tgatgttagg gtaattactg  10140
tcaaagactt attgttcgat ggcacttata aaggggtaaa atcttttatg cccgataatg  10200
cccgataatg cccgattgat gctacaaaat cccataatca taagcgataa tcccctaata  10260
gcttgtaatt cttgaaccgt agcgatttta gagtattcca aaaagaagaa ataaacaccg  10320
caaaatgtcg tatttcacat atataaacca aggtttttttg ccctaaaatc tttatgtttg  10380
tagtgtgatg ttgggtcaaa atggtcagaa aagttgcaag gtttttatgg atgcttacgc  10440
gcgcgagggg taagcatccc caaatagtta ctttatccta gtccatgccc atttattgcc  10500
gtcccgttcg gctttaaaaa agtgccaaaa ctcacaaggt gcaataaaaa gttctgtacc  10560
tttcgcaacc ctagataatc tttcaacagt tacttttttt cctattatct cggtacaaag  10620
tttggctagt ttctctttc cctcttttc aatcaagcct tcttgtatgc ccaactcatt  10680
gattaatctc tctattttta ccattatttc ccgttcaggt agtttatccc ctaaatcttc  10740
atcggggggc aatgtagggc attctgaagg ggcttttct tctgtctgga cattatctaa  10800
tattgaagta accaaactat cttcagtttt ttctattcct attaattcat attcggttac  10860
tgtatccgta tcaatatccg aataactatc tttatccgta ttagctattc ggttaagttt  10920
atccgttaac tcagaaacaa gactatatag cggttttagc ttttcttcta tcctgttatc  10980
taatacggat aagtttatac ggttatcatt atccgtatta gtatcattgg gcttttttgg  11040
tagttctacc ccctcataaa ccgcttttat tcccaattcc aacagactga taacagtatc  11100
ctttataatg ggtttttgc tgatatggtg aacttttgcc ccttccatca ttgcgatact  11160
ttctatctca ctcatcaact tatcgcttaa gtgaatctcg tatctgttta atcccttact  11220
```

-continued

```
ggttttattc atatccgttt actttattcg gttaacaatt ctattttata cgaataaaat  11280
attatacggt taactttata cgtttaacta ttttatctat acggataaca gtaataagtt  11340
attcgtatta gttatacgtt tacttttatc caaataaaat tagtgcattt aaactaaaag  11400
aatgatttta tcggagttga tagcattgga ttaacctaaa gatgtttata agctatatct  11460
gataagtatt taaggttatt ttgttattct gtttattgac attatcagaa taaaagaata  11520
gaatataatt gttgagagat aagaggttta agtgattatg gttaagaagt tagttggtta  11580
tgtcagggtc agtagtgaat cgcaagagga taacactagc ttacagaatc agatagagag  11640
aattgaagca tattgtatgg cttttggtta tgagttggta aaaatattca aagaggttgc  11700
cactggtaca aaagcagata ttgaaacccg tcctattttt aatgaagcta tagaatactt  11760
gaaacaggat aatgctaatg gaattattgc cttgaagcta gaccgaatcg cacggaatgc  11820
tttagatgta ttgcgtttgg ttcgtgaaac cttagaacca caaaataaaa tgttagtgtt  11880
actagatatt caggtagata cttcgacacc ttcaggaaaa atgattttaa ctgtaatgag  11940
tgccgttgct gaactcgaaa gagacatgat ctatgatcgc actcaggggg gtagaaagac  12000
taaagcccaa aagggcgggt atgcctacgg gaaacctaaa tttggctata agactgaaga  12060
aaaggaacta aaagaagatt cagcacaaca ggaaactatt aaactaatta agagacaccg  12120
taggtcaggg aaaagctacc agaaaatagc tgattatctc aatgcccaaa gtattcccac  12180
taaacaaggt aagaaatgga gttctagcgt cgtctatcga atctgtcagg aaaaagctgg  12240
ttaagtctgt ttatagatat ttagaattta ttgaataaaa atagtatgaa caataaatat  12300
ttatggacta accacgctcg gaaacgttta actgaacgat gggaaataaa agaatcatgg  12360
gttattgata ccatcgaaaa tcctgaacgt tcagaattta ttgttgatga gtcaggggaa  12420
aaatatcatt actataaaag aatagctaag tttaagaata gagtgttaga agtgataact  12480
tctgccaact caacacccac aagaataata accttttact ttaaccgtaa catgaggaaa  12540
aatttatgat tgttacttac gataatgaag ttgacgcaat ttattttaag ttaacggaaa  12600
ataaaattga tagcaccgaa cctcaaacag acaggattat cattgattac gatgaaagta  12660
ataatattgt tggcattgag gtattagatt ttaattatct tgtcaagaaa ggtttaaccg  12720
ttgctgattt accttttct gaagatgaaa gattaacagc ttctcaatat tttaattttc  12780
ctgttgctat ctaatccaga aggggcaata atccccttct ttcatcgagt tagacttaat  12840
atcacaaaag tcattttcat tttaccgttt cttttccaca gcgtccgtac gaataaaaaa  12900
cgcccggcgg caaccgagcg ttccacggta actaagatct ttaaatgaat ttttttctta  12960
aaaagttacc taaactatct actaatgtta ccataactaa aacaactaac aaaagggcag  13020
aaacttcctg atatttgagt aaacgtaatg ccccaataat ttcaaatcca atgccaccgg  13080
ctcccactgc gcctaatact agagaagctc taaaattgta ctcccaacga taaaatgtaa  13140
catcggcgat ttgtggtaaa acttggggta aaatactatg ataaatgatt tgtaaatgat  13200
ttgctccgac tgcttttgct gcttcaatag gtgcgttgtc tgtatgttct atggactcag  13260
caaaaaattt acctaccata ccaatagaat gaaatcccaa tgctaatacc ccaggaagtg  13320
cgccaaaccc aacagcggca acaaagataa ttcctagaag taattcagga atagctcttg  13380
ctatatttaa aataattctt gatacaaaat aaacgaaagg atggggactg gtattttgtg  13440
ctgccccgaa agtaataggc agagaaaaaa taacagccat tcctgttcct gcaatactca  13500
ttcctaaggt atcaattagt ggtttaatcc aatcagaagc acgagtaaaa tcgggaggca  13560
```

-continued

```
gcatttgtgc taccatttct aataggtcag gaattccttc agataagcgt tttccatcta  13620
ataaaccaac tacagcaaaa ctaataataa ttattattag caaaataatg atgtttatta  13680
gtgaacgata ccaaagaatc ttgtattggc gcaacagatt agaatattta tcttgattga  13740
ttgtcatttt tccaatattt gattaccaaa aattagggat aaccttataa ctttatgttt  13800
actttgattt gattctttgt ttagtaaaag aaaaaatctc acttgagagt ttaagatggt  13860
tatccctaaa tgaataattg atctttacag tagctaaacc ctcagattaa ttaagtttag  13920
caaaatcaag attgaggatt tttcctaagt ctcggacaac attataatcc ttgtcttcta  13980
ctgattgaaa cccttctgct ttaaatggtt ctaaaactgc cttatcttct agttctagaa  14040
aagcttgctt aatttgctgt tttaattgag gttctaagtc agatcgcatc gtccaaggat  14100
attggggaaa tggtttagat tcttctatta aaatgacttt attttcatca atggttccct  14160
tattaattaa agcggtataa atgggtttac ttaagccccc tgcttgggct tttccattgg  14220
caacagctac agctacagca tcatgagaac cgacaaatac ttcttgataa ttttcttctg  14280
cttttaagcc tttttccatt aacattgact taggaattaa atgactagag gtcgaggctt  14340
gatctccata agccatagtt tttccttcga ttttgtcata ggaatcaatt cctgcttctg  14400
cattaccaat aatgacagat ttataggtgg cttctccatc tttttctaac gctgcaaagg  14460
cttcgatatt acttttagtt ttggccaaaa catacgacaa aggaccaaaa taggctaagt  14520
ctaatcttcc attactcgct gcttcgatca tagaagaata atcggtactg acaaacaatt  14580
caacatcttt attcagtcgg tcttctaagt agctttctaa cccccttatta ttttgaatta  14640
cggtagatac tgattcatcg ggtaacaaag caactactaa ttttttaggg ttagcttttg  14700
tgtctgcttt gctattttca gggttattat tggatgtttg actattcggt gtactacaac  14760
caattagagt taatagggta aaagaaacaa caggggttaa ggattttttta aagatgaaac  14820
tgatcatacc aattttgagt caaataattt tactgttgat tataatgatt ttcttgaaaa  14880
aagcaagatt ttaatgattt tttaagtgtg atttagataa caattaacct gccttaatca  14940
aagaagaatt gtgataaatt ttttctaact ggtatgattg tatttctgac gggtgactat  15000
caaaaaggat gtttccatct gcaaggccaa taatgcgatc gccatagtct aaagcgaaat  15060
ctatttgatg taaactaacc actgccccaa taccatcttc ttgacaaatt tttttgagat  15120
tagttaatat cttatgagaa ctaccaggat ctaaactagc aacaggttca tctgctaaga  15180
gaaatctggg tttttgagct aaagctctgg ctattcctac ccgttgttgt tgtcctccac  15240
ttagttgttt aacaggagtt aaagctttat ttaataggcc aactctgtcc aaacaatcta  15300
aagcaatcat ttgatcaatt ttaggcaaag ggaaaaaact tcttaaggta gagtgatagg  15360
ctaaacgacc aactaaaaca tttttaaggg cagtttgtcg aggaattaat tgatgttgtt  15420
gaaaaatcat gcccgttttt tggcgatgtt ttcttaagat tttcgggtta tttagggttc  15480
ctaacccctc cacaataact tcacccttag taggaactgt tagaaaattg atacaacgta  15540
aaagggttga ttttcctgca ccagaagccc ctaaaagtac cgtaaattct cctggaatca  15600
attcaagaga aatattttct aaggccacgg ttccatcttt ataggtgaca ctaaggttat  15660
taagaaaaat atgcattgta attaatttct cctaattatg ttggtttacg ttaatgaaat  15720
ggattttcta atcttggttt aaagagctca ttataactag tgatggtgat gatggtgtac  15780
gtaggatcca gcagctttta caccaggata gggttgatta attgcaccca taggtttttc  15840
acctgctaaa gcctgtataa tattcattgc agcttgtctt tcaatttcta aacgtacttc  15900
ttttacagca ctacctaaat gaggtgtaaa aaaggtttgt gcggtgttat ctaataaggc  15960
```

```
tttgggaata gcttgaggtc tgtctgctct tatccactct tccatctcaa atacgtcggc  16020

agcatatcct gctaatttac cactagctaa agcagctata acggcattct cgtccacaac  16080

agaacctcta caagcattga ttaaataaga tcctgttttc atttttgcta aggcggtggc  16140

atcaattaaa tgtaatgtct ctgctgccat gggcaccata ggaacaacgt aatcacattt  16200

ctctaataat tcgtctaaag taactctttg tacatgccat gctttttctt gttctgcatt  16260

taaaggtata ggatcacaat ataataaatt catttcaaat cctgctaatc tttgagcaat  16320

agcacgtcct acagcaccca tacctataat tcctaaagtt ttaccggtta atccagaacc  16380

atataaagta ggtctccatc cttgaaaatg tccagaacgt atctgacgat caccttctaa  16440

catgtgtcta gttaaaccta ataataatcc aattgttaat tcggcggtag gaatagttaa  16500

taaatcaggt acgatggtta accaaacacc gtgtcttgta caggcgttta catcaaaatt  16560

atcataacct tttaaagcgg caccgatcac tcttaattta ggacattcct ctaaaaatgc  16620

agaatcaata gaatcaggca taaaggccat taaagcatca gcatctttgg ctctggcaat  16680

tacttcacta cgaggtaaag tttctcttgt tgtattggga atcacatctg cactagcact  16740

taataattct attatttcgg ggtgtaccca atgagttaat actactttag gtttcattga  16800

attcataagg ctgatcctcc ttaatatatt gaatacaaat aaatatttaa agacttatat  16860

acttaactgc ccaatacatt attaatttga ttcttaatat tttgtaactt tgactactaa  16920

ataaagacac attttctttt tacacataat tttaattcgt tttttgcatc tatcagggat  16980

gaaggcttag taattcggag agttcgctac gctcgttccg caaagcagta cggagttagt  17040

taggagcaaa tggccattcg cccgtacagg aagaagttat taattgtcga g           17091
```

<210> SEQ ID NO 9
<211> LENGTH: 17172
<212> TYPE: DNA
<213> ORGANISM: Artificial Sequence
<220> FEATURE:
<223> OTHER INFORMATION: Synthetic plasmid construct derived from p6.8 endogenous plasmid from Cyanobacterium sp. PTA-13311, plus ptxA,B,C, from Cyanothece sp. ATCC-51142, ptxD from Ralstonia sp. 4506, plus nitrate-inducible ethanologenic genes pdc and adh.

<400> SEQUENCE: 9

```
gtcgacaatt aataacttct tcctgtacgg gcgaatggcc atttgctcct aactaactcc     60

gtactgcttt gcggaacgag cgtagcgaac tctccgaatt actaagcctt catccctgat    120

agatgcaaaa aacgaattaa aattatgtgt aaaaagaaaa tgtgtcttta tttagtagtc    180

aaagttacaa aatattaaga atcaaattaa taatgtattg ggcagttaag tatataagtc    240

tttaaatatt tatttgtatt caatatatta aggaggatca gccttatgaa ttcttatacc    300

gtgggtactt atttagccga acgcttagtg caaattggtt taaaacatca ttttgccgtg    360

gctggggact ataatttagt gttattggat aacttattat taaataaaaa catggaacaa    420

gtgtattgtt gtaatgaatt aaattgtggt ttttctgctg aaggttatgc tagagctaaa    480

ggtgcagctg ctgctgttgt tacttattct gtgggtgctt tatctgcttt tgatgctatt    540

ggtggtgctt atgccgaaaa tttacccgtg attttaattt ctggtgcccc taataataat    600

gatcatgccg ctggacatgt tttacatcat gccttaggta aaaccgatta tcattatcaa    660

ttagaaatgg ccaaaaatat tactgctgct gccgaagcta tttatactcc tgaagaagcc    720

cctgccaaaa ttgatcatgt gattaaaacc gccttacgcg aaaaaaaacc cgtgtattta    780

gaaattgcct gtaatattgc ttctatgcct tgtgctgctc ctgggcctgc ttctgcttta    840
```

-continued

```
tttaatgatg aagcctctga tgaagctagt ttaaatgctg ccgtggaaga aaccttaaaa    900
tttattgcca atcgcgataa agttgccgtg ttagttggtt ctaaattaag agctgctggt    960
gctgaagaag ctgctgttaa atttgctgat gctttaggtg gtgcagttgc tactatggct   1020
gctgccaaat cttttttttcc cgaagaaaat ccccattata ttggaactag ttggggagaa   1080
gtttcttatc ctggtgtgga aaaaactatg aaagaagccg acgctgttat tgctttagcc   1140
cctgtgttta atgattattc taccactggt tggactgata ttcccgatcc caaaaaatta   1200
gttttagccg aacctcgttc tgttgttgtt aatggtgttc gctttccctc tgtgcattta   1260
aaagattatt taacccgctt agcccaaaaa gtttctaaaa aaactggtgc cttagatttt   1320
tttaaatctt taaatgcggg tgaattaaaa aaagctgctc ctgctgatcc ttctgctcct   1380
ttagttaatg ctgaaattgc ccgtcaagtt gaagccttat taaccccctaa tactaccgtt   1440
attgccgaaa ctggtgattc ttggtttaat gcccaacgca tgaaattacc taatggtgcc   1500
cgtgttgaat atgaaatgca atggggtcat attggttggt ctgtacctgc tgcttttggt   1560
tatgctgttg gtgctcctga acgtcgtaat attttaatgg tgggtgatgg ttcttttcaa   1620
ttaactgccc aagaagttgc ccaaatggtt cgcttaaaat tacccgttat tattttttta   1680
ataaataatt atggttatac cattgaagtg atgattcatg atgggccata taataatatt   1740
aaaaattggg attatgcggg tttaatggaa gtgtttaatg gtaatggtgg ttatgattct   1800
ggtgctggta aaggtttaaa agccaaaact ggtggtgaat tagctgaagc tattaaagtt   1860
gccttagcca atactgatgg gccaacctta attgaatgtt ttattggtcg cgaagattgt   1920
accgaagaat tagttaaatg ggtaaacgt gttgctgctg ctaattctcg caaacccgtg   1980
aataaattat tgtaaggatc cagcaaggtt tcatcccgac cccctcaggg tcgggatttt   2040
tttattgtga gctcaacttt agatattcgt agttggcaat gtcgtaaatg cggaacaata   2100
catggaaaac atatagattt gtaatgagaa aaagtgtaaa caaatattaa gaaaaagatc   2160
agaaaaattt aacaacacgt aataaaaaaa tgcgtcacta cgggttataa atttacatga   2220
aaggttaaaa cacttttctg agacgatttt gataaaaaag ttgtcaaaaa attaagtttc   2280
tttacaaatg cttaacaaaa acttggtttt aagcacaaaa taagagagac taatttgcag   2340
aagttttaca aggaaatctt gaagaaaaag atctaagtaa aacgactctg tttaaccaaa   2400
atttaacaaa tttaacaaaa caaactaaat ctattaggag attaactaca tatgagtgaa   2460
actaaattta aagcctatgc cgtaatgaat cctggtgaaa aattacaacc ctgggaatat   2520
gaacctgctc ctttacaggt agatgaaatt gaagtaagag ttactcacaa tggtttatgt   2580
cacactgact tacacatgag agataatgac tggaatgtta gtgagttccc cttagtagca   2640
ggtcatgaag ttgttggtga agtaaccgct gttggtgaaa aagtaaccag tcgtaaaaaa   2700
ggtgatagag ttggtgtagg ttggattcgt aattcttgtc gcgcttgtga ccattgttta   2760
caaggagaag agaacatttg tagagagggt tatactggtt taattgttgg tcatcacggt   2820
ggatttgctg atcgtgtacg tgtacctgct gacttcactt ataaaattcc tgatgcttta   2880
gatagtgcat ctgctgctcc tttattatgt gccggtatta ccgtttacac tcctttaaga   2940
acctacatta aacatcccgg tatgaaagta ggtgttatgg gtattggagg attaggacat   3000
ttagctatta aatttgctcg tgcaatggga gcagaagtta ctgcctttag taccagtcct   3060
aataaagaag cccaagccaa agaatttggt gctcatcatt tccaacaatg ggtactgct    3120
gaagaaatga aagctgttgc cggtaatttt gatttagttt tatctaccat ctctgctgaa   3180
```

-continued

```
actgactggg atgctgcctt ctctttatta gcaaataacg gtgttttatg tttcgtaggt   3240
attcccgtta gttctttaaa tgttccttta attcctttaa ttttcggaca aaaatctgtt   3300
gtaggttctg tagttggagg aagaagattc atggcagaaa tgttagagtt cgccgctgta   3360
aatcagatta aacctatgat cgaaactatg cccttatctc aagtaaatga agctatggat   3420
aaagttgccg ccaataaagc cagatataga attgtattat tatctgaata actagatcta   3480
cttctaaact gaaacaaatt tgagggtagg cttcattgtc tgcccttatt tttttattta   3540
ggaaaagtga acagactaaa gagtgttggc tctattgctt tgagtatgta aattaggcgt   3600
tgctgaatta aggtatgatt tttgacccct gcaggatcat cttgctgaaa aactcgagcg   3660
ctcgttccgc aaagcggtac ggagttagtt aggggctaat gggcattctc ccgtacagga   3720
aagagttaga agttattaat tatcaacaat tctcctttgc ctagtgcatc gttacctttt   3780
taattaaaac ataaggaaaa ctaataatcg taataattta acctcaaagt gtaaagaaat   3840
gtgaaattct gacttttata acgttaaaga gggaaaaatt agcagtttaa aatacctaga   3900
gaatagtctg ggtaagcat agagaattag attagttaag ttaatcaaat tcagaaaaaa   3960
taataatcgt aaatagttaa tctgggtgta tagaaaatga tccccttcat gataagattt   4020
aaactcgaaa agcaaaagcc aaaaaactaa cttccattaa aagaagttgt tacatataac   4080
gctataaaga aaatttatat atttggagga taccaaccat gtctcatatt caacgtgaaa   4140
ctagttgttc tcgccctcgt ttaaattcta atatggatgc cgatttatat ggttataaat   4200
gggctcgtga taatgttggt caatctggtg ctactattta tcgtttatat ggtaaacctg   4260
atgctcctga attattcttg aaacatggta aaggttctgt tgctaatgat gttactgatg   4320
aaatggttcg tttaaactgg ttgactgaat ttatgccttt acctactatt aaacatttta   4380
ttcgtactcc cgatgatgct tggttattaa ctactgctat tcctggtaaa actgcttttc   4440
aagttttaga agaatatcct gattctggtg aaaatattgt tgatgcttta gctgtttttt   4500
tacgtcgttt acattctatt cccgtttgta attgtccttt taattctgat cgtgtttttc   4560
gtttagctca agctcaatct cgtatgaata atggtttagt tgatgcttct gatttttgatg   4620
atgaacgtaa tggttggcct gttgaacaag tttggaaaga aatgcacaaa ttgttacctt   4680
tttctcctga ttctgttgtt actcatggtg atttttcttt agataatttg atctttgatg   4740
aaggtaaatt gattggttgt attgatgttg gtcgtgttgg tattgctgat cgttatcaag   4800
atttagctat tttatggaat tgtttaggtg aattttctcc ttctttacag aaacgtttat   4860
ttcagaaata tggtattgat aatcctgata tgaacaagtt acaatttcat ttaatgttgg   4920
acgagttctt ttaagaatta attcatgacc aaaatccctt aacgtgagtt ttcgttccac   4980
tgagcgtcag accccgtaga aaagatcaaa ggatcttctt gagatccttt ttttctgcgc   5040
gtaatctgct gctatttaaa ttacgtacac gtgttattac tttgttaacg acaattgtct   5100
taattaactg ggcctcatgg gccttccgct cactgcccgc tttccagtcg ggaaacctgt   5160
cgtgccagct ctgcagatga cggtgaaaac ctctgacaca tgcagctccc ggagacggtc   5220
acagcttgtc tgtaagcgga tgccgggagc agacaagccc gtcagggcgc gtcagcgggt   5280
gttggcgggt gtcggggcgc agccatgacc cagtcacgta gcgatagcgg agtgtatact   5340
ggcttaacta tgcggcatca gagcagattg tactgagagt gcaccatatg cggtgtgaaa   5400
taccgcacag atgcgtaagg agaaaatacc gcatcaggcg ctcttccgct tcctcgctca   5460
ctgactcgct gcgctcggtc gttcggctgc ggcgagcggt atcagctcac tcaaaggcgg   5520
taatacggtt atccacagaa tcaggggata acgcaggaaa gaacatgtga gcaaaaggcc   5580
```

agcaaaaggc caggaaccgt aaaaaggccg cgttgctggc gtttttccat aggctccgcc 5640
cccctgacga gcatcacaaa aatcgacgct caagtcagag gtggcgaaac ccgacaggac 5700
tataaagata ccaggcgttt ccccctggaa gctccctcgt gcgctctcct gttccgaccc 5760
tgccgcttac cggatacctg tccgcctttc tcccttcggg aagcgtggcg ctttctcata 5820
gctcacgctg taggtatctc agttcggtgt aggtcgttcg ctccaagctg ggctgtgtgc 5880
acgaaccccc cgttcagccc gaccgctgcg ccttatccgg taactatcgt cttgagtcca 5940
acccggtaag acacgactta tcgccactgg cagcagccac tggtaacagg attagcagag 6000
cgaggtatgt aggcggtgct acagagttct tgaagtggtg gcctaactac ggctacacta 6060
gaaggacagt atttggtatc tgcgctctgc tgaagccagt taccttcgga aaaagagttg 6120
gtagctcttg atccggcaaa caaaccaccg ctggtagcgg tggttttttt gtttgcaagc 6180
agcagattac gcgcagaaaa aaaggatctc aagaagatcc tttgatcttt tctactgcag 6240
aagcttgtta gacaccctgt catgtatttt atattattta tttcaccata cggattaagt 6300
gaaacctaat gaaaatagta ctttcggagc tttaacttta atgaaggtat gtttttttat 6360
agacatcgat gtctggttta acaataggaa aaagtagcta aaactcccat gaattaaaga 6420
aataacaagg tgtctaacaa cctgttatta agaatgttag aaaagactta acatttgtgt 6480
tgagttttta tagacattgg tgtctagaca tacggtagat aaggtttgct caaaaataaa 6540
ataaaaaaag attggactaa aaaacattta atttagtaca atttaattag ttattttttc 6600
gtctcaaatt ttgctttgtt gagcagaaat ttagataaaa aaatccccgt gatcagatta 6660
caatgtcgtt cattgtacga tgtgtcgaaa aatctttacg acactctaaa ctgaccacac 6720
gggggaaaaa gaaaactgaa ctaataacat catgatactc ggaaaaccta gcaattctca 6780
acccctaaac aaaagaaact tccaaaaccc tgaccatata aaggagtggc aacaatcagc 6840
aatcagtcaa gatttgatag cagaaaatct tgtatcggtt gctaatggtt ttgatgtact 6900
atttatcggc aataaatacc gaactaacac gggtgttctg tcacggcaca tattaaactc 6960
ctattctcat ttagaagatg gtggttcgta tggtagaaca tttgacccat ttaccaataa 7020
agaaatgcag tgggttcaat ttaaaccgaa tagaccaaga aaaggttcta ctggtaaggt 7080
aatcaaatat gaatcgccaa aggtgaacc tacaagagtt ctaatgccgt ttgtgcctat 7140
gaaaatatgg caacggatta gcgataagtt cggagtaccg attaatccga aaaaagatac 7200
tcacttttgg gaatgggtaa agaataatcc atcgataccg attgccatta cagaaggaaa 7260
taaaaaagct aattgcctat tatcctatgg ctatcctgct attgcctttg taggcatttg 7320
gaacggatta gagaaaataa atgatttctc gaaggaaaag cagttaaaag aggatttgaa 7380
atggttgtta tccaacggca accgaaatat taatatcatc tttgaccaag accagaaaca 7440
aaaaactgta attaatgtaa acaaagctat tttcgcttta tcttctctaa taagtagaaa 7500
tggtcataaa gttaatattg tgcaatggtt gccgtcaaaa ggtaaaggaa tagatgatta 7560
tttggtagct ttacctttg agaaaagaga aaatcattta gacaacttaa ttaaaattgc 7620
accatcattt aatttttggt caactaaata cttattcaag tgtcgtaaac cagatttaac 7680
cgtaaattgc cgttatttga gcgatgcagt aaaagaatta cctcaagagg atatagcatt 7740
aatagcacct cacggcacgg gtaaaacttc attagtagct actcacgtta agaatcggag 7800
ttatcacgga aggaaaacta tttcattggt gcatcttgaa agtttagcca aagctaatgg 7860
caacgcactt ggattatatt accgaaccga aaataatatt gaaaagcaat atcttggatt 7920

```
tagcttatgt gtagatagtt gccgtgataa gattaacggc attacaactg atattatttc   7980
aggtcaagat tattgccttt tcattgatga aattgaccaa gtaattccac acatccttaa   8040
cagtgaaact gaagtaagta agtatagatg caccatcatt gacacttttt ctgaactggt   8100
gagaaatgct gaacaggtca ttattgctga tgctgattta tccgatgtga cgattgacct   8160
aatagaaaac atcagaggta aaaaactata tgtaatcaag aatgaatatc agtatcaggg   8220
aatgactttt aacgccgttg gttcaccatt agaaatgatg gcaatgatgg gaaaatcggt   8280
gtcagaaggc aagaaattat ttattaacac cacatcccaa aaggcaaaaa gtaagtacgg   8340
cacaatcgct cttgagtctt atatttttgg tctaaataaa gaagcaaaga tattaagaat   8400
agactctgaa accactaaaa accctgaaca tccagcctat aaaatcattg accaagactt   8460
aaataatatc ctcaaagatt atgattatgt cattgcctca ccttgccttc aaacaggtgt   8520
cagtattacc ttaaaagggc attttgacca gcaatttaac ttttccagtg gaaacattac   8580
acctcattgc tttttacagc aaatgtggcg gttgagggat gcagaaattg aaagattcta   8640
ttatgtgccg aactcatcta acctcaatct cattgggaat aagtcaagtt caccatcaga   8700
ccttctaaag agcaataaca agatggcaac ggcaacggtt aaccttttgg gtagaatcga   8760
ctccgaatat tccctagagt atgaatcgca cggcatttgg cttgagacgt gggcaaaatt   8820
atcagcacgg cataacagtt caatgcgttg ttactctgaa attcttacct atctaattac   8880
gtctcaaggg cataaattaa atatcaacat tccctcacct cttgcagata ttaagaagct   8940
aaatgatgag gtaagtagta acagggaaaa ggtaaaaaat gagagatact ctcagaggtt   9000
aaactcacca gatattaacg atgcagaagc taccatactc gaatctaaag agcaaaaaat   9060
cggattgact ctcaatgaga gatgcaccct agaaaagcat aaagttaaga agcggtatgg   9120
gaatgtaaag atggatattc tcacctttga tgatgatgga ctatacccca aactcagact   9180
attttattac ctcaccatcg gtaaacctca tctcaaggct aatgacagaa aagctattgc   9240
caaaatgggc aatgacaata aaggcaagat tctatcaaaa gacttagtta ataaaactta   9300
ctccgctcgt gtgaaggtct tagagattct taaactaact gactttatcg acaatcttag   9360
agatgaactc ttaataactc ccaataatcc agctatcacc gattttaata atcttctgct   9420
aagagctaag aaggatttaa gagtattagg agtcaacatc ggaaaatatc caatggccaa   9480
cattaatgcc gtacttactc tcattggtca caaactttct gtaatgagag atgagttcgg   9540
aaaagagaaa aggataaaag tagatggtaa atcataccga tgttatcaac ttgaaacatt   9600
accagatttt accaatgata ctcttgacta ctggttagaa aatgatagcc aaaaagaagt   9660
aacagcaaca gaaaattact ccgaaaattt taacccttca aatagctaca atccagacag   9720
taagacactt tcagagggtg caaatttcct atatataaat aaagaagaat tgcatccaaa   9780
taaattgcac ctagaaataa aagaaggtgc tgaacttttt ttattcgggg taaaggtgat   9840
tgtgaaagga atcttggacg gggcagtaac tatattctct atgggtcaag aatacgattt   9900
atccctcaat gaactagagg ggatgttaac atcatgaact ttacaagaat ctttttaaag   9960
ggcgatcgca ccatgttaaa tgatggtaca tttgttcaga tatttgatat ttaccatgac  10020
cacgcattgg gagtgaccct tgaccttaag acagaaaaaa ttatttccga tgatgttagg  10080
gtaattactg tcaaagactt attgttcgat ggcacttata aaggggtaaa atcttttatg  10140
cccgataatg cccgataatg cccgattgat gctacaaaat cccataatca taagcgataa  10200
tcccctaata gcttgtaatt cttgaaccgt agcgatttta gagtattcca aaaagaagaa  10260
ataaacaccg caaaatgtcg tatttcacat atataaacca aggttttttg ccctaaaatc  10320
```

```
tttatgtttg tagtgtgatg ttgggtcaaa atggtcagaa aagttgcaag gtttttatgg  10380
atgcttacgc gcgcgagggg taagcatccc caaatagtta ctttatccta gtccatgccc  10440
atttattgcc gtcccgttcg gctttaaaaa agtgccaaaa ctcacaaggt gcaataaaaa  10500
gttctgtacc tttcgcaacc ctagataatc tttcaacagt tacttttttt cctattatct  10560
cggtacaaag tttggctagt ttctcttttc cctctttttc aatcaagcct tcttgtatgc  10620
ccaactcatt gattaatctc tctattttta ccattatttc ccgttcaggt agtttatccc  10680
ctaaatcttc atcggggggc aatgtagggc attctgaagg ggctttttct tctgtctgga  10740
cattatctaa tattgaagta accaaactat cttcagtttt ttctattcct attaattcat  10800
attcggttac tgtatccgta tcaatatccg aataactatc tttatccgta ttagctattc  10860
ggttaagttt atccgttaac tcagaaacaa gactatatag cggttttagc ttttcttcta  10920
tcctgttatc taatacggat aagtttatac ggttatcatt atccgtatta gtatcattgg  10980
gctttttggg tagttctacc ccctcataaa ccgcttttat tcccaattcc aacagactga  11040
taacagtatc ctttataatg ggttttttgc tgatatggtg aacttttgcc ccttccatca  11100
ttgcgatact ttctatctca ctcatcaact tatcgcttaa gtgaatctcg tatctgttta  11160
atcccttact ggttttattc atatccgttt actttattcg gttaacaatt ctattttata  11220
cgaataaaat attatacggt taactttata cgtttaacta ttttatctat acggataaca  11280
gtaataagtt attcgtatta gttatacgtt tacttttatc caaataaaat tagtgcattt  11340
aaactaaaag aatgatttta tcggagttga tagcattgga ttaacctaaa gatgtttata  11400
agctatatct gataagtatt taaggttatt ttgttattct gtttattgac attatcagaa  11460
taaaagaata gaatataatt gttgagagat aagaggttta agtgattatg gttaagaagt  11520
tagttggtta tgtcagggtc agtagtgaat cgcaagagga taacactagc ttacagaatc  11580
agatagagag aattgaagca tattgtatgg cttttggtta tgagttggta aaaatattca  11640
aagaggttgc cactggtaca aaagcagata ttgaaacccg tcctattttt aatgaagcta  11700
tagaatactt gaaacaggat aatgctaatg gaattattgc cttgaagcta gaccgaatcg  11760
cacggaatgc tttagatgta ttgcgtttgg ttcgtgaaac cttagaacca caaaataaaa  11820
tgttagtgtt actagatatt caggtagata cttcgacacc ttcaggaaaa atgattttaa  11880
ctgtaatgag tgccgttgct gaactcgaaa gagacatgat ctatgatcgc actcaggggg  11940
gtagaaagac taaagcccaa aagggcgggt atgcctacgg gaaacctaaa tttggctata  12000
agactgaaga aaaggaacta aaagaagatt cagcacaaca ggaaactatt aaactaatta  12060
agagacaccg taggtcaggg aaaagctacc agaaaatagc tgattatctc aatgcccaaa  12120
gtattcccac taaacaaggt aagaaatgga gttctagcgt cgtctatcga atctgtcagg  12180
aaaaagctgg ttaagtctgt ttatagatat ttagaattta ttgaataaaa atagtatgaa  12240
caataaatat ttatggacta accacgctcg gaaacgttta actgaacgat gggaaataaa  12300
agaatcatgg gttattgata ccatcgaaaa tcctgaacgt tcagaattta ttgttgatga  12360
gtcaggggaa aaatatcatt actataaaag aatagctaag tttaagaata gagtgttaga  12420
agtgataact tctgccaact caacacccac aagaataata accttttact ttaaccgtaa  12480
catgaggaaa aatttatgat tgttacttac gataatgaag ttgacgcaat ttattttaag  12540
ttaacggaaa ataaaattga tagcaccgaa cctcaaacag acaggattat cattgattac  12600
gatgaaagta ataatattgt tggcattgag gtattagatt ttaattatct tgtcaagaaa  12660
```

-continued ggtttaaccg ttgctgattt acctttttct gaagatgaaa gattaacagc ttctcaatat 12720
tttaattttc ctgttgctat ctaatccaga aggggcaata atccccttct ttcatcgagt 12780
tagacttaat atcacaaaag tcattttcat tttaccgttt cttttccaca gcgtccgtac 12840
gagagaatat aaaaagccag attattaatc cggctttttt attattttta aataaatttt 12900
tttctaagaa aattgcctaa tgaatcaact aaagtaacca ttactaatac gacaagcaat 12960
aaggcactaa cttcttgata tttcaataat ctcaaagcac caataatttc aaacccaata 13020
ccacctgcgc caacagcacc taatactaaa gaagctctaa aattatattc ccaacggtaa 13080
aaagttacat ccgcaatttg gggaagcact tggggtaaga tggaatgata tataatttga 13140
aggtggttag caccgaccgc tttagcagct tctattggag cattgtctgt atgttcaata 13200
gactccgcaa agaattttcc taccattcca atactatgaa aacctaaggc taatactcca 13260
ggtaatgcac caaaacctac tgcagcaaca aatataatcc ctaaaagcaa ttcaggaatc 13320
gctctagcaa tatttaaaat gattcttgat acaaaataga caaaaggatg aggagaagtg 13380
ttttgtgcgg ccccaaaagt tatgggcaat gaaaaaatta cggccatgcc agttccagct 13440
atggacatgc ccaaagtatc aattaaaggt ttgatccagt cagacgctct ggtaaagtca 13500
ggaggcaaca tttgtgcgac catttctaaa aggtctggaa tgccttcgga taagcgttta 13560
ccatctaaca aaccaactac tgcaaatgaa ataataataa taatcaataa aataataata 13620
ttaattaaag aacgatacca taaaatttta tattgtctta aaagattact atatttatcc 13680
tgattaatgg tcatgctttt tttaggaatt ctcctgttac acaatcagag tcaacgttta 13740
aaatacgctg gtcaattttg gattttatct tgcctagccc tcggaattaa atttctttaa 13800
aagaaactag gcaaggaatt aaattgattt ttaaatgtta gttaatagtg aagaatctaa 13860
gataaatata gactttcaac tattaacaat tattgttagt aaaaacggct ttatctgtta 13920
ttttataact tattttgccg tagattttcc cactaaatta gtgaaagttt acattcttaa 13980
tttaacttcg caaaatctaa gtttaaaatt tttccaagat cgcggacaac attataatct 14040
ttatcttcca cactctgaaa tccttctgct ttaaaaggtt ctaatacagc tttgtcttcc 14100
aactctaaaa atgcttgttt gatctgttgt ttaagctgtg gctcaagatc acttctcatg 14160
gtccaaggat attgaggaaa aggcttactt tcttcgatca aaataacctt gttttcatct 14220
attgttccct tattgattaa agcagtgtag atgggtttac ttaatccacc tgcttgagct 14280
tttccattag ccacggcgac cgcaacagca tcatgactcc caacaaaaac ttcttgataa 14340
ttttcttctg ctttaagtcc tttctccata agcattgatt taggaatcaa atgagaagag 14400
gtactagctt gatcaccata agccatagtt tttccttcaa ttttatcata actgtcaatg 14460
cccgcttcgg cattcccaat aattacagat ttataagtag cttcgccatc tttttctaag 14520
gcagcaaatg cttcgatgtt tgatttagtt ttcgctaaca cataacttaa gggcccaaag 14580
tacgctaaat ctaatcgtcc attggaagct gcttcaatca tactagaata atctgtacta 14640
acaaacaatt caacgtcttt atttaaacga tcctccaaat aggattctaa tcctttatta 14700
ttctgaatga ctgtactaac actttcatct ggtaataaag cgactactaa ctttttaggg 14760
tttgctttgg tgtccgcttt tgagttctca ggattgttat tactggtttg actattgggg 14820
gtagaacagc cgataagtgt taataaagta aaagacacaa caggtgttaa tgatttttta 14880
aatataaaag aaatcattgt gctgatcctc ctaattatgt tggtttacgt taatgaaatg 14940
gattttctaa tcttggttta aactatccag ctttgattaa actggaatta tgatagatct 15000
tttctaattg ataactttgg atttcactgg gatgactatc aaaaaggatg ttcccatctg 15060

-continued

```
ccaatccaat aattcggtcg ccataatcta aagcaaagtc aatctgatgc aaactaacta  15120
cagcacctat tccatcttct tgacaaattt ttttaagatt agttaagatt ttatgggaac  15180
tgccgggatc taatgatgcc acaggttcgt ccgctaaaag aaatctgggt ttctgagcta  15240
atgcacgcgc tatacctact ctctgttgtt gacccccact taattgtttc acaggggtta  15300
aagccttatt taataaaccc actctatcta aacagtctaa agcgatcatc tgatcaattt  15360
ttggtaaagg aaaaaaagat cttaaagtag aatgataagc taaacgtcca actaagacat  15420
ttttaagtgc tgtttgtctg ggtattaatt gatgttgttg aaaaatcatt cctgtttttt  15480
gtctgtgctt acgaagaatt tttggattat tcaaagttcc taaaccctca actataactt  15540
ccccttttggt aggaacggtt aaaaaattta tacatctcaa taaggtagat ttaccagctc  15600
cactagctcc caataaaacg gtaaactctc cggggatcaa ttctaaagaa atattttcca  15660
aagctacggt cccatcttta taggttacac ttaaattgtt taaaaaaatc attgtaatta  15720
atttctccta attatgttgg tttacgttaa tgaaatggat tttctaatct tggtttaaag  15780
agctcattat aactagtgat ggtgatgatg gtgtacgtag gatccagcag cttttacacc  15840
aggatagggt tgattaattg cacccatagg tttttcacct gctaaagcct gtataatatt  15900
cattgcagct tgtctttcaa tttctaaacg tacttctttt acagcactac ctaaatgagg  15960
tgtaaaaaag gtttgtgcgg tgttatctaa taaggctttg ggaatagctt gaggtctgtc  16020
tgctcttatc cactcttcca tctcaaatac gtcggcagca tatcctgcta atttaccact  16080
agctaaagca gctataacgg cattctcgtc cacaacagaa cctctacaag cattgattaa  16140
ataagatcct gttttcattt ttgctaaggc ggtggcatca attaaatgta atgtctctgc  16200
tgccatgggc accataggaa caacgtaatc acatttctct aataattcgt ctaaagtaac  16260
tctttgtaca tgccatgctt tttcttgttc tgcatttaaa ggtataggat cacaatataa  16320
taaattcatt tcaaatcctg ctaatctttg agcaatagca cgtcctacag cacccatacc  16380
tataattcct aaagttttac cggttaatcc agaaccatat aaagtaggtc tccatccttg  16440
aaaatgtcca gaacgtatct gacgatcacc ttctaacatg tgtctagtta aacctaataa  16500
taatccaatt gttaattcgg cggtaggaat agttaataaa tcaggtacga tggttaacca  16560
aacaccgtgt cttgtacagg cgtttacatc aaaattatca taacctttta aagcggcacc  16620
gatcactctt aatttaggac attcctctaa aaatgcagaa tcaatagaat caggcataaa  16680
ggccattaaa gcatcagcat ctttggctct ggcaattact tcactacgag gtaaagtttc  16740
tcttgttgta ttgggaatca catctgcact agcacttaat aattctatta tttcggggtg  16800
tacccaatga gttaatacta ctttaggttt cattgaattc atgactgttt ctctcttttt  16860
atctttacct ttgattctgt aaaaagaata tgaaattagg atgaaatgat tttcggtaaa  16920
taaacggtaa aaatactgcc ttgattttct tgactttcta aaattattct accaccatga  16980
ttaagcgcga tcgcatttgc aatagctaaa cctaatccgc aactgccttt ctctctattt  17040
cttgctttat tgattcgata aaaacgatta aaaattaatt tttgttcttc tttattaatg  17100
caaattcctg tatcaattat ttttataatg acttcttttt ttgttgtttc taaacatata  17160
gtaacttgac ca                                                      17172
```

<210> SEQ ID NO 10
<211> LENGTH: 9707
<212> TYPE: DNA
<213> ORGANISM: Artificial Sequence
<220> FEATURE:

<223> OTHER INFORMATION: Synthetic plasmid construct designed to create the knock-out the phosphate metabolism regulator gene PhoU, which is endogenous to Cyanobacterium sp. PTA-13311.

<400> SEQUENCE: 10

```
aaaaagttgt caaaaaatta agtttcttta caaatgctta acaaaaactt ggttttaagc     60
acaaaataag agagactaat ttgcagaagt tttacaagga aatcttgaag aaaaagatct    120
aagtaaaacg actctgttta accaaaattt aacaaattta acaaaacaaa ctaaatctat    180
taggagatta actaaaacca tggtaagatc aagtaacgac gtaacccagc aaggtagtag    240
acctaaaaca aagttgggag gctcaagtat gggtatcatt cgcacttgta ggttagggcc    300
cgatcaagtg aaatctatgc gagctgcttt agatcttttt ggtagagaat ttggtgatgt    360
tgcaacttat agtcaacatc aaccagattc cgactatttg ggaaatcttt tacgttctaa    420
aacattcatt gcattagcag catttgatca ggaagctgtt gtcggtgcat tagccgctta    480
tgttttaccc aagtttgaac aacctcgttc tgagatctat atctacgatt tagcggtatc    540
tggcgagcat cgtcgccaag ggatagcaac agcgttaatc aatttgttaa agcatgaagc    600
taatgctctt ggtgcctatg tgatttacgt tcaagcggac tatggagatg atcctgccgt    660
agccttgtat accaaacttg gaattagaga agaagttatg cactttgata ttgatccttc    720
tactgctact taacaattcg ttcaagccga gtcacactgg ctcaccttcg gtgggccttt    780
ctgcgtttat atactagaga gagaatataa aaagccagat tattaatccg gctttttat     840
tatttgaagt tcctattctc tagaaagtat aggaacttca tttaaattac gtacacggcg    900
gccgctgcct accttcaccg acaaatttat atcgaactca actaaatcaa acattcaggc    960
tgaacaacag aggtttattt gacccaaacc tgagctttgg ataagctgaa agtattattt   1020
tctcctagtc agaaaacctt atagcttctt agaaataacg ataaaattgc cttaatccga   1080
actgacgtta aatatattca acccctactt ccccctctca ccctctcccc tcatctcctc   1140
atcaccctaa cacctacaac ctgacacctg acatctaacc ttatcggata ttcttaaacc   1200
gaactgaggt tgacccaaag acctgtaaat gataaatatag cctagacata aaaccttgat  1260
cgccccttgg aatatagata attatgggaa aaatttggga gttagacttt tattctcgtc   1320
caattattga tgaaaataac aaaaaacgtt gggaaatcct catctgtgaa agtcctacca   1380
ctatagacac cgatacaagc caattatttc gctattctca attttgcgcc aatacagaag   1440
ttaactccat tactcttcaa aatgcgatcg caactgccat agaaaaagca ggagaaactc   1500
ccagtaaaat ccgcttcttt cgtcgtcaaa tgaataacat gattcttaaa ggatgtgaag   1560
atgcggggat tccagccctt gcatcccgtc atacttatac tctcaatcaa tggttagaag   1620
agagaatgac atcattttat cccctccaag aaggctatga cgaaaaaacc accattgccg   1680
cttctgttca atatcctcaa accaacccag taaatcttcc tgatgcttta aaaggagata   1740
aaaaagacaa atgggcatta gttagtttaa atgggaaaga tttagaagaa atgcccgaat   1800
gggatatagg ttttagagag gcgtttcccc taaaaatagc caatatatct ccagacacca   1860
aaattccggg gctaattatc ttttcctccc gtgctttacc tcttgcagga tggatgtctg   1920
gactggaatt aggttactta agattagata gaggaaagtt cccctgtatt tgcttagaaa   1980
caggggtgag cgatagttgg atattagtta acttgacgga caaaaacacc ttatctgagg   2040
cagaaggctt tgaaaatacg aaaaaacagg ctaatggagt tcattttta gccattcaat    2100
cttctcctga atctcagtcc tttgaggctt tttggctact tttagaacag tcaagtaaca   2160
ataattagca aggggcaaag gcaattagta attaaggtaa ggcaatgggc aatagtgaat   2220
```

-continued

```
aattaaaaat taaaaattaa gaactaaaaa ctcctaactc tcatcctcat tacttattac   2280
ccattactcc cctaaacttg caacctgcca cctgaaacct gaaacctgaa acctctctat   2340
aattattatc acacttattc tactcaccat gaccgataaa attataaaaa ttgcagtaat   2400
aggggatgtt cacgatcttt ggaatgagtt tgatcatgag gcgttggaat tttgcaagt    2460
ggacttagtc ttatttgtgg gagattttgg caatgagtca attcccttaa ttagtcgaat   2520
tgctcaatta aatataccta aagcaataat attaggtaat catgatgctt ggtttagtgc   2580
cacggaatgg gggagaaaaa aatgtcctta cgatcgcacc ttggaagaca gagtacaaca   2640
acagttagac atactaggaa aatctcatgt tggttatagc tatcttgact ttcccgaatt   2700
agatatttct gtggtgggta gtcgcccttt tagttggggg ggttcaaaat ggaaatgtga   2760
agaattttat cgagaaaaat atgcgatcga aaatttccat cagtcttcag acaaaatcat   2820
cgcctctgta aataaagctc aagcccaaca gataattttt gttggtcata atggaccttt   2880
tggtttaggt gcaaatccag aagatacttg cggtagagat tggaaacctt tgggggggaga   2940
ctttggcgat cctgatttc  aagaagcgat aaaatacact caagaattag gcaaaaatgt   3000
accattagtc acctttggtc atatgcacca tagcttaaga catactaaag atagattaag   3060
aaccattatt aaccaagatg aacataaaac aatttatttg aacgccgcct ccactcctcg   3120
tattcaagaa attgagggac aaaaaatcca taaattttcc cttgttaccc tagatgcccg   3180
aatcgttacc aagattgatt taatcggtat cagtgaaaag atgaaaataa aagaagcaat   3240
taacctctat ggtaaatgaa ttttaagaat agaaaggtca tcattaaaat tactagaatg   3300
gttgactttt tctatctgct taattaaatg ttgcaattcg cctttatatt ttgcttgggt   3360
atccactaat aaactaataa agttttctaa cccccaaata ttctcgtttt cttgctcaat   3420
ttcgtaaata ccatcactga aaatatataa ataactatcg ggtttaacca gacataaact   3480
ctgatcaaat tctacatcct caatcatgcc cactggtaaa ctaggagtct ttaatttctc   3540
atatctccac tgattgtctt cttgataaat caatatagct ggaggatgcc ccgccgaaga   3600
atatattagc tcatgggtat cggtattata caccccatac catatagtaa agtaattgag   3660
gcgatcgcta tccatttgaa aaagacgatt taattctgtg ataattgtcc aaggttgata   3720
aggatttgtg ttgtatagtg aattattacg aaccaaatta agaatagaca cagataacaa   3780
agctgaatga ataccatgac ctgcaacatc tagtaaataa atagcgatat tctcctcatc   3840
caaccaataa taatcaaaaa tatctcctcc caattttgaa gatggaataa atttttgttc   3900
tacggataaa ttatgttcct ctggggaagg taacaagata tcaatctaga atgacggtga   3960
aaacctctga cacatgcagc tcccggagac ggtcacagct tgtctgtaag cggatgccgg   4020
gagcagacaa gcccgtcagg gcgcgtcagc gggtgttggc gggtgtcggg gcgcagccat   4080
gacccagtca cgtagcgata gcggagtgta tactggctta actatgcggc atcagagcag   4140
attgtactga gagtgcacca tatgcggtgt gaaataccgc acagatgcgt aaggagaaaa   4200
taccgcatca ggcgctcttc cgcttcctcg ctcactgact cgctgcgctc ggtcgttcgg   4260
ctgcggcgag cggtatcagc tcactcaaag gcggtaatac ggttatccac agaatcaggg   4320
gataacgcag gaaagaacat gtgagcaaaa ggccagcaaa aggccaggaa ccgtaaaaag   4380
gccgcgttgc tggcgttttt ccataggctc cgcccccctg acgagcatca caaaaatcga   4440
cgctcaagtc agaggtggcg aaacccgaca ggactataaa gataccaggc gtttccccct   4500
ggaagctccc tcgtgcgctc tcctgttccg accctgccgc ttaccggata cctgtccgcc   4560
```

-continued

```
tttctccctt cgggaagcgt ggcgctttct catagctcac gctgtaggta tctcagttcg   4620

gtgtaggtcg ttcgctccaa gctgggctgt gtgcacgaac cccccgttca gcccgaccgc   4680

tgcgccttat ccggtaacta tcgtcttgag tccaacccgg taagacacga cttatcgcca   4740

ctggcagcag ccactggtaa caggattagc agagcgaggt atgtaggcgg tgctacagag   4800

ttcttgaagt ggtggcctaa ctacggctac actagaagga cagtatttgg tatctgcgct   4860

ctgctgaagc cagttacctt cggaaaaaga gttggtagct cttgatccgg caaacaaacc   4920

accgctggta gcggtggttt ttttgtttgc aagcagcaga ttacgcgcag aaaaaaagga   4980

tctcaagaag atcctttgat cttttctaat gcattttcag acaaaaataa attcgatgat   5040

caaataaaaa aagtccttgt ttaataagat ttataataat ttaagatcca ttccttgtaa   5100

ttgaatatta atagtaaact ctaatgccag tatttgaaac ggacaccgaa gaaaaatcag   5160

agccagtatc agccaattca tcccttgcta atccttctcc cacccatcat aaagccaata   5220

acggaataat gagtgtttta aggaatatta gttttcttat tctctggcta ggacaaattt   5280

tttctcaatt ggcggataag atttatttag ttttaatgat cgccttaatt agtgctaact   5340

ttcagactca aggagaaagt atcagttcat gggtatcatt aattatgata gcttttacta   5400

tacctgcaat tttatttggt tctttggctg gagtttatgt tgatcgatgg tcgaaaaaaa   5460

gtgttttagt tgtctctaat ctcggtagag gtatattggt tttaatcttg cctttttgct   5520

tgttaattaa taaacaagaa atgggctttt tctctttacc ttggtcattt tggttacttt   5580

tattagttac tttctccgtc tccacattaa ctcaattttt tgccccagcc gaacaagcaa   5640

caattccttt aatcgtcaga aaaaaagact tattggcagc aaattctcta tataccacaa   5700

caatgatggc tatgttaatc attggttttg cagttggtga gcctttattg gaaataacct   5760

ataactgggg tgagaatttt tcttttgctt atggaaaaga gttgctagta ggaggatgtt   5820

atcttttggc gggaattgta ttgatgacaa tgcgcagtcg ggaaaaggat aaggatagac   5880

aacaacaaga aaatcatcct tgggaagata taaaagatgg tttacgatac ttgcaaaaaa   5940

atcatcgagt gcgcaatgct ttatttcaat tagttatttt attttctatt tttgcggctt   6000

tggcagtgtt agcggtgcgt ttagcggaaa ctatacccgg aatggaggct gatcaatttg   6060

gctatttatt ggccgcaacg ggcattggca ttgctattgg tgcagtattt gttactcatc   6120

agggtaaaat gattcctcat gctcgactta gtttttgggg ttcaatgggt atgggagcgg   6180

cattgagtgg cttgtctgtg gctactaaca atttgatttt ggctttacta atgacggtta   6240

ttttgggtat ttttgcggct ttggtgggtg taccgatgca aacgactatt caagcagaaa   6300

ccccttctga tatgcgtggt aaggtttttg gtttgcaaaa taatgcggtt aatattgctt   6360

tgtctttacc tttagcttta gccggaattg cggaaactta ttttggctta aggattgttt   6420

tgatgattct tgcctcttta gctgtttcgg gtatggcttt aacttcttta attactggta   6480

aatcggggaa ctaattgggt atggattgct tcatactaag taatagatat ttttattttt   6540

attgttactc aactatgtta tttcatcaaa gtaataggaa atttatgaaa gtcggctctc   6600

aattttttt agtttgtggt ttggctgttt ttggtgttag tttggggatt gttcctgagt   6660

acaatcaggg ttcaatttct attgaatcta aagctatggc gcaaaatgtt tctgatgaag   6720

atttaaaaaa atatgcccaa gctgcgatcg aaattgagaa tttacgcaaa actacttata   6780

gtaatataga aggaattgtt ggtaaatcta tggggcaaat gagttgtaac cagcgacaaa   6840

gtttcagtca acttcctgat aatgcccgta acatggcgat cgaatattgt gatcagtcag   6900

aaactattgt caaaaatcat ggcttaagtg ttaatcgttt taatcaaata actcagcaag   6960
```

tcaaacaaaa tcccagttta aaacaacgtt tgcaatctat tattggacaa atgtagttta 7020
gaagttatta attattcact ccaacactat ttacccttgc cccttgccct ttcttgattg 7080
ctaaaaatta taaacatctt caataaccct tacccacccc tgtgctaaag aagctaaaat 7140
gcgatcgcct ttttcctttg tagcggaggt tgcatccccc atcacaccac tatcgcttaa 7200
ctcttttgtt aaccaagcaa agggtaattt tccctccatt gacaataaac tgttgggtgc 7260
aagattacga gggtattctt tgaccgctaa atccattttt acttgttggg gcagtaaagc 7320
taacattaaa ctggtttcag catccccagc gtgaattccc cattcttgct cttcttccgt 7380
tagcagttcg tttgtgatgt ttggaactct ccaagtaaaa aaaggaaaaa catctaaatc 7440
gggaaatttt tgatgtaaat cacgggcaac tatttccata acttggggtt gtccgccgtg 7500
ggagttcatt aagattattt ttctaaatcc agctttgtaa atgctttctg ccatttctag 7560
gattaaagtg tatagagttt gagaactaat cgtaatagtt ccagcaaatc catcgtgttc 7620
attagattta ccataataaa gagtaggtaa agcaaaagca ggaattttgt cggatagtaa 7680
cgccaacgct ttccccaaaa ctccctcact aattgccgaa tctactacta aaggtaaatg 7740
ataaccgtgt tgctcgatcg cacctatggg ttgaataatt actgtgtttt ccttattgga 7800
cattttctca atttcttgcc atgttaaata ggcaaaaaaa cgatgaggag gtataaaacc 7860
atgaatcatt ttcaaaaaaa atattttatt tttcagcttt gttaccaata taacactaca 7920
taatcacttt tttcgagata gaataaagac ctaaataagg atcattaaag ggattaattt 7980
cgggataaaa aaagtggcat tatcaaatca actcgtcgac gaagttccta ttctctagaa 8040
agtataggaa cttccaaaaa acccctcaag acccgtttag aggccccaag gggttatgct 8100
agttaacatt gaccagcacc ctgactaggt ttacaaacgt aaaaagtttc tttaattcca 8160
gtttttgctt cgtattgttc tgcaacggct tgttgtactg cgggaactaa ctcttcagga 8220
attaaagcaa caatacaacc accaaaacct ccaccagtca ttctaacacc acctttgtca 8280
ccgattacag ctttaacgat ttctactaag gtgtcaattt gaggaacggt aatttcaaaa 8340
tcatctctca tagaagcgtg agattcggcc attaattctc ccattctttt taagtctcct 8400
tgttctaatg cacttgcggc ttctacagtt ctggcgtttt cggttaaaat atgtctaaca 8460
cgtttagcaa cgataggatc taattcatgg gcaacggcat taaattcttc aatggtaaca 8520
tctcttaaag caggttgttg gaaaaaacgg gcaccagttt cacattgttc acgacgagtg 8580
ttgtattcac ttcctactaa agtacgttta aaattagagt tgatgataac tactgcaaca 8640
cctttaggca tagaaacggc tttagtacct aaagaacgac aatcgattaa taaagcatgg 8700 tctttttac ctaaagcaga gattaattga tccataatac cacaattaca accaacgaat 8760
tgattctcgg cctcttgacc atttaatgcg atttgggcac catctaaagg taaatgatat 8820
aactgttgta aaacggttcc aacagctacc tctaaagaag cactagaact taaacctgct 8880
ccttggggaa cgttaccact gattaccatg tctacaccac caaaagaatt gtttcttaat 8940
tgtaagtgtt taacaacacc acgtacataa tttgcccact gatagttttc gtgagctaca 9000
atgggggcat ctaaagaaaa ttcatctaat tggttttcat aatcggctgc cataacacga 9060
actttacggt cgtctctagg agcacaagaa attacagttt gatagtcgat agcacagggt 9120
aatacgaaac catcattata atcagtatgc tcaccaatta aattaacacg accaggagct 9180
tgaatggtat gggtggcagg gtatccaaaa gcattagcga ataaactttg ggttttctct 9240
tttaaaggca tgctaaactt tttcctcatt tttacctaat cttccatacc atggtgacag 9300

-continued

```
gagaatatga aatgaggatg aaatgatgct ttaattattc atctgcttac ttttccttac   9360

gaaccattgt tgtaattctt cctcggtaat tctgccacta gctaaggttt ggatgatatg   9420

tactacttcc acttcagaag cagtaaagtg agaaccattg agcattaaaa aggttactcc   9480

actaataaaa cctgttcttt tattaccatc aataaaggga tgatttttaa ctatgctgaa   9540

ggtataagta gaagctaagg atgagatatt cctgcagtga gaaaaagtgt aaacaaatat   9600

taagaaaaag atcagaaaaa tttaacaaca cgtaataaaa aaatgcgtca ctacgggtta   9660

taaatttaca tgaaaggtta aaacactttt ctgagacgat tttgata                 9707
```

```
<210> SEQ ID NO 11
<211> LENGTH: 1011
<212> TYPE: DNA
<213> ORGANISM: Ralstonia sp. strain 4506

<400> SEQUENCE: 11

atgaagccca aagtcgtcct cacccactgg gtgcacccgg aaatcatcga attgttgtcc     60

gctagcgccg atgttatccc caacaccaca cgggaaacct tgccgcgttc tgaggtaatt    120

gcgcgagcca aagatgcgga tgcactcatg gctttcatgc cggacagcat cgacagcgcg    180

tttctcgagg aatgtccaaa gctgcgtgtc atcggcgccg cgcttaaagg ctatgataac    240

ttcgatgtca acgcctgcac acgccacggt gtatggctta cgattgtgcc ggatttgctt    300

acgatcccga ccgctgaact gactatcggc cttcttctcg gtttgacaag gcatatgctg    360

gaaggcgata ggcaaatccg tagcggacac ttccaaggct ggcggccgac actatatggc    420

tctggtttga caggaaaaac gcttggcatc attggtatgg gggcggtcgg ccgtgcaatc    480

gcccagcgct tggctggctt tgaaatgaat ctcttgtatt gcgatccgat tccgctcaat    540

gccgaacaag aaaaggcttg gcacgtacag cgcgtcacgc tcgatgaact gctcgaaaaa    600

tgtgattatg tcgtgccgat ggttccgatg gccgcagaga cactgcatct gatcgatgcc    660

accgcgttgg ccaagatgaa aaccggtagc tacctgatca atgcatgtcg cggctcggtc    720

gtggatgaga atgcggtgat agcagcactg gcgtctggaa aactagctgg atatgcagcc    780

gatgtcttcg agatggaaga atggatacgc gctgatcgcc cgcaggctat ccccaaggcg    840

ctgctcgaca atacggcaca aacgtttttt acgccgcatt tgggatcggc ggtcaaggaa    900

gttcggcttg aaatcgagcg gcaggcagcg atgaacatca tccaggcact cgctggtgaa    960

aaaccgatgg gcgcgattaa tcagccgtat ccgggagtaa aggcggcgtg a            1011
```

```
<210> SEQ ID NO 12
<211> LENGTH: 340
<212> TYPE: PRT
<213> ORGANISM: Ralstonia sp. strain 4506

<400> SEQUENCE: 12

Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
            20                  25                  30

Thr Leu Pro Arg Ser Glu Val Ile Ala Arg Ala Lys Asp Ala Asp Ala
        35                  40                  45

Leu Met Ala Phe Met Pro Asp Ser Ile Asp Ser Ala Phe Leu Glu Glu
    50                  55                  60

Cys Pro Lys Leu Arg Val Ile Gly Ala Ala Leu Lys Gly Tyr Asp Asn
65                  70                  75                  80
```

```
Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
    210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu
    290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

Gly Ser Tyr Val
            340
```

<210> SEQ ID NO 13
<211> LENGTH: 1041
<212> TYPE: DNA
<213> ORGANISM: Ralstonia sp. strain 4506

<400> SEQUENCE: 13

```
atgaaaccta aagtagtatt aactcattgg gtacaccccg aaataataga attattaagt      60

gctagtgcag atgtgattcc caatacaaca agagaaactt tacctcgtag tgaagtaatt     120

gccagagcca aagatgctga tgctttaatg gcctttatgc ctgattctat tgattctgca     180

tttttagagg aatgtcctaa attaagagtg atcggtgccg ctttaaaagg ttatgataat     240

tttgatgtaa acgcctgtac aagacacggt gtttggttaa ccatcgtacc tgatttatta     300

actattccta ccgccgaatt aacaattgga ttattattag gtttaactag acacatgtta     360

gaaggtgatc gtcagatacg ttctggacat tttcaaggat ggagacctac tttatatggt     420

tctggattaa ccggtaaaac tttaggaatt ataggtatgg gtgctgtagg acgtgctatt     480

gctcaaagat tagcaggatt tgaaatgaat ttattatatt gtgatcctat acctttaaat     540

gcagaacaag aaaaagcatg gcatgtacaa agagttactt tagacgaatt attagagaaa     600
```

| | | |
|---|---|---|
| tgtgattacg ttgttcctat ggtgcccatg gcagcagaga cattacattt aattgatgcc | 660 | |
| accgccttag caaaaatgaa aacaggatct tatttaatca atgcttgtag aggttctgtt | 720 | |
| gtggacgaga atgccgttat agctgcttta gctagtggta aattagcagg atatgctgcc | 780 | |
| gacgtatttg agatggaaga gtggataaga gcagacagac ctcaagctat tcccaaagcc | 840 | |
| ttattagata acaccgcaca aacctttttt acacctcatt taggtagtgc tgtaaaagaa | 900 | |
| gtacgtttag aaattgaaag acaagctgca atgaatatta tacaggcttt agcaggtgaa | 960 | |
| aaacctatgg gtgcaattaa tcaaccctat cctggtgtaa aagctgctgg atcctacgta | 1020 | |
| caccatcatc accatcacta g | 1041 | |

<210> SEQ ID NO 14
<211> LENGTH: 346
<212> TYPE: PRT
<213> ORGANISM: Ralstonia sp. strain 4506

<400> SEQUENCE: 14

Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
            20                  25                  30

Thr Leu Pro Arg Ser Glu Val Ile Ala Arg Ala Lys Asp Ala Asp Ala
        35                  40                  45

Leu Met Ala Phe Met Pro Asp Ser Ile Asp Ser Ala Phe Leu Glu Glu
    50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
    210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu 290 295 300

Ile Glu Arg Gln Ala Ala Met Asn Ile Ile Gln Ala Leu Ala Gly Glu
305 310 315 320

Lys Pro Met Gly Ala Ile Asn Gln Pro Tyr Pro Gly Val Lys Ala Ala
325 330 335

Gly Ser Tyr Val His His His His His His
340 345

<210> SEQ ID NO 15
<211> LENGTH: 999
<212> TYPE: DNA
<213> ORGANISM: Cyanothece sp. ATCC51142

<400> SEQUENCE: 15
atgaatcaaa aacctaaagt tgtgattacc cattgggttc atccagaaat cattgactat 60
ttaactccac attgtgagct tattcttaat caaacaaaag aaaccttaac ccgtgaagaa 120
gttattaata gaagcaaaga tgctcaaggt ttaatggttt ttatgccaga ttatattgat 180
gtaaattttt tagaagcctg tcctcaatta aaagtaattt caggagcctt aagaggctat 240
gataattttg atgtagaagc ttgcacaaag cgaaatattt ggtttactat tgttcctgat 300
ttattagctg cacctacagc agaattaacc ataggattac tactaatatt agcccgtaga 360
atggtagaag gcgatcgcct aattcgttcg ggtaattttc agggttggaa acctcaatta 420
tacagtacag gattattaaa taagaccctc ggaattattg gtatgggcaa gttaggaaaa 480
gccttgacaa aacggttaat gggctttgat atgaccctgt tatatcatga taaaattact 540
ctaacaagcc aacaagaaag agattggaaa attaccaaaa cctctctaga agaattatta 600
acaaaaagtg attatgttgt gttaatggtt cccttagttc ctgataccta tcatttaatt 660
aatgagaata gtttaaaaat gatgaaacct aatagttttt taattaatcc ttgtcggggt 720
tccatagtag atgaaaccgc cgtagctact gccattaaat caggacattt agccgggtat 780
gctgctgatg tttttgaaat ggaagattgg gcgatcgcca accgtcctca aagcattaat 840
caaaccttat taactgatat aaaccatact ttttttacac cccatttagg ctcagccgtt 900
aatgaggttc gtcgtgatat tgccctagaa gcagccaaaa atattatcga agttctctca 960
gaaaacagac cacaaggtgc tgtaaatggt atcgtatag 999

<210> SEQ ID NO 16
<211> LENGTH: 332
<212> TYPE: PRT
<213> ORGANISM: Cyanothece sp. ATCC51142

<400> SEQUENCE: 16

Met Asn Gln Lys Pro Lys Val Val Ile Thr His Trp Val His Pro Glu
1 5 10 15

Ile Ile Asp Tyr Leu Thr Pro His Cys Glu Leu Ile Leu Asn Gln Thr
20 25 30

Lys Glu Thr Leu Thr Arg Glu Glu Val Ile Asn Arg Ser Lys Asp Ala
35 40 45

Gln Gly Leu Met Val Phe Met Pro Asp Tyr Ile Asp Val Asn Phe Leu
50 55 60

Glu Ala Cys Pro Gln Leu Lys Val Ile Ser Gly Ala Leu Arg Gly Tyr
65 70 75 80

Asp Asn Phe Asp Val Glu Ala Cys Thr Lys Arg Asn Ile Trp Phe Thr
85 90 95

-continued

```
Ile Val Pro Asp Leu Leu Ala Ala Pro Thr Ala Glu Leu Thr Ile Gly
            100                 105                 110

Leu Leu Leu Ile Leu Ala Arg Arg Met Val Glu Gly Asp Arg Leu Ile
        115                 120                 125

Arg Ser Gly Asn Phe Gln Gly Trp Lys Pro Gln Leu Tyr Ser Thr Gly
    130                 135                 140

Leu Leu Asn Lys Thr Leu Gly Ile Ile Gly Met Gly Lys Leu Gly Lys
145                 150                 155                 160

Ala Leu Thr Lys Arg Leu Met Gly Phe Asp Met Thr Leu Leu Tyr His
                165                 170                 175

Asp Lys Ile Thr Leu Thr Ser Gln Gln Glu Arg Asp Trp Lys Ile Thr
            180                 185                 190

Lys Thr Ser Leu Glu Glu Leu Leu Thr Lys Ser Asp Tyr Val Val Leu
        195                 200                 205

Met Val Pro Leu Val Pro Asp Thr Tyr His Leu Ile Asn Glu Asn Ser
    210                 215                 220

Leu Lys Met Met Lys Pro Asn Ser Phe Leu Ile Asn Pro Cys Arg Gly
225                 230                 235                 240

Ser Ile Val Asp Glu Thr Ala Val Ala Thr Ala Ile Lys Ser Gly His
                245                 250                 255

Leu Ala Gly Tyr Ala Ala Asp Val Phe Glu Met Glu Asp Trp Ala Ile
            260                 265                 270

Ala Asn Arg Pro Gln Ser Ile Asn Gln Thr Leu Leu Thr Asp Ile Asn
        275                 280                 285

His Thr Phe Phe Thr Pro His Leu Gly Ser Ala Val Asn Glu Val Arg
    290                 295                 300

Arg Asp Ile Ala Leu Glu Ala Ala Lys Asn Ile Ile Glu Val Leu Ser
305                 310                 315                 320

Glu Asn Arg Pro Gln Gly Ala Val Asn Gly Ile Val
                325                 330
```

<210> SEQ ID NO 17
<211> LENGTH: 740
<212> TYPE: DNA
<213> ORGANISM: Cyanothece sp. ATCC51142

<400> SEQUENCE: 17

```
atgctttttc ttaataacct tagtgtcacc tataaagatg gaaccgtggc cttagaaaat     60

atttctcttg aattgattcc aggagaattt acggtacttt taggggcttc tggtgcagga    120

aaatcaaccc ttttacgttg tatcaatttt ctaacagttc ctactaaggg tgaagttatt    180

gtggaggggt taggaaccct aaataacccg aaaatcttaa gaaaacatcg ccaaaaaacg    240

ggcatgattt ttcaacaaca tcaattaatt cctcgacaaa ctgcccttaa aaatgtttta    300

gttggtcgtt tagcctatca ctctacctta agaagttttt tccctttgcc taaaattgat    360

caaatgattg ctttagattg tttggacaga gttggcctat taaataaagc tttaactcct    420

gttaaacaac taagtggagg acaacaacaa cgggtaggaa tagccagagc tttagctcaa    480

aaacccagat ttctcttagc agatgaacct gttgctagtt tagatcctgg tagttctcat    540

aagatattaa ctaatctcaa aaaaatttgt caagaagatg gtattggggc agtggttagt    600

ttacatcaaa tagatttcgc tttagactat ggcgatcgca ttattggcct tgcagatgga    660

aacatccttt ttgatagtca cccgtcagaa atacaatcat accagttaga aaaaatttat    720

cacaattctt ctttgattaa                                                 740
```

-continued

<210> SEQ ID NO 18
<211> LENGTH: 750
<212> TYPE: DNA
<213> ORGANISM: Cyanothece sp. ATCC51142

<400> SEQUENCE: 18

```
atgatttttt taaacaattt aagtgtaacc tataaagatg ggaccgtagc tttggaaaat      60

atttctttag aattgatccc cggagagttt accgttttat tgggagctag tggagctggt     120

aaatctacct tattgagatg tataaatttt ttaaccgttc ctaccaaagg ggaagttata     180

gttgagggtt taggaacttt gaataatcca aaaattcttc gtaagcacag acaaaaaaca     240

ggaatgattt ttcaacaaca tcaattaata cccagacaaa cagcacttaa aaatgtctta     300

gttggacgtt tagcttatca ttctacttta agatcttttt ttcctttacc aaaaattgat     360

cagatgatcg ctttagactg tttagataga gtgggtttat taaataaggc tttaacccct     420

gtgaaacaat taagtggggg tcaacaacag agagtaggta tagcgcgtgc attagctcag     480

aaacccagat ttcttttagc ggacgaacct gtggcatcat tagatcccgg cagttcccat     540

aaaatcttaa ctaatcttaa aaaaatttgt caagaagatg gaataggtgc tgtagttagt     600

ttgcatcaga ttgactttgc tttagattat ggcgaccgaa ttattggatt ggcagatggg     660

aacatccttt ttgatagtca tcccagtgaa atccaaagtt atcaattaga aaagatctat     720

cataattcca gtttaatcaa agctggatag                                      750
```

<210> SEQ ID NO 19
<211> LENGTH: 246
<212> TYPE: PRT
<213> ORGANISM: Cyanothece sp. ATCC51142

<400> SEQUENCE: 19

```
Met Leu Phe Leu Asn Asn Leu Ser Val Thr Tyr Lys Asp Gly Thr Val
1               5                   10                  15

Ala Leu Glu Asn Ile Ser Leu Glu Leu Ile Pro Gly Glu Phe Thr Val
            20                  25                  30

Leu Leu Gly Ala Ser Gly Ala Gly Lys Ser Thr Leu Leu Arg Cys Ile
        35                  40                  45

Asn Phe Leu Thr Val Pro Thr Lys Gly Glu Val Ile Val Glu Gly Leu
    50                  55                  60

Gly Thr Leu Asn Asn Pro Lys Ile Leu Arg Lys His Arg Gln Lys Thr
65                  70                  75                  80

Gly Met Ile Phe Gln Gln His Gln Leu Ile Pro Arg Gln Thr Ala Leu
                85                  90                  95

Lys Asn Val Leu Val Gly Arg Leu Ala Tyr His Ser Thr Leu Arg Ser
            100                 105                 110

Phe Phe Pro Leu Pro Lys Ile Asp Gln Met Ile Ala Leu Asp Cys Leu
        115                 120                 125

Asp Arg Val Gly Leu Leu Asn Lys Ala Leu Thr Pro Val Lys Gln Leu
    130                 135                 140

Ser Gly Gly Gln Gln Gln Arg Val Gly Ile Ala Arg Ala Leu Ala Gln
145                 150                 155                 160

Lys Pro Arg Phe Leu Leu Ala Asp Glu Pro Val Ala Ser Leu Asp Pro
                165                 170                 175

Gly Ser Ser His Lys Ile Leu Thr Asn Leu Lys Lys Ile Cys Gln Glu
            180                 185                 190

Asp Gly Ile Gly Ala Val Val Ser Leu His Gln Ile Asp Phe Ala Leu
```

```
        195                 200                 205

Asp Tyr Gly Asp Arg Ile Ile Gly Leu Ala Asp Gly Asn Ile Leu Phe
    210                 215                 220

Asp Ser His Pro Ser Glu Ile Gln Ser Tyr Gln Leu Glu Lys Ile Tyr
225                 230                 235                 240

His Asn Ser Ser Leu Ile
                245
```

```
<210> SEQ ID NO 20
<211> LENGTH: 921
<212> TYPE: DNA
<213> ORGANISM: Cyanothece sp. ATCC51142

<400> SEQUENCE: 20

atgatcagtt tcatctttaa aaaatcctta acccctgttg tttcttttac cctattaact      60

ctaattggtt gtagtacacc gaatagtcaa acatccaata ataaccctga aaatagcaaa     120

gcagacacaa aagctaaccc taaaaaatta gtagttgctt tgttacccga tgaatcagta     180

tctaccgtaa ttcaaaataa taaggggtta gaaagctact tagaagaccg actgaataaa     240

gatgttgaat tgtttgtcag taccgattat tcttctatga tcgaagcagc gagtaatgga     300

agattagact tagcctattt tggtcctttg tcgtatgttt tggccaaaac taaaagtaat     360

atcgaagcct ttgcagcgtt agaaaaagat ggagaagcca cctataaatc tgtcattatt     420

ggtaatgcag aagcaggaat tgattcctat gacaaaatcg aaggaaaaac tatggcttat     480

ggagatcaag cctcgacctc tagtcattta attcctaagt caatgttaat ggaaaaaggc     540

ttaaaagcag aagaaaatta tcaagaagta tttgtcggtt ctcatgatgc tgtagctgta     600

gctgttgcca atggaaaagc ccaagcaggg ggcttaagta aacccattta taccgcttta     660

attaataagg gaaccattga tgaaaataaa gtcattttaa tagaagaatc taaaccattt     720

ccccaatatc cttggacgat gcgatctgac ttagaacctc aattaaaaca gcaaattaag     780

caagcttttc tagaactaga agataaggca gttttagaac catttaaagc agaagggttt     840

caatcagtag aagacaagga ttataatgtt gtccgagact taggaaaaat cctcaatctt     900

gattttgcta aacttaatta a                                               921

<210> SEQ ID NO 21
<211> LENGTH: 921
<212> TYPE: DNA
<213> ORGANISM: Cyanothece sp. ATCC51142

<400> SEQUENCE: 21

atgatttctt ttatatttaa aaaatcatta acacctgttg tgtcttttac tttattaaca      60

cttatcggct gttctacccc caatagtcaa accagtaata acaatcctga gaactcaaaa     120

gcggacacca aagcaaaccc taaaaagtta gtagtcgctt tattaccaga tgaaagtgtt     180

agtacagtca ttcagaataa taaaggatta gaatcctatt tggaggatcg tttaaataaa     240

gacgttgaat tgtttgttag tacagattat tctagtatga ttgaagcagc ttccaatgga     300

cgattagatt tagcgtactt tgggccctta agttatgtgt tagcgaaaac taaatcaaac     360

atcgaagcat ttgctgcctt agaaaaagat ggcgaagcta cttataaatc tgtaattatt     420

gggaatgccg aagcgggcat tgacagttat gataaaattg aaggaaaaac tatggcttat     480

ggtgatcaag ctagtacctc ttctcatttg attcctaaat caatgcttat ggagaaagga     540

cttaaagcag aagaaaatta tcaagaagtt tttgttggga gtcatgatgc tgttgcggtc     600
```

-continued gccgtggcta atggaaaagc tcaagcaggt ggattaagta aacccatcta cactgcttta 660
atcaataagg gaacaataga tgaaaacaag gttattttga tcgaagaaag taagcctttt 720
cctcaatatc cttggaccat gagaagtgat cttgagccac agcttaaaca acagatcaaa 780
caagcatttt tagagttgga agacaaagct gtattagaac cttttaaagc agaaggattt 840
cagagtgtgg aagataaaga ttataatgtt gtccgcgatc ttggaaaaat tttaaactta 900
gattttgcga agttaaatta a 921

<210> SEQ ID NO 22
<211> LENGTH: 306
<212> TYPE: PRT
<213> ORGANISM: Cyanothece sp. ATCC51142

<400> SEQUENCE: 22

Met Ile Ser Phe Ile Phe Lys Lys Ser Leu Thr Pro Val Val Ser Phe
1 5 10 15

Thr Leu Leu Thr Leu Ile Gly Cys Ser Thr Pro Asn Ser Gln Thr Ser
20 25 30

Asn Asn Asn Pro Glu Asn Ser Lys Ala Asp Thr Lys Ala Asn Pro Lys
35 40 45

Lys Leu Val Val Ala Leu Leu Pro Asp Glu Ser Val Ser Thr Val Ile
50 55 60

Gln Asn Asn Lys Gly Leu Glu Ser Tyr Leu Glu Asp Arg Leu Asn Lys
65 70 75 80

Asp Val Glu Leu Phe Val Ser Thr Asp Tyr Ser Ser Met Ile Glu Ala
85 90 95

Ala Ser Asn Gly Arg Leu Asp Leu Ala Tyr Phe Gly Pro Leu Ser Tyr
100 105 110

Val Leu Ala Lys Thr Lys Ser Asn Ile Glu Ala Phe Ala Ala Leu Glu
115 120 125

Lys Asp Gly Glu Ala Thr Tyr Lys Ser Val Ile Ile Gly Asn Ala Glu
130 135 140

Ala Gly Ile Asp Ser Tyr Asp Lys Ile Glu Gly Lys Thr Met Ala Tyr
145 150 155 160

Gly Asp Gln Ala Ser Thr Ser Ser His Leu Ile Pro Lys Ser Met Leu
165 170 175

Met Glu Lys Gly Leu Lys Ala Glu Glu Asn Tyr Gln Glu Val Phe Val
180 185 190

Gly Ser His Asp Ala Val Ala Val Ala Val Ala Asn Gly Lys Ala Gln
195 200 205

Ala Gly Gly Leu Ser Lys Pro Ile Tyr Thr Ala Leu Ile Asn Lys Gly
210 215 220

Thr Ile Asp Glu Asn Lys Val Ile Leu Ile Glu Glu Ser Lys Pro Phe
225 230 235 240

Pro Gln Tyr Pro Trp Thr Met Arg Ser Asp Leu Glu Pro Gln Leu Lys
245 250 255

Gln Gln Ile Lys Gln Ala Phe Leu Glu Leu Glu Asp Lys Ala Val Leu
260 265 270

Glu Pro Phe Lys Ala Glu Gly Phe Gln Ser Val Glu Asp Lys Asp Tyr
275 280 285

Asn Val Val Arg Asp Leu Gly Lys Ile Leu Asn Leu Asp Phe Ala Lys
290 295 300

Leu Asn
305

<210> SEQ ID NO 23
<211> LENGTH: 807
<212> TYPE: DNA
<213> ORGANISM: Cyanothece sp. ATCC51142

<400> SEQUENCE: 23
atgacaatca atcaagataa atattctaat ctgttgcgcc aatacaagat tctttggtat 60
cgttcactaa taaacatcat tattttgcta ataataatta ttattagttt tgctgtagtt 120
ggtttattag atggaaaacg cttatctgaa ggaattcctg acctattaga aatggtagca 180
caaatgctgc ctcccgattt tactcgtgct tctgattgga ttaaaccact aattgatacc 240
ttaggaatga gtattgcagg aacaggaatg gctgttattt tttctctgcc tattactttc 300
ggggcagcac aaaataccag tccccatcct ttcgtttatt ttgtatcaag aattatttta 360
aatatagcaa gagctattcc tgaattactt ctaggaatta tctttgttgc cgctgttggg 420
tttggcgcac ttcctggggt attagcattg ggatttcatt ctattggtat ggtaggtaaa 480
ttttttgctg agtccataga acatacagac aacgcaccta ttgaagcagc aaaagcagtc 540
ggagcaaatc atttacaaat catttatcat agtattttac cccaagtttt accacaaatc 600
gccgatgtta cattttatcg ttgggagtac aattttagag cttctctagt attaggcgca 660
gtgggagccg gtggcattgg atttgaaatt attggggcat tacgtttact caaatatcag 720
gaagtttctg cccttttgtt agttgtttta gttatggtaa cattagtaga tagtttaggt 780
aactttttaa gaaaaaaatt catttaa 807

<210> SEQ ID NO 24
<211> LENGTH: 806
<212> TYPE: DNA
<213> ORGANISM: Cyanothece sp. ATCC51142

<400> SEQUENCE: 24
atgaccatta atcaggataa atatagtaat cttttaagac aatataaaat tttatggtat 60
cgttctttaa ttaatattat tattttattg attattatta ttatttcatt tgcagtagtt 120
ggtttgttag atggtaaacg cttatccgaa ggcattccag accttttaga aatggtcgca 180
caaatgttgc ctcctgactt taccagagcg tctgactgga tcaaaccttt aattgatact 240
ttgggcatgt ccatagctgg aactggcatg gccgtaattt tttcattgcc cataactttt 300
ggggccgcac aaaacacttc tcctcatcct tttgtctatt ttgtatcaag aatcatttta 360
aatattgcta gagcgattcc tgaattgctt ttagggatta tatttgttgc tgcagtaggt 420
tttggtgcat tacctggagt attagcctta ggttttcata gtattggaat ggtaggaaaa 480
ttctttgcgg agtctattga acatacagac aatgctccaa tagaagctgc taaagcggtc 540
ggtgctaacc accttcaaat tatatatcat tccatcttac cccaagtgct tccccaaatt 600
gcggatgtaa ctttttaccg ttgggaatat aattttagag cttctttagt attaggtgct 660
gttggcgcag gtggtattgg gtttgaaatt attggtgctt tgagattatt gaaatatcaa 720
gaagttagtg ccttattgct tgtcgtatta gtaatggtta ctttagttga ttcattaggc 780
aattttctta gaaaaaaatt tattta 806

<210> SEQ ID NO 25
<211> LENGTH: 268
<212> TYPE: PRT
<213> ORGANISM: Cyanothece sp. ATCC51142

<400> SEQUENCE: 25

Met Thr Ile Asn Gln Asp Lys Tyr Ser Asn Leu Leu Arg Gln Tyr Lys
1               5                   10                  15

Ile Leu Trp Tyr Arg Ser Leu Ile Asn Ile Ile Ile Leu Leu Ile Ile
            20                  25                  30

Ile Ile Ile Ser Phe Ala Val Val Gly Leu Leu Asp Gly Lys Arg Leu
        35                  40                  45

Ser Glu Gly Ile Pro Asp Leu Leu Glu Met Val Ala Gln Met Leu Pro
    50                  55                  60

Pro Asp Phe Thr Arg Ala Ser Asp Trp Ile Lys Pro Leu Ile Asp Thr
65                  70                  75                  80

Leu Gly Met Ser Ile Ala Gly Thr Gly Met Ala Val Ile Phe Ser Leu
                85                  90                  95

Pro Ile Thr Phe Gly Ala Ala Gln Asn Thr Ser Pro His Pro Phe Val
            100                 105                 110

Tyr Phe Val Ser Arg Ile Ile Leu Asn Ile Ala Arg Ala Ile Pro Glu
        115                 120                 125

Leu Leu Leu Gly Ile Ile Phe Val Ala Ala Val Gly Phe Gly Ala Leu
    130                 135                 140

Pro Gly Val Leu Ala Leu Gly Phe His Ser Ile Gly Met Val Gly Lys
145                 150                 155                 160

Phe Phe Ala Glu Ser Ile Glu His Thr Asp Asn Ala Pro Ile Glu Ala
                165                 170                 175

Ala Lys Ala Val Gly Ala Asn His Leu Gln Ile Ile Tyr His Ser Ile
            180                 185                 190

Leu Pro Gln Val Leu Pro Gln Ile Ala Asp Val Thr Phe Tyr Arg Trp
        195                 200                 205

Glu Tyr Asn Phe Arg Ala Ser Leu Val Leu Gly Ala Val Gly Ala Gly
    210                 215                 220

Gly Ile Gly Phe Glu Ile Ile Gly Ala Leu Arg Leu Leu Lys Tyr Gln
225                 230                 235                 240

Glu Val Ser Ala Leu Leu Leu Val Val Leu Val Met Val Thr Leu Val
                245                 250                 255

Asp Ser Leu Gly Asn Phe Leu Arg Lys Lys Phe Ile
            260                 265

<210> SEQ ID NO 26
<211> LENGTH: 1320
<212> TYPE: DNA
<213> ORGANISM: Desulfotignum sp.

<400> SEQUENCE: 26
atgaaagatg ctacagctaa agataaatat cctgaatttg aaggcctcgg ccttacagat 60
agtgaacagg taagttacga cagatttaga ttttggaagg ttgtgatctt ggtgtctatc 120
tggtatagtt tttattatct gggaagactc aactggggaa tgtgtatgcc ctggatgatt 180
aaagaccttg gaattactaa aacgcaggcc ggagtgggag caaccgtctt gttctggtcc 240
tacgcttttg gaacgctcat aagcgggaaa cttggggata catatggtgc cagagttatg 300
aataccattg gcggcatcgg cacagtaatt ttaaacatta ttgtagcaag tatggcaaga 360
ataaatataa tgctcattcc atgggggttt aacggattca tacagggcca agcatatgcg 420
cccacaaaca atatgataac ccagtggtat cctaaggcaa aaagaggttt ggccacgggt 480
atttttgcaa cctccatggg ggtagcatct ttatttgtgt ggttgattac cggcactgtg 540
gcagcccatt atgggtggag agccgccttt acttatccct tgctattttg cacgcttccg 600
ttgacgattt tgtttttat attagcccga tcaaaaccta aagatgcggg ttatcccgag 660
tacaaagaaa caatgacgaa cacgatttca agtaaggcgg aagaattgag ggatgaccaa 720
atatcgggtt tcaaagcttg gggcctttta tttggcaatt ggaaattcgt ctgccttgcg 780
gtagcttctt tcatgttgta tatgggaaga tacggtcttt taacctgggt gccgctttat 840
tatgcagaaa ccgctggcat taatttaaag aaaattccaa ttgccaccat agcgttgccg 900
ttaggaatgg cggttggtcc cataattgcc ggatggatct ctgatcgttt cttcaaggcg 960
aaacgatatc aaatcctcac aatctatatg ctagcgttca caacgattat gattatattg 1020
gcgagcgcgg gtctgaagac actaggtcta cctctttctt tcttcttgct cgccataggg 1080
ggattctttg tcctcgggtc ggtcggtctt gtttttacta cagcctgtga ttttggcgga 1140
aggcgaatgg caggcactgc tgtcggatcc gttaactttt ttaactatat gggagcaggc 1200
acgcagggtt tcgttattgg tatgattcta gatgcaacaa aaaattgggg tatcgtattt 1260
ggtcttcttt ccggatgtgc cattcttgga atcattctgg tcaacatcgt tagggaataa 1320

<210> SEQ ID NO 27
<211> LENGTH: 1320
<212> TYPE: DNA
<213> ORGANISM: Desulfotignum sp.

<400> SEQUENCE: 27
atgcatgatg ctactgctaa agacaaatac cctgagttcg aaggtttagg attaaccgat 60
agtgaacaag ttagttatga tagatttcgt ttttggaaag tggttatatt agtgtctatt 120
tggtattctt tttactactt aggaagatta aattggggta tgtgtatgcc ttggatgatt 180
aaagatttag gtattacaaa aacccaagca ggtgttggtg ctactgtttt attttggtct 240
tatgctttcg gaacattaat atctggaaaa ttaggtgaca cttatggagc cagagtaatg 300
aataccattg gtggtattgg aactgtaata ttaaacataa ttgtagcctc tatggctcgt 360
ataaatatta tgttaattcc ttggggattt aatggattta ttcaaggtca ggcttatgcc 420
cccactaata acatgattac acaatggtat cccaaagcaa aaagaggatt agcaactgga 480
atatttgcta cctctatggg agtggcaagt ttattcgttt ggttaatcac tggtactgtt 540
gctgctcatt atggttggcg tgctgctttt acatacccctt tattattttg tactttacct 600
ttaactatct tattttttat attagcaaga agtaaaccca aagatgccgg ttatcctgaa 660
tataaagaaa caatgaccaa taccattagt agtaaagccg aagaattacg tgatgatcaa 720
atatctggtt ttaaagcctg gggtttatta tttggtaatt ggaaatttgt ttgcttagcc 780
gttgcaagtt ttatgttata tatgggacgt tatggtttat taacctgggt tcctttatat 840
tatgctgaaa cagccggaat taatttaaaa aaaattccca tagctactat tgccttaccc 900
ttaggaatgg cagttggacc tataattgca ggttggatct ctgatagatt ttttaaagcc 960
aaaagatacc aaattttaac catatacatg ttagcattta ctaccattat gattatctta 1020
gcaagtgcag gtttaaaaac tttaggttta cctttatctt tctttttatt agcaatcggt 1080
ggattttttg tgttaggaag tgtgggttta gtttttacca ctgcatgtga ttttggtggt 1140
cgtagaatgg ccggaacagc agtgggaagt gtaaattttt ttaattatat gggagcagga 1200
acccaaggtt ttgttattgg tatgatatta gatgctacta aaaattgggg aattgtattt 1260
ggtttattat ctggttgtgc aatattagga atcatcttag taaatatagt aagagagtag 1320

<210> SEQ ID NO 28
<211> LENGTH: 439
<212> TYPE: PRT
<213> ORGANISM: Desulfotignum sp.

<400> SEQUENCE: 28

```
Met His Asp Ala Thr Ala Lys Asp Lys Tyr Pro Glu Phe Glu Gly Leu
1               5                   10                  15

Gly Leu Thr Asp Ser Glu Gln Val Ser Tyr Asp Arg Phe Arg Phe Trp
            20                  25                  30

Lys Val Val Ile Leu Val Ser Ile Trp Tyr Ser Phe Tyr Tyr Leu Gly
        35                  40                  45

Arg Leu Asn Trp Gly Met Cys Met Pro Trp Met Ile Lys Asp Leu Gly
    50                  55                  60

Ile Thr Lys Thr Gln Ala Gly Val Gly Ala Thr Val Leu Phe Trp Ser
65                  70                  75                  80

Tyr Ala Phe Gly Thr Leu Ile Ser Gly Lys Leu Gly Asp Thr Tyr Gly
                85                  90                  95

Ala Arg Val Met Asn Thr Ile Gly Gly Ile Gly Thr Val Ile Leu Asn
            100                 105                 110

Ile Ile Val Ala Ser Met Ala Arg Ile Asn Ile Met Leu Ile Pro Trp
        115                 120                 125

Gly Phe Asn Gly Phe Ile Gln Gly Gln Ala Tyr Ala Pro Thr Asn Asn
    130                 135                 140

Met Ile Thr Gln Trp Tyr Pro Lys Ala Lys Arg Gly Leu Ala Thr Gly
145                 150                 155                 160

Ile Phe Ala Thr Ser Met Gly Val Ala Ser Leu Phe Val Trp Leu Ile
                165                 170                 175

Thr Gly Thr Val Ala Ala His Tyr Gly Trp Arg Ala Ala Phe Thr Tyr
            180                 185                 190

Pro Leu Leu Phe Cys Thr Leu Pro Leu Thr Ile Leu Phe Phe Ile Leu
        195                 200                 205

Ala Arg Ser Lys Pro Lys Asp Ala Gly Tyr Pro Glu Tyr Lys Glu Thr
    210                 215                 220

Met Thr Asn Thr Ile Ser Ser Lys Ala Glu Glu Leu Arg Asp Asp Gln
225                 230                 235                 240

Ile Ser Gly Phe Lys Ala Trp Gly Leu Leu Phe Gly Asn Trp Lys Phe
                245                 250                 255

Val Cys Leu Ala Val Ala Ser Phe Met Leu Tyr Met Gly Arg Tyr Gly
            260                 265                 270

Leu Leu Thr Trp Val Pro Leu Tyr Tyr Ala Glu Thr Ala Gly Ile Asn
        275                 280                 285

Leu Lys Lys Ile Pro Ile Ala Thr Ile Ala Leu Pro Leu Gly Met Ala
    290                 295                 300

Val Gly Pro Ile Ile Ala Gly Trp Ile Ser Asp Arg Phe Phe Lys Ala
305                 310                 315                 320

Lys Arg Tyr Gln Ile Leu Thr Ile Tyr Met Leu Ala Phe Thr Thr Ile
                325                 330                 335

Met Ile Ile Leu Ala Ser Ala Gly Leu Lys Thr Leu Gly Leu Pro Leu
            340                 345                 350

Ser Phe Phe Leu Leu Ala Ile Gly Gly Phe Phe Val Leu Gly Ser Val
        355                 360                 365

Gly Leu Val Phe Thr Thr Ala Cys Asp Phe Gly Gly Arg Arg Met Ala
    370                 375                 380
```

-continued

```
Gly Thr Ala Val Gly Ser Val Asn Phe Phe Asn Tyr Met Gly Ala Gly
385                 390                 395                 400

Thr Gln Gly Phe Val Ile Gly Met Ile Leu Asp Ala Thr Lys Asn Trp
                405                 410                 415

Gly Ile Val Phe Gly Leu Leu Ser Gly Cys Ala Ile Leu Gly Ile Ile
            420                 425                 430

Leu Val Asn Ile Val Arg Glu
        435


<210> SEQ ID NO 29
<211> LENGTH: 645
<212> TYPE: DNA
<213> ORGANISM: Cyanobacterium sp. PTA-13311

<400> SEQUENCE: 29

atggtcgagg gtagcaggtt acaaagacat actagcgaag tggctcaaga cgttctaaga      60

atgggagctt tagtggaaga gtcttttcgt tatagccatc aagccttatt tgaaggagac     120

ttagaaacag ttgctttaat tacaaaccaa gatatagaaa ttgatcgcta ctatcgtcat     180

atagaaatga ggtgtgctac aatattaaca ttacaagccc cagtggctca agacttaaga     240

atattgagtg cttttatgca attagtcagg gatttggaaa gaatcggaga ctatgccaaa     300

gatttaggac aaatagctat aaaactcgcc ctctatccat cccattcctg tatgcctgaa     360

ttagccgcca tgtcaaaaca cgctcaagtc atgttagcta aagcaatggt tgcgttaagc     420

gagttagact ctcaggcagg agaaaaaatt aaactcctag atgataccgt agataatgcc     480

tatgacaagc tctatcacac ccttgcacaa caaagggaca tcaagggagt agtagaacct     540

attatcttat tagctttagc aattcgccat atagaaagaa tggctgatca tgctacaaat     600

atagcccaaa gagtatcgta tattgtcacg ggagaacgaa attaa                     645


<210> SEQ ID NO 30
<211> LENGTH: 214
<212> TYPE: PRT
<213> ORGANISM: Cyanobacterium sp. PTA-13311

<400> SEQUENCE: 30

Met Val Glu Gly Ser Arg Leu Gln Arg His Thr Ser Glu Val Ala Gln
1               5                   10                  15

Asp Val Leu Arg Met Gly Ala Leu Val Glu Glu Ser Phe Arg Tyr Ser
            20                  25                  30

His Gln Ala Leu Phe Glu Gly Asp Leu Glu Thr Val Ala Leu Ile Thr
        35                  40                  45

Asn Gln Asp Ile Glu Ile Asp Arg Tyr Tyr Arg His Ile Glu Met Arg
    50                  55                  60

Cys Ala Thr Ile Leu Thr Leu Gln Ala Pro Val Ala Gln Asp Leu Arg
65                  70                  75                  80

Ile Leu Ser Ala Phe Met Gln Leu Val Arg Asp Leu Glu Arg Ile Gly
                85                  90                  95

Asp Tyr Ala Lys Asp Leu Gly Gln Ile Ala Ile Lys Leu Ala Leu Tyr
            100                 105                 110

Pro Ser His Ser Cys Met Pro Glu Leu Ala Ala Met Ser Lys His Ala
        115                 120                 125

Gln Val Met Leu Ala Lys Ala Met Val Ala Leu Ser Glu Leu Asp Ser
    130                 135                 140

Gln Ala Gly Glu Lys Ile Lys Leu Leu Asp Asp Thr Val Asp Asn Ala
145                 150                 155                 160
```

```
Tyr Asp Lys Leu Tyr His Thr Leu Ala Gln Gln Arg Asp Ile Lys Gly
                165                 170                 175

Val Val Glu Pro Ile Ile Leu Leu Ala Leu Ala Ile Arg His Ile Glu
            180                 185                 190

Arg Met Ala Asp His Ala Thr Asn Ile Ala Gln Arg Val Ser Tyr Ile
        195                 200                 205

Val Thr Gly Glu Arg Asn
    210


<210> SEQ ID NO 31
<211> LENGTH: 278
<212> TYPE: DNA
<213> ORGANISM: Cyanobacterium sp. PTA-13311

<400> SEQUENCE: 31

aattaataac ttcttcctgt acgggcgaat ggccatttgc tcctaactaa ctccgtactg      60

ctttgcggaa cgagcgtagc gaactctccg aattactaag ccttcatccc tgatagatgc     120

aaaaaacgaa ttaaaattat gtgtaaaaag aaaatgtgtc tttatttagt agtcaaagtt     180

acaaaatatt aagaatcaaa ttaataatgt attgggcagt taagtatata agtctttaaa     240

tatttatttg tattcaatat attaaccgag gacaaatt                              278


<210> SEQ ID NO 32
<211> LENGTH: 246
<212> TYPE: DNA
<213> ORGANISM: Cyanobacterium sp. PTA-13311

<400> SEQUENCE: 32

ccaatatctt gtcatacata cttatttgcc tcactattag ccctatatgt ctctattgta      60

tttttctttt tctcctattc ctagatcttg taatgaatca ttactctctg aaatatagct     120

actaatttta tggttgtttg taaaatatat taacaaatga acaataaatc atattttgtg     180

ttaatctaat tattagacaa ctactgaatt tatattcaga tattcacaga taggagaatt     240

ttgatt                                                                 246


<210> SEQ ID NO 33
<211> LENGTH: 162
<212> TYPE: DNA
<213> ORGANISM: Cyanobacterium sp. PTA-13311

<400> SEQUENCE: 33

tattattttt cgtttatatg cagatttaga ataaacaaaa ttcatttact gcaaattttc      60

aaaaaaatgt gactaaacat acaaaataaa gaaaaaataa agttttaaat ttatgtacat     120

caaacttaag aaatgtttaa attacttaga aatttatagt tc                         162


<210> SEQ ID NO 34
<211> LENGTH: 433
<212> TYPE: DNA
<213> ORGANISM: Cyanobacterium sp. PTA-13311

<400> SEQUENCE: 34

tttatatata aactcgaata aaattatcaa tataaagtca aactatatct atcctatttt      60

aactgctatt ggtaagtccc ttaattagtg ttggggtgaa tagattttaa aagggcaaac     120

ccccctttat cctccctcga gaggggggag ggcaaaaggc aaggggcaag ggaaaaatta     180

agaattaaga attaaaaact ccgaacacct gtaggggcga atagccattc gcttcccctc     240
```

-continued

```
atccccccat ctccccaaca ccctaagccc ctactcgtta ctcatttatt tacatcattt    300

atttacatca ttaagaaaag taacaaattt tgacaagtag tcttttgaca ggaaaaagca    360

aattctcgaa gatgaaaaca atagaaaaaa attcaatctt acagtaacga tgaaaaaact    420

tttaggctta att                                                       433
```

<210> SEQ ID NO 35
<211> LENGTH: 299
<212> TYPE: DNA
<213> ORGANISM: Cyanobacterium sp. PTA-13311

<400> SEQUENCE: 35

```
tgtctcaaaa agacaggttt tttttatgaa agtaataaga aataagtaga agtgaggagt     60

tggaaagata ggattaagaa ttaggagtta actattttca ttctttattc ttccattgcc    120

cattgagaaa tcatatctaa aatcagcaac gccaaatttt agatgcaaaa taaccataaa    180

taaaatgcag aaaaaagaat actttagatc ttccgtatca gaagatacat ttcttaacaa    240

aatctggtga caagattaaa cacacgaaat ccgaggtttt atatattgat tagtcctag     299
```

<210> SEQ ID NO 36
<211> LENGTH: 536
<212> TYPE: DNA
<213> ORGANISM: Cyanobacterium sp. PTA-13311

<400> SEQUENCE: 36

```
attctgtgaa ttgattagat ttgaggtttt ttaagaggtt gattaccttg cctccaaaaa     60

aatcataaca cactaatgct ctatatgaaa gggctttaga cccataggtt tttgagaaaa    120

aaacttgcta actctcggac aatgtcagca taactaaagt caattctttt cgtactttat    180

aattgtctat aatttaatat acaactgttc tgaaactagt tttctctac attccttagt     240

tttatctgag taaggttgct tgtaacttaa cttcggttgg gcctaaaaat atccgattag    300

gagcaggtgt cagactttaa ttaattatta attattaatt gcttattgcc aaccctcggc    360

gacaccactt tttcatcagc cccagataaa gattgatgtt ttagttttgt ttctttttat    420

cccctaattc aactaataca agtaaaacta aggttgttta tcaaaaatga tggttgatgt    480

ttgggtaaat tttaagatat tatgaaaaga aaatgaataa aaaatgaaaa atcttt        536
```

<210> SEQ ID NO 37
<211> LENGTH: 320
<212> TYPE: DNA
<213> ORGANISM: Cyanobacterium sp. PTA-13311

<400> SEQUENCE: 37

```
gaatatctca tccttagctt ctacttatac cttcagcata gttaaaaatc atccctttat     60

tgatggtaat aaaagaacag gttttattag tggagtaacc tttttaatgc tcaatggttc    120

tcactttact gcttctgaag tggaagtagt acatatcatc caaaccttag ctagtggcag    180

aattaccgag gaagaattac aacaatggtt cgtaaggaaa agtaagcaga tgaataatta    240

aagcatcatt tcatcctcat ttcatattct cctgtcacca tggtatggaa gattaggtaa    300

aaatgaggaa aaagtttatt                                                320
```

<210> SEQ ID NO 38
<211> LENGTH: 309
<212> TYPE: DNA
<213> ORGANISM: Cyanobacterium sp. PTA-13311

<400> SEQUENCE: 38

```
atacatggtt ggttcactga cttttacccc agttttctct ttgaacaatt ggcataactc     60

tgaaaaaatc agatcgggct tttgttgaat tatttgttca atcaaagcaa aaccgtgatt    120

gtctattttc tttttttcc caccactcat agataaaaat ttatcccgaa ctcaggttat    180

attaagttcg gatgatcact taagataatt gatcagattg gttaagatag agaaaaattc    240

tttttcatag tgatttcata attgatagtt acaataacga ttattattta gtaaaaagat    300

tttcaaatc                                                            309


<210> SEQ ID NO 39
<211> LENGTH: 330
<212> TYPE: DNA
<213> ORGANISM: Cyanobacterium sp. PTA-13311

<400> SEQUENCE: 39

tggtcaagtt actatatgtt tagaaacaac aaaaaaagaa gtcattataa aaataattga     60

tacaggaatt ggcattaata aagaagaaca aaaattaatt tttaatcgtt tttatcgaat    120

caataaagca agaaatagag agaaaggcag ttgcggatta ggtttagcta ttgcaaatgc    180

gatcgcgctt aatcatggtg gtagaataat tttagaaagt caagaaaatc aaggcagtat    240

ttttaccgtt tatttaccga aaatcatttc atcctaattt catattcttt tgacagaatc    300

aaaggtaaag ataaaaagag agaaacagtc                                     330


<210> SEQ ID NO 40
<211> LENGTH: 359
<212> TYPE: DNA
<213> ORGANISM: Cyanobacterium sp. PTA-13311

<400> SEQUENCE: 40

cctcaactac aagttctttt atatattact ttaacctgag ttttggataa gctgaaagca     60

ttattttctc gtagtcagaa aaccttatag cttcttagaa ataacgataa aattacctta    120

atccgaactg acgttaaata tattcacccc tatcacccca aaaccctaag cccctacttc    180

ccccttccc ttcatcacct catcccccca tcccctaaca cttaacctta ttctttattc    240

ttaaaccgaa ctgaggtgaa gttgcagaat acccatgggg ggttacagca ttgtagaaaa    300

ataaatattc tttcattatt aaggttgttt ggtaaaaata tgtgaaaacc ctaataatt     359


<210> SEQ ID NO 41
<211> LENGTH: 239
<212> TYPE: DNA
<213> ORGANISM: Cyanobacterium sp. PTA-13311

<400> SEQUENCE: 41

ggggacagac atatttttat cataatggta aattcataat aattttagac ttttttttgc     60

aaaaattaat ctcactctct tctttcccta tctcccattg tttcttatat cccaatgccc    120

caatacccaa agctcagaaa ataggtatta gcgaagaggt gttgatcccc tcccctagca    180

aaatatactc ctatatagta aagtgagaaa gtgaagaaat aagatcaagt tcgcaattt     239


<210> SEQ ID NO 42
<211> LENGTH: 290
<212> TYPE: DNA
<213> ORGANISM: Cyanobacterium sp. PTA-13311

<400> SEQUENCE: 42

ttgacgattg tattgactta cgccaaatgg cttaccctca tagtgaatag ttgataatta     60
```

-continued agaattaaaa atcccgttca cgacagaagg gagtgtaaga gccttcggtg cgaactctca 120
tcttccctga aacctgacac ctgaaacctg acacctgaaa cctgacacct catctcccta 180
atcccctaat tttaatgaaa aaataccctg agtgggcatt gaaaaaaaag aaaagttgtt 240
cgactatgaa ataagaattc tgcacttcgt gagaaaaaag gaaatgaaat 290

<210> SEQ ID NO 43
<211> LENGTH: 355
<212> TYPE: DNA
<213> ORGANISM: Cyanobacterium sp. PTA-13311

<400> SEQUENCE: 43
ctatttaact aggaaaaggt aaagttaaaa ggacaagggt aaataattaa aaattaagaa 60
ttaagaactt ctaactctca ttactcatta cttatttcct cctctcaccc cttctcctga 120
tcacctcttc tcctcaatac tcggaactca tttccccatg gtgtgacact caaatcaaaa 180
gtctgttatt gactttcaga tgaaatatta ctatgataac aatatccccc ctatgggtat 240
ataaaaatat gagcgatatt agttaaaaat caaatttgga tttttttct gaaaatattt 300 taagattaag taaagataag taaagaaatt ataagcaatt ttgttaaatc atacc 355

<210> SEQ ID NO 44
<211> LENGTH: 619
<212> TYPE: DNA
<213> ORGANISM: Cyanobacterium sp. PTA-13311

<400> SEQUENCE: 44
ctcacactga aaatattgcc acaagaaata aagatcaagc aataatcctg actaaaaagg 60
aataaagtaa ttatcctttt cctgatatgt tatctgactt gttgtttctt agtcatgttc 120
cttccatttt tatttttgtt tttatcattt ttattacaaa aatttcttaa tagggctaaa 180
gcatttagtt agttttttag ctctcaacaa gttgactaat caatataatg ccctaagtta 240
atttgccctt ggtttgacgg aggatattgg aaaaaagaaa cttctcgttg tatttcacag 300
ggaaaagggg gaaattttat taataactaa acaatagaaa ataattattt atttatatta 360
ttttgtgaac aaatgttcaa gaattaaagt gtaataagaa aatttatttt tttatattta 420
tttaaaactt agatataagc ctaaaggtct gaaattatta ttagacaatc aattgattca 480
gaggtaatag ttttttactt aaaaatattt tttcaaaatt atcccctatt tgggtattga 540
aaaataaata aattcaagta ataatataca gaataaagga aaatctaatc ttaaaaattt 600
tgtgtgtgag gaattgaaa 619

<210> SEQ ID NO 45
<211> LENGTH: 496
<212> TYPE: DNA
<213> ORGANISM: Cyanobacterium sp. PTA-13311

<400> SEQUENCE: 45
caaatcacga gaatttatgt agggactatt ttgggttgac ggtggagagt atgtcgccct 60
tgaattatga cccgaagatg aagatgtcgg ggaggtggaa ggacggtctt taagaggttt 120
aacatcaaag ttggtcataa tctctgtccc tgtttgataa ctactattta attttgagtt 180
gttttaggta catcaaaata cccaaatcct tactctcccc tcaatataca acaaaaaaaa 240
ctttttgatt cactttagtc ataaaaatta gaatttatct accgaaatat tacataaatg 300
taatgtatat attttctgat ttattccgtg tgagccatga ttcataattt ataattcata 360
atttctaaat atgcccctac aatggatata gaatgtcatt ttaattatag gtatcataat 420

```
cgtggtagtt actccggaaa aaactattga atcaaattca gtctcacctg ctacagatag    480

agtagccgtt attctt                                                    496


<210> SEQ ID NO 46
<211> LENGTH: 283
<212> TYPE: DNA
<213> ORGANISM: Cyanobacterium sp. PTA-13311

<400> SEQUENCE: 46

ctacaggggc aagatttggc ggaaatctat atgtggattc tctttcaagt gaagaaggtg     60

cagtgccgac ttatctggac ttattagaat acgatattcg cactattact aatggtttgt    120

tagcaggagt gaacaattaa aaattttttc ctaattgacg aataaaaaat caatgtcaac    180

taatagttaa caatactctc tgaaaaccaa aaattgtcaa ccaaaacata acataatttt    240

tacccaaaaa cctcatttat aaactttaag gataaaatca atg                      283


<210> SEQ ID NO 47
<211> LENGTH: 299
<212> TYPE: DNA
<213> ORGANISM: Cyanobacterium sp. PTA-13311

<400> SEQUENCE: 47

gggattagag agttcaaagt taggaatgag gtgtcaggtt ttaggtttca ggtttagggg     60

agcaatgaga aagaggtttc aggtttcagg tgtcaggttg caggtgtcac aggtgatgag    120

gggatggggg atgaggggga aacaagtaag taataagtgt tcggagtttt taattcttaa    180

ttcttaattt ttcctttgcc tcttgccttt tgccttgtct taattactaa tttctaatta    240

aaatgattgt gttttctagt ttagtctcat ggttacttga acccttacag catagtttt     299


<210> SEQ ID NO 48
<211> LENGTH: 416
<212> TYPE: DNA
<213> ORGANISM: Cyanobacterium sp. PTA-13311

<400> SEQUENCE: 48

ttacaaacgg cgggaattat tatggtagta gcgatgttag taaccccggg tgcgatcgca     60

tatttactta cagatcgttt tgatcaaatg ttaatcttat caatagttag tagtgttcta    120

tcttgtgttt taggcactta tttaagttat cattttgatg tttctacggg gggaagtatt    180

gtcgttttaa tgaccataat ttttatttta gcgatgattt ttgctcctaa atatggcatc    240

atcaatcaaa ataccaaaat atattctgct taacttgttt actgatactt caaataatca    300

tataacctat cttccgagtt aaaaataatg gatattatcc aactgaggtc gagaatagag    360

tttctttttt gatagaattt ttttacacca gttattcatt actatcatgg gataat        416


<210> SEQ ID NO 49
<211> LENGTH: 412
<212> TYPE: DNA
<213> ORGANISM: Cyanobacterium sp. PTA-13311

<400> SEQUENCE: 49

taatatagtg attattataa atgcaatgtg aatcaaacct atattttacc gtacattgac     60

catggaactt aatttgaggt gattagtaga gggtgcgatc gccctatttg tcaaataata    120

aagataacat ttgacattgc tgattgaaga cataaaacac agaaaaaatc aggtaaaaat    180

ataaagctaa agtctaaata tggtttactt ttgccttcga cttacaacaa aaaatcatag    240
```

ctagaatcac caacgcctaa tattttattt agctgaaatt ttgggatgaa ctttttgtaa 300
aaatcggggg tctaaaaata tagcaaccac gatattaaat aactgagtga ttattttaat 360
ctattggggg cttattaact aaatacttgc atttttatgg agggttttaa tt 412

<210> SEQ ID NO 50
<211> LENGTH: 364
<212> TYPE: DNA
<213> ORGANISM: Cyanobacterium sp. PTA-13311

<400> SEQUENCE: 50
aaagattatt ttctacagaa gcaacccttt catcttccga attttcagga atttcctgct 60
tttgtttctg aatattagca taggcggctt ttgcccactc taaagaaggt tgagactgaa 120
tttctgaggt ttcagaagga gcattagatt gtttatcttc aacaacagga ggtttttgtt 180
caatattttc cttattctct tttttacggc gaaaccaatt aaacataatg attgtgcata 240
aatattcgtt aatatattgt aaccctagaa aggaatcggt ttcaggttta tccccagaga 300
atgtgaacct ttacagaaag taaaaagtct aaaatcgtag caacaataaa tcacagaaat 360
tgag 364

<210> SEQ ID NO 51
<211> LENGTH: 304
<212> TYPE: DNA
<213> ORGANISM: Cyanobacterium sp. PTA-13311

<400> SEQUENCE: 51
gcgattatca accacgaaaa catacaatta ttatcaaacc tgctgagaaa ttatccacag 60
aaatagatgt ttctgcgaag ggaaaatggg cttttcattg ccatttaatg tatcacatgg 120
atgtgggaat gtttcggact attaatgtta tttcctaaaa aataatagta ttaaagccta 180
aaatttttat aaaaaaattc atgtctttta ttagggtgag cattcttcct ttatgtctcc 240
ttattttacc tctttagagg taactacaaa cttaatcaaa aaatttagat aattaattat 300
atca 304

<210> SEQ ID NO 52
<211> LENGTH: 490
<212> TYPE: DNA
<213> ORGANISM: Cyanobacterium sp. PTA-13311

<400> SEQUENCE: 52
catctttact tttgactaac atttcatagg tatcatgacg aaaatttttt agtctgttat 60
atttgttcat gtagagagat tttaatttgt gattatttta ttttctctct atttttcttt 120
tttgtcttgt ccttcctcat ttttctctac atttagtcta aactacagct ctttaatctt 180
cagtttctct ttcctcctct tcctcatcaa ggtaatcatc ccaattaata tcttcttctt 240
gttctaattt gggttgagat tgttgtttat caatcatatt tcatactcct aaaactttct 300
tacttattta tcagttactt tttacccatt tatgcaatag tgtagaaatt tttttcgatc 360
gagttaatta atttttattt caaccatatc taaataattc ttgatggaca ttctagttaa 420
ctagaaggtt taagctaaaa ataattattg atattgcctt cggtataact aactatatcc 480
agagaaaaag 490

<210> SEQ ID NO 53
<211> LENGTH: 306
<212> TYPE: DNA
<213> ORGANISM: Cyanobacterium sp. PTA-13311

<400> SEQUENCE: 53
ctcaagagat agttaaaaaa caaatagctt tagtctatca attaatcgaa ttatttttac 60
aaacaaattt tcataaaccc atagaactag aggaggaagt tatttatgtt taaaaatcta 120
aaagagtttt atattcccct aaaacccccct tagtaagagt gactttttttc atcatttgcc 180
tgtaaattct cctcttttaa taagagagct agggtgtttt aaaagaggat tttattgctt 240
tccaattcta actacttcaa aaacttattt tatactcaat aatttattaa tcaagaggaa 300
attacc 306

<210> SEQ ID NO 54
<211> LENGTH: 464
<212> TYPE: DNA
<213> ORGANISM: Cyanobacterium sp. PTA-13311

<400> SEQUENCE: 54
tcgagcgctc gttccgcaaa gcggtacgga gttagttagg ggctaatggg cattctcccg 60
tacaggaaag agttagaagt tattaattat caacaattct cctttgccta gtgcatcgtt 120
acctttttaa ttaaaacata aggaaaacta ataatcgtaa taatttaacc tcaaagtgta 180
aagaaatgtg aaattctgac ttttataacg ttaaagaggg aaaaattagc agtttaaaat 240
acctagagaa tagtctgggg taagcataga gaattagatt agttaagtta atcaaattca 300
gaaaaaataa taatcgtaaa tagttaatct gggtgtatag aaaatgatcc ccttcatgat 360
aagatttaaa ctcgaaaagc aaaagccaaa aaactaactt ccattaaaag aagttgttac 420
atataacgct ataaagaaaa tttatatatt tggaggatac caac 464

<210> SEQ ID NO 55
<211> LENGTH: 541
<212> TYPE: DNA
<213> ORGANISM: Cyanobacterium sp. PTA-13311

<400> SEQUENCE: 55
aatagttgat aattactcgt tactcattac tcacttaaac ctgccacctg atacctgcca 60
cctctccccc catcacctca tcccctcaac attccgaacc ccttgacact ttgaactaaa 120
attgtattaa agtgcaaatc tggacggggt taaccagtgt gacttataat agtaaacgct 180
gtttttttata ataaataagc taaatattta aaaactatga gtaaatatac actaaatggt 240
actagacgta agcagaaaag aacctccggt ttccgcgccc gtatgagaac caaaaatggt 300
agaaaagtaa ttcaagctcg tcgtaataag ggtagaaaaa gattagcagt ataaaattac 360
tgttaaataa ggaagctaag tttagcattt taagtttgat attactaatc attaaattta 420
ctgtgaaata taggtgggac taccatcaaa gcatcgactg aaacggcgtt taaatttcca 480
atctgtttat caacagggta ttcgccgctc tagtcgttat tttattgtcc gagggttacg 540
g 541

<210> SEQ ID NO 56
<211> LENGTH: 569
<212> TYPE: DNA
<213> ORGANISM: Cyanobacterium sp. PTA-13311

<400> SEQUENCE: 56
ctccgcttaa aaaatttcat ttttcgatca aaaaagacaa attattacta attagctcat 60
ggcaataaat aatcagtagt aatctgtttt cacattttat tgttaatttt tattattgct 120

-continued aatatcaacc ttttctactt ctgcttaata ttttatttat gctcaatggg aaaatctgaa 180
ataagattga gaacagtgtt accaatagaa gtatttaagg tttaaagcat accttaaaga 240
taacattttt ttttgaaaag agtcaaatta tttttgaaag gctgatattt ttgatattta 300
ctaatatttt atttatttct ttttccctta aaataagagc taaatctgtt tttattatca 360
tttatcaagc tctattaata cctcaacttt ttcaagaaaa aataataata atttttccct 420
ctattctcat gaccttttag gaaaattaat tttagaaaaa ctattgacaa acccataaaa 480
aatgagataa gattatagat tgtcactggt attttatact agaggcaaat tatatttata 540
tatacaaaaa tgctgtataa aaaacatct 569

<210> SEQ ID NO 57
<211> LENGTH: 163
<212> TYPE: DNA
<213> ORGANISM: Cyanobacterium sp. PTA-13311

<400> SEQUENCE: 57
agtaaagatt atcaccaaca tctgaaacct gacttcatca actgaggaaa taaccactgt 60
ggctgtgttt aaaatcgact gcgtagcaag taaaactcaa aaaaatcaag gtcaatacgg 120
aaagtttgtg cttgaaccct tagaaaaagg acaaggcata act 163

<210> SEQ ID NO 58
<211> LENGTH: 301
<212> TYPE: DNA
<213> ORGANISM: Cyanobacterium sp. PTA-13311

<400> SEQUENCE: 58
ctacatcaac taatcaaaag ttaagaaaaa agatagaaac gcccatgaat attaaagatt 60
aatctgtgtc ctttaacttt ttatcccctt aaaagagcat aactaaaaca ttgatagatt 120
ttataaagaa aagtaacaaa atcttgactt aaatgagaaa ggattaaaaa ccaaagcctt 180
atctgaggga atgttaaaca aattttaaat attgttaagc aagaaccaca atggtgacaa 240
atagccctta tcatcttcag taatgtagta gtttaagtat ttgtcgagag aggaatccct 300
c 301

<210> SEQ ID NO 59
<211> LENGTH: 299
<212> TYPE: DNA
<213> ORGANISM: Cyanobacterium sp. PTA-13311

<400> SEQUENCE: 59
gatcgaattt ttgactattt aataatttct ttactattca taatatctca aaagacttct 60
atctttttaa gtaaactacc tcctctaaga ataaacactt attgactata ttccttttta 120
gttataaaat ggcatttaaa gttactcaaa atatttgcaa tcattctaca aaacatagtg 180
tatttccttg tattaagcgt attgtgtcct gttagataat gtaggaaaga ttgtgagttg 240
ataggtgata aatacataac tcattagaca acaagataaa gttgtaggag ttctaaatt 299

<210> SEQ ID NO 60
<211> LENGTH: 261
<212> TYPE: DNA
<213> ORGANISM: Cyanobacterium sp. PTA-13311

<400> SEQUENCE: 60
aagagtttgg catttttatt ggtaagacta ttctgagaaa aatgtgacaa tttgttaaaa 60
tatttgctag aaatagaaaa agtaatttgg caaagatact taaatcgtat cgaaaaacgg 120

```
agttacatta actctaactc atgctatatt aagaaaagtt aattgcagat cagtattatt    180

gctgagtagc agtgccgtct ccaataatat aaagagagac aatataaaag taaaacttga    240

caagttaaaa aaagaaagat t                                              261


<210> SEQ ID NO 61
<211> LENGTH: 396
<212> TYPE: DNA
<213> ORGANISM: Cyanobacterium sp. PTA-13311

<400> SEQUENCE: 61

aactttagat attcgtagtt ggcaatgtcg taaatgcgga acaatacatg gaaaacatat     60

agatttgtaa tgagaaaaag tgtaaacaaa tattaagaaa aagatcagaa aaatttaaca    120

acacgtaata aaaaaatgcg tcactacggg ttataaattt acatgaaagg ttaaaacact    180

tttctgagac gattttgata aaaaagttgt caaaaaatta agtttcttta caaatgctta    240

acaaaaactt ggttttaagc acaaaataag agagactaat ttgcagaagt tttacaagga    300

aatcttgaag aaaaagatct aagtaaaacg actctgttta accaaaattt aacaaattta    360

acaaaacaaa ctaaatctat taggagatta actaca                              396
```

CYANOBACTERIAL STRAINS CAPABLE OF UTILIZING PHOSPHITE

CROSS-REFERENCE TO RELATED APPLICATIONS

This application claims the benefit of U.S. Provisional Application No. 62/410,577, filed on Oct. 20, 2016, the disclosure of which is hereby incorporated by reference.

STATEMENT REGARDING FEDERALLY SPONSORED RESEARCH

Not applicable.

REFERENCE TO SEQUENCE LISTING

This application contains a sequence listing submitted by EFS-Web, thereby satisfying the requirements of 37 C.F.R. §§ 1.821-1.825. The sequence listing, created on Jul. 29, 2016, contains 61 sequences and is 218 KB in size.

FIELD OF THE INVENTION

The present invention relates to genetically modified cyanobacterial cells that are capable of utilizing phosphite as a phosphorus source.

BACKGROUND OF THE INVENTION

Cyanobacterial cultures for the production of biofuels or other products are often grown as an axenic or nearly axenic "monoculture" to improve yields of the product. Once the culture reaches a large scale, the requirement for light for photosynthesis often results in the culture being grown outdoors in non-axenic conditions, such as open ponds, non-sterile tubes, or plastic transparent containers. The cost of keeping a cyanobacterial production culture from becoming contaminated, however, is a major obstacle, particularly for the outdoor, large-scale, commercial production of a product of interest. Although the growth system can be pre-cleaned or pre-sterilized before the cyanobacterial culture is added, it is often difficult to keep contaminants out of the system, particularly during longer culture run times, such as 20 days or more.

The use of various drugs such as antibiotics for the prevention of contamination with microorganisms other than the cyanobacterial production strains can also be used, where the cyanobacterial culture is maintained by introducing an antibiotic-resistance gene into the cyanobacterial host cell and culturing the cells in a culture medium containing an antibiotic corresponding to the antibiotic-resistance gene. However, a culturing method that uses an antibiotic may not be suitable for use at a larger scale.

Cyanobacterial production systems typically utilize culture media that are formulated to provide the nutrients necessary for the growth of a host cell, such as carbon, nitrogen, phosphorus, sulfur, and other major nutrients. Some cell cultures also require additional components, such as trace minerals and metals. These nutrients provide a suitable growth environment for the cyanobacterial strain of choice and, unfortunately, for many potential contaminating organisms. Thus, the cyanobacterial production strain is required to compete directly with contaminant organisms in the cell culture for nutrients.

What is needed in the art is a method of growing cyanobacterial cultures in a way that reduces the growth of contaminating organisms such as heterotrophic bacteria, so that the cyanobacterial cells can grow and produce the product of interest at maximal yields in a production environment.

SUMMARY OF THE INVENTION

The present invention relates to genetically modified cyanobacterial cells that are capable of utilizing phosphite as a phosphorus source. The modified cyanobacteria can more effectively produce a product of interest. The capability of phosphite utilization allows the modified cyanobacterial cells to grow and make products of interest more efficiently and productively, with fewer side effects caused by contamination, allowing the cultures to remain healthy and productive for a much longer period of time. This can provide a competitive advantage for the cyanobacteria relative to contaminating organisms that have a lesser ability to utilize phosphite as a phosphorus source.

In an aspect of the invention, a genetically modified cyanobacterial cell for the production of a product of interest is provided, having at least one recombinant gene that encodes a phosphite dehydrogenase enzyme that catalyzes the oxidation of phosphite to phosphate; an operon having at least one recombinant phosphite transporter gene encoding at least one phosphite transporter protein for transporting phosphite into the cell; and at least one recombinant production gene encoding a polypeptide for the production of the product of interest.

The phosphite dehydrogenase enzyme can be, for example, heterologous to the cyanobacterial cell. The phosphite dehydrogenase enzyme can be, for example, a phosphite dehydrogenase EC:1.20.1.1. The phosphite dehydrogenase enzyme can be capable of using NAD(H) or NADP (H) as a cofactor. The phosphite dehydrogenase can be, for example, from *Cyanothece* or *Ralstonia*. The recombinant phosphite dehydrogenase gene can encode, for example, a polypeptide that has a sequence identity of greater than 60% to the protein sequence of the phosphite dehydrogenase enzyme from *Cyanothece* (SEQ ID NO: 16) or from *Ralstonia* (SEQ ID NO: 12). The recombinant phosphite dehydrogenase gene can encode, for example, a polypeptide that has a sequence identity of greater than 95% to the protein sequence of the phosphite dehydrogenase enzyme from *Cyanothece* (SEQ ID NO: 16) or from *Ralstonia* (SEQ ID NO: 12). The recombinant phosphite dehydrogenase gene can be operably linked to a constitutive or regulatable promoter. The regulatable promoter can be, for example, a metal-regulatable promoter, a nitrate-regulatable promoter, or a phosphorus-regulatable promoter.

The at least one recombinant phosphite transporter operon can have, for example, three genes encoding three phosphite transporter proteins. At least one of the phosphite transporter genes can be derived from a different organism than the phosphite dehydrogenase gene. The at least one phosphite transporter gene can be, for example, from *Desulfotignum phosphitoxidans* or *Cyanothece*. The at least one phosphite transporter protein(s) can be chosen from, for example, PtxA, PtxB, PtxC, or PtdC. The recombinant phosphite transporter operon can have, for example, a nucleic acid sequence having a sequence identity of at least 60% to at least one of the ptxABC operon sequences SEQ ID NO:17 (ptxA gene sequence from *Cyanothece* sp.) or SEQ ID NO: 20 (ptxB gene sequence from *Cyanothece* sp.) or SEQ ID NO: 23 (ptxC gene sequence from *Cyanothece* sp.). The recombinant phosphite transporter operon can have a gene encoding a protein that has a sequence identity of greater than 60% to the protein sequence of PtdC from *Desulfotignum phosphitoxidans* (SEQ ID NO: 28). Further, the recombinant phosphite transporter gene can be operably linked to a regulatable or constitutive promoter. The regulatable promoter can be selected from a group consisting of: a metal-regulatable promoter, a nitrate-regulatable promoter, and a phosphorus-regulatable promoter.

The cell can have a further modification of a gene encoding an endogenous repressor protein which in its native form represses the expression of a phosphate transporter protein in the cyanobacterial cell. The modification can be a knockout resulting in an inactivation of the gene encoding an endogenous repressor protein. The modification can be a knockdown, for example, resulting in a decrease in expression or function of the gene encoding an endogenous repressor protein. The endogenous repressor can be PhoU or a homolog. The modification of the gene encoding the endogenous repressor protein results in cellular metabolism consistent with a constant phosphorus starvation mode, resulting in an increase in the rate of phosphate uptake into the cell, and, optionally, an increase in polyphosphate storage in the cell. The at least one recombinant production gene can encode, for example, a pyruvate decarboxylase enzyme and an alcohol dehydrogenase enzyme.

The gene encoding the pyruvate decarboxylase enzyme and the gene encoding the alcohol dehydrogenase enzyme can be, for example, on the same operon. The gene encoding the pyruvate decarboxylase enzyme and the gene encoding the alcohol dehydrogenase enzyme can be operably linked to different promoters. The promoter operably linked to the gene encoding the pyruvate decarboxylase enzyme can be a regulatable promoter. The promoter operably linked to the alcohol dehydrogenase enzyme can be, for example, a constitutive promoter. The product of interest can be, for example, ethanol.

In another aspect of the invention, a recombinant expression cassette having at least one recombinant phosphite transporter gene encoding an enzyme that can be at least a part of a transporter system for phosphite, and at least one recombinant phosphite dehydrogenase gene encoding an enzyme that catalyzes the oxidation of phosphite to phosphate is provided, where the expression cassette provides sufficient expression of the enzymes in a genetically modified cyanobacterial cell having the expression cassette to confer an ability on the genetically modified cyanobacterial cell to metabolize phosphite as a phosphorus source for supporting growth of the cyanobacterial cell. The promoter can be operably linked to at least one of the genes, and can be regulatable (such as a metal-regulatable promoter or a nutrient-regulatable promoter) or can be constitutive. The recombinant expression cassette can be located on a chromosome or on an extrachromosomal plasmid.

In yet another aspect of the invention, a method of propagating a genetically modified cyanobacterial cell is provided, by obtaining a genetically modified cyanobacterial cell as described above, and growing the recombinant cyanobacterial cell in a medium containing phosphite as a source of phosphorus. The phosphorus source in the medium can be, for example, at least 80% phosphite. The medium can have, for example, a phosphate concentration of less than about 20 μM.

In yet another aspect of the invention, a method of producing a product of interest is provided, by providing a cell as described above, and growing the cell in a medium having phosphite as a source of phosphorus, so that the cell produces the product of interest. The cell can be grown, for example, under non-axenic conditions, such as growing in the presence of contaminating heterotrophic organisms. Some of the contaminating heterotrophic organisms can be less able to utilize phosphite as a source of phosphorus in comparison to the genetically modified host cell. The product of interest can be, for example, an alcohol, a biofuel, an alkane, a nutraceutical, a pharmaceutical, a lipid, a carbohydrate, biomass, a protein, an amino acid, a cell extract, or a pigment. The product of interest can be, for example, ethanol. The genetically modified host cells can have a faster rate of phosphite uptake in comparison to the rate of phosphite uptake of at least some of the contaminating heterotrophic organisms. The presence of contaminant cells can be maintained, for example, below $1\times10^6$ colony forming units per milliliter (CFU/mL), preferably below $1\times10^4$ CFU/mL, after about 30 days of cultivation. The growth of contaminant cells can be reduced or inhibited by limiting availability of phosphate in the medium to less than 5 μM. The contaminating heterotrophic organisms can be present, for example, in at least a 5-fold lower concentration than when a normal amount of phosphate is provided to the medium.

In another aspect of the invention, the use of a cyanobacterial cell as described above for producing the product of interest in the presence of contaminating heterotrophic organisms in a cyanobacterial culture having phosphite as the main phosphorus source is provided, where the ratio of contaminating heterotrophic organisms to cyanobacterial cells is less than when phosphate can be the main source of phosphorus in the medium. The growth of the contaminating heterotrophic organisms can be reduced or inhibited by limiting availability of phosphate in the cyanobacterial culture. More product can accumulate in the culture than when phosphate is used as the main source of phosphorus in the medium.

In another aspect of the invention, a method of producing a product of interest from cyanobacteria is provided, by providing a genetically modified cyanobacterial cell as described earlier, where the phosphite dehydrogenase gene and at least one of the recombinant production genes are present on the same extrachromosomal plasmid; and growing the genetically modified cyanobacterial cell in a medium having phosphite as the main source of phosphorus, under conditions to produce the product of interest, where the at least one recombinant production gene remains functional in the host cyanobacterial cell for a longer period of time than it would remain functional in an otherwise identical cyanobacterium that does not have the phosphite dehydrogenase gene, cultured under identical conditions but growing on phosphate instead of phosphite. The extrachromosomal plasmid can remain intact in the cell for a longer period of time than it would in a similar but non-phosphite utilizing cyanobacterial cell growing on phosphate as the main source of phosphorus. The recombinant production gene can be a gene involved in the production of ethanol. The production gene can encode, for example, a pyruvate decarboxylase. The phosphite dehydrogenase gene and at least one of the recombinant production genes can both be under the control of one regulatable promoter. The production gene can remain intact in the cell culture for a longer period of time than it would remain intact in a cell culture of an otherwise identical cyanobacterium, but having the phosphite dehydrogenase gene and at least one of the recombinant production genes controlled by different promoters, cultured under identical conditions. The production gene can be located, for example, upstream of the phosphite dehydrogenase gene.

BRIEF DESCRIPTION OF THE DRAWINGS

FIG. 5 is a table of several of the plasmid constructs discussed herein. The strain identification numbers, plasmid identification numbers, genotypes, promoters, and SEQ ID NOs. are indicated.

DETAILED DESCRIPTION

Figure 1:
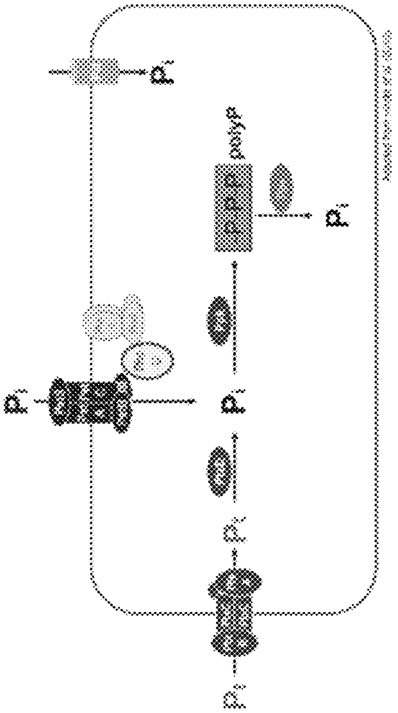
FIG. 1 is a schematic diagram of possible phosphate and/or phosphite uptake, utilization, and storage systems found in cyanobacteria.

As an alternative to the use of costly antibiotics and other chemicals in large scale culture systems, cyanobacteria can be designed to effectively utilize alternative nutrient components that are not utilized by many contaminants. Although contaminating organisms would still be likely to be present in the culture, their growth can be limited such that they are no longer a major challenge to the cyanobacterial production process.

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture Biotechnology And Applied Phycology (2003) Richmond, A.; (ed.), Blackwell Publishing; and "The Cyanobacteria, Molecular Biology, Genomics and Evolution", Edited by Antonia Herrero and Enrique Flores, Caister Academic Press, Norfolk, UK, 2008.

All publications and patent applications mentioned in this specification are herein incorporated by reference to the same extent as if each individual publication or patent application was specifically and individually indicated to be incorporated by reference.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

The term "cyanobacterium" refers to a member from the group of photoautotrophic prokaryotic microorganisms which can utilize solar energy and fix carbon dioxide. Cyanobacteria are also referred to as blue-green algae.

The terms "host cell" and "recombinant host cell" are intended to include a cell suitable for metabolic manipulation, e.g., which can incorporate heterologous polynucleotide sequences, e.g., which can be transformed. The term is intended to include progeny of the cell originally transformed. In particular embodiments, the cell is a prokaryotic cell, e.g., a cyanobacterial cell. The term "recombinant host cell" is intended to include a cell that has already been selected or engineered to have certain desirable properties and to be suitable for further genetic enhancement.

The terms "phosphorus" and "P" refer to a chemical element that is a nutrient source for cell growth. Phosphorus can be present in several different forms, such as phosphoric acid, phosphorus acid, hypophosphorous acid, phosphate, and phosphite. Salts with various compounds, such as calcium, potassium, sodium, are also common forms.

The term "phosphate" means phosphoric acid ($PO_4^{3-}$) and related salts, such as sodium salt, potassium salt, and calcium salt.

The term "phosphite" means phosphorous acid ($H_3PO_3$) and related salts. Other common names for phosphite include, for example, phosphonic acid, phosphonate, and phosphorous acid. Phosphite may be provided as any suitable phosphite compound or combination of phosphite compounds. Exemplary forms of phosphite include, but are not limited to phosphite salts of sodium, potassium, ammonium, calcium, or magnesium, or any combination thereof. An example of a sodium salt of phosphite is $Na_2HPO_3$ pentahydrate. Phosphite can be oxidized to phosphate.

The terms "phosphite dehydrogenase", "phosphonate dehydrogenase", "NAD:phosphite oxidoreductase", and "PtxD" refer to a protein in the class EC 1.20.1.1, which can catalyze the following reactions:

$$\text{phosphite}+NAD(P)^{+}+H_2O\rightarrow\text{phosphate}+NAD(P)H+H^{+}$$

or $$\text{phosphonate}+NAD(P)^{-}+H_2O\rightarrow\text{phosphate}+NAD(P)H+H^{+}$$

The term "phosphite transporter" refers to a protein or complex that is capable of importing phosphite into the cyanobacterial cell. This can be an ABC transporter complex of several polypeptides (such as PtxA,B,C). ABC transporters belong to the ATP-Binding Cassette (ABC) superfamily, which uses the hydrolysis of ATP to provide energy for the transport. ABC transporters are involved in the export or import of a wide variety of substrates. The major function of ABC import systems is to provide essential nutrients to cells. ABC transporters typically have two conserved regions: a highly conserved ATP binding cassette (ABC) and a less conserved transmembrane domain (TMD).

The polypeptide "PtxA" refers to a "phosphite transport system ATP binding protein" having a Transporter Classification number of TC 3.A.1.9.1. The polypeptide is homologous to a "phosphonate transport ATP binding protein (PhnC)".

The polypeptide "PtxB" refers to a "phosphite transport system substrate binding protein" having a Transporter Classification number of TC 3.A.1.9.1. The polypeptide is homologous to a "phosphonate transport system substrate binding protein (PhnD)".

The polypeptide "PtxC" refers to a "phosphite transport system permease protein" having a Transporter Classification number of TC 3.A.1.9.1. The polypeptide is homologous to a "phosphonate transport system permease protein (PhnE)".

The term "phosphite transporter" can also encompass other types of phosphite transporter systems or phosphonate transporter systems, such as the single protein phosphite transport system that is exemplified by the PtdC protein from *Desulfotignum phosphitoxidans*, an organophosphate: inorganic phosphate antiporter (OPA) family protein.

The term "phosphate transporter" refers to a protein or complex that is capable of importing phosphate into the cyanobacterial cell. The transporter protein can be, for example, a membrane-bound protein.

The term "phosphate metabolism regulating protein" refers to a protein that modulates (either increases or decreases), inter alia, the entry of phosphate into the cell. It can be a regulatory protein that regulates the expression or the activity of other proteins involved in the phosphate uptake process. In an embodiment, the phosphate metabolism regulating protein is PhoU, and its elimination from the cell can lead to an increase in phosphate uptake rates. PhoU is a global phosphate response regulator which is responsible for the repression of the high affinity PstSCAB uptake system in cyanobacteria and also regulates expression of other genes involved in the response to phosphate limitation. Other genes encoding proteins involved in the phosphate transport system can be genetically modified to alter the rate of entry of phosphate into the cell.

As used herein, the term "biomass" refers to the cellular material produced from the cyanobacterial cultures. Biomass can be comprised of lipids, protein, and /or carbohydrates. Biomass can be obtained from axenic or non-axenic cyanobacterial cell cultures. A cyanobacterial biomass can be in a liquid, or condensed to a paste, or can be substantially dried. At least some of the cell components can have been previously removed, such as a product (for example, ethanol), or a lipid, or another compound, leaving the remaining material as biomass. Cyanobacterial biomass can also mean whole, live or dead cells.

"Competent to express" refers to a host cell that provides a sufficient cellular environment for expression of endogenous and/or exogenous polynucleotides.

As used herein, the term "genetically modified" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

The terms "polynucleotide" and "nucleic acid" also refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids can be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be recombinantly introduced into the host cell.

In one aspect the invention also provides nucleic acids which are at least 50%, 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994, Nucleic Acids Research 22: 4673-4680). A nucleotide sequence or an amino acid sequence can also be used as a so-called "query sequence" to perform a search against public nucleic acid or protein sequence databases in order, for example, to identify further unknown homologous promoters, which can also be used in embodiments of this invention. In addition, any nucleic acid sequences or protein sequences disclosed in this patent application can also be used as a "query sequence" in order to identify yet unknown sequences in public databases, which can encode for example new enzymes, which could be useful in this invention. Such searches can be performed using the algorithm of Karlin and Altschul (1990, Proceedings of the National Academy of Sciences U.S.A. 87: 2,264 to 2,268), modified as in Karlin and Altschul (1993, Proceedings of the National Academy of Sciences U.S.A. 90: 5,873 to 5,877). Such an algorithm is incorporated in the NBLAST and XBLAST programs of Altschul et al. (1990, Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997, Nucleic Acids Research, 25: 3,389 to 3,402).

In one aspect the invention also provides amino acid sequences which are at least 50%, 55%, 60%, 70%, 80% 90%, 95%, 97%, 99%, or 99.5% identical to the amino acid sequences disclosed herein.

Database entry numbers given in the following are for the CyanoBase, the genome database for cyanobacteria (bacteria.kazusa.orjp/cyanobase/index.html); Nakamura et al. "CyanoBase, the genome database for *Synechocystis* sp. Strain PCC 6803: status for the year 2000", Nucleic Acid Research, 2000, Vol. 18, page 72.

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacterium." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non- equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "expressed endogenously" refers to polynucleotides that are native to the host cell and are naturally expressed in the host cell.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

An "endogenous plasmid" is one that is from the host cyanobacterial cell itself, rather than being obtained from a different organism. One exemplary endogenous plasmid is the p6.8 plasmid from *Cyanobacterium* sp. PTA-13311. This plasmid, when carrying inserted genes, is able to remain in the cell at a relatively high copy number.

A "heterologous plasmid" is derived from other than the host cyanobacterial cell.

The phrase "operably linked" means that the nucleotide sequence of the nucleic acid molecule or gene of interest is linked to the regulatory sequence(s) in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription. The term "promoter" is also intended to include a polynucleotide segment that can transcriptionally control a gene of interest that it does or does not transcriptionally control in nature. In one embodiment, the transcriptional control of a promoter results in an increase in expression of the gene of interest. In an embodiment, a promoter is placed 5' to the gene of interest. A heterologous promoter can be used to replace the natural promoter, or can be used in addition to the natural promoter. A promoter can be endogenous with regard to the host cell in which it is used or it can be a heterologous polynucleotide sequence introduced into the host cell.

The term "regulatable promoter" refers to a promoter that can up-regulate or down-regulate the transcription of its operably linked gene by the presence or absence of a compound, an environmental factor, or another stimulus. For example, certain promoters can be up-regulated ("inducible") by the presence of a nutrient, while other promoters are up-regulated by the absence of the nutrient.

The term "phosphorus-regulatable promoter" is a promoter that is regulated by the presence or absence of phosphorus. For example, the pstS promoter is a phosphorus-regulatable promoter that is induced under phosphorus starvation conditions.

The term "metal-regulatable promoter" is a promoter that is regulated by the level of a specific metal ion in the culture medium.

The term "nitrate-regulatable promoter" is a promoter that is regulated by the level of nitrate in the culture medium.

The term "inducible promoter" is a regulatable promoter that up-regulates an operably linked gene in response to certain stimuli (such as nutrient availability, nutrient starvation, heat shock, environmental stress, cold stress, salt stress, mechanical stress, light exposure, etc.), leading to the transcription of the gene.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). The recombinant nucleic acid molecule (e.g., a recombinant DNA molecule) also includes an isolated nucleic acid molecule or gene of the present invention.

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence.

The term "endogenous gene" refers to a native gene in its natural location in the genome of an organism.

A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6, 50, 100, 200, 500, 1,000, to about 1,500 or more consecutive nucleotides of a polynucleotide according to the invention.

The term "open reading frame," abbreviated as "ORF," refers to a length of nucleic acid sequence, either DNA, cDNA or RNA, that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, "substantially similar" refers to nucleic acid fragments wherein changes in one or more nucleotide bases results in substitution of one or more amino acids, but do not affect the functional properties of the protein encoded by the DNA sequence. The term "substantially similar" also refers to modifications of the nucleic acid fragments of the instant invention such as deletion or insertion of one or more nucleotide bases that do not substantially affect the functional properties of the resulting transcript.

The terms "restriction endonuclease" and "restriction enzyme" refer to an enzyme that binds and cuts within a specific nucleotide sequence within double stranded DNA.

The term "expression", as used herein, refers to the transcription and stable accumulation mRNA derived from a nucleic acid or polynucleotide. Expression may also refer to translation of mRNA into a protein or polypeptide.

An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term "codon" refers to a triplet of nucleotides coding for a single amino acid.

The term "codon-anticodon recognition" refers to the interaction between a codon on an mRNA molecule and the corresponding anticodon on a tRNA molecule.

The term "codon bias" refers to the fact that different organisms use different codon frequencies.

The terms "codon optimization," "codon improvement," and "codon optimization" refer to the modification of at least some of the codons present in a heterologous gene sequence from a triplet code that is not generally used in the host organism to a triplet code that is more common in the particular host organism. This can result in a higher expression level of the gene of interest.

The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, spectinomycin, kanamycin, hygromycin, and the like.

A "polypeptide" is a polymeric molecule comprised of covalently linked amino acid residues. A "protein" is a polypeptide that performs a structural or functional role in a living cell.

A "heterologous protein" refers to a protein not naturally produced in the cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids).

The term "fragment" of a polypeptide refers to a polypeptide whose amino acid sequence is shorter than that of the reference polypeptide. Such fragments of a polypeptide according to the invention may have a length of at least about 2, 50, 100, 200, or 300 or more amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements.

As used herein, the phrase "increased activity" refers to any genetic modification resulting in increased levels of enzyme function in a host cell. As known to one of ordinary skill in the art, enzyme activity may be increased by increasing the level of transcription, either by modifying promoter function or by increasing gene copy number; increasing translational efficiency of an enzyme messenger RNA, e.g., by modifying ribosomal binding; or by increasing the stability of an enzyme, which increases the half-life of the protein, leading to the presence of more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Biomedical Engineering Handbook (2000) Bronzino, J. D., Springer, ISBN 354066808X).

The terms "pyruvate decarboxylase" and "Pdc" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide.

The terms "alcohol dehydrogenase" and "Adh" refer to an enzyme that facilitates the interconversion between alcohols and aldehydes or ketones. An "adh gene" refers to the gene encoding an enzyme that facilitates the interconversion between alcohols and aldehydes or ketones, "Pdc/Adh" refers to the Pdc and Adh enzymes collectively. A "pdc/adh cassette" refers to a nucleic acid sequence encoding a Pdc enzyme and an Adh enzyme.

The term "ethanologenic cassette" refers to any polynucleotide sequence that encodes enzymes capable of producing ethanol alone or in combination with other exogenous or endogenous enzymes. In a certain embodiment, an ethanologenic cassette comprises genes encoding an alcohol dehydrogenase and a pyruvate decarboxylase.

The term "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

The term "polymerase chain reaction," also termed "PCR," refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

The term "knockdown" refers to a partial suppression of the expression of a target gene. A knockdown can occur, for example, when antisense is used. Some expression may still remain when using antisense, so this term is used rather than "knockout".

The term "knockout" generally refers to a partial or complete suppression of the expression of at least a portion of a protein encoded by an endogenous DNA sequence in a cell. As used herein, the "knockout" relates to the deletion or insertional inactivation of a target gene.

The term "knockout construct" refers to a nucleic acid sequence that is designed to decrease or suppress expression of a protein encoded by endogenous DNA sequence in a cell. The knockout construct is inserted into a cell, and integrates with the genomic DNA of the cell in such a position so as to prevent or interrupt transcription of the native DNA sequence. Such insertion usually occurs by homologous recombination. The knockout construct nucleic acid sequence may comprise (1) a full or partial sequence of the gene to be suppressed, (2) a full or partial promoter sequence of the gene to be suppressed, or (3) combinations thereof. Typically, the knockout construct is inserted into a cyanobacterial host cell and is integrated into the cell genomic DNA to delete a target gene, usually by the process of homologous recombination.

The phrases "disruption of the gene" and "gene disruption" refer to a deletion or insertion of a nucleic acid sequence into one region of the native DNA sequence and/or the promoter region of a gene so as to decrease or prevent expression of that gene in the cell as compared to the wild-type or naturally occurring sequence of the gene.

The term "environmental stress" means a stress caused by the area surrounding the growing cell. Exemplary environmental stresses include heat stress, cold stress, pH stress, nutrient stress, high oxygen stress, and the like. An environmental stress can cause slower growth and can also trigger altered biosynthetic pathways.

The term "plurality" means more than one.

Phosphite as a Phosphorus Source

Microorganisms have evolved to utilize different forms of nutrient sources, such as phosphorus. Phosphorus is available in the environment in several forms. The phosphate form of phosphorus is more generally available in the natural environment, in comparison to other forms, such as phosphite or organic phosphorus sources. Further, phosphate is the form that most organisms can utilize most effectively. Phosphate is also the form that is most commonly used in cyanobacterial culture media. A schematic diagram of possible phosphate and/or phosphite uptake, utilization, and storage systems is shown in FIG. 1.

Most microorganisms take up and utilize phosphite poorly, if at all. To demonstrate this, as shown in Example 3 and in FIG. 2, 14 strains of bacterial contaminants found in cyanobacterial photobioreactors were isolated, purified, and tested for their ability to grow on phosphite. The strains either grew poorly or not at all when the only source of phosphorus present in the medium was phosphite.

Two fungal strains that were isolated from outdoor cyanobacterial cultures were also tested for their ability to utilize phosphite—both of these strains utilized phosphite poorly (Example 4).

Thus, a cyanobacterial cell that is able to take up and adequately utilize phosphite can have a growth advantage when grown in the presence of phosphite over contaminants that utilize only phosphate. In an embodiment, cyanobacteria can be genetically modified to utilize alternative forms of phosphorus, such as phosphite, and can have a higher likelihood of out-competing contaminating heterotrophic bacteria and other organisms for phosphorus when it is supplied as phosphite.

Figure 3:
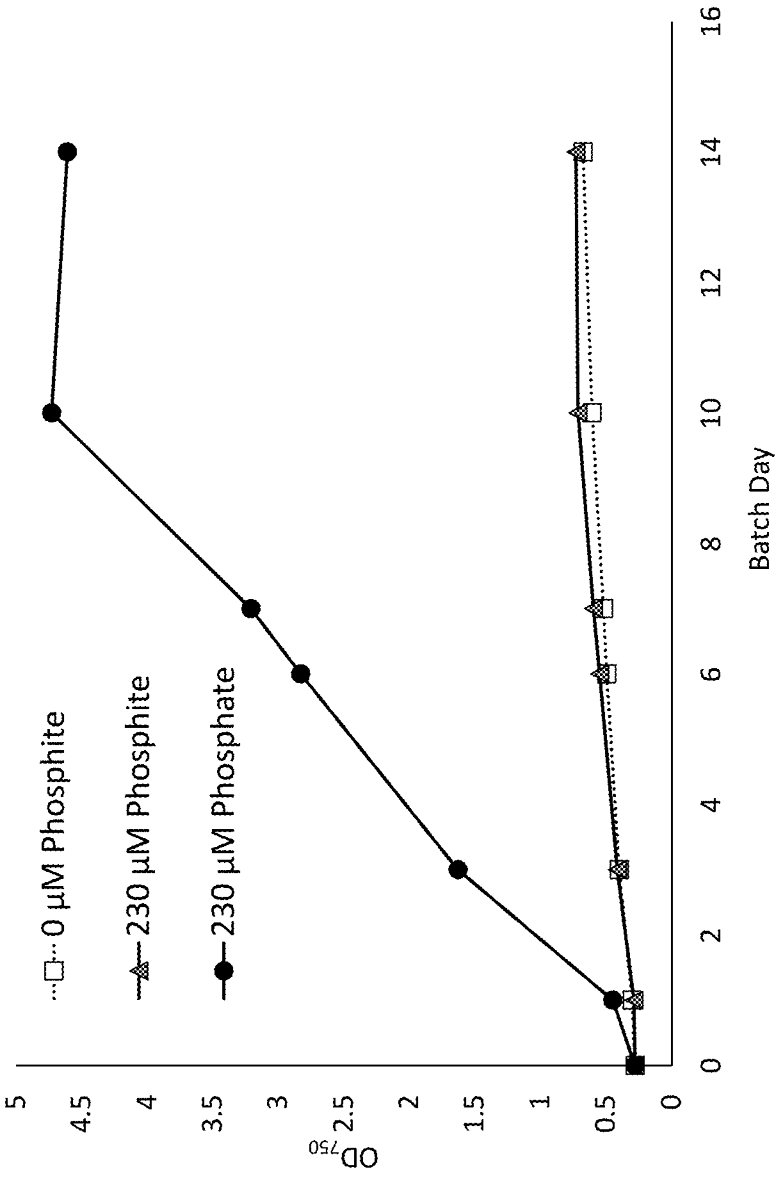
FIG. 3 is a line graph showing the cell growth ($OD_{750}$) of wild type *Cyanobacterium* sp. PTA-13311 ("AB1"), in medium containing 230 μM phosphate (black circles), 230 μM phosphite (grey triangles), or no P source (empty squares). The cyanobacterial culture was previously grown on P-free medium for two rounds to reach a P-starvation stage. The graph shows that while the wild type strain can grow well on phosphate, it does not, without further modification, have the ability to utilize phosphite.

The cyanobacterial production strain *Cyanobacterium* sp. PTA-13311 ("AB1") is currently being utilized as a base organism for ethanol production, particularly due to its fast growth and its ability to withstand environmental stresses. Unfortunately, however, this cyanobacterial strain (as well as most other cyanobacterial strains) does not, by itself, take up or utilize phosphite (Example 5; FIG. 3). The genes involved in phosphite utilization and uptake would accordingly need to be identified and transferred into the cyanobacterial production strain in order to allow it to grow on phosphite.

The phosphite dehydrogenase enzyme has been described previously (Costas, et al., (2001), "Purification and characterization of a novel phosphorus-oxidizing enzyme from *Pseudomonas stutzeri* WM88," J. Biol. Chem. 276:17429-17436; Vrtis et al. (2001), "Phosphite dehydrogenase: An unusual phosphoryl transfer reaction," J. Am. Chem. Soc. 123:2672-2673). The international application publication number WO2010/058298, to Herrera-Estrella, teaches transgenic plants and fungi that have been modified by the addition of the phosphite dehydrogenase (ptxD) gene from Pseudomonas stutzeri to utilize phosphite as a phosphorus source.

US patent application US20040091985 to Metcalf teaches a phosphite dehydrogenase enzyme from several microorganisms, including *Pseudomonas stutzeri* and cyanobacteria such as Nostoc sp. PCC 7120. The PtxD gene was transferred to E. coli, where it was produced at high levels, followed by purification, in order to aid in the biochemical characterization of the enzyme.

Higher plants have previously been genetically modified to utilize phosphite. Lopez-Arredondo (2012), for example, described the production of transgenic *Arabidopsis* and tobacco plants that were engineered with a ptxD gene derived from *Pseudomonas stutzeri* in order to utilize phosphite. Fertilization of the transformed plants with phosphite resulted in vigorous growth and increased biomass while also controlling nearby weed growth. In comparison, the control plants died a few days after fertilization with phosphite ("Engineering phosphorus metabolism in plants to produce a dual fertilization and weed control system", Nature Biotechnology, 30:889-893).

Most (but not all) microorganisms are incapable of utilizing phosphite. Loera-Quezada (2015), noting that certain strains of bacteria and cyanobacteria are capable of utilizing phosphite as the sole P source, attempted to utilize phosphite as a P source for several eukaryotic algal species. The algal cells grew poorly if phosphite was present in the medium (along with phosphate), and did not survive with phosphite as the sole source of P. They concluded that although phosphite was non-toxic to the algae, the algae cells were unable to metabolize it ("Phosphite cannot be used as a phosphorus source but is non-toxic for microalgae", Plant Science 231: 124-130).

Most cyanobacterial species are capable of taking up and transporting phosphate into the cell. However, only a few cyanobacteria have the natural capability for phosphite uptake. Some of these phosphite-utilizing organisms have been found, and their phosphite uptake genes (such as, for example, ptxA,B,C) have been identified. The phosphite utilizing organisms also typically contain genes that encode a phosphite dehydrogenase enzyme (PtxD) that can catalyze the conversion of phosphite to phosphate.

Recombinant Expression of Phosphite Dehydrogenase (PtxD and homologs) in Cyanobacteria In an embodiment, the genes for phosphite utilization, as well as the genes encoding proteins involved in phosphite uptake into the cell, have been identified and transferred to cyanobacterial strains that have been genetically modified to produce ethanol or other products of interest. The growth advantage this provides allows the genetically modified cyanobacterial strains to produce the product of interest in a non-axenic culture.

Because most heterotrophic bacteria utilize phosphite poorly, a culture of cyanobacteria engineered to utilize phosphite that has been contaminated with such heterotrophic bacteria has a better chance of surviving, thriving, and producing product for a longer time than a cyanobacterial culture that only utilizes phosphate. Furthermore, consumption of a product secreted by the cyanobacteria by contaminating heterotrophic bacteria is less likely to occur.

The gene encoding phosphite dehydrogenase is capable of catalyzing the transformation of phosphite to phosphate, once the phosphite molecule is transported to the interior of the cyanobacterial cell. The gene encoding phosphite dehydrogenase can be obtained from any suitable source. Other names for phosphite dehydrogenase include, for example, phosphonate dehydrogenase and NAD:phosphite oxidoreductase. In an embodiment, any enzyme that is capable of oxidizing phosphite to phosphate would be suitable. In an embodiment, the phosphite dehydrogenase enzyme belongs to the enzyme class EC: 1.20.1.1. The purification and characterization of a phosphite dehydrogenase was described, for example, in Costas et al., (2001) "Purification and characterization of a novel phosphorus-oxidizing enzyme from *Pseudomonas stutzeri* WM88," Jour. Biol. Chem., 276:17429-17436.

In an embodiment, the phosphite dehydrogenase gene is obtained from a cyanobacterial cell. In another embodiment, the phosphite dehydrogenase can be obtained from a member of the genus *Ralstonia*, such as, for example, *Ralstonia* sp. strain 4506.

In another embodiment, the phosphite dehydrogenase gene can be obtained from a member of the cyanobacterial genus *Cyanothece*, such as *Cyanothece* sp. ATCC 51142. The gene can be codon optimized for optimal expression in the cyanobacterial strain of interest.

Other exemplary prokaryotic PtxD homologs include, for example, WP_004629224.1 from *Ralstonia pickettii*; WP_046983515.1 from *Delftia lacustris*; WP_029043082.1 from *Cupriavidus* sp. WS; EFP65990.1 from *Ralstonia* sp. 5_7_47FAA;WP_004757466.1 from *Acinetobacter*; WP_044432324.1 from *Acinetobacter*; WP_011610233.1 from *Trichodesmium erythraeum*; and WP_008277007.1 from *Cyanothece* sp. CCY0110.

Figure 4:
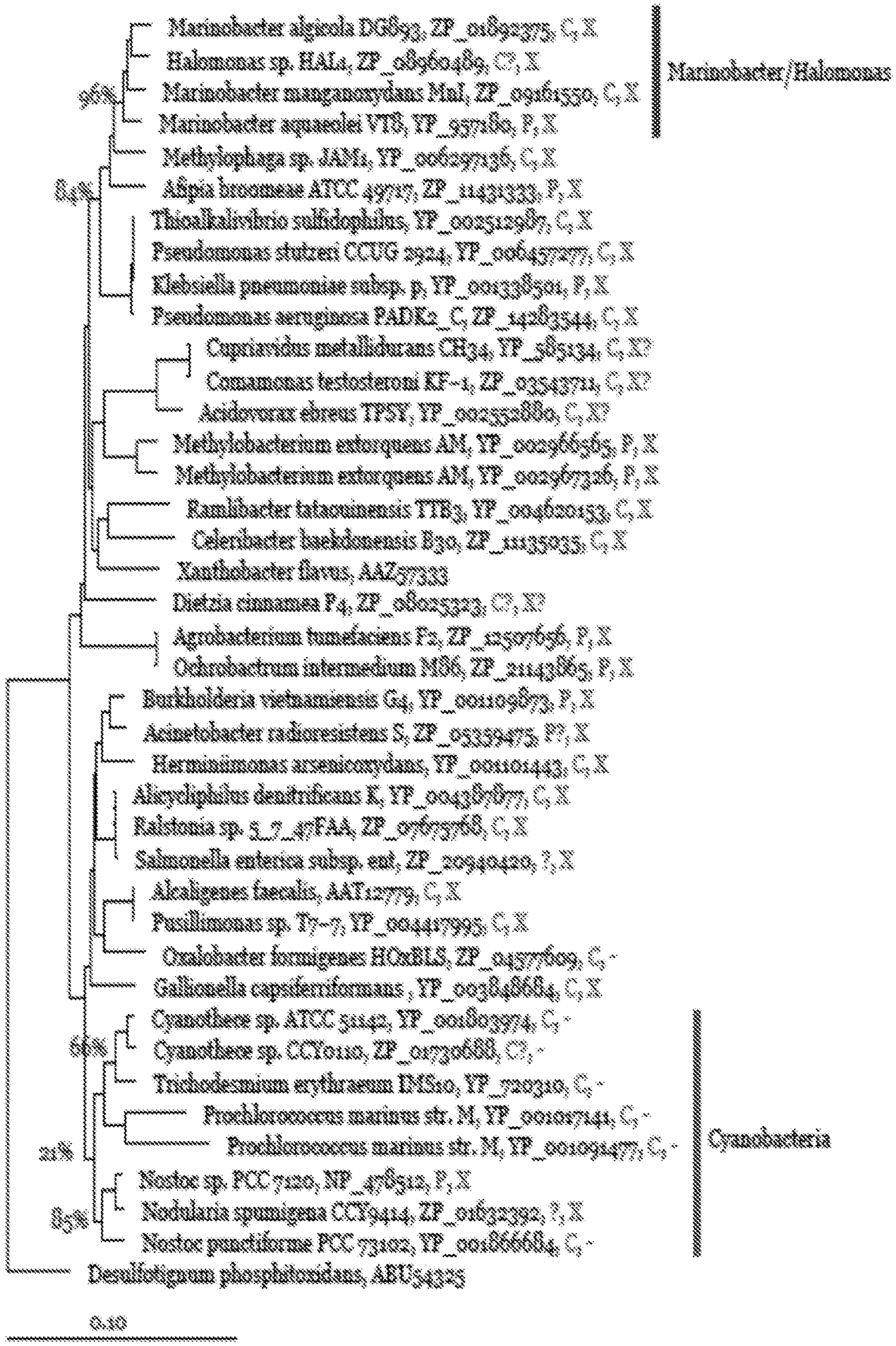
FIG. 4 is a maximum likelihood phylogenetic tree for phosphite dehydrogenase PtxD, based on 272 positions of an amino acid alignment. Bootstrap values are indicated. The strain name and GenBank accession number of the protein are listed on each leaf, along with whether the gene is located on the chromosome ('C') or a plasmid ('P'), and if the ptx operon contains the PtxE regulator 'X'). A question mark with 'X' indicates that a regulator was found in the correct position or near the operon, but it is not similar to ptxE. A dash in place of an 'X' indicates that the strain lacks a regulator near the ptx operon.

The phosphite dehydrogenase gene or protein sequence can be, for example, at least 50%, 55%, 60%, 65%, 70%, 75%, 80%, 85%, 90%, 95%, 97%, or 99% identical to the phosphite dehydrogenase sequence of Ralstonia sp. strain 4506 or *Cyanothece* sp. ATCC 51142. Exemplary phosphite dehydrogenase sequences are listed below in Table 1. In an embodiment, the phosphite dehydrogenase gene can be obtained from other genera of cyanobacteria, or from other types of microorganisms such as bacteria, fungi, yeast, or eukaryotic algae. FIG. 4 is a phylogenetic tree of several phosphite dehydrogenase sequences.

The expression of the phosphite dehydrogenase gene can be controlled by its own separate promoter, or the phosphite dehydrogenase gene can be part of an operon. The gene can be present on an extrachromosomal plasmid. In an embodiment, the phosphite dehydrogenase gene is present on the same extrachromosomal plasmid that carries an ethanol production cassette. In an embodiment, the phosphite dehydrogenase gene is regulatable by a copper-inducible promoter. In an embodiment, the phosphite dehydrogenase gene is regulatable by a phosphorus-regulatable promoter such as the pstS phosphorus-starvation-inducible promoter. In another embodiment, the phosphite dehydrogenase gene is controlled by a constitutive promoter.

TABLE 1

Phosphite Dehydrogenase Sequences

| Name | Source Organism | Nucleic acid sequence | Codon-optimized sequence | Protein sequence |
|---|---|---|---|---|
| Phosphite Dehydrogenase (PtxD) | *Ralstonia* sp. strain 4506 | SEQ ID NO: 11 | — | SEQ ID NO: 12 |
| Phosphite Dehydrogenase (PtxD) - codon optimized with His Tag | *Ralstonia* sp. strain 4506 | — | SEQ ID NO: 13 | SEQ ID NO: 14 |
| Phosphite Dehydrogenase (PtxD) | *Cyanothece* sp. ATCC 51142 | SEQ ID NO: 15 | — | SEQ ID NO: 16 |

As shown herein, modifying a cyanobacterial production strain so that it is capable of utilizing phosphite (rather than just phosphate) allows for an improved competitive advantage. Many contaminating organisms (both prokaryotic and eukaryotic) are incapable of utilizing phosphite, so if that is the only phosphorus source in the medium, the cyanobacterial cells carrying the gene can grow at a normal rate, while contaminants are unable to proliferate.

This system is particularly useful when the cyanobacterial production product is ethanol, as it helps keep heterotrophic contaminants from consuming the ethanol product, because the contaminants will grow very slowly or not at all in a phosphite medium. Unfortunately, even if phosphate is not added to the medium, it may "leak" out of the cyanobacterial cells themselves (through cell death or by other means) and may be present in the medium at a low level.

Recombinant Expression of a Phosphite Transporter System

In addition to the phosphite dehydrogenase enzyme, an additional protein complex is often needed to allow the transport of the phosphite molecule into the cyanobacterial cell. The cyanobacterium *Cyanothece* ATCC 51142, for example, contains a phosphite transporter system that is encoded by three or more genes, including ptxA, ptxB, and ptxC. This operon also includes ptxD. The cyanobacterial species *Ralstonia* sp. strain 4506 was also found to contain an operon containing three phosphite transporter genes (ptxA,B,C).

The operon (or separate genes) encoding the phosphite transporter complex can be obtained from any other suitable source organism. The phosphite dehydrogenase gene and at least one of the phosphite transporter complex genes can be derived from the same organism or from different source organisms. In an embodiment, these genes are obtained from another cyanobacterial species.

TABLE 2

Multi-Gene Phosphite Transporter (ABC transporter from *Cyanothece* sp. ATCC 51142)

| Name | Source Organism | Nucleic acid sequence | Codon-optimized sequence | Protein sequence |
|---|---|---|---|---|
| phosphite transport system ATP binding protein (PhnC or PtxA) | *Cyanothece* sp. ATCC 51142 | SEQ ID NO: 17 | SEQ ID NO: 18 | SEQ ID NO: 19 |
| phosphite transport system substrate binding protein (PhnD or PtxB) | *Cyanothece* sp. ATCC 51142 | SEQ ID NO: 20 | SEQ ID NO: 21 | SEQ ID NO: 22 |
| phosphite transport system permease protein (PhnE or PtxC) | *Cyanothece* sp. ATCC 51142 | SEQ ID NO: 23 | SEQ ID NO: 24 | SEQ ID NO: 25 |

One system that is present in several microbial species is the three gene ptxA,B,C, transporter system. In an embodiment, the operon is obtained from *Cyanothece*. The genes can be codon-optimized for optimal expression in the cyanobacterial strain of interest. In yet another embodiment, the genes encoding the three transporter proteins PtxA, PtxB, and PtxC can be obtained from different source organisms, or the genes can be modified as needed.

In an embodiment, the ptxA protein is SEQ ID NO: 19, as shown above, or can have at least 80%, 85%, 90%, 95%, 97%, or 99% identity to SEQ ID NO: 19. In yet another embodiment, the ptxA protein can be, for example, WP_008277010.1 from *Cyanothece* sp. CCY0110; WP_011610230.1 from *Trichodesmium erythraeum*; or WP_012409717.1 from *Nostoc punctiforme*.

In an embodiment, the PtxB protein is SEQ ID NO: 22, or can have, for example, at least 80%, 85%, 90%, 95%, 97%, or 99% identity to SEQ ID NO: 22. PtxB homologs can include, for example, WP_047156767.1 from *Trichodesmium erythraeum*; and WP_010994146.1 from *Nostoc* sp. PCC 7120.

The PtxC sequence can be, for example, SEQ ID NO: 25, or can have, for example, at least 80%, 85%, 90%, 95%, 97%, or 99% identity to SEQ ID NO: 25. Other exemplary PtxC homologs include, for example, WP_009544750.1 from *Cyanothece* sp. ATCC 51472; WP_008277008.1 from *Cyanothece* sp. CCY0110; WP_011610232.1 from *Trichodesmium erythraeum*; and WP_014707853.1 from *Methylophaga nitratireducenticrescens*.

In an embodiment, the PtxA, PtxB, or PtxC transporter system genes are chosen from a cyanobacterial species. This is because it may be difficult for a host cell to import phosphite if it is genetically modified to contain a transport system from an unrelated organism. Entry of phosphite into the cyanobacterial host cell may be quite different than it would be in, for example, a eukaryotic cell, or even in a non-photosynthetic bacterial cell. Such an unrelated transport protein could, for example, have difficulty localizing to the correct location for proper function. Thus, in an embodiment, it is an advantage to use cyanobacterial transporter genes to allow the phosphite to enter the cell.

In another embodiment, the phosphite transporter system that is utilized is a system encoded by a single gene. For example, in an embodiment, the phosphite transporter gene is obtained from the organism *Desulfotignum phosphitoxidans*. This transporter system is encoded by only one gene.

The gene can be codon-optimized for improved expression in the cyanobacterial host cell, if desired.

TABLE 3

Single Gene Phosphite Transporter

| Name | Source Organism | Nucleic acid sequence | Codon-optimized sequence | Protein sequence |
|---|---|---|---|---|
| Phosphite Transporter (PtdC) | *Desulfotignum phosphitoxidans* | SEQ ID NO: 26 | SEQ ID NO: 27 | SEQ ID NO: 28 |

The phosphite transporter proteins can be, for example, at least 50%, 55%, 60%, 65%, 70%, 75%, 80%, 85%, 90%, 95%, 97%, or 99% identical to the phosphite transporter proteins of *Cyanothece* sp. ATCC 51142 or *Desulfotignum phosphitoxidans*. In an embodiment, the genes encoding the phosphite transporter can be obtained from other genera of cyanobacteria, or from other types of microorganisms such as bacteria, fungi, yeast, or eukaryotic algae. In another embodiment, the phosphite transporter protein can be, for example, at least 50%, 55%, 60%, 65%, 70%, 75%, 80%, 85%, 90%, 95%, 97%, or 99% identical WP_006968136.1 from *Desulfotignum phosphitoxidans*; or ABU54328.1 from *Desulfotignum phosphitoxidans* DSM 13687.

The phosphite transporter genes can be on the same operon as the phosphite dehydrogenase, or the genes can be on a different operon. The expression of at least one of the genes can be controlled by a constitutive promoter. The expression of at least one of the genes can be controlled by a regulatable promoter, such as an inducible promoter.

The Phosphite-Utilizing Cyanobacterial Strains Can Out-Compete Contaminants

In many situations, such as outdoor large-scale cyanobacterial production facilities, cyanobacterial culture systems are likely to be non-axenic. If so, the new phosphite-utilizing cyanobacterial strains can out-compete non-phosphite utilizing contaminants, including many bacteria and fungi, for phosphorus when phosphite is supplied as the sole phosphorus source.

Many bacteria and fungi utilize phosphate, but not phosphite. When these species are contaminants in a cyanobacterial culture with phosphite-utilizing strains such as those provided herein, such contaminants typically grow poorly, if at all, when phosphite is the main or sole phosphorus source in the medium. Other bacterial contaminant strains can utilize both phosphite and phosphate.

In some cases, although the initial inoculum is typically axenic, it may become contaminated during growth in outdoor, large-scale systems. By the use of phosphite-utilizing cyanobacteria with a medium comprising phosphite rather than phosphate, the contamination (if any) will be delayed, and any contaminant organisms will be likely to grow slowly enough so as not to be a hindrance to the cyanobacterial growth and accumulation of product.

Consumption of Product Such as Ethanol by Contaminating Microorganisms

Another advantage of the invention is related to the fact that many contaminants actually consume the ethanol that is produced by the modified ethanologenic cyanobacteria. Left unchecked in a phosphate-containing system, some of these contaminants can grow to the point where most or even all of the ethanol produced in the culture is consumed by the contaminants. However, when these contaminants are starved for phosphorus, they typically grow poorly or not at all. Ethanol or other products that accumulate in the culture medium are thus not consumed, or are consumed at a much lower rate. The cyanobacterial cultures can be run for much longer times, and can accumulate much more ethanol, by using this method.

Figure 19A:
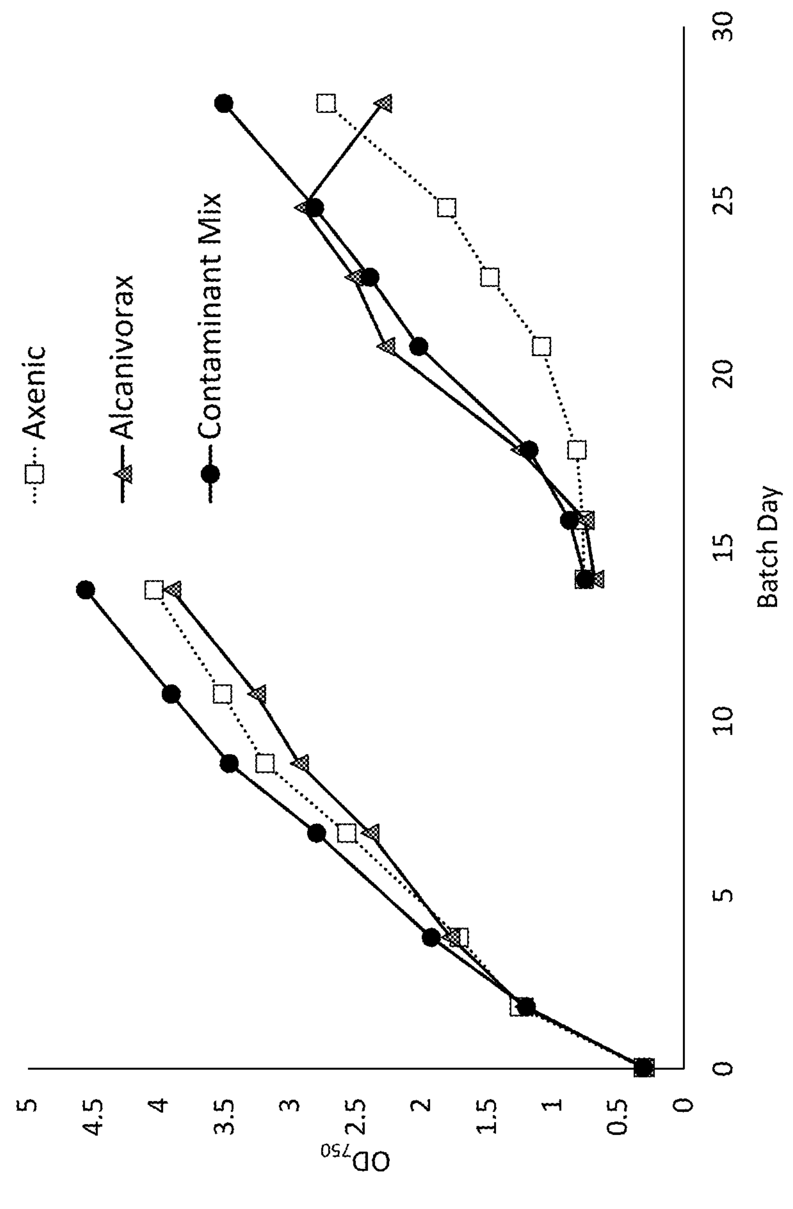
FIG. 19A is a line graph showing the cyanobacterial cell growth (in $OD_{750}$) of the phosphite-utilizing cyanobacterial strain AB0701, spiked with either the bacterial contaminant *Alcanivorax*, or with a "contaminant mix", when grown on phosphite as the sole phosphorus source. Empty squares: Axenic culture. Grey triangles: Culture with *Alcanivorax* added. Black circles: Culture with a contaminant mix added.
Figure 19B:
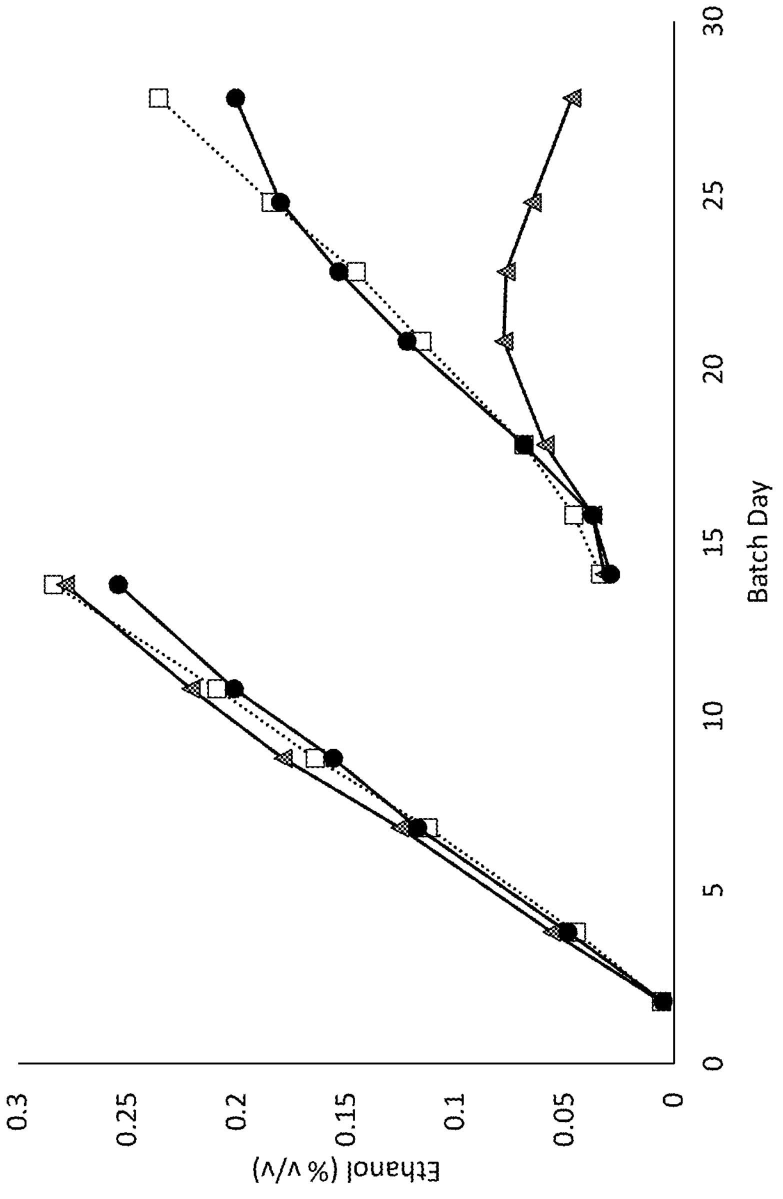
FIG. 19B is a line graph showing the ethanol levels (in % v/v) in the culture medium for the same time period as in FIG. 19A. Empty squares: Axenic culture. Grey triangles: Culture with *Alcanivorax* added. Black circles: Culture with a contaminant mix added. The ethanol accumulation is increased by use of phosphite rather than phosphate as a phosphorus source (compare to FIG. 18B). This is particularly noticeable during the second batch after day 14.

Cultures of the Phosphite-Utilizing Cyanobacterial Strains Can Accumulate More Product Cultures of the new phosphite-utilizing cyanobacterial strains are less likely to become contaminated, and if they do become contaminated, the contaminant growth is typically slower than would occur if the cultures are grown on phosphate as the phosphorus source. Because of this, the cyanobacterial cultures can accumulate more product. When ethanol is the product made by the cyanobacteria, for example, as shown in FIG. 19B and Example 17, more product can be accumulated, and if contamination occurs, it is less pronounced than with a phosphate system. Thus, cultures can be kept producing for a longer amount of time before the system is re-started. The cyanobacterial cultures can be grown for, for example, 1, 2, 3, 4, 5, 6, or more months, to produce the product of interest.

Plasmids Containing the Phosphite-Utilizing Genes Have Increased Genetic Stability When the phosphite-utilizing genes (also termed “phosphite genes” herein) are present on a plasmid in the cyanobacterial host cell, that plasmid can have an increased stability when the cultures are grown on phosphite as the phosphorus source. Thus, other genes of interest (such as the ethanologenic cassette) can be added to the same plasmid and will be more likely to remain on the plasmid and in the host cell, because cells that have lost the plasmid harboring the phosphite gene(s) would not be able to survive on phosphite as the only phosphorus source. Similarly, cells that have lost some (but not all) of the copies of plasmids containing the phosphite utilizing genes would not be able to compete well in a phosphite-only medium. Thus, the presence of the phosphite genes creates a strong selection pressure, increasing the likelihood of keeping the phosphite genes, neighboring genes (such as genetically modified production genes), and the entire plasmid in the cell. This provides a simple system to ensure transgene stability in a host cell.

Co-localizing Phosphite-utilizing Genes with Production Genes to Increase Genetic Stability of Production Genes In an embodiment, the phosphite dehydrogenase gene, or other genes required for phosphite utilization in cyanobacteria, can be located on the same operon as at least one production gene. This can further increase the stability of the production gene when the cultures are grown in phosphite as the phosphorus source. This is because an inactivation, deletion, insertion, or certain other mutations of the production gene would be more likely to also negatively affect the phosphite utilization gene if it is located near the production gene, and particularly if it is downstream of the production gene, and controlled by the same inducible promoter. If the upstream production gene is inactivated, it is likely that the downstream gene in the same operon would also exhibit reduced expression.

In an embodiment, a single operon containing at least a promoter, at least one production gene, and at least one phosphite utilization gene are present on a plasmid, or are present in the chromosomal DNA. In an embodiment, the construct is fully segregated.

In an embodiment, the product production gene is a pdc gene, and the product is ethanol. In an embodiment, a regulatable promoter, such as an inducible promoter, controls both the pdc gene and the phosphite dehydrogenase gene. In this way, phosphate can be used as the phosphorus source during scale-up, after which the inducing agent is added to initiate phosphite utilization, along with the production of the product. A suitable example of this system is described in Example 20.

The Method can be Improved Further by a Knock-out of the Phosphate Metabolism Regulatory Gene PhoU As mentioned herein, most contaminating bacterial species utilize phosphate, but are relatively poor at utilizing phosphite. However, even when the only source of phosphorus that is fed to the cyanobacterial cell culture is phosphite, typically some amount of phosphate can still be found in the medium, allowing the contaminants to survive and grow. The source of this residual phosphate is unknown, but may be from leakage of the cyanobacterial cells, cyanobacterial cell death, trace contamination in medium components, or even the slight non-biological conversion of phosphite to phosphate that can occur in aqueous medium over time. Even a small amount of phosphate in the medium can cause contaminant growth, so a method has been devised to allow the cyanobacterial cells to take up any residual amounts of phosphate rapidly.

In an embodiment, the competitive advantage of a cyanobacterial cell genetically modified to utilize phosphite can be further improved by modifying the cell so that it also allows for faster uptake of any residual phosphate, particularly if it is present at a low level in the medium. This was achieved by the use of a knockout of the phosphate metabolism regulator PhoU. With the knockout of this gene, cyanobacterial cells can more quickly consume residual amounts of phosphate that may be present in the medium. This prevents phosphate-utilizing contaminating microorganisms from obtaining the phosphate needed for their own growth. The PhoU knockout, in combination with the phosphite utilization genes, allows the cyanobacterial host cells to more successfully out-compete contaminants for phosphorus. Even when contamination does occur, growth of the contaminants is delayed, and the cultures can accumulate the product of interest (such as ethanol) to higher levels.

To accomplish this, a knock-out of the phosphate metabolism regulatory gene phoU can be performed. This results in much faster uptake of phosphate from the medium into the cyanobacterial cell, independent of the levels of phosphate or phosphite in the medium or already in the cell. The nucleic acid sequence of the phoU gene endogenous to *Cyanobacterium* sp. PTA-13311, for example, is shown in SEQ ID NO: 29. The amino acid sequence of the PhoU protein endogenous to *Cyanobacterium* sp. PTA-13311 is shown in SEQ ID NO: 30.

In general, this knock-out allows for phosphate released from the cells to the medium to be taken up faster by the cyanobacterial production cultures than by many of the contaminating organisms that may be present. In this way, the genetically modified cyanobacteria can both 1) utilize an uncommonly used source of phosphorus and 2) quickly take up the commonly used phosphorus source phosphate, if it becomes present in the medium. Accordingly, it is likely that this combination is particularly effective in providing a competitive advantage to the cyanobacterial production cells.

Exemplary Phosphite Utilization Gene Cassettes

Several configurations of phosphite dehydrogenase genes in combination with phosphite uptake genes have been prepared and tested. The table present in FIG. 5 lists several constructs that have been prepared, as well as the genotype, host strain, promoter type, Ptx or Pt transporter type, and the sequence identification number.

New cyanobacterial strains having different sources of the genes, as well as combinations thereof, different promoters for their induction, as well as various gene cassettes for ethanol production, were prepared and examined. The strains have been tested both without and with the production of a product of interest (ethanol in these cases). Some of the strains have also been tested in the presence of bacterial contaminants, to determine whether the modified cyanobacteria can better out-compete common heterotrophic bacterial contaminants.

Preparation of Recombinant Vectors for Genetic Modification of Cyanobacteria

Cyanobacteria can be modified by the addition of phosphite dehydrogenase genes and phosphite transport genes, and can also be modified to produce ethanol or other products of interest. The DNA comprising the genes described herein can be amplified by polymerase chain reaction (PCR) using specific primers. The amplified PCR fragments were digested with the appropriate restriction enzymes and cloned into either a self-replicating plasmid or a plasmid designed for genome integration. An antibiotic resistance cassette for selection of positive clones can be present on the appropriate plasmid.

In an embodiment, the nucleic acids of interest can be amplified from nucleic acid samples using amplification techniques. PCR can be used to amplify the genes from genomic DNA, mRNA, cDNA, genomic libraries, or from cDNA libraries. PCR and other in vitro amplification methods can also be useful, for example, to clone nucleic acid sequences that code for proteins to be expressed, to make nucleic acids to use as probes for detecting the presence of the desired mRNA or DNA in samples, and for nucleic acid sequencing.

To use isolated sequences in the above techniques, recombinant DNA vectors suitable for transformation of cyanobacteria can be prepared. Techniques for transformation are well known and described in the technical and scientific literature. For example, a DNA region containing one or more of the genes described herein can be combined with transcriptional and other regulatory sequences which will direct the transcription of the gene or genes in the transformed cyanobacteria.

Transformation vectors for genetic modification of cyanobacterial cells can be derived from endogenous plasmids, or can be from heterologous sources. The cyanobacterial host strain *Cyanobacterium* sp. PTA-13311, for example, contains endogenous plasmids. In combination with other genotypic and phenotypic attributes, these endogenous plasmids differentiate *Cyanobacterium* sp. PTA-13311 from other *Cyanobacterium* strains.

A transformation vector derived from endogenous plasmid p6.8 from *Cyanobacterium* sp. PTA-13311 was developed. In an embodiment, this transformation vector can be used to transform the *Cyanobacterium* sp. PTA-13311 strain from which it was derived.

The endogenous p6.8 plasmid was isolated by an in vitro transposition reaction with an EZ-Tn5 R6K γ Ori/Kan-2 transposition kit from Epicentre (Madison Wis., USA) by following the manufacturer's protocol. The plasmid 6.8 has been modified for use as a transformation vector containing genes of interest for the production of products of interest.

In an embodiment, the phosphite utilization genes are located on the same plasmid as the genes of interest for the production of products of interest. In another embodiment, at least one of the inserted genes is located on a different plasmid or on the cyanobacterial chromosome. In an embodiment, the genes of interest are inserted into the cyanobacterial chromosome. When the cell is polyploid, the gene insertions can be present in all of the copies of the chromosome, or in some of the copies of the chromosome. In another embodiment, the inserted genes are present on an extrachromosomal plasmid. The extrachromosomal plasmid can be derived from an outside source, such as, for example, RSF10-based plasmid vectors, or it can be derived from an endogenous plasmid from the cyanobacterial cell or from another species of cyanobacteria.

In an embodiment, the inserted genes are present on an extrachromosomal plasmid, wherein the plasmid has multiple copies per cell. The plasmid can be present, for example, at about 1, 3, 5, 8, 10, 15, 20, 30, 40, 50, 60, 70, 80, 90, or more copies per host cyanobacterial cell. In an embodiment, the plasmids are fully segregated. In another embodiment, the inserted genes are present on one cassette driven by one promoter. In another embodiment, the inserted genes are present on separate plasmids, or on different cassettes. In yet another embodiment, a transformation vector from the above-described p6.8 endogenous plasmid can be used to transform cyanobacteria from a broad range of genera.

Codon Improvement of Recombinant Genes

The inserted genes can be modified for optimal expression by modifying the nucleic acid sequence to accommodate the cyanobacterial cell's protein translation system. This method utilizes codon improvement (sometimes referred to as codon optimization or codon adaptation), which can be performed to increase the expression level of foreign genes such as antibiotic resistance genes, genes for production of ethanol or other products of interest, and any other inserted genes to be expressed in the host cell.

The underlying rationale is that the codon usage frequency of highly expressed genes is generally correlated to the host cognate tRNA abundance. (Bulmer, Nature 325: 728-730; 1987). Modifying the nucleic acid sequences in this manner ("codon improvement") of the recombinant gene can be performed for improved expression in the cyanobacterial host cell. Codon improvement can also be performed by adapting the codon usage of the recombinant gene to the codon usage in the host cell. In an embodiment, only 2% to 6% or 1% to 10% of the codons of variants of recombinant genes are codon improved. In another embodiment, highly codon improved variants of recombinant genes, at least 25%, to at least 50%, 65% or even at least 70% of the codons have been changed. In another embodiment, recombinant genes are used which are not codon improved.

Codon improvement of heterologously derived genes (such as genes encoding antibiotic resistance genes, the phosphite uptake and utilization genes, and the recombinant genes for the production of products of interest, such as genes in an ethanologenic cassette) was guided by the *Cyanobacterium* sp. PTA-13311 codon usage table derived from ribosomal proteins and highly expressed genes (such as photosynthesis genes). To improve heterologous gene expression, original gene sequences of interest (such as *Z. mobilis* pdc and *Synechocystis* sp. PCC 6803 adh) were assessed with the online software OPTIMIZER (Puigbò P, Guzmán E, Romeu A, & Garcia-Vallvé S (2007), (OPTIMIZER: a web server for optimizing the codon usage of DNA sequences *Nucleic Acids Research* 35(suppl 2):W126-W131), based on the codon-usage table derived from the *Cyanobacterium* sp. PTA-13311 genome.

The codon adaptation index is a measure of directional synonymous codon usage bias, and its potential applications, (see Nucleic Acids Research 15(3):1281-1295). The effective number of codons (see, Wright F (1990) Gene 87(1):23-29) are designed to match those of highly expressed genes (such as ribosomal proteins) in the *Cyanobacterium* sp. PTA-13311 genome. The resulting polynucleotides using improved codons were further modified and optimized to avoid the presence of any known or predicted putative *Cyanobacterium* sp. PTA-13311 endonuclease restriction sites (AvaI, BsaHI, KasI, XhoI etc.); internal Shine-Dalgarno sequence and RNA destabilizing sequences; an internal terminator sequence; and a repeat sequence of greater than about 10 bp (see, Welch et al., PLOS One 4, e7002; 2009; and Welch et al., Journal of the Royal Society; Interface 6 (Suppl 4), S467-S476; 2009).

In an embodiment, the nucleic acid sequences of the recombinant genes are modified so that they will have improved expression in cyanobacteria. For example, the selectable marker gene that confers gentamycin or kanamycin resistance was codon optimized for higher expression in cyanobacteria. In an embodiment, as a result of codon improvement, the GC % of the antibiotic resistance genes decreased from 40-53% to 33-40%, which is similar to that of *Cyanobacterium* sp. PTA-13311 coding genes (about 36% on average). The codon adaptation index of the codon improved antibiotic resistance genes is significantly improved from less than 0.4 to greater than 0.8, which is similar to that of *Cyanobacterium* sp. PTA-13311 endogenous genes.

Table 4, below, depicts the codon usage statistics within the cyanobacterial strain *Cyanobacterium* sp. PTA-13311.

TABLE 4

Codon Usage Table for *Cyanobacterium* sp. PTA-13311

| Amino Acid | Codon | Fraction | Number | Frequency (/1000) |
|---|---|---|---|---|
| Ala | GCA | 0.293 | 20724 | 18.356 |
| Ala | GCC | 0.214 | 15144 | 13.414 |
| Ala | GCG | 0.14 | 9870 | 8.742 |
| Ala | GCT | 0.353 | 24915 | 22.068 |
| Arg | AGA | 0.347 | 16040 | 14.207 |
| Arg | AGG | 0.09 | 4158 | 3.683 |
| Arg | CGA | 0.106 | 4886 | 4.328 |
| Arg | CGC | 0.131 | 6043 | 5.353 |
| Arg | CGG | 0.039 | 1813 | 1.606 |
| Arg | CGT | 0.288 | 13329 | 11.806 |
| Asn | AAC | 0.22 | 14609 | 12.94 |
| Asn | AAT | 0.78 | 51712 | 45.804 |
| Asp | GAC | 0.193 | 11063 | 9.799 |
| Asp | GAT | 0.807 | 46399 | 41.098 |
| Cys | TGC | 0.218 | 2501 | 2.215 |
| Cys | TGT | 0.782 | 8976 | 7.95 |
| Gln | CAA | 0.806 | 43747 | 38.749 |
| Gln | CAG | 0.194 | 10554 | 9.348 |
| Glu | GAA | 0.787 | 60690 | 53.756 |
| Glu | GAG | 0.213 | 16451 | 14.571 |
| Gly | GGA | 0.324 | 22709 | 20.114 |
| Gly | GGC | 0.125 | 8720 | 7.724 |
| Gly | GGG | 0.151 | 10542 | 9.338 |
| Gly | GGT | 0.401 | 28065 | 24.859 |
| His | CAC | 0.251 | 4859 | 4.304 |
| His | CAT | 0.749 | 14516 | 12.858 |
| Ile | ATA | 0.195 | 18334 | 16.239 |
| Ile | ATC | 0.19 | 17872 | 15.83 |
| Ile | ATT | 0.616 | 57964 | 51.342 |
| Leu | CTA | 0.088 | 10776 | 9.545 |
| Leu | CTC | 0.058 | 7129 | 6.314 |
| Leu | CTG | 0.033 | 4040 | 3.578 |
| Leu | CTT | 0.116 | 14162 | 12.544 |
| Leu | TTA | 0.571 | 69559 | 61.612 |
| Leu | TTG | 0.133 | 16235 | 14.38 |
| Lys | AAA | 0.836 | 59396 | 52.61 |
| Lys | AAG | 0.164 | 11694 | 10.358 |
| Met | ATG | 1 | 20093 | 17.797 |
| Phe | TTC | 0.172 | 8420 | 7.458 |

TABLE 4-continued

Codon Usage Table for *Cyanobacterium* sp. PTA-13311

| Amino Acid | Codon | Fraction | Number | Frequency (/1000) |
|---|---|---|---|---|
| Phe | TTT | 0.828 | 40450 | 35.829 |
| Pro | CCA | 0.169 | 7746 | 6.861 |
| Pro | CCC | 0.275 | 12613 | 11.172 |
| Pro | CCG | 0.066 | 3012 | 2.668 |
| Pro | CCT | 0.491 | 22560 | 19.982 |
| Ser | AGC | 0.088 | 6435 | 5.7 |
| Ser | AGT | 0.306 | 22393 | 19.835 |
| Ser | TCA | 0.14 | 10217 | 9.05 |
| Ser | TCC | 0.102 | 7465 | 6.612 |
| Ser | TCG | 0.044 | 3196 | 2.831 |
| Ser | TCT | 0.321 | 23473 | 20.791 |
| Thr | ACA | 0.26 | 15649 | 13.861 |
| Thr | ACC | 0.236 | 14251 | 12.623 |
| Thr | ACG | 0.083 | 5024 | 4.45 |
| Thr | ACT | 0.42 | 25340 | 22.445 |
| Trp | TGG | 1 | 14964 | 13.254 |
| Tyr | TAC | 0.187 | 7364 | 6.523 |
| Tyr | TAT | 0.813 | 31912 | 28.266 |
| Val | GTA | 0.28 | 18541 | 16.423 |
| Val | GTC | 0.117 | 7778 | 6.889 |
| Val | GTG | 0.184 | 12184 | 10.792 |
| Val | GTT | 0.419 | 27713 | 24.547 |
| End | TAA | 0.63 | 2495 | 2.23 |
| End | TAG | 0.22 | 848 | 0.76 |
| End | TGA | 0.15 | 591 | 0.53 |

Choice of Promoters

Any desired promoter can be used to regulate the expression of the inserted genes. Exemplary promoter types include but are not limited to, for example, constitutive promoters, regulatable promoters such as inducible promoters (e.g., by nutrient starvation, heat shock, mechanical stress, environmental stress, metal concentration, light exposure, etc.), endogenous promoters, heterologous promoters, and the like. Additional promoters that can be used are described, for example, in U.S. Pat. Nos. 6,699,696, 9,650,642, 8,163,516, 8,404,466, 9,315,820, 9,765,364, 9,551,014, 9,476,067, 8,848,369, 9,315,832, 9,157,101, 9,127,297, 9,493,794, 9,493,795, and International Patent Application Nos. PCT/EP2012/067534, PCT/US2013/065568, PCT/US2013/065574, PCT/US2015/000210, all of which are incorporated herein by reference in their entireties.

The inserted genes can be controlled by one promoter, or they can be controlled by different individual promoters. The promoter sequences can be derived, for example, from the host cell, from another organism, or can be synthetically derived.

The recombinant gene(s) can be under the transcriptional control of a constitutive promoter. In this way, a sustained level of transcription and, therefore, enzymatic activity of the corresponding protein can be maintained during the whole period of cultivation. For example, the constitutive promoter can be endogenous to the cyanobacterial cell. This has the advantage that no recombinant transcription factor has to be present in the host cell. The endogenous promoter is usually well-recognized by the metabolically enhanced cyanobacterial cell without the need to introduce further genetic modifications.

Suitable constitutive promoters include, without limitation, the PrpsL promoter (Gene ID: ABICyano1_orf1758), PpsaA promoter (ABICyano1_orf3243), PpsbB (ABICyano1_orf2107), PcpcB promoter (ABICyano1_orf2472), PatpG (ABICyano1_orf1814), PrbcL promoter (ABICyano1_orf1369), PpetE promoter (ABICyano1_orf2417), and variations thereof. Further suitable endogenous constitutive promoters from genes with unknown function exhibiting appropriate transcriptional activity include, without limitation, the promoters of Gene IDs ABICyano_orf1924, ABICyano_orf1997, ABICyano_orf3446, ABICyano_orf0865, ABICyano_orf1919, ABICyano_orf3278, ABICyano_orf1181, ABICyano_orf1627, ABICyano_orf0265 and ABICyano_orf2536, ABICyano_orf0615, and variants thereof.

In an embodiment, the promoters can be derived from the cyanobacterial strain *Cyanobacterium* sp. PTA-13311, or they can be derived from another cyanobacterium or from another organism. In an embodiment, the promoters can be about 60%, 70%, 75%, 80%, 85%, 90%, 95%, 97%, 99%, or 100% identical to the promoter sequences described herein.

The promoters can be regulatable promoters, such as inducible promoters. For example, certain promoters are up-regulated by the presence of a compound, while other promoters can be up-regulated by the absence of a compound (also termed "repressible").

Various promoters that can be used include promoters that are regulatable by the presence (or in other promoters, by the absence) of inductors such as different metal ions, different external stimuli such as heat, cold or light. In some embodiments, the regulatable or inducible promoters are induced under conditions such as nutrient starvation, stationary growth phase, heat shock, cold shock, oxidative stress, salt stress, light, darkness, metal ions, organic chemical compounds, and combinations thereof. For example, a particularly tight control of the expression of gene can be achieved if a gene is under the transcriptional control of a Zn-, Ni-, or Co-inducible promoter. Exemplary Zn-regulatable promoters and their variants are described, for example, in International Application No. PCT/EP2013/077496. Exemplary Zn, Ni, and Co-regulatable promoters are described, for example, in International Application No. PCT/2012/076790, both of which are incorporated by reference herein in their entireties.

In a further embodiment, the regulatable or inducible promoter is inducible by a change of a metal-ion concentration. Such a change of metal-ion concentration includes for instance the addition or depletion of certain metal ions. Suitable inducible promoters include, without limitation, the PziaA promoter, the PsmtA promoter, PaztA promoter, the PcorT promoter, the PnrsB promoter, the PpetJ promoter, the Porf0316 promoter, the Porf0221 promoter, the Porf0223 promoter, the Porf3126 promoter, the PmntC promoter, and variations thereof.

Preferably, the regulatable or inducible promoter is endogenous to the cyanobacterial cell. An endogenous inducible promoter is usually well-recognized by the metabolically enhanced cyanobacterial cell without the need to introduce further genetic modifications.

In further embodiments, the choice of regulatable or inducible promoters can include, but are not limited to, PntcA, PnblA, PisiA, PpetJ, PggpS, PpsbA2, PsigB, PlrtA, PhtpG, PnirA, PnarB, PnrtA, PhspA, PclpB1, PhliB, PcrhC, PziaA, PsmtA, PcorT, PnrsB, PnrsB916, PaztA, PbmtA, Pbxal, PzntA, PczrB, PnmtA, PpstS, and the like.

The regulatable or inducible promoter can, for instance, also be a nitrate inducible promoter. Suitable nitrate inducible promoters include, without limitation, the PnirA promoter, the PnrtA promoter, the PnarB promoter, and variations thereof.

In certain other preferred embodiments, truncated or partially truncated versions of these promoters including only a small portion of the native promoters upstream of the transcription start point, such as the region ranging from −35 to the transcription start can often be used. Furthermore, introducing nucleotide changes into the promoter sequence, e.g. into the TATA box, the operator sequence, 5'-untranslated region and/or the ribosomal binding site (RBS) can be used to tailor or optimize the promoter strength and/or its induction conditions, e.g. the concentration of inductor required for induction. In some preferred variants, the different inducible promoters are inducible by different metal ions.

The promoters hspA, clpB1, and hliB can be induced by heat shock (raising the growth temperature of the host cell culture from 30° C. to 40° C.), cold shock (such as, for example, reducing the growth temperature of the cell culture from 30° C. to 20° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium and the promoters psaA and psbA2 can be induced by low light or high light conditions. The promoter htpG can be induced by osmotic stress and heat shock. The promoter crhC can be induced by cold shock. An increase in copper concentration can be used in order to induce the promoter petE, whereas the promoter petJ is induced by decreasing the copper concentration. Additional details of these promoters can be found, for example, in PCT/EP2009/060526, which is incorporated by reference herein in its entirety.

In an embodiment, the promoters of any of the above embodiments may be selected from the endogenous inducible promoters identified in *Cyanobacterium* sp. with the ATCC accession number PTA-13311 listed in Table 5, below, and variants thereof.

TABLE 5

*Cyanobacterium* sp. ABICyano1 endogenous promoter sequences

| Promoter | Sequence | SEQ ID NO: |
|---|---|---|
| PnirA | AATTAATAACTTCTTCCTGTACGGGCGAATGGCCATTTGCTCCTAAC<br>TAACTCCGTACTGCTTTGCGGAACGAGCGTAGCGAACTCTCCGAATT<br>ACTAAGCCTTCATCCCTGATAGATGCAAAAAACGAATTAAAATTATG<br>TGTAAAAAGAAAATGTGTCTTTATTTAGTAGTCAAAGTTACAAAATA<br>TTAAGAATCAAATTAATAATGTATTGGGCAGTTAAGTATATAAGTCT<br>TTAAATATTTATTTGTATTCAATATATTAACCGAGGACAAATT | 31 |
| Porf3126 (PsmtA) | CCAATATCTTGTCATACATACTTATTTGCCTCACTATTAGCCCTATAT<br>GTCTCTATTGTATTTTTCTTTTTCTCCTATTCCTAGATCTTGTAATGAA<br>TCATTACTCTCTGAAATATAGCTACTAATTTTATGGTTGTTTGTAAAA | 32 |

TABLE 5-continued

*Cyanobacterium* sp. ABICyano1 endogenous promoter sequences

| Promoter | Sequence | SEQ ID NO: |
|---|---|---|
| | TATATTAACAAATGAACAATAAATCATATTTTGTGTTAATCTAATTA<br>TTAGACAACTACTGAATTTATATTCAGATATTCACAGATAGGAGAAT<br>TTTGATT | |
| PnrtA | TATTATTTTTCGTTTATATGCAGATTTAGAATAAACAAAATTCATTTA<br>CTGCAAATTTTCAAAAAAATGTGACTAAACATACAAAATAAAGAAA<br>AAATAAAGTTTTAAATTTATGTACATCAAACTTAAGAAATGTTTAAA<br>TTACTTAGAAATTTATAGTTC | 33 |
| Porf3461 (petJ) | TTTATATATAAACTCGAATAAAATTATCAATATAAAGTCAAACTATA<br>TCTATCCTATTTTAACTGCTATTGGTAAGTCCCTTAATTAGTGTTGGG<br>GTGAATAGATTTTAAAAGGGCAAACCCCCCTTTATCCTCCCTCGAGA<br>GGGGGGAGGGCAAAAGGCAAGGGGCAAGGGAAAAATTAAGAATTA<br>AGAATTAAAAACTCCGAACACCTGTAGGGGCGAATAGCCATTCGCT<br>TCCCCTCATCCCCCCATCTCCCCAACACCCTAAGCCCCTACTCGTTAC<br>TCATTTATTTACATCATTTATTTACATCATTAAGAAAAGTAACAAATT<br>TTGACAAGTAGTCTTTTGACAGGAAAAAGCAAATTCTCGAAGATGA<br>AAACAATAGAAAAAAATTCAATCTTACAGTAACGATGAAAAAACTT<br>TTAGGCTTAATT | 34 |
| PnarB | TGTCTCAAAAAGACAGGTTTTTTTATGAAAGTAATAAGAAATAAGT<br>AGAAGTGAGGAGTTGGAAAGATAGGATTAAGAATTAGGAGTTAACT<br>ATTTTCATTCTTTATTCTTCCATTGCCCATTGAGAAATCATATCTAAA<br>ATCAGCAACGCCAAATTTTAGATGCAAAATAACCATAAATAAAATG<br>CAGAAAAAAGAATACTTTAGATCTTCCGTATCAGAAGATACATTTCT<br>TAACAAAATCTGGTGACAAGATTAAACACACGAAATCCGAGGTTTT<br>ATATATTGATTAGTCCTAG | 35 |
| Porf1071 (PmntC) | ATTCTGTGAATTGATTAGATTTGAGGTTTTTTAAGAGGTTGATTACCT<br>TGCCTCCAAAAAAATCATAACACACTAATGCTCTATATGAAAGGGCT<br>TTAGACCCATAGGTTTTTGAGAAAAAAACTTGCTAACTCTCGGACAA<br>TGTCAGCATAACTAAAGTCAATTCTTTTCGTACTTTATAATTGTCTAT<br>AATTTAATATACAACTGTTCTGAAACTAGTTTTTCTCTACATTCCTTA<br>GTTTTATCTGAGTAAGGTTGCTTGTAACTTAACTTCGGTTGGGCCTAA<br>AAATATCCGATTAGGAGCAGGTGTCAGACTTTAATTAATTATTAATT<br>ATTAATTGCTTATTGCCAACCCTCGGCGACACCACTTTTTCATCAGCC<br>CCAGATAAAGATTGATGTTTTAGTTTTGTTTCTTTTTATCCCCTAATT<br>CAACTAATACAAGTAAAACTAAGGTTGTTTATCAAAAATGATGGTTG<br>ATGTTTGGGTAAATTTTAAGATATTATGAAAAGAAAATGAATAAAA<br>AATGAAAAATCTTT | 36 |
| Porf0221 | GAATATCTCATCCTTAGCTTCTACTTATACCTTCAGCATAGTTAAAAA<br>TCATCCCTTTATTGATGGTAATAAAAGAACAGGTTTTATTAGTGGAG<br>TAACCTTTTTAATGCTCAATGGTTCTCACTTTACTGCTTCTGAAGTGG<br>AAGTAGTACATATCATCCAAACCTTAGCTAGTGGCAGAATTACCGAG<br>GAAGAATTACAACAATGGTTCGTAAGGAAAAGTAAGCAGATGAATA<br>ATTAAAGCATCATTTCATCCTCATTTCATATTCTCCTGTCACCATGGT<br>ATGGAAGATTAGGTAAAAATGAGGAAAAAGTTTATT | 37 |
| Porf0223 | ATACATGGTTGGTTCACTGACTTTTACCCCAGTTTTCTCTTTGAACAA<br>TTGGCATAACTCTGAAAAAATCAGATCGGGCTTTTGTTGAATTATTT<br>GTTCAATCAAAGCAAAACCGTGATTGTCTATTTTCTTTTTTTTCCCAC<br>CACTCATAGATAAAAATTTATCCCGAACTCAGGTTATATTAAGTTCG<br>GATGATCACTTAAGATAATTGATCAGATTGGTTAAGATAGAGAAAA<br>ATTCTTTTTCATAGTGATTTCATAATTGATAGTTACAATAACGATTAT<br>TATTTAGTAAAAAGATTTTCAAATC | 38 |
| Porf0316 | TGGTCAAGTTACTATATGTTTAGAAACAACAAAAAAAGAAGTCATT<br>ATAAAAATAATTGATACAGGAATTGGCATTAATAAAGAAGAACAAA<br>AATTAATTTTTAATCGTTTTTATCGAATCAATAAAGCAAGAAATAGA<br>GAGAAAGGCAGTTGCGGATTAGGTTTAGCTATTGCAAATGCGATCG<br>CGCTTAATCATGGTGGTAGAATAATTTTAGAAAGTCAAGAAAATCA<br>AGGCAGTATTTTTACCGTTTATTTACCGAAAATCATTTCATCCTAATT<br>TCATATTCTTTTGACAGAATCAAAGGTAAAGATAAAAAGAGAGAAA<br>CAGTC | 39 |
| Porf0128 | CCTCAACTACAAGTTCTTTTATATATTACTTTAACCTGAGTTTTGGAT<br>AAGCTGAAAGCATTATTTTCTCGTAGTCAGAAAACCTTATAGCTTCT<br>TAGAAATAACGATAAAATTACCTTAATCCGAACTGACGTTAAATATA<br>TTCACCCCTATCACCCCAAAACCCTAAGCCCCTACTTCCCCCTTTCCC<br>TTCATCACCTCATCCCCCCATCCCCTAACACTTAACCTTATTCTTTAT<br>TCTTAAACCGAACTGAGGTGAAGTTGCAGAATACCCATGGGGGGTT<br>ACAGCATTGTAGAAAAATAAATATTCTTTCATTATTAAGGTTGTTTG<br>GTAAAAATATGTGAAAACCCTAATAATT | 40 |

TABLE 5-continued

*Cyanobacterium* sp. ABICyano1 endogenous promoter sequences

| Promoter | Sequence | SEQ ID NO: |
|---|---|---|
| Porf1486 | GGGGACAGACATATTTTTATCATAATGGTAAATTCATAATAATTTTA<br>GACTTTTTTTTGCAAAAATTAATCTCACTCTCTTCTTTCCCTATCTCCC<br>ATTGTTTCTTATATCCCAATGCCCCAATACCCAAAGCTCAGAAAATA<br>GGTATTAGCGAAGAGGTGTTGATCCCCTCCCCTAGCAAAATATACTC<br>CTATATAGTAAAGTGAGAAAGTGAAGAAATAAGATCAAGTTCGCAA<br>TTT | 41 |
| Porf3293 | TTGACGATTGTATTGACTTACGCCAAATGGCTTACCCTCATAGTGAA<br>TAGTTGATAATTAAGAATTAAAAATCCCGTTCACGACAGAAGGGAG<br>TGTAAGAGCCTTCGGTGCGAACTCTCATCTTCCCTGAAACCTGACAC<br>CTGAAACCTGACACCTGAAACCTGACACCTCATCTCCCTAATCCCCT<br>AATTTTAATGAAAAAATACCCTGAGTGGGCATTGAAAAAAAAGAAA<br>AGTTGTTCGACTATGAAATAAGAATTCTGCACTTCGTGAGAAAAAAG<br>GAAATGAAAT | 42 |
| Porf3621 | CTATTTAACTAGGAAAAGGTAAAGTTAAAAGGACAAGGGTAAATAA<br>TTAAAAATTAAGAATTAAGAACTTCTAACTCTCATTACTCATTACTT<br>ATTTCCTCCTCTCACCCCTTCTCCTGATCACCTCTTCTCCTCAATACTC<br>GGAACTCATTTCCCCATGGTGTGACACTCAAATCAAAAGTCTGTTAT<br>TGACTTTCAGATGAAATATTACTATGATAACAATATCCCCCCTATGG<br>GTATATAAAAATATGAGCGATATTAGTTAAAAATCAAATTTGGATTT<br>TTTTTCTGAAAATATTTTAAGATTAAGTAAAGATAAGTAAAGAAATT<br>ATAAGCAATTTTGTTAAATCATACC | 43 |
| Porf3635 | CTCACACTGAAAATATTGCCACAAGAAATAAAGATCAAGCAATAAT<br>CCTGACTAAAAAGGAATAAAGTAATTATCCTTTTCCTGATATGTTAT<br>CTGACTTGTTGTTTCTTAGTCATGTTCCTTCCATTTTTATTTTTGTTTT<br>TATCATTTTTATTACAAAAATTTCTTAATAGGGCTAAAGCATTTAGTT<br>AGTTTTTTAGCTCTCAACAAGTTGACTAATCAATATAATGCCCTAAG<br>TTAATTTGCCCTTGGTTTGACGGAGGATATTGGAAAAAAGAAACTTC<br>TCGTTGTATTTCACAGGGAAAAGGGGGAAATTTTTATTAATAACTAAA<br>CAATAGAAAATAATTATTTATTTATATTATTTTGTGAACAAATGTTCA<br>AGAATTAAAGTGTAATAAGAAAATTTATTTTTTTATATTTATTTAAA<br>ACTTAGATATAAGCCTAAAGGTCTGAAATTATTATTAGACAATCAAT<br>TGATTCAGAGGTAATAGTTTTTTACTTAAAAATATTTTTTCAAAATTA<br>TCCCCTATTTGGGTATTGAAAAATAAATAAATTCAAGTAATAATATA<br>CAGAATAAAGGAAAATCTAATCTTAAAAATTTTGTGTGTGAGGAATT<br>GAAA | 44 |
| Porf3164 | CAAATCACGAGAATTTATGTAGGGACTATTTTGGGTTGACGGTGGAG<br>AGTATGTCGCCCTTGAATTATGACCCGAAGATGAAGATGTCGGGGA<br>GGTGGAAGGACGGTCTTTAAGAGGTTTAACATCAAAGTTGGTCATA<br>ATCTCTGTCCCTGTTTGATAACTACTATTTAATTTTGAGTTGTTTTAG<br>GTACATCAAAATACCCAAATCCTTACTCTCCCCTCAATATACAACAA<br>AAAAAACTTTTTGATTCACTTTAGTCATAAAAATTAGAATTTATCTA<br>CCGAAATATTACATAAATGTAATGTATATATTTTCTGATTTATTCCGT<br>GTGAGCCATGATTCATAATTTATAATTCATAATTTCTAAATATGCCCC<br>TACAATGGATATAGAATGTCATTTTAATTATAGGTATCATAATCGTG<br>GTAGTTACTCCGGAAAAAACTATTGAATCAAATTCAGTCTCACCTGC<br>TACAGATAGAGTAGCCGTTATTCTT | 45 |
| Porf1072 | CTACAGGGGCAAGATTTGGCGGAAATCTATATGTGGATTCTCTTTCA<br>AGTGAAGAAGGTGCAGTGCCGACTTATCTGGACTTATTAGAATACG<br>ATATTCGCACTATTACTAATGGTTTGTTAGCAGGAGTGAACAATTAA<br>AAATTTTTTCCTAATTGACGAATAAAAAATCAATGTCAACTAATAGT<br>TAACAATACTCTCTGAAAACCAAAAATTGTCAACCAAAACATAACA<br>TAATTTTTACCCAAAAACCTCATTTATAAACTTTAAGGATAAAATCA<br>ATG | 46 |
| Porf1074 | GGGATTAGAGAGTTCAAAGTTAGGAATGAGGTGTCAGGTTTTAGGTT<br>TCAGGTTTAGGGGAGCAATGAGAAAGAGGTTTCAGGTTTCAGGTGT<br>CAGGTTGCAGGTGTCACAGGTGATGAGGGGATGGGGGATGAGGGGG<br>AAACAAGTAAGTAATAAGTGTTCGGAGTTTTTAATTCTTAATTCTTA<br>ATTTTTCCTTTGCCTCTTGCCTTTTGCCTTGTCTTAATTACTAATTTCT<br>AATTAAAATGATTGTGTTTTCTAGTTTAGTCTCATGGTTACTTGAACC<br>CTTACAGCATAGTTTT | 47 |
| Porf01075 | TTACAAACGGCGGGAATTATTATGGTAGTAGCGATGTTAGTAACCCC<br>GGGTGCGATCGCATATTTACTTACAGATCGTTTTGATCAAATGTTAA<br>TCTTATCAATAGTTAGTAGTGTTCTATCTTGTGTTTTAGGCACTTATT<br>TAAGTTATCATTTTGATGTTTCTACGGGGGGAAGTATTGTCGTTTTAA<br>TGACCATAATTTTTATTTTAGCGATGATTTTTGCTCCTAAATATGGCA<br>TCATCAATCAAAATACCAAAATATATTCTGCTTAACTTGTTTACTGAT | 48 |

TABLE 5-continued

*Cyanobacterium* sp. ABICyano1 endogenous promoter sequences

| Promoter | Sequence | SEQ ID NO: |
|---|---|---|
| | ACTTCAAATAATCATATAACCTATCTTCCGAGTTAAAAATAATGGAT ATTATCCAACTGAGGTCGAGAATAGAGTTTCTTTTTTGATAGAATTTT TTTACACCAGTTATTCATTACTATCATGGGATAAT | |
| Porf1542 | TAATATAGTGATTATTATAAATGCAATGTGAATCAAACCTATATTTT ACCGTACATTGACCATGGAACTTAATTTGAGGTGATTAGTAGAGGGT GCGATCGCCCTATTTGTCAAATAATAAAGATAACATTTGACATTGCT GATTGAAGACATAAAACACAGAAAAAATCAGGTAAAAATATAAAGC TAAAGTCTAAATATGGTTTACTTTTGCCTTCGACTTACAACAAAAAA TCATAGCTAGAATCACCAACGCCTAATATTTTATTTAGCTGAAATTTT GGGATGAACTTTTTGTAAAAATCGGGGGTCTAAAAATATAGCAACC ACGATATTAAATAACTGAGTGATTATTTTAATCTATTGGGGGCTTAT TAACTAAATACTTGCATTTTTATGGAGGGTTTTAATT | 49 |
| Porf1823 | AAAGATTATTTTCTACAGAAGCAACCCTTTCATCTTCCGAATTTTCAG GAATTTCCTGCTTTTGTTTCTGAATATTAGCATAGGCGGCTTTTGCCC ACTCTAAAGAAGGTTGAGACTGAATTTCTGAGGTTTCAGAAGGAGC ATTAGATTGTTTATCTTCAACAACAGGAGGTTTTTGTTCAATATTTTC CTTATTCTCTTTTTTACGGCGAAACCAATTAAACATAATGATTGTGCA TAAATATTCGTTAATATATTGTAACCCTAGAAAGGAATCGGTTTCAG GTTTATCCCCAGAGAATGTGAACCTTTACAGAAAGTAAAAAGTCTAA AATCGTAGCAACAATAAATCACAGAAATTGAG | 50 |
| Porf0222 | GCGATTATCAACCACGAAAACATACAATTATTATCAAACCTGCTGAG AAATTATCCACAGAAATAGATGTTTCTGCGAAGGGAAAATGGGCTTT TCATTGCCATTTAATGTATCACATGGATGTGGGAATGTTTCGGACTA TTAATGTTATTTCCTAAAAAATAATAGTATTAAAGCCTAAAATTTTT ATAAAAAAATTCATGTCTTTTATTAGGGTGAGCATTCTTCCTTTATGT CTCCTTATTTTACCTCTTTAGAGGTAACTACAAACTTAATCAAAAAA TTTAGATAATTAATTATATCA | 51 |
| Porf3232 | CATCTTTACTTTTGACTAACATTTCATAGGTATCATGACGAAAATTTT TTAGTCTGTTATATTTGTTCATGTAGAGAGATTTTAATTTGTGATTAT TTTATTTTCTCTCTATTTTTCTTTTTTGTCTTGTCCTTCCTCATTTTTCT CTACATTTAGTCTAAACTACAGCTCTTTAATCTTCAGTTTCTCTTTCC TCCTCTTCCTCATCAAGGTAATCATCCCAATTAATATCTTCTTCTTGT TCTAATTTGGGTTGAGATTGTTGTTTATCAATCATATTTCATACTCCT AAAACTTTCTTACTTATTTATCAGTTACTTTTTACCCATTTATGCAAT AGTGTAGAAATTTTTTTCGATCGAGTTAATTAATTTTTATTTCAACCA TATCTAAATAATTCTTGATGGACATTCTAGTTAACTAGAAGGTTTAA GCTAAAAATAATTATTGATATTGCCTTCGGTATAACTAACTATATCC AGAGAAAAAG | 52 |
| Porf3749 | CTCAAGAGATAGTTAAAAAACAAATAGCTTTAGTCTATCAATTAATC GAATTATTTTTACAAACAAATTTTCATAAACCCATAGAACTAGAGGA GGAAGTTATTTATGTTTAAAAATCTAAAAGAGTTTTATATTCCCCTA AAACCCCCTTAGTAAGAGTGACTTTTTTCATCATTTGCCTGTAAATTC TCCTCTTTTAATAAGAGAGCTAGGGTGTTTTAAAAGAGGATTTTATT GCTTTCCAATTCTAACTACTTCAAAAACTTATTTTATACTCAATAATT TATTAATCAAGAGGAAATTACC | 53 |
| PrbcL (Prbc) | TCGAGCGCTCGTTCCGCAAAGCGGTACGGAGTTAGTTAGGGGCTAAT GGGCATTCTCCCGTACAGGAAAGAGTTAGAAGTTATTAATTATCAAC AATTCTCCTTTGCCTAGTGCATCGTTACCTTTTTAATTAAAACATAAG GAAAACTAATAATCGTAATAATTTAACCTCAAAGTGTAAAGAAATG TGAAATTCTGACTTTTATAACGTTAAAGAGGGAAAAATTAGCAGTTT AAAATACCTAGAGAATAGTCTGGGGTAAGCATAGAGAATTAGATTA GTTAAGTTAATCAAATTCAGAAAAAATAATAATCGTAAATAGTTAAT CTGGGTGTATAGAAAATGATCCCCTTCATGATAAGATTTAAACTCGA AAAGCAAAAGCCAAAAAACTAACTTCCATTAAAAGAAGTTGTTACA TATAACGCTATAAAGAAAATTTATATATTTGGAGGATACCAAC | 54 |
| PrnpA | AATAGTTGATAATTACTCGTTACTCATTACTCACTTAAACCTGCCACC TGATACCTGCCACCTCTCCCCCCATCACCTCATCCCCTCAACATTCCG AACCCCTTGACACTTTGAACTAAAATTGTATTAAAGTGCAAATCTGG ACGGGGTTAACCAGTGTGACTTATAATAGTAAACGCTGTTTTTTATA ATAAATAAGCTAAATATTTAAAAACTATGAGTAAATATACACTAAAT GGTACTAGACGTAAGCAGAAAAGAACCTCCGGTTTCCGCGCCCGTA TGAGAACCAAAAATGGTAGAAAAGTAATTCAAGCTCGTCGTAATAA GGGTAGAAAAAGATTAGCAGTATAAAATTACTGTTAAATAAGGAAG CTAAGTTTAGCATTTTAAGTTTGATATTACTAATCATTAAATTTACTG TGAAATATAGGTGGGACTACCATCAAAGCATCGACTGAAACGGCGT TTAAATTTCCAATCTGTTTATCAACAGGGTATTCGCCGCTCTAGTCGT TATTTTATTGTCCGAGGGTTACGG | 55 |

TABLE 5-continued

Cyanobacterium sp. ABICyano1 endogenous promoter sequences

| Promoter | Sequence | SEQ ID NO: |
|---|---|---|
| PrpsL | CTCCGCTTAAAAAATTTCATTTTTCGATCAAAAAAGACAAATTATTA CTAATTAGCTCATGGCAATAAATAATCAGTAGTAATCTGTTTTCACA TTTTATTGTTAATTTTTATTATTGCTAATATCAACCTTTTCTACTTCTG CTTAATATTTTATTTATGCTCAATGGGAAAATCTGAAATAAGATTGA GAACAGTGTTACCAATAGAAGTATTTAAGGTTTAAAGCATACCTTAA AGATAACATTTTTTTTTGAAAAGAGTCAAATTATTTTTGAAAGGCTG ATATTTTTGATATTTACTAATATTTTATTTATTTCTTTTTCCCTTAAAA TAAGAGCTAAATCTGTTTTTATTATCATTTATCAAGCTCTATTAATAC CTCAACTTTTTCAAGAAAAAATAATAATAATTTTTCCCTCTATTCTCA TGACCTTTTAGGAAAATTAATTTTAGAAAAACTATTGACAAACCCAT AAAAAATGAGATAAGATTATAGATTGTCACTGGTATTTTATACTAGA GGCAAATTATATTTATATATACAAAAATGCTGTATAAAAAACATCT | 56 |
| PrpoA | AGTAAAGATTATCACCAACATCTGAAACCTGACTTCATCAACTGAGG AAATAACCACTGTGGCTGTGTTTAAAATCGACTGCGTAGCAAGTAAA ACTCAAAAAAATCAAGGTCAATACGGAAAGTTTGTGCTTGAACCCTT AGAAAAAGGACAAGGCATAACT | 57 |
| PpsaA | CTACATCAACTAATCAAAAGTTAAGAAAAAAGATAGAAACGCCCAT GAATATTAAAGATTAATCTGTGTCCTTTAACTTTTTATCCCCTTAAAA GAGCATAACTAAAACATTGATAGATTTTATAAAGAAAAGTAACAAA ATCTTGACTTAAATGAGAAAGGATTAAAAACCAAAGCCTTATCTGA GGGAATGTTAAACAAATTTTAAATATTGTTAAGCAAGAACCACAAT GGTGACAAATAGCCCTTATCATCTTCAGTAATGTAGTAGTTTAAGTA TTTGTCGAGAGAGGAATCCCTC | 58 |
| PpsbA2 | GATCGAATTTTTGACTATTTAATAATTTCTTTACTATTCATAATATCT CAAAAGACTTCTATCTTTTTAAGTAAACTACCTCCTCTAAGAATAAA CACTTATTGACTATATTCCTTTTTAGTTATAAAATGGCATTTAAAGTT ACTCAAAATATTTGCAATCATTCTACAAAACATAGTGTATTTCCTTGT ATTAAGCGTATTGTGTCCTGTTAGATAATGTAGGAAAGATTGTGAGT TGATAGGTGATAAATACATAACTCATTAGACAACAAGATAAAGTTG TAGGAGTTCTAAATT | 59 |
| PpsbD | AAGAGTTTGGCATTTTTATTGGTAAGACTATTCTGAGAAAAATGTGA CAATTTGTTAAAATATTTGCTAGAAATAGAAAAAGTAATTTGGCAAA GATACTTAAATCGTATCGAAAAACGGAGTTACATTAACTCTAACTCA TGCTATATTAAGAAAAGTTAATTGCAGATCAGTATTATTGCTGAGTA GCAGTGCCGTCTCCAATAATATAAAGAGAGACAATATAAAAGTAAA ACTTGACAAGTTAAAAAAAGAAAGATT | 60 |
| PcpcB | AACTTTAGATATTCGTAGTTGGCAATGTCGTAAATGCGGAACAATAC ATGGAAAACATATAGATTTGTAATGAGAAAAAGTGTAAACAAATAT TAAGAAAAAGATCAGAAAAATTTAACAACACGTAATAAAAAAATGC GTCACTACGGGTTATAAATTTACATGAAAGGTTAAAACACTTTTCTG AGACGATTTTGATAAAAAAGTTGTCAAAAAATTAAGTTTCTTTACAA ATGCTTAACAAAAACTTGGTTTTAAGCACAAAATAAGAGAGACTAA TTTGCAGAAGTTTTACAAGGAAATCTTGAAGAAAAAGATCTAAGTA AAACGACTCTGTTTAACCAAAATTTAACAAATTTAACAAAACAAACT AAATCTATTAGGAGATTAACTACA | 61 |

In certain other preferred embodiments, truncated or partially truncated versions of these promoters including only a small portion of the native promoters upstream of the transcription start point, such as the region ranging from −35 to the transcription start can often be used. Furthermore, introducing nucleotide changes into the promoter sequence, e.g. into the TATA box, the operator sequence and/or the ribosomal binding site (RBS) can be used to tailor or optimize the promoter strength and/or its induction conditions, e.g. the concentration of inductor required for induction.

Products of Interest Produced by the Cyanobacterial Host Cells

In certain embodiments, a variety of different products of interest can be produced using the genetically modified cyanobacterial host cells. Plasmid vectors disclosed herein (either endogenous to the cyanobacterial strain, or heterologous) can be used to carry a gene or genes involved in various biosynthetic pathways that produce a product of interest in the cyanobacterial cell. Exemplary products of interest include, but are not limited to, organic carbon compounds, alcohols, fatty acids, oils, carotenoids, proteins, amino acids, cell extracts, colorants or pigments such as phycocyanin, enzymes, biofuels, biomass, nutraceuticals, beauty products such as lotions, skin products, and hair products, vitamins, pharmaceuticals, and the like.

In an embodiment, the 6.8 kb endogenous plasmid vector from the cyanobacterial strain *Cyanobacterium* sp. PTA-13311 is genetically enhanced to include recombinant genes encoding enzymes that produce a product of interest. In an embodiment, the 6.8 kb endogenous plasmid vector from *Cyanobacterium* sp. PTA-13311 is used as the backbone of a vector useful for introducing exogenous polynucleotides for the production of a product of interest.

The production of 1,2-propanediol in cyanobacteria is described, for example, in PCT/US2013/65568. The production of 1,3-propanediol in cyanobacteria is described in PCT/US2013/065574. The production of isoprene in cyanobacteria is described in PCT/EP2012/067534. Additional information on compounds that can be produced from cyanobacteria can be found, for example, in PCT/EP2009/000892 and in PCT/EP2009/060526, and all of the above are incorporated by reference herein in their entirety. Genes involved in the biosynthetic pathway for the production of a product of interest can be inserted into cyanobacterial host cell, either in a plasmid or in the cyanobacterial chromosome.

In one embodiment, propanol and butanol are products of interest. Similar to ethanol, they can be produced by fermentation processes. In certain embodiments, genes encoding enzymes involved in isopropanol and isobutanol fermentation are incorporated into recombinant vectors and transformed into a cyanobacterial host cell. Examples of enzymes involved in isopropanol fermentation include acetyl-CoA acetyltransferase (EC 2.3.1.9), acetyl-CoA: acetoacetyl-CoA transferase (EC 2.8.3.8), acetoacetate decarboxylase (EC 4.1.1.4) and isopropanol dehydrogenase (EC 1.1.1.80). Examples of enzymes involved in isobutanol fermentation include acetolactate synthase (EC 2.2.1.6), acetolactate reductoisomerase (EC 1.1.1.86), 2,3-dihydroxy-3-methylbutanoate dehydratase (EC 4.2.1.9), a-ketoisovalerate decarboxylase (EC 4.1.1.74), and alcohol dehydrogenase (EC 1.1.1.1).

In another embodiment, ethylene is produced as a product of interest. In an embodiment, at least one recombinant gene encodes an enzyme for ethylene formation. Examples of enzymes involved in the production of ethylene include ethylene forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene forming enzyme is synthesized by the enzyme 1-aminocyclopropane-1-carboxylic acid synthase (EC 4.4.1.14) from the amino acid methionine.

In another embodiment, the product of interest is isoprene. In an embodiment the recombinant vector used to transform a cyanobacterial host cell for the production of isoprene includes at least one recombinant gene encoding an enzyme such as isoprene synthase. Isoprene synthase (EC 4.2.3.27) catalyzes the chemical reaction from dimethylallyl diphosphate to isoprene and pyrophosphate.

In another embodiment, products of interest are terpenes and terpenoids. Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl diphosphate synthase (EC 2.5.1.1), which catalyzes the reaction of dimethylallyl diphosphate and isopentenyl diphosphate yielding farnesyl diphosphate. Another example is geranylgeranyl diphosphate synthase (EC 2.5.1.29), which catalyzes the reaction between transfarnesyl diphosphate and isopentenyl diphosphate yielding pyrophosphate and geranylgeranyl diphosphate.

In and embodiment, the product of interest is hydrogen, and the recombinant genes can, for example, encode for hydrogenase. In an embodiment, hydrogenase is an enzyme catalyzing the following reaction: $12H^{+}+12X(reduced)\rightarrow 6 H_2$ 12X(oxidized), where X is an electron carrier such as ferredoxin.

In an embodiment, examples of products of interest include non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities that are of pharmacological relevance. Hybrids of non-ribosomal peptides and polyketides also exist, exhibiting both peptide and polyketide parts. Recombinant genes for the production of non-ribosomal peptides as products of interest are encoded by, for example, gene clusters encoding non-ribosomal peptide synthetases (NRPS). NRPS are characteristic modular multidomain enzyme complexes encoded by modular non-ribosomal peptide synthetase gene clusters. Examples for non-ribosomal peptide synthetases are actinomycin synthetase and gramicidin synthetase.

In an embodiment, polyketides are products of interest. In general, there are two distinct groups of polyketides, the reduced polyketides of type I, macrolides, and the aromatic polyketides of type II. Type I polyketides are synthesized by modular polyketide synthases (PKS), which are characteristic modular multidomain enzyme complexes encoded by modular PKS gene clusters. Examples for recombinant genes useful for encoding enzymes for the production of type I polyketides are the rapamycin synthase gene cluster and the oleandomycin synthase gene cluster. One example for a recombinant gene for type II polyketides is the actinorhodin polyketide synthase gene cluster.

In another embodiment, hybrids of polyketides and non-ribosomal peptides are products of interest. Examples for recombinant genes for the production of hybrids of polyketides and non-ribosomal peptides are the microcystin synthetase gene cluster, microginin synthetase gene cluster, and myxothiazole synthetase gene cluster.

In another embodiment, alkaloids are products of interest. Alkaloids are a group of compounds containing mostly basic nitrogen atoms and which are synthesized by many organisms, including plants. Alkaloids have highly complex chemical structures and pronounced pharmacological activities. Examples for biosynthetic enzymes for alkaloids which can be encoded by recombinant genes for the production of the compound are strictosidine synthase, which catalyzes the reaction of tryptamine and secologanin to form 3a(S)-strictosidine. Strictosidine is a precursor for the biosynthetic pathway of ajmaline and it also initiates all pathways leading to an entire monoterpene indole alkaloid family. Another example of an enzyme that could be encoded by a recombinant gene is strictosidine glucosidase from the ajmaline biosynthetic pathway. This enzyme is able to activate strictosidine by deglycosylation, thus generating an aglycon which is the precursor for more than 2,000 monoterpenoid indole alkaloids.

In an embodiment, additional examples of enzymes encoded by at least one recombinant gene are (R,S)-3'-hydroxy-N-methylcoclaurine 4'-O-methyltransferase (4'OMT) which is central to the biosynthesis of most tetrahydrobenzylisoquinolin-derived alkaloids; berberine bridge enzyme (BBE) of the sanguinarine pathway; (R,S)-reticuline 7-O-methyltransferase (7OMT) part of laudanosine formation; as well as salutaridinol 7-O-acetyltransferase (SalAT) and codeinone reductase involved in the production of morphine.

In yet another embodiment, vitamins are products of interest. Vitamins are organic compounds that are essential nutrients for certain organisms and act mainly as cofactors in enzymatic reactions but can also have further importance, e.g. as antioxidants. In plants, vitamin C can be made via the L-ascorbic acid (L-AA) biosynthetic pathway starting from D-glucose. In an embodiment, recombinant genes encoding enzymes involved in vitamin C synthesis are disclosed and include hexokinase, glucose-6-phosphate isomerase, mannose-6-phosphate isomerase, phosphomannomutase, mannose-1-phosphate guanylyltransferase, GDP-mannose-3,5-epimerase, GDP-L-galactose phosphorylase, L-galactose 1-phosphate phosphatase, L-galactose dehydrogenase, and L-galactono-1,4-lactone dehydrogenase.

In another embodiment, an amino acid is the product of interest. Amino acids as products of interest include naturally occurring amino acids as well as amino acid derivatives. The amino acid can be, for example, naturally occurring in the cell, naturally occurring in another organism, or a non-naturally occurring amino acid.

In an embodiment, lactams are products of interest. Lactams are cyclic amides and the prefix indicates how many carbon atoms (apart from the carbonyl moiety) are present in the ring. For example, β-lactam (2 carbon atoms outside the carbonyl, 4 ring atoms in total), γ-lactam (3 and 5), δ-lactam (4 and 6). One example for a γ-lactam is pyrrolidone, a colorless liquid which is used in industrial settings as a high-boiling, non-corrosive, polar solvent for a wide variety of applications. Pyrrolidone is also an intermediate in the manufacture of polymers such as polyvinylpyrrolidone and polypyrrolidone.

In another embodiment, ethers are products of interest. Ethers are a class of organic compounds that contain an ether group, an oxygen atom connected to two alkyl or aryl groups of general formula R-O-R. An example of an ether is tetrahydrofuran (THF) which is a colorless, water-miscible organic liquid. THF is a heterocyclic compound and is one of the most polar ethers miscible in many solvents. THF is also useful as a solvent and as a precursor to polymers. Other examples of ethers that are products of interest include naturally occurring ethers such as divinyl ether oxylipins. Enzymes involved in the biosynthesis of divinyl ether oxylipins include lipoxygenase and divinyl ether synthase.

In yet another embodiment, alkanes (also known as saturated hydrocarbons) are products of interest. Alkanes consist only of the elements carbon (C) and hydrogen (H), i.e. hydrocarbons. When the carbon and hydrogen atoms of alkanes are linked together exclusively by single bonds, the alkanes are saturated alkanes. Each carbon atom must have 4 bonds (either C—H or C—C bonds), and each hydrogen atom must be joined to a carbon atom (H—C bonds). The simplest possible alkane is methane, $CH_4$. There is no limit to the number of carbon atoms that can be linked together. Alkanes, observed throughout nature, are produced directly from fatty acid metabolites. A two gene pathway, widespread in cyanobacteria, is responsible for alkane biosynthesis. In an embodiment, these genes may be part of the recombinant vector and include genes encoding acyl-ACP reductase (EC 1.3.1.9) which converts a fatty acyl-ACP into a fatty aldehyde that may subsequently be converted into an alkane/alkene by an aldehyde decarbonylase (EC 4.1.99.5).

In an embodiment, biopolymers such as polyhydroxyalkanoates (PHAs) are products of interest. PHAs are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB) but many other polymers of this class are produced by a variety of organisms. PHAs include poly-4-hydroxybutyrate (P4HB), polyhydroxyvalerate (PHV), polyhydroxyhexanoate (PHH), polyhydroxyoctanoate (PHO) and their copolymers. In an embodiment, recombinant genes encoding enzymes involved in P3HB synthesis are part of recombinant vectors. These genes include genes encoding β-ketothiolase (EC 2.3.1.9) that produces acetoacetyl-CoA which is converted to (R)-3-hydroxybutyryl-CoA (3HBCoA) by NADPH-dependent acetoacetyl-CoA reductase (EC 1.1.1.36). The 3HBCoA is subsequently polymerized by poly(3-hydroxyalkanoate) synthase (EC 2.3.1) and is converted to P3HB.

In an embodiment, esters, including fatty acid esters, are a product of interest. Simple esters with lower chain alcohols (methyl-, ethyl-, n-propyl-, isopropyl- and butyl esters) are used as emollients in cosmetics and other personal care products and as lubricants. Esters of fatty acids with other alcohols, such as sorbitol, ethylene glycol, diethylene glycol and polyethylene glycol are consumed in foods, personal care, paper, water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMEs, usually obtained from vegetable oils by transesterification with methanol. The esterification of the ethanol with the acyl moieties of coenzyme A thioesters of fatty acids can be obtained enzymatically by a nonspecific long chain alcohol O-fatty-acyltransferase (EC 2.3.1.75) from *Acinetobacter baylyi* strain ADP1, for example.

In an embodiment, the product of interest is a colorant, such as phycocyanin, phycobiliprotein, or a derivative thereof. Other colorants of interest can be, for example, allophycocyanin, phycoerythrin, or phycoerythrocyanin, and the like. The genes for the production of the colorant can be endogenous to the cyanobacterial cell, or can be exogenously derived.

The product of interest can also be a pigment such as a carotenoid. The genes for the production of a carotenoid of interest can be endogenous to the cyanobacterial cell, or can be exogenously derived. Exemplary carotenoids that can be obtained from cyanobacterial cultures include, but are not limited to, lutein, zeaxanthin, beta-carotene, astaxanthin, canthaxanthin, and the like.

In an embodiment, the product of interest is an amino acid, or a derivative thereof In yet another embodiment, the product of interest is a cell extract.

In another embodiment, the product of interest is an industrial enzyme. The enzyme can be endogenous to the cell or can be exogenously derived. An exogenously derived gene encoding an enzyme of interest can be inserted into the plasmid vector or integrated into the genome of the cyanobacteria. A culture of the cells is grown, the cells are harvested, and the enzyme of interest is isolated and purified.

In an embodiment, the genetically modified cyanobacterial host cell contains the entire sequences of recombinant genes that encode for all of the enzymes used in a cascade of enzymatically catalyzed reactions that results in the production of a product of interest.

In an embodiment, a first protein encoded by a first recombinant gene can produce a first intermediate which is further converted by a second protein encoded by a second recombinant gene into a second intermediate, which then in turn is further converted by a third protein encoded by a third recombinant gene into a third intermediate such that a sequence of reactions provide intermediates for the next enzyme leading to the eventual production of a product of interest. In an embodiment, the recombinant genes encoding the enzymes that catalyze the sequence of reactions can be introduced into the desired cyanobacterial host cells.

In an embodiment, the product of interest is biomass. The methods described herein can allow cyanobacterial cultures to grow faster and to a higher cell density, with less competition from other organisms, and can thus result in a higher biomass harvest at the end of the culture run.

In an embodiment, the products of interest that are produced from the genetically modified cyanobacterial host cells can be removed intermittently as the culture grows, or the compounds can be separated at the end of a batch growth period. The cultures can be grown indoors, or can be grown outdoors in enclosed containers such as bioreactors, or in another suitable type of container.

Production of Ethanol in Genetically Modified Cyanobacterial Host Cells

In an embodiment, the product of interest that is produced by the cyanobacterial host cell is ethanol. Genes encoding the enzymes pyruvate decarboxylase and alcohol dehydrogenase can be transformed to the cell, either on a plasmid vector or at a location on the cyanobacterial chromosome.

In an embodiment, the 6.8 kb endogenous plasmid vector from the cyanobacterial strain *Cyanobacterium* sp. PTA-13311 ("p6.8") is genetically enhanced to include recombinant genes encoding enzymes that produce a product of interest. In an embodiment, the 6.8 kb endogenous plasmid vector from *Cyanobacterium* sp. PTA-13311 is used as the backbone of a vector useful for introducing exogenous polynucleotides for the production of a product of interest.

In an embodiment, a plasmid vector is prepared which comprises one or more recombinant genes encoding an enzyme used in ethanol production. In an embodiment, the genes are adh and pdc. The gene pdc encodes pyruvate decarboxylase (Pdc), which catalyzes the conversion of pyruvate to acetaldehyde. The gene adh encodes alcohol dehydrogenase (Adh) which catalyzes the interconversion between acetaldehyde and ethanol. Thus, Pdc and Adh act in concert to produce ethanol. In another embodiment, the gene is adhE which encodes an AdhE enzyme (alcohol dehydrogenase E) which catalyzes the interconversion between acetyl-coenzyme A and ethanol.

Ethanol produced by the cyanobacterial cells can be measured by any means well known in the art. In an embodiment, the ethanol produced is measured using gas chromatographic analysis of a growth media and/or the headspace above a growth media.

In an embodiment, Pdc activity is measured by a photometric kinetic reaction that can be monitored at 340 nm using a spectrophotometer. Pyruvate is enzymatically converted to acetaldehyde by pyruvate decarboxylase, which is reduced to ethanol by alcohol dehydrogenase coupled to NADH or NADPH oxidation.

In particular embodiments, the Adh enzyme is, for example, a $Zn^{2+}$-dependent alcohol dehydrogenase such as Adhl from *Zymomonas mobilis* (ZmAdh) or the Adh enzyme from *Synechocystis* sp. PCC 6803 (SynAdh encoded by the synadh gene). Alternatively or in addition, the enzyme is an iron-dependent alcohol dehydrogenase (e.g. AdhII from *Z. mobilis*). The $Zn^{2+}$-dependent alcohol dehydrogenase can, for example, be an alcohol dehydrogenase enzyme having at least 60%, 70%, 80%, 90% or even more than 90% sequence identity to the amino acid sequence of $Zn^{2+}$ dependent alcohol dehydrogenase from *Synechocystis* sp. PCC 6803. Relative to other alcohol dehydrogenases, SynAdh (annotated open reading frame s1r1192 from the *Synechocystis* sp. PCC 6803 genome) favors higher overall ethanol production because the reduction of acetaldehyde to ethanol is preferred to the reaction from ethanol to acetaldehyde. Thus, in an embodiment, a SynAdh encoding recombinant gene is useful for production of ethanol in a host cell.

AdhE is an iron-dependent, bifunctional enzyme that interconverts acetyl coenzyme A to ethanol. One characteristic of iron-dependent alcohol dehydrogenases (e.g. AdhE and AdhII) is their sensitivity to oxygen. In an embodiment, AdhE used to transform *Cyanobacterium* sp. PTA-13311 is derived from *E. coli* or from thermophilic organisms such as *Thermosynechococcus elongatus* BP-1.

Genes encoding other types of ADH enzymes, such as those described in PCT/EP2014/062594, which is incorporated by reference herein in its entirety, can be used to produce ethanol in cyanobacterial host cells. Thus, genes encoding ADH enzymes derived from *Arthrospira platensis, Arthronema africanum, Chroococcidiopsis* sp., *Synechococcus* sp., *Lyngbya* sp., *Cyanothece* sp., and *Cyanobacterium* sp. can be used. In a preferred embodiment, the ADH enzyme is derived from *Lyngbya* sp.

In an embodiment, pyruvate decarboxylase can be derived from, for example, *Zymomonas mobilis, Zymobacter palmae* or the yeast *Saccharomyces cerevisiae*. In an embodiment, nucleic acid sequences, protein sequences and properties of ethanologenic enzymes such as alcohol dehydrogenases and pyruvate decarboxylases disclosed herein, can be found within PCT patent application WO 2009/098089 A2, which is hereby incorporated for this purpose.

In an embodiment, ethanologenic cassettes are introduced into the cyanobacterial host cells and those host cells are used for the production of ethanol. Ethanologenic cassettes disclosed herein vary in promoters used as well as the source of adh and pdc genes.

Transformation of Cyanobacterial Cells

Cyanobacteria can be transformed by several suitable methods. Exemplary cyanobacteria that can be transformed with the constructs described herein include but are not limited to *Synechocystis, Synechococcus, Acaryochloris, Anabaena, Thermosynechococcus, Chamaesiphon, Chroococcus, Cyanobacterium, Cyanobium, Dactylococcopsis, Gloeobacter, Gloeocapsa, Gloeothece, Microcystis, Prochlorococcus, Prochloron, Chroococcidiopsis, Cyanocystis, Dermocarpella, Myxosarcina, Pleurocapsa, Stanieria, Xenococcus, Arthrospira, Borzia, Crinalium, Geitlerinema, Halospirulina, Leptolyngbya, Limnothrix, Lyngbya, Microcoleus, Cyanodictyon, Aphanocapsa, Oscillatoria, Planktothrix, Prochlorothrix, Pseudanabaena, Spirulina, Starria, Symploca, Trichodesmium, Tychonema, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema, Tolypothrix, Cyanothece, Phormidium, Adrianema*, and the like.

Exemplary methods suitable for transformation of Cyanobacteria, include, as nonlimiting examples, natural DNA uptake (Chung, et al. (1998) FEMS Microbiol. Lett. 164: 353-361; Frigaard, et al. (2004) Methods Mol. Biol. 274: 325-40; Zang, et al. (2007) J. Microbiol. 45: 241-245), conjugation, transduction, glass bead transformation (Kindle, et al. (1989) J. Cell Biol. 109: 2589-601; Feng, et al. (2009) Mol. Biol. Rep. 36: 1433-9; U.S. Pat. No. 5,661, 017), silicon carbide whisker transformation (Dunahay, et al. (1997) Methods Mol. Biol. (1997) 62: 503-9), biolistics (Dawson, et al. (1997) Curr. Microbiol. 35: 356-62; Hallmann, et al. (1997) Proc. Natl. Acad. USA 94: 7469-7474; Jakobiak, et al. (2004) Protist 155:381-93; Tan, et al. (2005) J. Microbiol. 43: 361-365; Steinbrenner, et al. (2006) Appl Environ. Microbiol. 72: 7477-7484; Kroth (2007) Methods Mol. Biol. 390: 257-267; U.S. Pat. No. 5,661,017) electroporation (Kjaerulff, et al. (1994) Photosynth. Res. 41: 277-283; Iwai, et al. (2004) Plant Cell Physiol. 45: 171-5; Ravindran, et al. (2006) J. Microbiol. Methods 66: 174-6; Sun, et al. (2006) Gene 377: 140-149; Wang, et al. (2007) Appl. Microbiol. Biotechnol. 76: 651-657; Chaurasia, et al. (2008) J. Microbiol. Methods 73: 133-141; Ludwig, et al. (2008) Appl. Microbiol. Biotechnol. 78: 729-35), laser-mediated transformation, or incubation with DNA in the presence of or after pre-treatment with any of poly(amidoamine) dendrimers (Pasupathy, et al. (2008) Biotechnol. J. 3: 1078-82), polyethylene glycol (Ohnuma, et al. (2008) Plant Cell Physiol. 49: 117-120), cationic lipids (Muradawa, et al. (2008) J. Biosci. Bioeng. 105: 77-80), dextran, calcium phosphate, or calcium chloride (Mendez-Alvarez, et al. (1994) J. Bacteriol. 176: 7395-7397), optionally after treatment of the cells with cell wall-degrading enzymes (Perrone, et al. (1998) Mol. Biol. Cell 9: 3351-3365). Biolistic methods (see, for example, Ramesh, et al. (2004) Methods Mol. Biol. 274: 355-307; Doestch, et al. (2001) Curr. Genet. 39: 49-60; all incorporated herein by reference in their entireties).

Culturing the Cyanobacterial Cells

In an embodiment, the product of interest is synthesized in cyanobacterial cultures by preparing host cyanobacterial cells having the gene constructs discussed herein, growing cultures of the cells, and harvesting the product.

The choice of culture medium can depend on the cyanobacterial species. In an embodiment of the invention, BG-11 medium (as shown in Example 1) can be used as the basic medium for growing cyanobacteria. When salt water species are grown, NaCl is added to the culture medium. The medium is also adjusted as needed for a particular experiment. For example, the medium may be modified by replacing phosphate with phosphite, or by substituting urea for nitrate, as needed for a particular situation. This is further described in the example section.

In an embodiment, the cells are grown autotrophically, and the only carbon source is $CO_2$. In another embodiment, the cells are grown mixotrophically, for example with the addition of a carbon source such as glycerol along with $CO_2$.

The cultures can be grown indoors or outdoors. The light cycle indoors can be set as desired, for example: continuous light, or 16 hours on and 8 hours off, or 14 hours on and 10 hours off, or 12 hours on and 2 hours off.

In an embodiment, the cyanobacteria are grown in enclosed bioreactors in quantities of at least about 100 ml, 500 ml, 1 liter, 1.5 liters, 5 liters, 10 liters, 50 liters, 100 liters, 500 liters, 1000 liters, 2000 liters, 5,000 liters, or more. In an embodiment, the cyanobacterial cell cultures are grown in flexible photobioreactors made of a clear plastic material.

In another embodiment, the cultures are grown indoors, with continuous light. In another embodiment, the cultures are grown outdoors in an open pond type of photobioreactor.

EXAMPLES

Example 1

Culture Medium for Cyanobacterial Growth

Artificial Seawater medium ("ASW") was the standard medium used for cultivation of marine cyanobacteria strains. The ASW medium uses the standard cyanobacterial medium BG-11 as its base, with the addition of the salts listed below. This medium is also known as mBG-11 medium.

TABLE 6

| Culture Medium Components Artificial Seawater Medium | |
|---|---|
| Compound | Amount in 1 L (g) |
| NaCl | 25.84 |
| $MgSO_4$•$7H_20$ | 6.36 |
| $MgCl_2$•$6H_2O$ | 5.06 |
| KCl | 0.62 |
| $CaCl_2$•$2H_2O$ | 1.36 |

Before use, 1 ml stock solutions of ferric ammonium citrate, phosphate, and trace metal solution is added to the medium.

TABLE 7

| Additional Components for Medium | | | |
|---|---|---|---|
| Component | Stock Solution g * $L^{-1}$ in $dH_2O$ | mL * $L^{-1}$ | mM |
| Fe—$NH_4$-citrate | 6 | 1 | 0.022 |
| $K_2HPO_4$ × $3H_20$ | 52.49 | 1 | 0.229 |
| Trace metals | | 1 | |

The following is a basic recipe for the common cyanobacterial culture medium "BG-11":

TABLE 8

| Basic BG-11 Medium Recipe | |
|---|---|
| Compound | Amount |
| BG-11 Medium | |
| $NaNO_3$ | 1.5 g |
| $K_2HPO_4$ | 0.04 g or 1 mL of prepared stock solution |
| $MgSO_4$•$7H_2O$ | 0.075 g |
| $CaCl_2$•$2H_2O$ | 0.036 g |
| Citric acid | 0.006 g |
| Ferric ammonium citrate | 0.006 g or 1 mL of prepared stock solution |
| EDTA (disodium salt) | 0.001 g |
| $NaCO_3$ | 0.02 g |
| Trace metal mix A5 | 1.0 ml |
| Distilled water | to 1.0 L |
| — | — |
| Composition of Trace Metal Mix | |
| $H_3BO_3$ | 2.86 g |
| $MnCl_2$•$4H_2O$ | 1.81 g |
| $ZnSO_4$•$7H_2O$ | 0.222 g |
| $NaMoO_4$•$2H_2O$ | 0.39 g |
| $CuSO_4$•$5H_2O$ | 0.079 g |
| $Co(NO_3)_2$•$6H_2O$ | 49.4 mg |
| Distilled water | to 1.0 L |

The medium was also modified based on the choice of inducible promoters for the chosen added constructs. Thus, the nitrogen source and amount, as well as the amount and timing of any added copper was dependent on the strain and the promoters used to control the expression of the ethanol cassette or phosphite utilization genes, respectively. Further, the phosphorus source (such as phosphate or phosphite) and amount were modified as indicated for individual experiments.

Unless noted otherwise, the following standard growth conditions were used: mBG-11 medium; 38 mL min' aeration rate with 15% $CO_2$ supply on demand; pH 7.3+/−0.1 as the set-point for $CO_2$ delivery during the day; a light cycle of 12 hours light/12 hours dark. The temperature cycle was set at 25° C. (during the dark phase) and 35° C.-37° C. (during the light phase) The light intensity was set at approximately 350 μmol photons $m^{-2}s^{-1}$ from one side of the vertical photobioreactors.

Example 2

Long-Term Cultivation in 0.5 L Photobioreactors (PBRs) and 1.2 L Vertical Photobioreactors (vPBRs)

1. Cultivation in 0.5 L PBRs

For scale up, the cyanobacterial culture was maintained under repressed conditions, using mBG-11 (35 psu) with ammonium and urea (2 mM of each) instead of nitrate as nitrogen source, 5 mM TES was used as buffer. For plasmid maintenance and contamination control, kanamycin (150 mg $L^{-1}$) was used. For induction of ethanol production, cells were switched back to normal mBG-11 with nitrate and no ammonium/urea. Cells were cultivated in 0.5 L round Schott bottles. Mixing was achieved using a magnetic stir bar at continuous 250 rpm. The gas flow rate was continuously 15 ml $min^{-1}$ with $CO_2$ enriched air (5% $CO_2$). A light/dark period of 12 h:12 h was applied. Illumination of cultures was done with fluorescence lamps (Sylvana Grolux FHO 39 W/T5/GRO). The cultures were illuminated from two sides with a photon flux density (PFD) of 230 μmol photons $m^2s^{-1}$ each.

2. Cultivation in 1.2 L vertical vPBRs

The strains were scaled up in 1 liter mBG-11 with 0.5% continuous $CO_2$ supply and continuous illumination with a PFD of 200-300 μmol photons $m^{-2}s^{-1}$. The strains were cultivated under repressed conditions in media containing 2 mM ammonium and 2 mM urea as the nitrogen source. Furthermore 200 mg/L kanamycin was added and 5 mM TES buffer was used to keep the pH at 8.0.

1.2 L vPBRs were inoculated at a cell density of $OD_{750nm}$=0.5 in mBG-11 medium (35 psu) containing kanamycin (200 mg/L). The strains were cultivated at pH 7.3±0.01. $CO_2$ (15% $CO_2$ in air) was injected into the liquid phase in a pH controlled manner with continuous aeration (38 mL/min). The vPBRs were illuminated from one side using fluorescent bulbs with a PFD of 230 μmol photons $m^{-2}s^{-1}$ during the photoperiod of 12 hours. The temperature profile ranged from 25° C. during the dark period and 37° C. during the light period.

Vapor loss correction: An average value of 2.5% ethanol vapor loss per day was assumed in order to compensate for the ethanol loss through vapor phase. The value 2.5% was calculated from several evaporation tests with ethanol spiked medium in 1.2L vPBRs under these standardized conditions, where the decline of ethanol in the liquid phase had been determined experimentally. Nutrients were added several times during the cultivation. Ethanol production rates were calculated by subtracting ethanol values from the first day and the last day divided by the number of cultivation days.

Example 3

Most Heterotrophic Contaminants Do Not Utilize Phosphite Efficiently

The following experiment confirmed that most bacterial organisms that contaminate cyanobacterial cultures do not have the ability to utilize phosphite (or utilize phosphite inefficiently). A contaminated outdoor cyanobacterial photobioreactor was sampled for contaminating heterotrophic bacteria, and the sample strains were isolated and purified.

Bacterial Minimal Media ("BMM") was prepared, containing the following components per liter of ASW: 1 mL Trace Metal Mix, 1 mL ferric ammonium citrate solution, 1 g sodium pyruvate, 0.1 g ammonium chloride, 10 mM Tris (ph 7.5), 10 mL RPMI amino acid solution (Sigma R7131), and 10 mL of BME vitamin solution (Sigma B6891).

Figure 2:
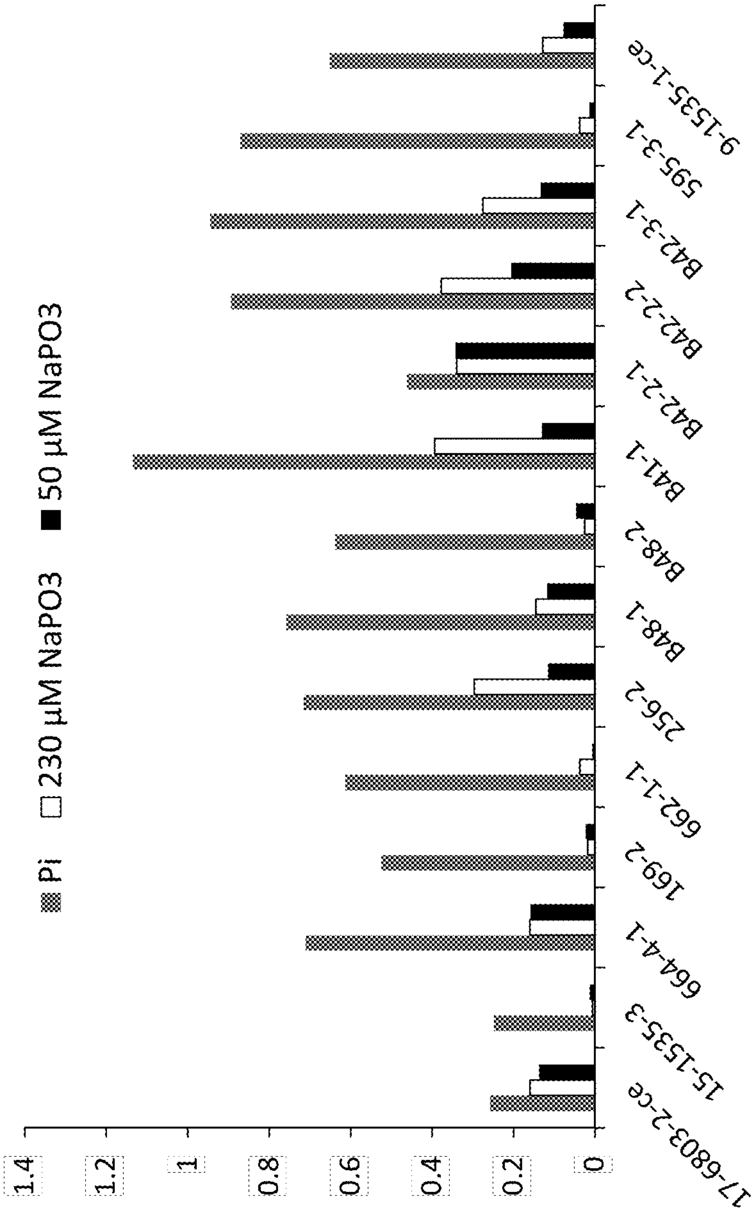
FIG. 2 is a bar graph showing cell growth (average $\Delta OD_{600}$) of isolated contaminant bacterial strains inoculated on bacterial minimal medium (BMM) broth for 48 hours in either phosphate or two concentrations of phosphite (50 and 230 μM). The $\Delta OD_{600}$ was calculated as ΔOD=OD48 hours (+P)−$OD_{48\ hours}$ (−P).

Several of the strains were then grown in bacterial minimal medium with either 50 μM or 230 μM $NaPO_3$ as the sole phosphorus source. After 48 hours, the $OD_{600}$ was measured to determine bacterial cell growth. As shown in FIG. 2, six of the strains had negligible growth on phosphite as the only phosphorus source, and eight of the strains had relatively slow growth on phosphite (slower than with phosphate, but slightly higher than with no phosphorus in the medium).

Example 4

Common Fungal Contaminants Do Not Grow Well on Phosphite

Two fungal strains were obtained from outdoor contaminated cultures. These strains were isolated, purified, and identified as a *Fusarium* and *Cladosporium*. The two isolates were then tested to determine whether they were capable of growth when the only phosphorus source was phosphite.

The assay was conducted on fungal minimal medium (FMM) agar. The medium contained the following components per liter of ASW: 1 mL Trace Metal Mix, 1 mL ferric ammonium citrate solution, 10 g sucrose, 1.0 g sodium nitrate, and 10 mM Tris (ph 7.5).

The two isolated contaminant strains (*Fusarium* and *Cladosporium*) were plated on FMM containing 230 ΞM phosphate, FMM containing 230 μM sodium phosphite, and P-free FMM. After four consecutive transfers, the *Fusarium* and *Cladosporium* isolates displayed decreased growth in P-free medium while maintaining high growth in the control phosphate treatments. Further, both of the fungal test strains grew more slowly in sodium phosphite than in P-free medium.

Example 5

Wild Type *Cyanobacterium* sp. PTA-13311 Does Not Utilize Phosphite

The wild type cyanobacterial strain, *Cyanobacterium* sp. PTA-13311, was tested to determine whether it was capable of utilizing phosphite as a sole phosphorus source. The strain was first grown for 3 weeks on phosphorus-free medium to reach a phosphorus limitation stage. The strain was then pelleted and resuspended in growth medium with either 230 μM phosphite (as $Na_2HPO_3$), 230 μM phosphate (as $K_2HPO_4$), or no P source. Cells were grown in 0.5 L PBRs at a light intensity of 250 μmol photons $m^{-2}s^{-1}$ light from one side, with a light cycle of 12 hours light/12 hours dark, at a temperature of 28° C. After 14 days, the cyanobacterial cells growing on phosphite showed no improved growth compared to cells grown in P-free medium, while comparable cells growing in phosphate had exponential growth over the same period (FIG. 3). Thus, it was concluded that the Wild Type (WT) *Cyanobacterium* sp. PTA-13311 strain, without further modification, does not have the ability to utilize phosphite.

Example 6

Identification of the ptxABCD Genes in Other Organisms

Although most cyanobacterial strains (including the *Cyanobacterium* sp. PTA-13311 strain previously chosen to be suitable as the host strain for commercial-scale ethanol production) do not utilize phosphite, some cyanobacterial strains are actually able to utilize phosphite. A search of the publicly available sequence databases found that the ptxABCDE operon is found in proteobacteria, cyanobacteria, and actinobacteria (FIG. 4). Bacteria harboring a biochemical pathway (ptxABCDE operon) for the oxidation of reduced phosphorus (i.e. phosphite) were identified by performing a BLAST search (world wide web: blast.ncbi.nlm.nih.gov) using the blastp algorithm and the PtxD protein from *Pseudomonas stutzeri* (YP_006457277) as the query sequence. Sequences producing significant alignment were examined for the presence of the phosphite dehydrogenase (PTDH) conserved domain (cd12157).

Phylogenetic analysis of the ptxD gene showed that well-supported clades did not form based on taxonomy, although similar organisms did group together. For example, strains of the genera *Halomonas* and *Marinobacter* grouped together but were separate from other γ-proteobacteria such as *Pseudomonas* and *Salmonella* (non-ptxE like). The cyanobacteria strains formed three well-supported clades that grouped together, but the clade had a low bootstrap value (21%). Most of the bacteria strains harboring ptxD also contained the ABC transporter genes. In contrast, not all strains contained ptxE. Further, some strains lacked a transcriptional regulator nearby. Other strains were found to have a different type of regulator. The operon was located on either the chromosome (75% of the strains) or a plasmid (<25% of the strains). Only one strain, *Methylobacterium extorquens*, contained more than one copy of the operon, with two copies on its megaplasmid.

Example 7

Codon Optimization

Some of the phosphite utilization genes that were chosen for insertion into the cyanobacterial host cells were codon optimized for optimal expression in *Cyanobacterium* sp. PTA-13311. The ptxD gene sequence from the bacterium *Ralstonia*, for example, was codon optimized. In some cases, such as for the ptxABC phosphite transporter and ptxD phosphite dehydrogenase genes, both codon-optimized and non-codon-optimized variants were cloned. Codon modification of heterologous genes for optimal expression in *Cyanobacterium* sp. PTA-13311 was performed utilizing the codon usage table shown in Table 4.

Example 8

General Cloning Methods Used to Generate Plasmid Vectors

The plasmid vectors used herein were produced using PCR-based cloning techniques and the Invitrogen GENEART® Seamless Cloning and Assembly Kit from Life Technologies (Carlsbad, Calif., USA). Heterologous phosphite utilization genes were synthetically produced by custom synthesis. The plasmid backbone used was pAB1Cyano1-6.8, which is a synthetic derivative of an endogenous 6.8 kB extrachromosomal plasmid of *Cyanobacterium* sp. PTA-13311.

The ethanologenic plasmid backbones used were #1904 (pAB1-6.8::PnirA*2-pdc(AB1opt1)-TdsrA-PcpcB-ADH111-TrbcS) or #1938 (Porf0316- pdc(AB1opt1)-TdsrA-PcpcB-adh111 (AB1opt)-Trbc, respectively, also synthetic derivatives of the endogenous 6.8 kB extrachromosomal plasmid pAB1Cyano1-6.8 of *Cyanobacterium* sp. PTA-13311.

Example 9

Construction of Phosphite Utilization Plasmid Vectors and Ethanologenic Plasmid Vectors Several plasmid vectors were constructed to add various phosphite utilization genes to *Cyanobacterium* sp. PTA-13311. The phosphite dehydrogenase gene (ptxD) from various sources, as well as genes to transport phosphite into the cell (either multi-gene systems ptxA,B,C, or single gene systems such as the ptdC from *Desulfotignum phosphitoxidans*). FIG. 5 shows a summary of the different constructs that were prepared.

Plasmid annotations were made using "vector NTI" software (Thermo Fisher Scientific Inc., Waltham, Mass.). Abbreviations: CDS (coding DNA sequence); RBS (ribosome binding site); ORF (open reading frame); Km (kanamycin resistance gene). Asterisks (*) or (**), optionally followed by a number, denote recombinantly modified genes or promoters. All of the plasmids listed below were transformed to *Cyanobacterium* sp. PTA-13311 ("ABICyano1") or ("AB1").

Plasmid construct #1904 (pAB1-6.8::PnirA*2-pdc (AB1opt1)-TdsrA-PcpcB-ADH111-TrbcS) is present in a control ethanologenic control strain AB0250, without the phosphite utilization genes, in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Plasmid construct #1938 (Porf0316- pdc(AB1opt1)-TdsrA-PcpcB-adh111 (AB1opt)-Trbc) is present in an ethanologenic control strain AB0012, without modification of phosphite utilization or phosphate uptake genes, in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Figure 6:
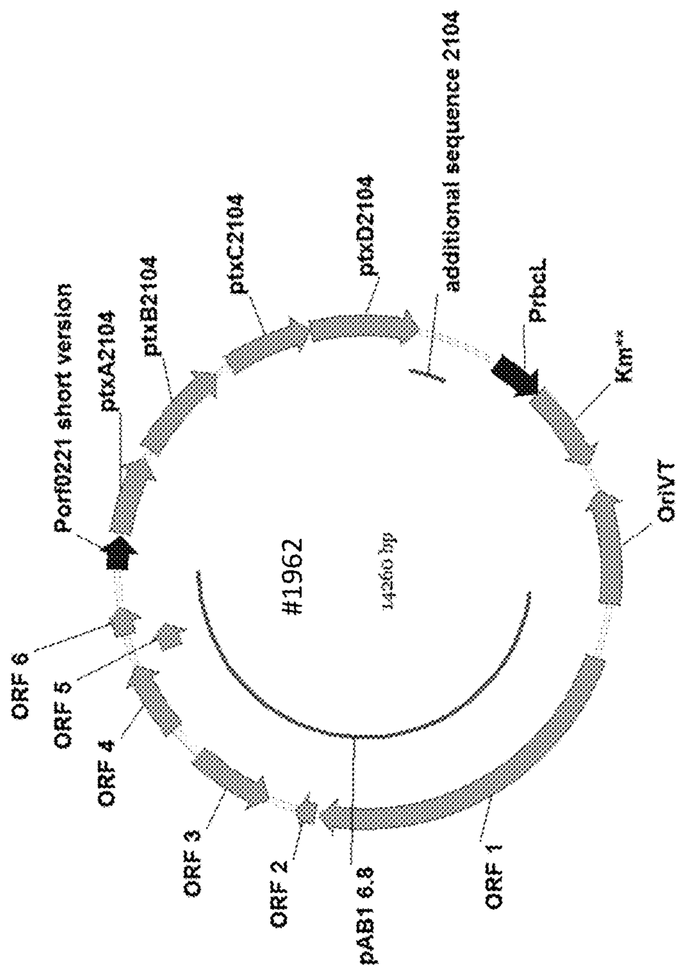
FIG. 6 is a map of the plasmid #1962 (SEQ ID NO: 1), present in cyanobacterial strain AB0493, as indicated in the table in FIG. 5. The plasmid construct is a synthetic derivative of an endogenous 6.8 kB extrachromosomal plasmid of *Cyanobacterium* sp. PTA-13311, Porf221-ptxABCD2104, having copper-inducible expression of phosphite utilization genes from *Cyanothece*, which are present in a single operon.

Plasmid construct #1962 (pAB1_6.8::Porf221-ptxABCD2104; SEQ ID NO: 1; FIG. 6) is present in strain AB0493 for copper inducible expression of phosphite utilization genes in a non-ethanologenic *Cyanobacterium* sp. PTA-13311 ("AB1") wild-type background. The plasmid construct is a synthetic derivative of an endogenous 6.8 kB extrachromosomal plasmid of *Cyanobacterium* sp. PTA-13311.

Figure 7:
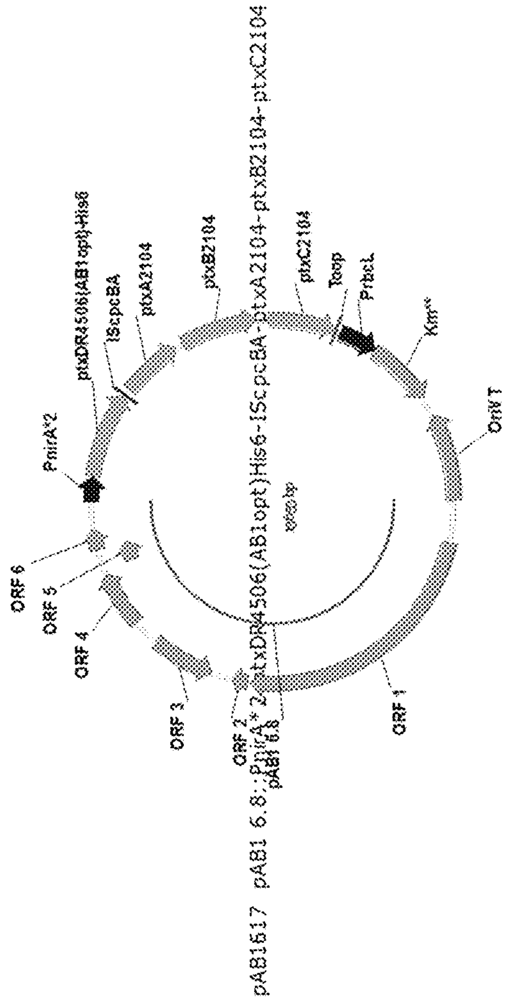
FIG. 7 is a map of the plasmid AB1617 (SEQ ID NO: 2), present in cyanobacterial strain AB0524, as indicated in the table in FIG. 5. The plasmid construct is a synthetic derivative of an endogenous 6.8 kB extrachromosomal plasmid of *Cyanobacterium* sp. PTA-13311, containing PnirA*2-ptxDR4506(AB1opt)-His6-IScpcBA-ptxABC2104-Toop, which allows nitrate inducible expression of phosphite utilization genes.

Plasmid construct pAB1617 (pAB1_6.8::PnirA*2-ptxDR4506(AB1opt)-His6-IScpcBA-ptxABC2104-Toop; SEQ ID NO: 2; FIG. 7) is present in strain AB0524 for nitrate inducible expression of phosphite utilization genes in a non-ethanologenic *Cyanobacterium* sp. PTA-13311 ("AB1") wild-type background. The plasmid construct is a synthetic derivative of an endogenous 6.8 kB extrachromosomal plasmid of *Cyanobacterium* sp. PTA-13311.

Figure 8:
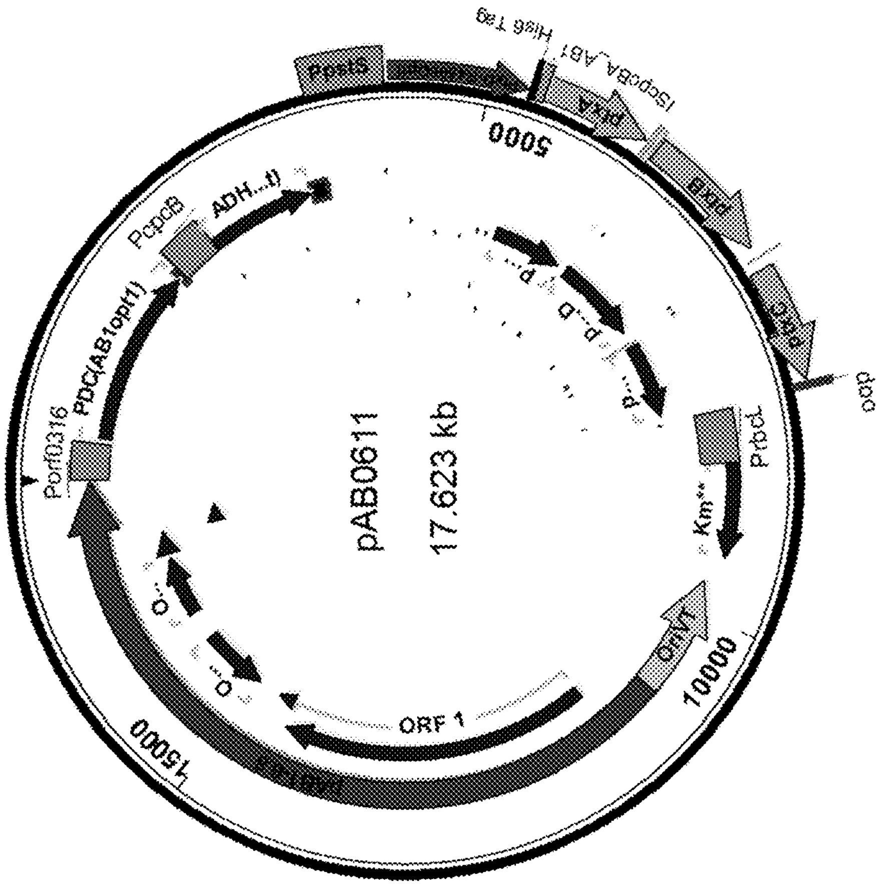
FIG. 8 is a map of the ~17.6 kB plasmid pAB0611 (SEQ ID NO: 3), which is present in cyanobacterial strain AB701, as indicated in the table in FIG. 5. The plasmid construct is a synthetic derivative of an endogenous 6.8 kB extrachromosomal plasmid of *Cyanobacterium* sp. PTA-13311, containing Porf0316-pdc(AB1opt1)-TdsrA-PcpcB-adh111 (AB1opt)-TrbcS-PpstS_ptxDR4506(AB1opt)-His6_IScpcBA_ptxABC2104, having phosphorus-regulatable (P-starvation inducible) expression of phosphite utilization genes, plus a copper inducible ethanol cassette.

Plasmid construct pAB611 (pAB1_6.8::Porf0316-pdc (AB1opt1)-TdsrA-PcpcB-adh111(AB1opt)-TrbcS-PpstS_ptxDR4506(AB1opt)-His6_IScpcBA_ptxABC2104;

SEQ ID NO: 3; FIG. 8) is present in strain AB0701 allowing for phosphorus regulatable (P-starvation inducible) expression of phosphite utilization genes, plus a copper inducible ethanol cassette, in a wild-type *Cyanobacterium* sp. PTA-13311 background. The plasmid construct is a synthetic derivative of an endogenous 6.8 kB extrachromosomal plasmid of *Cyanobacterium* sp. PTA-13311. This construct was prepared from the parent plasmid pAB0609, with the original ptdC-Dp(Opt1) gene replaced by ptxABC2104 operon. To prepare the plasmid, the parent vector pAB0609 was digested with NsiI and XhoI to remove the ptdC-Dp(Opt1) gene. The NsiI/XhoI digested ptxABC2104 operon from pAB1617 was ligated with digested pAB0609. Transformation was performed using nitrate-free plates with kanamycin selection for transformation. Testing for transformants was performed by the use of PCR, using PtxD-R4506-753F/2104ptxA-599R, which would be expected to generate a PCR product of 980 bp using the following primers:

```
PtxD-R4506-753F:
                                    (SEQ ID NO: 4)
5'-TGCTTTAGCTAGTGGTAAATTAGC-3'

2104ptxA-599R:
                                    (SEQ ID NO: 5)
5'-CTAACCACTGCCCCAATACCATC-3'
```

Figure 9:
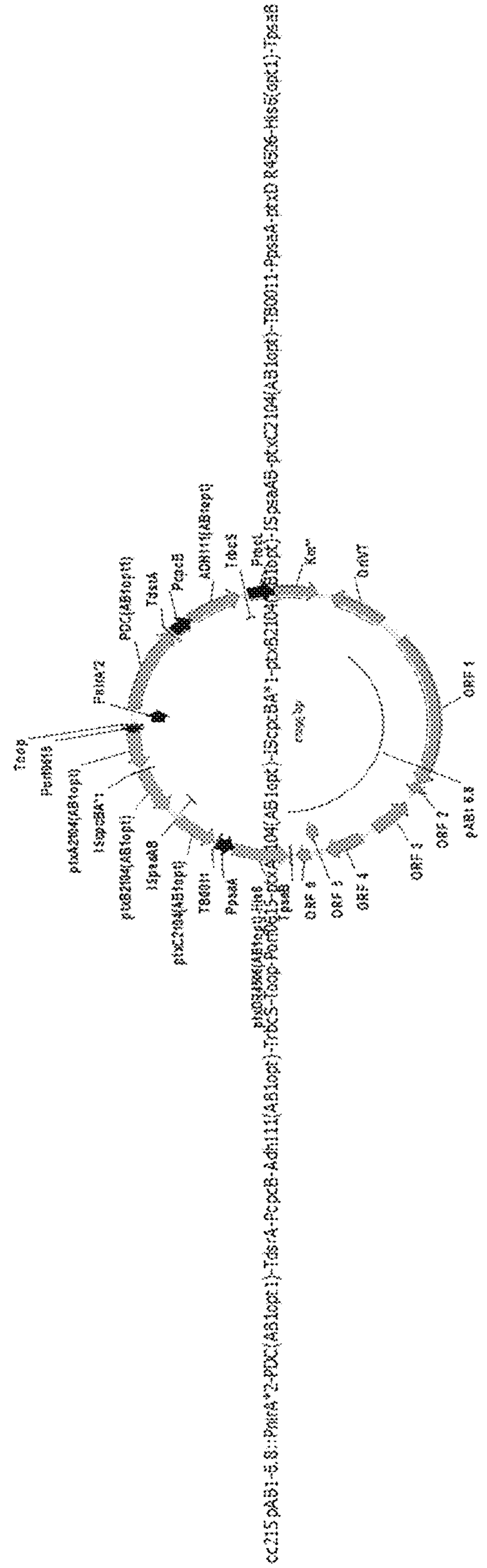
FIG. 9 is a map of the plasmid cc215 (SEQ ID NO: 6), present in cyanobacterial strain AB0762, as indicated in the table in FIG. 5. The plasmid construct is a synthetic derivative of an endogenous 6.8 kB extrachromosomal plasmid of *Cyanobacterium* sp. PTA-13311, containing PnirA*2-pdc (AB1opt1)-TdsrA-PcpcB-ADH111(AB1opt)-TrbcS-Toop-Porf00615-ptxA2104(AB1opt)-IScpcBA*1-ptxB2104 (AB1opt)-ISpsaAB-ptxC2104(AB1opt)-TB0011-PpsaA-ptxDR4506(AB1opt)-His6-TpsaB, which has constitutive expression of the phosphite utilization genes, plus a nitrate inducible ethanol cassette.

Plasmid construct cc215 (pAB1_6.8:: PnirA*2-pdc(AB1opt1)-TdsrA-PcpcB-ADH111(AB1opt)-TrbcS-Toop-Porf00615-ptxA2104(AB1opt)-IScpcBA*1-ptxB2104(AB1opt)-ISpsaAB-ptxC2104(AB1opt)-TB 0011-PpsaA-ptxDR4506(AB1opt)-His6-TpsaB; SEQ ID NO: 6; FIG. 9) is present in strain AB0762 allowing for constitutive expression of the phosphite utilization genes, plus a nitrate inducible ethanol cassette, in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Figure 10:
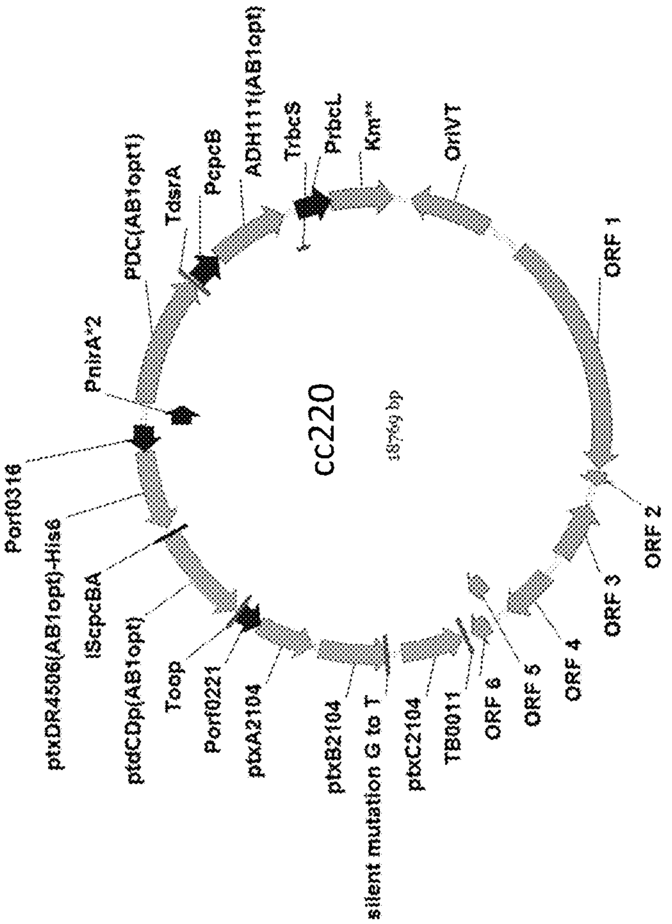
FIG. 10 is a map of the plasmid cc220 (SEQ ID NO: 7) present in cyanobacterial strain AB764, as indicated in the table in FIG. 5. The plasmid construct is a synthetic derivative of an endogenous 6.8 kB extrachromosomal plasmid of *Cyanobacterium* sp. PTA-13311, containing PnirA*2-pdc (AB1opt1)-TdsrA-PcpcB-ADH111(AB 1opt)-TrbcS-Porf0316-ptxDR4506(AB1opt)-His6-IScpcBA-ptdCDp (AB1opt)-Toop-Porf0221-ptxABC2104-TB0011, allowing copper inducible expression of phosphite utilization genes with two phosphite transporters and a nitrate inducible ethanol cassette.

Plasmid construct cc220 (pAB1_6.8:: PnirA*2-pdc(AB1opt1)-TdsrA-PcpcB-ADH111(AB1opt)-TrbcS-Porf0316- ptxDR4506(AB1opt)-His6-IScpcBA-ptdCDp(AB1opt)-Toop-Porf0221-ptxABC2104-TB0011; SEQ ID NO: 7; FIG. 10) is present in AB0764 allowing for copper inducible expression of phosphite utilization genes with two phosphite transporters and a nitrate inducible expression of the ethanol cassette, in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Figure 11:
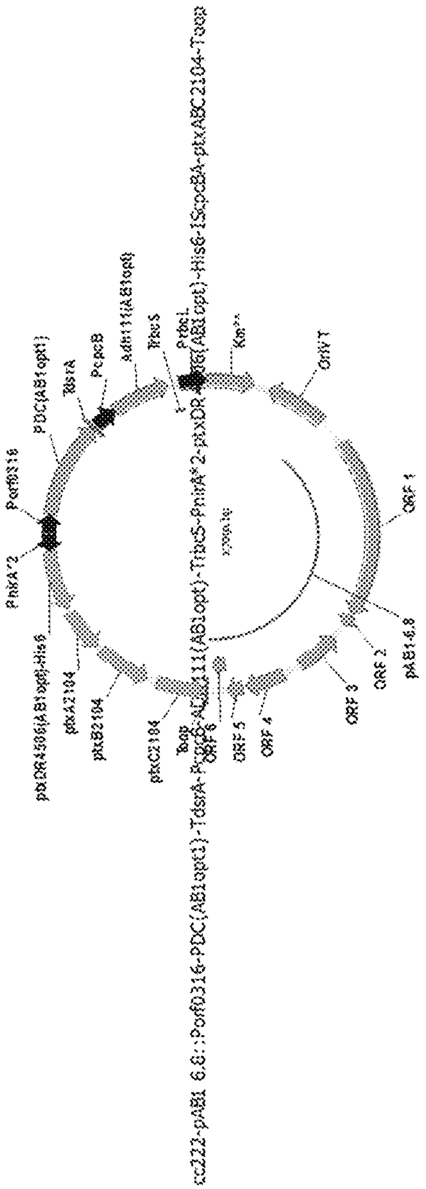
FIG. 11 is a map of the plasmid cc222 (SEQ ID NO: 8), present in cyanobacterial strain AB0765, as indicated in the table in FIG. 5. The plasmid construct is a synthetic derivative of an endogenous 6.8 kB extrachromosomal plasmid of *Cyanobacterium* sp. PTA-13311, containing Porf0316-pdc (AB1opt1)-TdsrA-PcpcB-ADH111(AB1opt)-TrbcS-PnirA*2-ptxDR4506(AB1opt)-His6-IScpcBA-ptx-ABC2104-Toop, which allows nitrate inducible expression of phosphite utilization genes, plus copper inducible expression of the ethanol cassette.

Plasmid construct cc222 (pAB 1_6.8:: Porf0316-pdc(AB1opt1)-TdsrA-PcpcB-ADH111(AB1opt)-TrbcS-PnirA*2-ptxDR4506(AB1opt)-His6-IScpcBA-ptxABC2104-Toop; SEQ ID NO: 8; FIG. 11) present in strain AB0765 harbors a nitrate inducible expression cassette of phosphite utilization genes, plus copper inducible expression of the ethanol cassette, in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Figure 12:
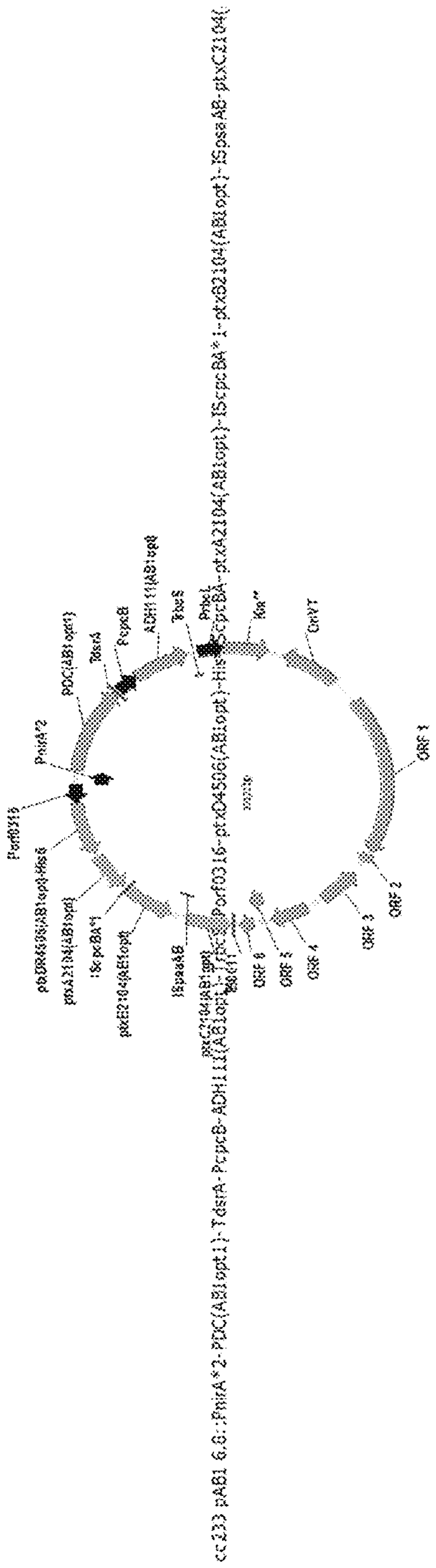
FIG. 12 is a map of the plasmid cc233 (SEQ ID NO: 9), present in cyanobacterial strain AB0766, as indicated in the table in FIG. 5. The plasmid construct is a synthetic derivative of an endogenous 6.8 kB extrachromosomal plasmid of *Cyanobacterium* sp. PTA-13311, containing PnirA*2-pdc (AB1opt1)-TdsrA-PcpcB-ADH111(AB1opt)-TrbcS-Porf0316-ptxDR4506(AB1opt)-His6-IScpcBA-ptxA2104 (AB1opt)-IScpcBA*1-ptxB2104(AB1opt)-ISpsaAB-ptxC2104(AB1opt)-TB0011, which allows copper inducible expression of the phosphite utilization genes, and a nitrate inducible ethanol cassette.

Plasmid construct cc233 (pAB1-6.8:: PnirA*2-pdc(AB1opt1)-TdsrA-PcpcB-ADH111(AB1opt)-TrbcS-Porf0316-ptxDR4506(AB1opt)-His6-IScpcBA-ptxA2104(AB1opt)-IScpcBA*1-ptxB2104(AB1opt)-ISpsaAB-ptxC2104(AB1opt)-TB0011; SEQ ID NO: 9; FIG. 12) present in strain AB0766 harbors a copper inducible expression cassette of the phosphite utilization genes, and a nitrate inducible ethanol cassette in a wild-type *Cyanobacterium* sp. PTA-13311 background. The plasmid construct is a synthetic derivative of an endogenous 6.8 kB extrachromosomal plasmid of *Cyanobacterium* sp. PTA-13311.

Figure 13:
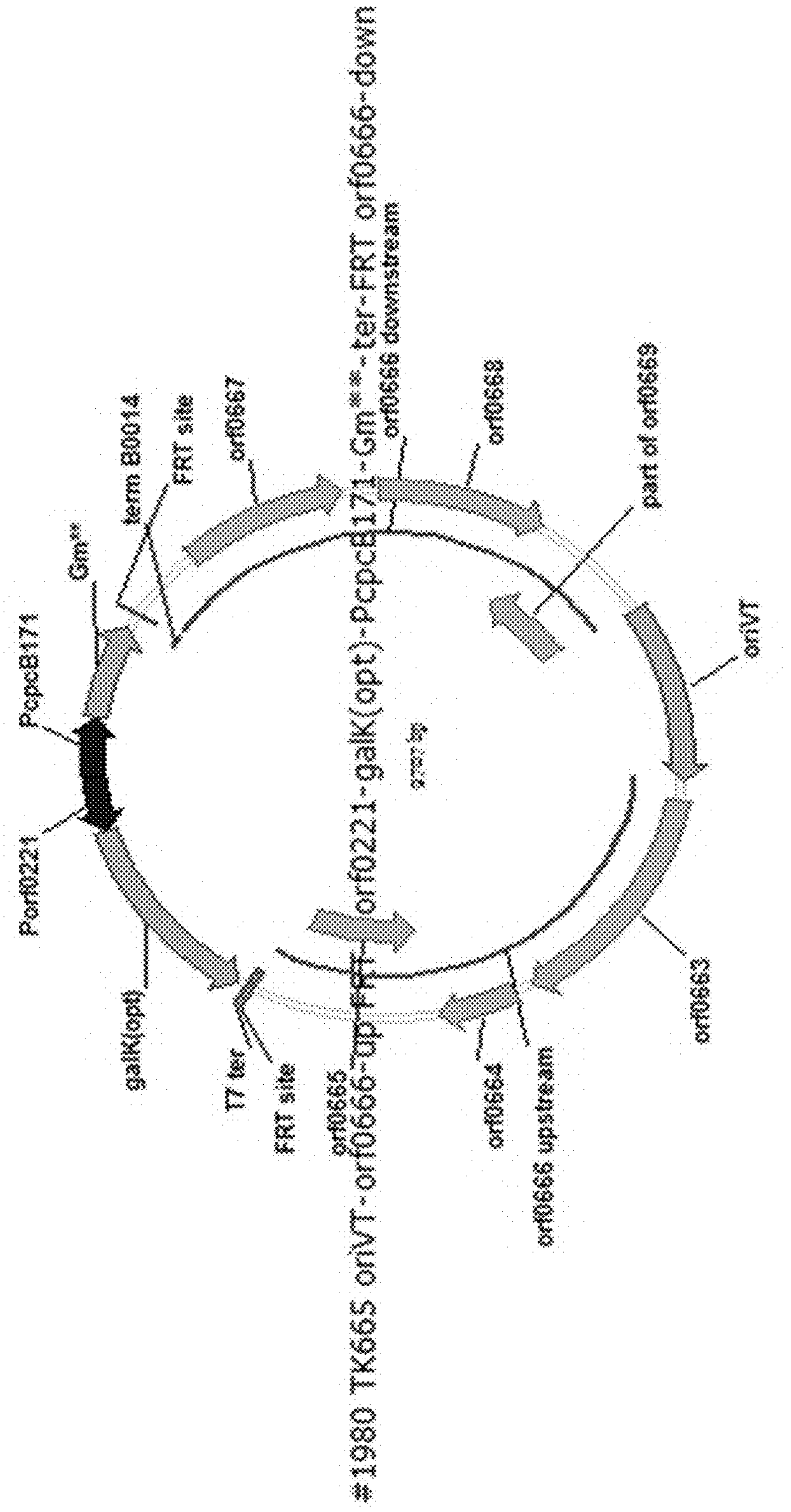
FIG. 13 is a map of the plasmid #1980 (SEQ ID NO: 10), which was used to generate cyanobacterial knock-out strain AB0040, as indicated in the table in FIG. 5. The strain AB0040 is *Cyanobacterium* sp. PTA-13311 having a knock-out of the phosphate transport regulator gene phoU (orf0666). This results in a faster rate of phosphate uptake into the cell, when phosphate is present in the medium.

Cyanobacterial strain AB0040 (ΔAB1_orf0666) is *Cyanobacterium* sp. PTA-13311 having a knockout of the phosphate metabolism regulatory gene phoU (orf0666) (FIG. 13). This results in a faster rate of phosphate uptake into the cell, when phosphate is present in the medium.

Plasmid construct cc233 (pAB1-6.8::PnirA*2-pdc(AB1opt1)-TdsrA-PcpcB-ADH111(AB1opt)-TrbcS-Porf0316-ptxDR4506(AB1opt)-His6-IScpcBA-ptxA2104(AB1opt)-IScpcBA*1-ptxB2104(AB1opt)-ISpsaAB-ptxC2104(AB1opt)-TB0011) present in strain AB0793 contains copper inducible expression cassette of the phosphite utilization genes and a nitrate inducible ethanol cassette in a AphoU background. The plasmid construct is a synthetic derivative of an endogenous 6.8 kB extrachromosomal plasmid of *Cyanobacterium* sp. PTA-13311.

Example 10

Transformation of *Cyanobacterium* sp. PTA-13311

Due to a significant layer of extracellular polymeric substances (EPS) outside the cell of the production strain *Cyanobacterium* sp. PTA-13311 ("AB1"), the following method was used to decrease the EPS layer prior to conjugation. The method involved several steps: treatment of cells with N-acetylcysteine (NAC); washing steps that utilize NaCl; a treatment with lysozyme and subsequent washing. Firstly, 200 ml of an exponentially growing culture ($0.5<OD_{750nm}<1$) was incubated with N-acetylcysteine (NAC) for 2 days at 16° C. at 0.1 mg/ml final concentration without shaking. The culture was then pelleted at 4400 rpm and washed with 0.9% NaCl containing 8 mM EDTA. The cell pellet was resuspended in 0.5 M sucrose and incubated for 60 minutes at room temperature (RT) with slow shaking at 85 rpm. Cells were then centrifuged and resuspended in 40 ml of a solution containing 50 mM Tris pH 8.0, 10 mM EDTA pH 8.0, 4% sucrose, and 20-40 µg/ml lysozyme. After incubation at RT for 10-15 minutes, cells were centrifuged and washed three times using different washing solutions, namely i) with 30 mM Tris containing 4% sucrose and 1 mM EDTA, ii) with 100 mM Tris containing 2% sucrose and iii) with BG-11 medium. All centrifugation steps before the lysozyme treatment were performed at 4400 rpm for 10 min at 10° C., all centrifugations after the lysozyme treatment were performed at 2400 rpm for 5 minutes at 4° C. The cells were then resuspended in 400 µl BG-11 culture medium containing Tris/sucrose buffer and used for gene transfer via conjugation.

Triparental mating was performed as follows. *E. coli* strain J53 bearing a conjugative RP4 plasmid and *E. coli* strain HB101 bearing the plasmid cargo to be introduced into *Cyanobacterium* sp. PTA-13311 and the pRL528 helper plasmid for in vivo methylation were used. *E. coli* strains were grown in LB broth supplemented with the appropriate antibiotics overnight at 37° C. with shaking at 100 rpm. An aliquot of 3 to 5 ml of each culture was centrifuged, washed twice with LB medium and resuspended in 200 µL LB medium. Subsequently, the *E. coli* strains were mixed, centrifuged and resuspended in 100 µL BG-11 medium. A 100 µL aliquot of the resuspended cyanobacterial cells and the *E. coli* cultures were mixed and applied onto a membrane filter (Millipore GVWP, 0.22 µm pore size) placed on the surface of solid BG-11 medium supplemented with 5%

LB. Petri dishes were incubated under dim light of 5 μmol photons $m^{-2}s^{-1}$ for two days. Cells were then resuspended in fresh BG-11 medium and plated onto selective medium containing 10 and 15 μg/ml kanamycin, respectively. The following selection conditions were used: light intensity approximately 20-40 μmol photons $m^{-2}s^{-1}$ at a temperature of approximately 28° C. Transformants were visible after approximately 10-14 days. The transformant colonies were then plated on BG-11 medium containing 15 μg/ml kanamycin and then stepwise transferred to higher kanamycin concentrations up to kanamycin 60 μg/ml to aid in the selection process.

Example 11

Characterization of the New Phosphite-Utilizing Cyanobacterial Host Cells

The new phosphite utilization strain AB0766, containing the phosphite dehydrogenase gene from *Ralstonia* sp. strain 4506, and the phosphite uptake genes ptxABC from *Cyanothece* sp. ATCC-51142, codon optimized for optimal expression in *Cyanobacterium* sp. PTA-13311, was tested to confirm that the modified strain was capable of utilizing phosphite. Both strains were also modified to contain an ethanologenic (pdc/adh) construct.

The cultures were grown in triplicates over a 24 day period in 1.2 L indoor photobioreactors, under a 12 hour on/12 hour off light cycle, essentially following the culture method of Example 2, above. Cell density ($OD_{750}$), chlorophyll, and ethanol production were measured periodically. At day 10, additional nutrients and phosphorus (as $PO_4$ or $PO_3$) were added to the culture.

Figure 14A:
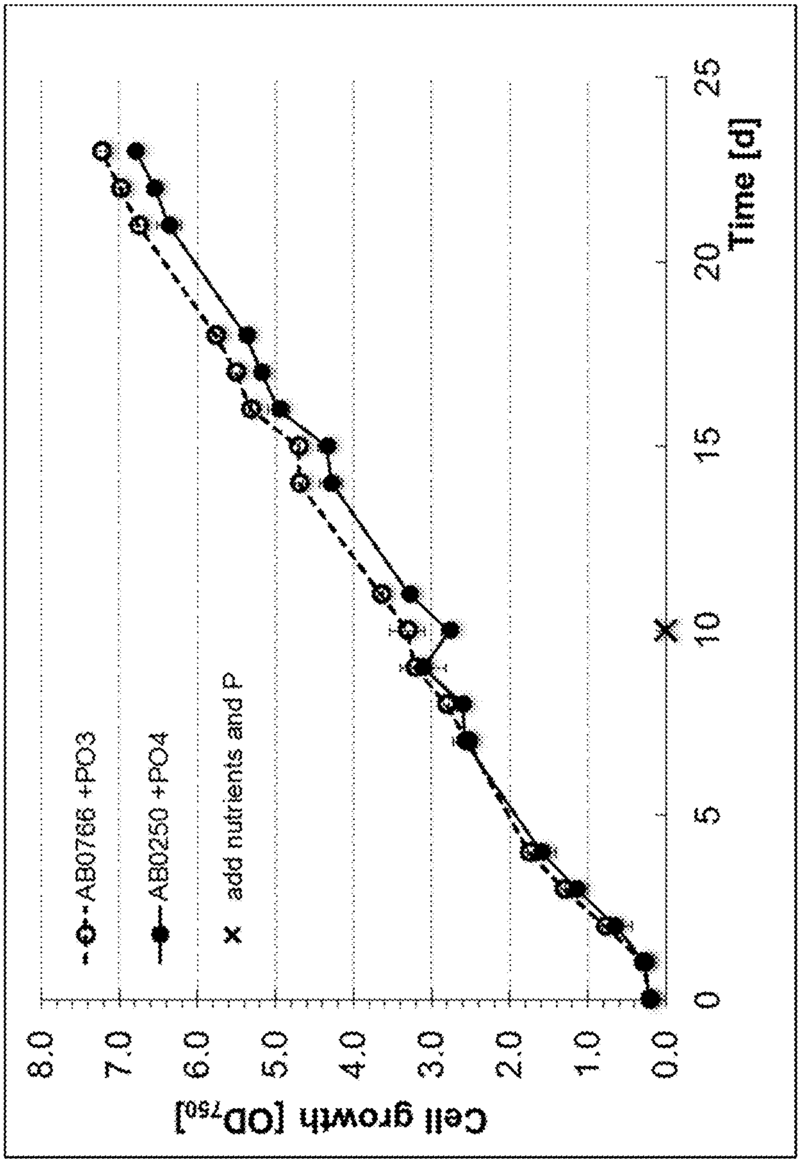
FIG. 14A is a graph showing the comparative cell growth ($OD_{750}$) of the phosphite-utilizing, ethanologenic strain AB0766 on phosphite as the phosphorus source, with the control ethanologenic strain AB0250 on phosphate as the phosphorus source. Additional nutrients and the indicated P source were added at day 10. The graph shows similar cell growth in the two strains.
Figure 14B:
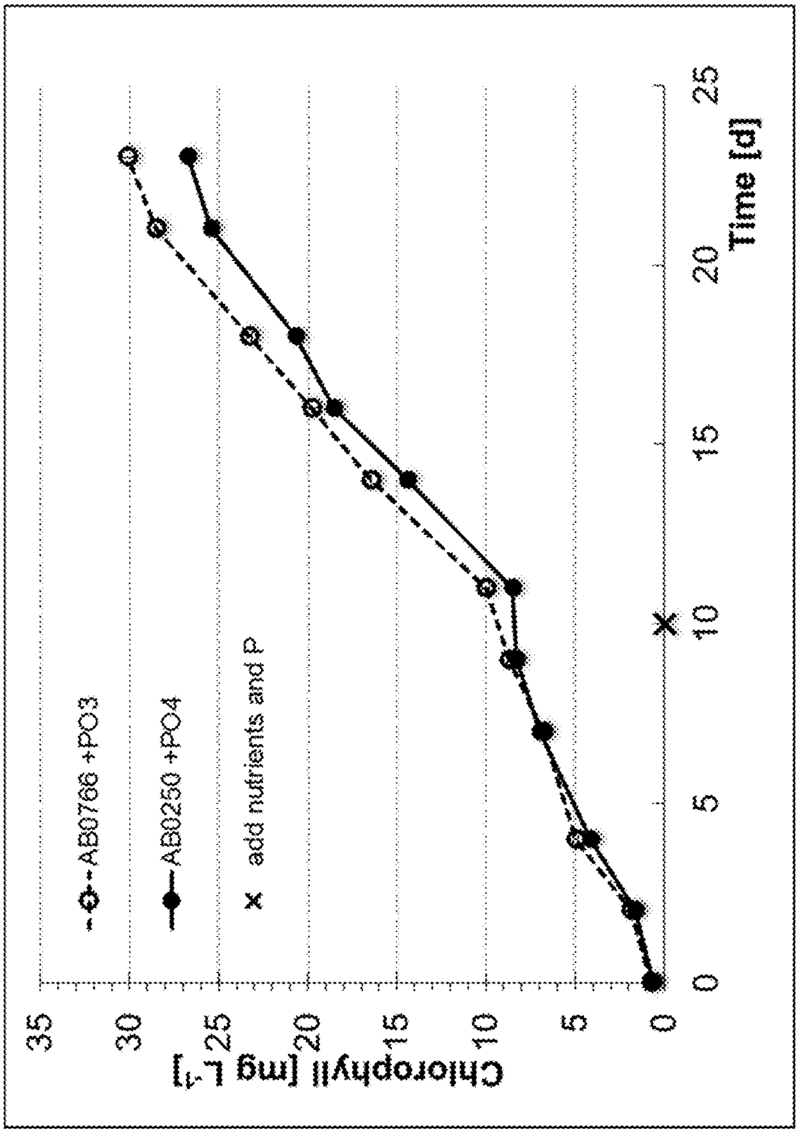
FIG. 14B is a graph showing the comparative chlorophyll content (in mg/L) of the phosphite-utilizing, ethanologenic strain AB0766 on phosphite as the phosphorus source, with the control ethanologenic strain AB0250 on phosphate as the phosphorus source. The graph shows similar chlorophyll content in the two strains.
Figure 14C:
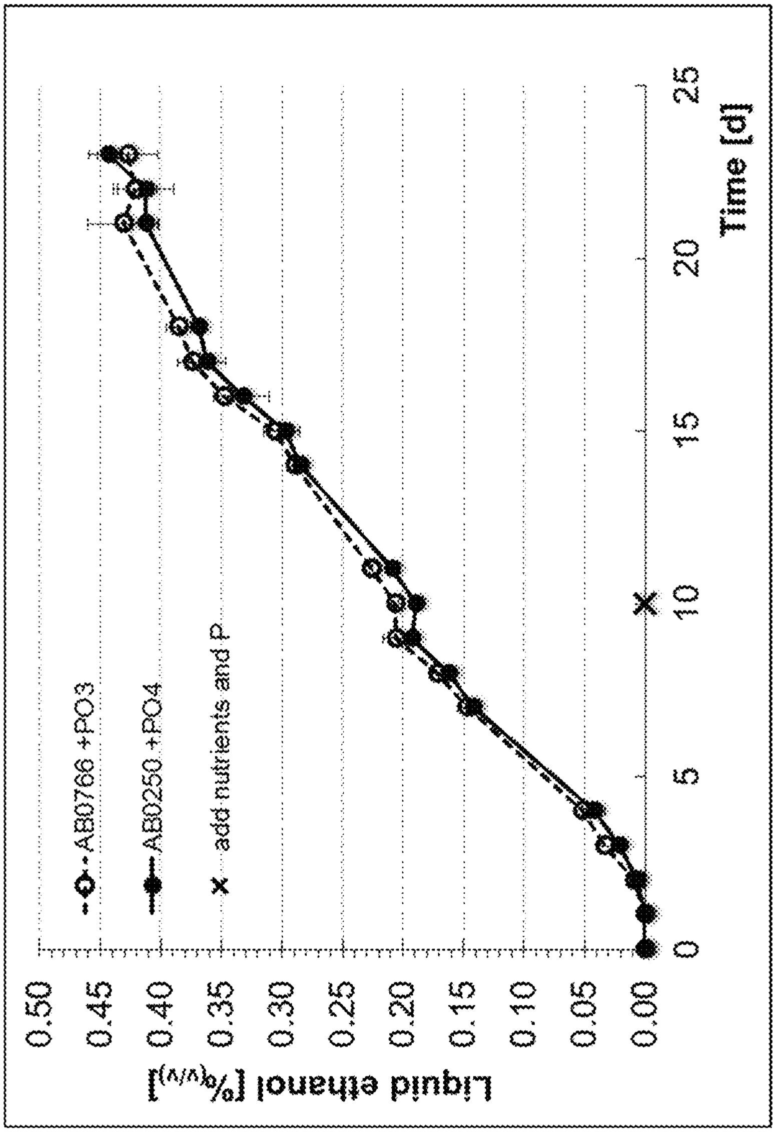
FIG. 14C is a graph showing comparative ethanol production (in % v/v) of the phosphite-utilizing, ethanologenic strain AB0766 on phosphite as the phosphorus source, with the control ethanologenic strain AB0250 on phosphate as the phosphorus source. The graph shows similar ethanol production in the two strains.

As shown in FIG. 14A, the cell growth measurements were similar between the phosphite utilization strain grown on phosphite (AB0766) and a control strain (AB0250) grown on phosphate. The chlorophyll levels and ethanol production were also comparable between the phosphite utilizer strain (AB0766) and the phosphate utilizer strain (AB250) (FIG. 14B). Lastly, the ethanol production (% v/v) was also similar between the two strains (FIG. 14C).

Thus, cyanobacterial cells that are not able to grow on phosphite can be modified with phosphite uptake and utilization genes from other organisms. As demonstrated here, the modified cells have a similar growth rate, chlorophyll content, and ethanol production as ethanologenic cyanobacterial cells that are grown on phosphate.

Example 12

The New Phosphite-Utilizing Cyanobacterial Strains Can Switch Between Utilization of Phosphate and Phosphite The new phosphite utilization strains are capable of utilizing both phosphate and phosphite. As shown in the above experiments, cell growth rates and ethanol production levels were similar when the new strains are fed either phosphate or phosphite as the sole source of phosphorus. Because the new strains can utilize both sources of phosphorus, the modified host cell cultures can also switch back and forth between the use of phosphate and phosphite, without sacrificing production levels. Since many contaminating organisms are unable to utilize both phosphorus sources efficiently, switching back and forth between phosphate and phosphite as the sole phosphorus source is useful for contamination control.

To demonstrate the phosphorus source switching capability, and to see whether these changes affect ethanol production, the cultures were grown on one phosphorus source first, then diluted and switched to the other phosphorus source. Additionally, a one-time, bulk feeding of the phosphorus source at the beginning of the run was compared with the feeding of smaller intermittent doses of phosphorus over time.

The following copper-regulatable ethanologenic strains with the indicated phosphite gene modifications were used: Control strain was AB0012: (Porf0316-pdc(AB1opt1)-TdsrA-PcpcB-adh111 (AB1opt)-TrbcS). The phosphite utilization strain was AB0701 (Porf0316- pdc(AB1opt1)-TdsrA-PcpcB-adh111 (AB1opt)-TrbcS-PpstS-ptxDR4506His-IScpcBA-ptxABC2104-Toop-).

The cells were inoculated at an initial cell density of 0.2 $OD_{750}$ in 500-mL vertical photobioreactors with 350 mL culture medium (1× NWW+BG-11-P-free+17 mM Nitrate+P-source).

The photobioreactors receiving an intermittent dose of P-source were fed as follows: the cultures received 35 μM P-source at inoculation, and at every increase of 1.0 $OD_{750}$, starting at 1.0 $OD_{750}$. The photobioreactor cultures that received a bulk dose of P-source at the beginning of the culture were given 230 μM of the indicated P-source.

Copper induction of ethanologenesis was initiated when cell density reached approximately 1 $OD_{750}$ by addition of 0.85 μM $CuSO_4$ per $OD_{750}$. The light was set at approximately 350 μmol photons $m^{-2}s^{-1}$ on one side, with a 12 hour/12 hour photoperiod. The cultures were given continuous aeration with 25 SCCM inflow, and $CO_2$ was added at a constant rate, from 1-6% ramped manually during the light period with 0.25% during the dark period. The cultures were grown for 41 days, with one 20× dilution to new medium at day 20.

Figure 15:
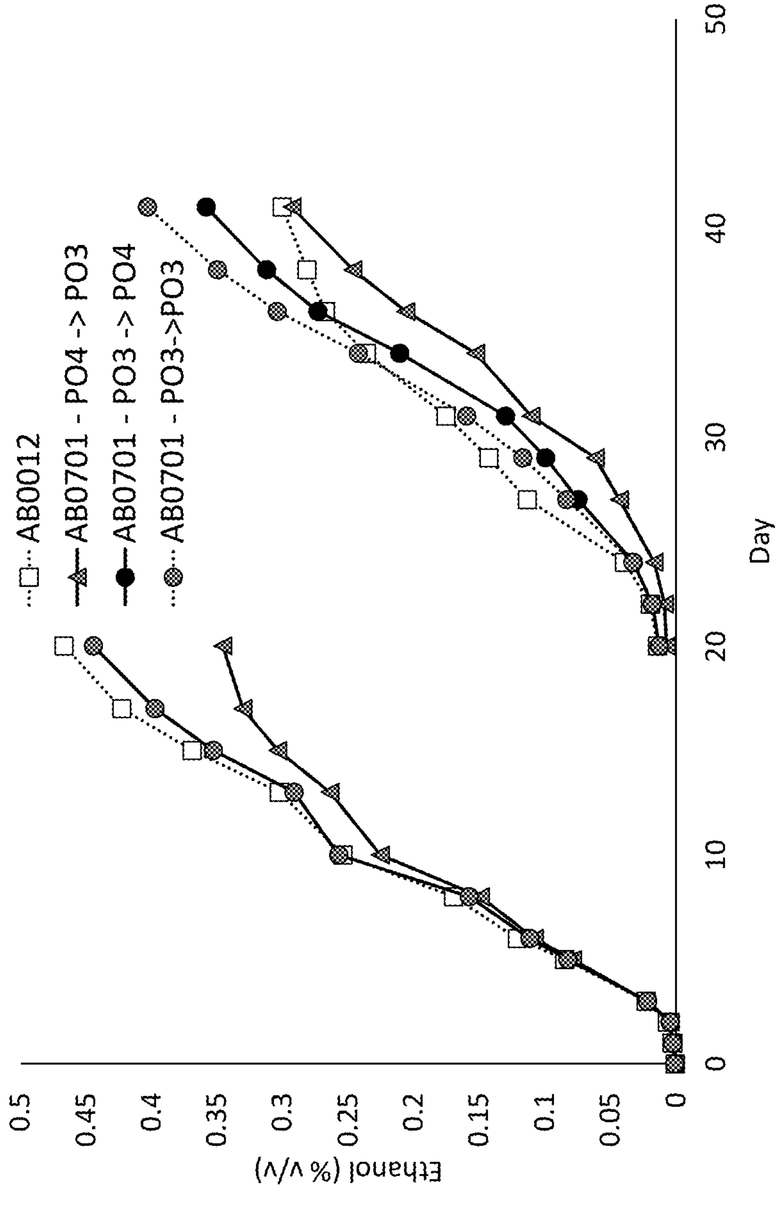
FIG. 15 is a line graph showing the ethanol production (in % v/v) of a phosphite-utilizing, ethanologenic strain AB0701 on either phosphate or phosphite as the phosphorus source, in comparison to the control ethanologenic strain AB0012 (see FIG. 5), growing with phosphate as the sole phosphorus source. At day 20, two of the cultures were switched from one form of phosphorus to the other, showing that this change in phosphorus source does not affect ethanol production.

At day 20, the cells were diluted 20-fold in culture medium, with the phosphorus source switched as indicated in FIG. 15.

Empty square: control strain AB0012 (not capable of utilizing phosphite).

Grey circle: phosphite-utilizing strain AB0701, grown on phosphite for the first 19 days, then grown in new medium, again with phosphite.

Grey triangle: phosphite-utilizing strain AB0701, grown on phosphate for the first 19 days, then switched to phosphite.

Black circle: phosphite-utilizing strain AB0701, grown on phosphite for the first 19 days, then switched to phosphate.

The graph shows that the cells were able to produce comparable amounts of ethanol when they were switched to a different phosphorus source (either phosphite to phosphate or phosphate to phosphite). Thus, either phosphate or phosphite can be used as needed, and the phosphorus source can be switched from one to another without affecting ethanol production.

Example 13

Figure 16:
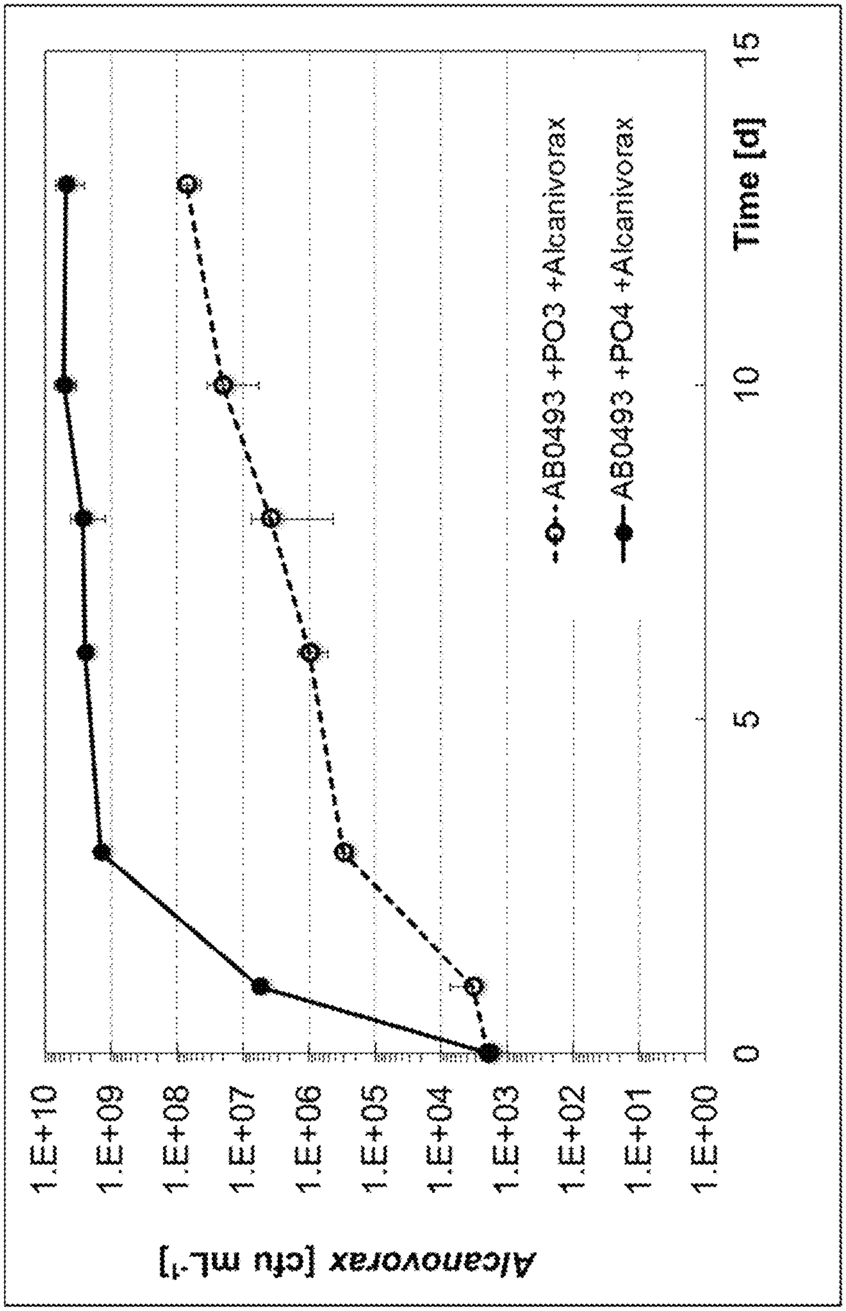
FIG. 16 is a line graph showing that certain contaminants grow poorly on $PO_3$. The common contaminant bacterium *Alcanivorax* was added to an axenic culture containing the phosphite utilizing cyanobacterial strain AB0493, with either phosphate or phosphite as the sole phosphorus source. The *Alcanivorax* cell count (in CFU/ml), was determined over a 13 day growth period. *Alcanivorax* grew well when $PO_4$ was the sole phosphorus source, but grew poorly when the sole phosphorus source was $PO_3$.

Contaminating Bacteria Have a Lower Cell Density When the Cyanobacterial Culture is Grown on Phosphite Previous research found that outdoor cultivated ethanologenic cyanobacterial cultures often became contaminated with bacterial species such as *Alcanivorax*. To determine whether the new phosphite-utilizing cyanobacterial strains would have an advantage over the wild type phosphate utilizing cyanobacteria when grown in a non-axenic culture, the following experiment was performed in 1.2 L vertical photobioreactors using a 12/12 hour light cycle essentially following the method described in Example 2. The non-ethanologenic phosphite utilizing strain AB0493 was spiked with the common heterotrophic bacterial contaminant *Alcanivorax* to mimic outdoor contaminated growth conditions. *Alcanivorax* grew poorly when phosphite was the sole phosphorus source, in comparison to phosphate (FIG. 16). This graph demonstrates that the phosphite-utilizing cyanobacterial strains are less likely to become highly contaminated in outdoor production cultures.

Example 14

Figure 17:
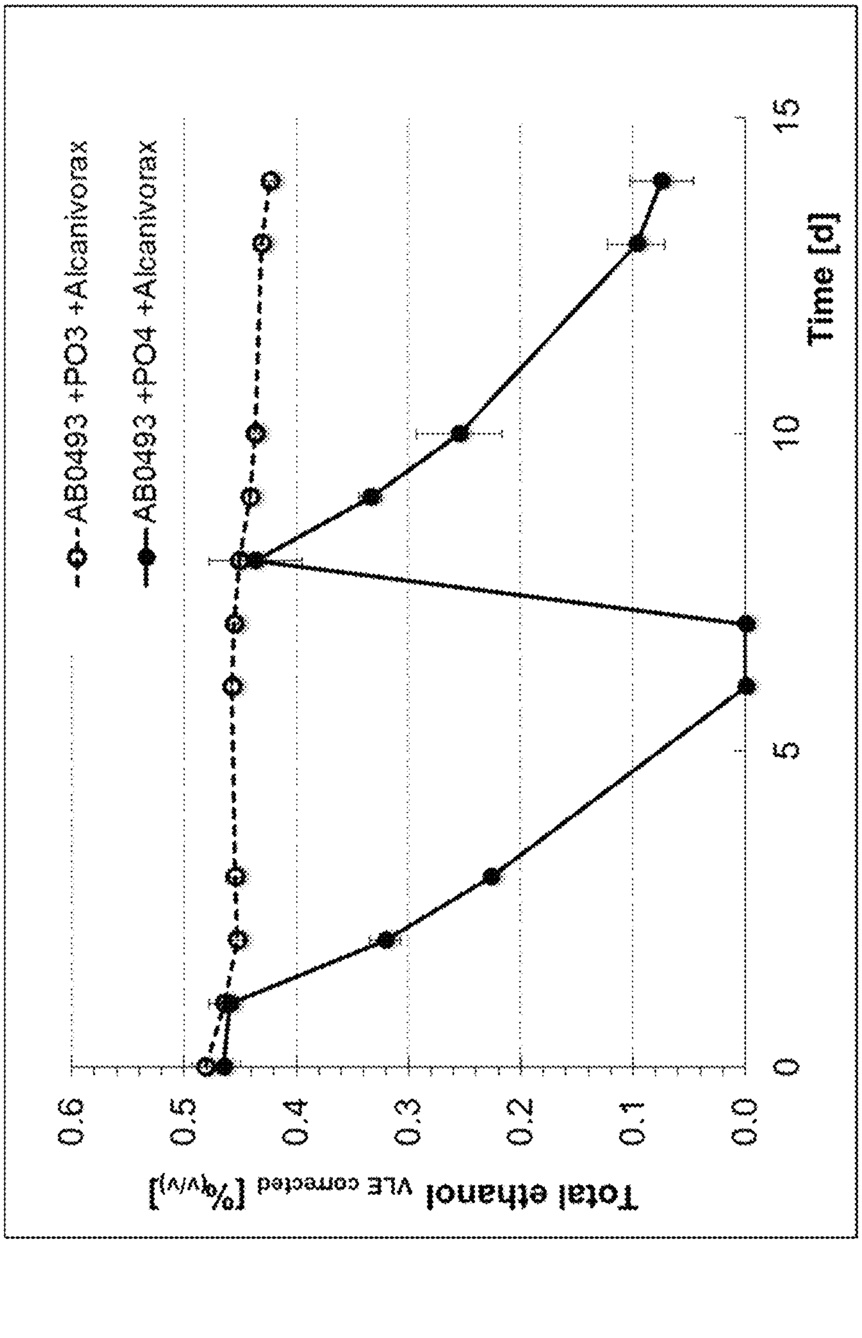
FIG. 17 is a line graph showing the bacterial consumption of artificially added (spiked) ethanol in a culture of the phosphite utilizing cyanobacterial strain AB0493, which was artificially contaminated with the bacterium *Alcanivorax*, grown in either phosphate or phosphite as the sole phosphorus source. At day 8 a second dose of ethanol was added to the culture grown on phosphate. The *Alcanivorax* strain was incapable of consuming the artificially added ethanol when the sole phosphorus source was $PO_3$. However, when the sole phosphorus source was phosphate, *Alcanivorax* was able to rapidly consume the added ethanol.

Contaminating Bacteria are Less Able to Consume Spiked Ethanol When the Phosphorus Source is Phosphite In addition to the problem of rapid growth of certain bacterial contaminants such as *Alcanivorax* in the cyanobacterial production cultures, these contaminants can also consume most or even all of the ethanol that is produced by the ethanologenic cyanobacterial cultures. To test whether this would also be the case when phosphite was used as the sole phosphorus source instead of phosphate, an amount of ethanol was added (spiked) at day 0 and day 8 to the combined cyanobacteria and *Alcanivorax* culture (the mixed culture of non-ethanologenic phosphite utilizing strain AB0493 and *Alcanivorax* as described in the above experiment). The ethanol levels were then measured throughout the culture run. It was found that ethanol consumption by *Alcanivorax* was significantly lowered when the phosphorus source was phosphite rather than phosphate (FIG. 17).

Example 15

Characterization of Artificially Contaminated Ethanologenic, Phosphite-Utilizing Cyanobacterial Cultures The following several experiments were performed to determine whether cells cultured on phosphite would produce comparable amounts of ethanol as when grown on phosphate alone, as well as what effect the phosphite system has on contaminants.

For this series of experiments (FIG. 18A-FIG. 20B), a different phosphite-utilizing strain was used. The cyanobacterial strain AB0701 (Porf0316-pdc (AB1opt1)-TdsrA-PcpcB-adh111 (AB1opt)-TrbcS-PpstS-ptxDR4506His-IScpcBA-ptxABC2104-Toop-), contained ethanologenic genes under the regulation of a copper-inducible promoter, as well as phosphite utilization genes. The strain was grown in vertical photobioreactors in mBG-11 medium (with BG-11 nutrients, but free of P, N, and Cu), with the addition of 17 mM nitrate, 25 μM phosphite or phosphate. As the culture grew, the following nutrients were added intermittently: 35 μM phosphate (as phosphoric acid) or phosphite (as phosphorous acid) with 0.85 uM Copper per $OD_{750}$. The cultures had a starting inoculation density of 0.3 $OD_{750}$. The cultures received light in a 12 hour on/12 hour off cycle, at 300 μmol photons $m^{-2}s^{-1}$, with a temperature of approximately 32° C.

To mimic the longer-term culture growth in outdoor large-scale, commercial systems, the cultures were grown in two semi-continuous batches. The treatments were run in duplicates, with the results of each treatment shown (FIG. 18A-FIG. 20B). After a 14 day first batch, the culture was harvested, and a portion of the culture was diluted into new medium at a starting cell density of 0.3 $OD_{750}$. In some of the cultures, the phosphorus source was switched (phosphate or phosphite) during the second batch to determine the effect of the phosphorus-source switch on ethanol levels, contamination levels, and ethanol consumption by contaminants.

Example 16

Phosphate Control: Some Common Contaminating Bacteria Consume the Ethanol Produced by the Cyanobacterial Cultures The AB701 cultures (growing in phosphate as the sole source of phosphorus) were spiked with either the contaminant bacteria *Alcanivorax* or spiked with a mixture of contaminating bacteria, and the cultures were analyzed intermittently for cell density and ethanol production.

Figure 18A:
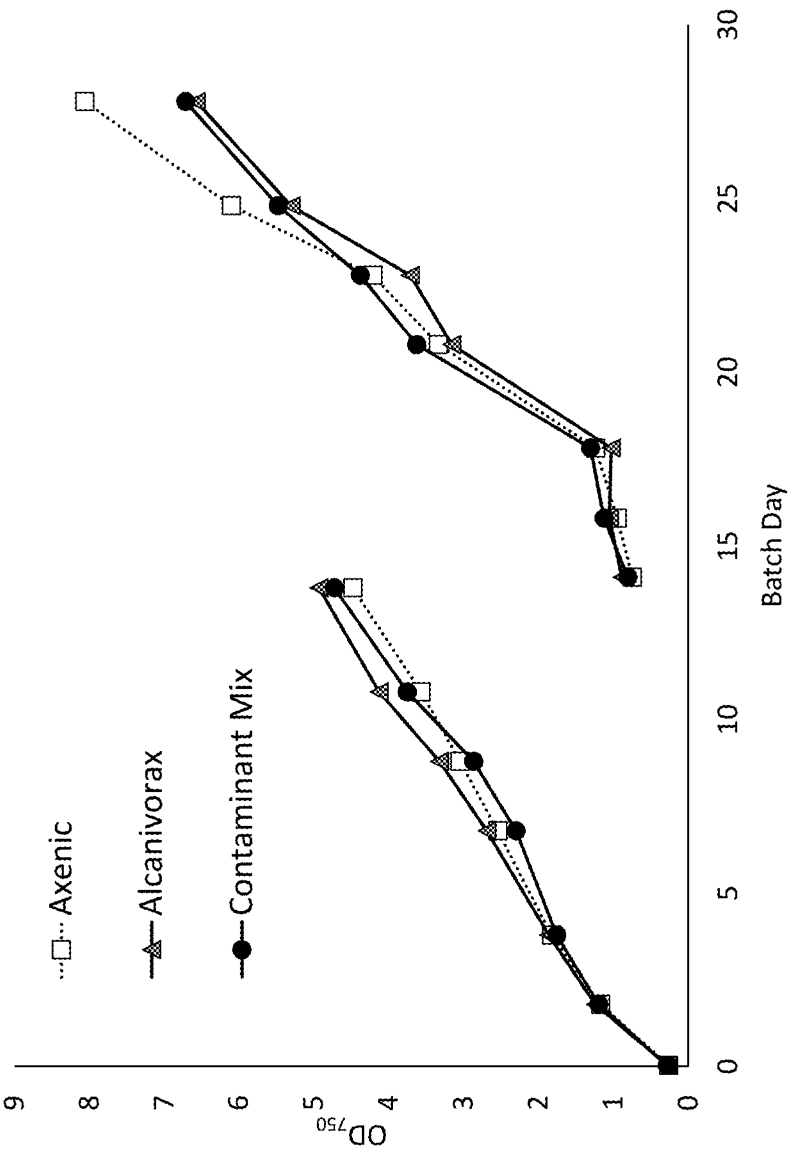
FIG. 18A is a line graph showing the cyanobacterial cell growth (in $OD_{750}$) of the phosphite-utilizing cyanobacterial strain AB0701, spiked with either the bacterial contaminant *Alcanivorax*, or with a "contaminant mix", when grown on phosphate as the sole phosphorus source. Empty squares: Axenic culture. Grey triangles: Culture with *Alcanivorax* added. Black circles: Culture with a contaminant mix added. At day 14, the cultures were harvested, and a portion was re-suspended in new medium.

The cyanobacterial cell growth (as measured by $OD_{750}$) was not affected by the contamination (FIG. 18A).

Figure 18B:
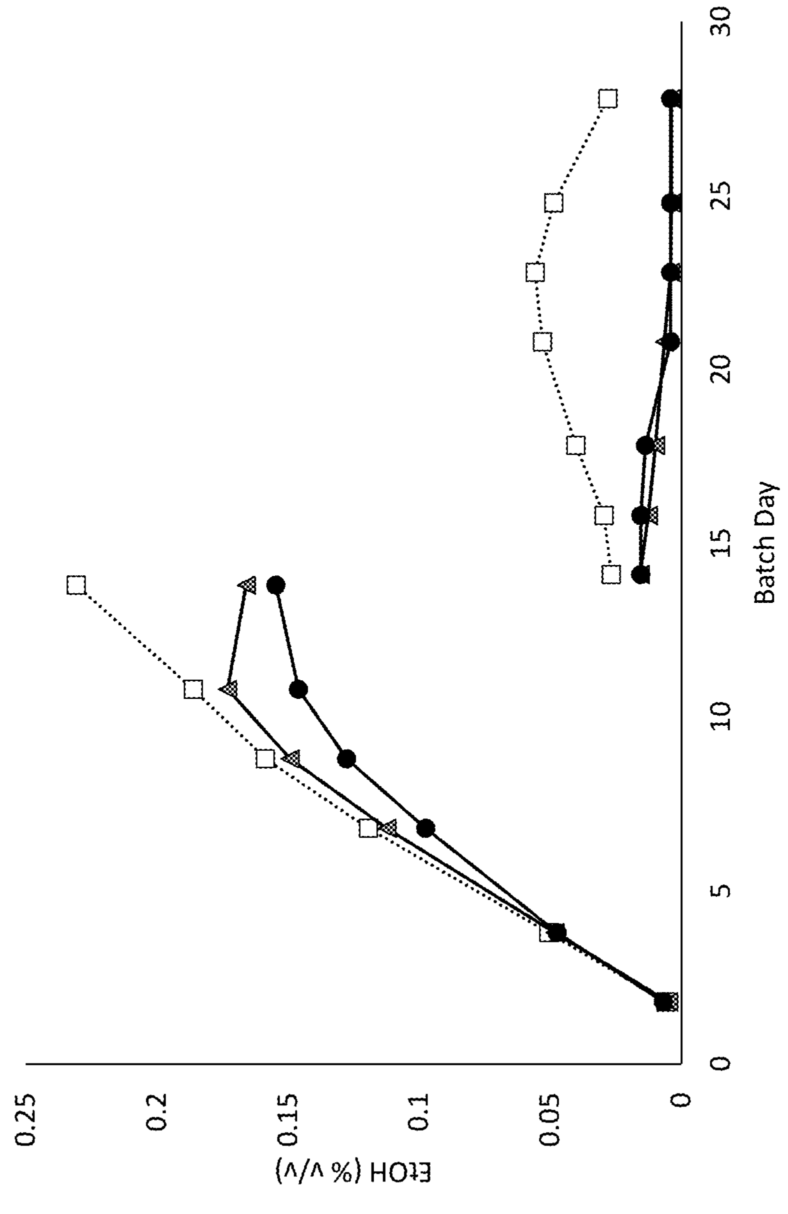
FIG. 18B shows the ethanol levels (in % v/v) in the culture media for the same time period as for FIG. 18A. Empty squares: Axenic culture. Grey triangles: Culture with *Alcanivorax* added. Black circles: Culture with a contaminant mix added. The graph shows that the ethanol consumption was rapid when the culture was grown on phosphate. By the second batch, most of the ethanol was consumed by the contaminants.

However, ethanol production was affected by the presence of the contaminants (FIG. 18B). The ethanol production dropped as compared to the axenic controls. When the cultures were harvested and re-suspended at a low density in new medium at day 14 (to mimic outdoor production procedures), the ethanol yield decreased, in part due to consumption by the contaminant bacteria. Thus, when cultures were grown solely on phosphate for both first and second batches, the contaminants could grow easily and they consumed a considerable amount of ethanol.

Example 17

Growth of the Cyanobacterial Cultures on Phosphite as the Sole Phosphorus Source Yields More Ethanol Over Time, and With Less Ethanol Consumption by Contaminating Bacteria In another experiment, the AB701 phosphite-utilizing cultures, growing in phosphite as the sole source of phosphorus, were spiked with either the contaminant bacteria *Alcanivorax* or spiked with a mixture of contaminating bacteria, and the cultures were analyzed intermittently for cell density and ethanol production. The cultures were grown for 14 days, and were then harvested and re-suspended at a low density in new medium at day 14 to produce a second batch (again, to mimic outdoor production procedures) (FIG. 19A; FIG. 19B).

When the phosphite-utilizing cyanobacterial strains were grown with phosphite as the only phosphorus source, ethanol yields (FIG. 19B) were higher than with the phosphate-fed cultures (FIG. 18B; see Example 16). This was particularly noticeable at the end of the second batch. Further, the cultures grown in phosphite had a 10-fold lower CFU (colony forming units) count of contaminating bacteria (data not shown). Although the ethanol consumption was lessened when phosphite was the phosphorus source rather than phosphate, some ethanol was still consumed, particularly when the contaminant was Alcanivorax (FIG. 19B, grey triangle).

As can be seen by the ethanol production graph (FIG. 19B), the use of phosphite can increase the amount of ethanol that accumulates in the cultures, and can also increase the amount of time that the culture is capable of yielding a high level of ethanol production.

Example 18

P-Source Switching: Phosphate to Phosphite Switching

Because the modified cyanobacterial strains described herein can utilize two sources of phosphorous, being able to switch from one source to another during the course of a long culture run in an outdoor, non-axenic environment may allow the modified cyanobacterial strains to better out-compete contaminating organisms that have accumulated in the culture. This possibility was tested by the following two experiments.

In one experiment, cultures of the modified cyanobacterial cells (with both phosphite and phosphate utilization capabilities) that were either axenic, treated with Alcanivorax alone, or treated with a mixture of contaminants ("contaminant mix") were grown with phosphate as the sole phosphorus source for the first 14 days. The cells were then harvested and re-inoculated into new medium, switching to phosphite as the sole phosphorus source for the remainder of the culture run. Optical density and ethanol levels in the culture were measured.

Figure 20A:
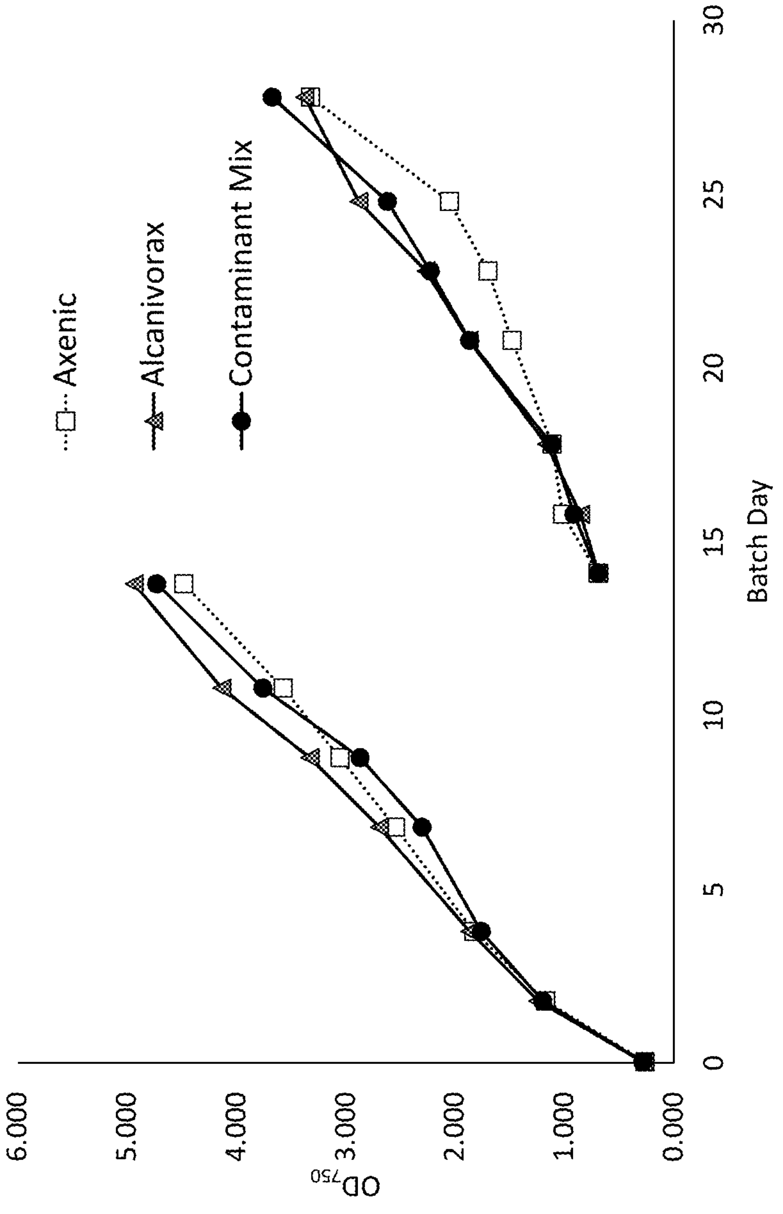
FIG. 20A is a line graph showing cell growth (in $OD_{750}$) of the phosphite-utilizing cyanobacterial strain AB0701, intentionally contaminated with either the bacterial contaminant *Alcanivorax*, or with a "contaminant mix", when grown with phosphate for the first 14 days, then switched to growth on phosphite for the second batch. Empty squares: Axenic culture. Grey triangles: Culture with *Alcanivorax* added. Black circles: Culture with a contaminant mix added.
Figure 20B:
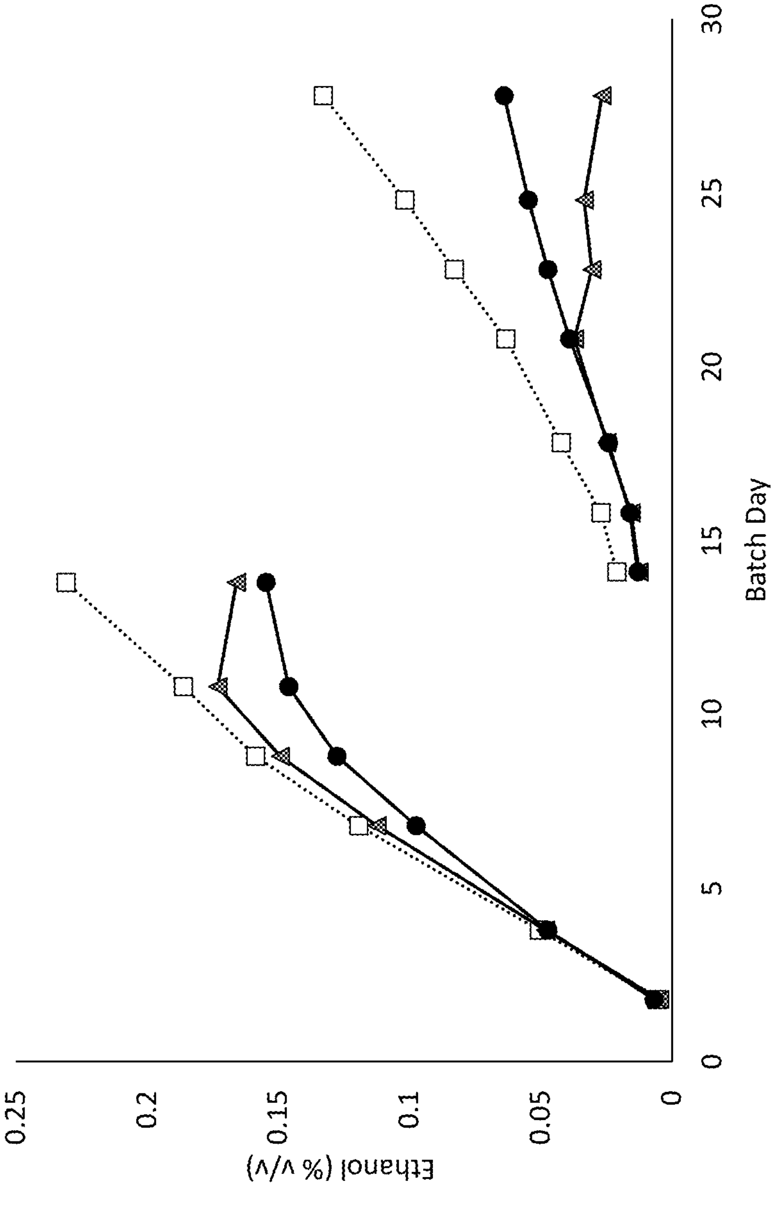
FIG. 20B is a line graph showing ethanol levels (in % v/v) in the culture media for the culture described in FIG. 20A. The switching from phosphate to phosphite after dilution does not appear to diminish cell growth or ethanol production and ethanol accumulation is increased by switching to phosphite rather than continuing with phosphate as the phosphorus source (compare to FIG. 18B). Empty squares: Axenic culture. Grey triangles: Culture with *Alcanivorax* added. Black circles: Culture with a contaminant mix added.

As shown in FIG. 20A, the cyanobacterial cell density of the phosphate ($1^{st}$ batch) and phosphite ($2^{nd}$ Batch) cultures was similar, whether axenic or non-axenic. However, the ethanol levels of the second batch grown on phosphite (FIG. 20B) differed from the batch grown on phosphate both before and after dilution (FIG. 18B). Axenic cultures accumulated, as expected, the most ethanol during the first batch. During the second batch, when the system was switched to phosphite, while the axenic cultures again generally accumulated higher ethanol levels, some ethanol also accumulated even in the contaminated batches. This ethanol accumulation was higher than in cultures that remained on phosphate after dilution (FIG. 18B). Thus, switching from one phosphorus source to another, particularly when the contamination level rises, can, in some cases, result in a lessening of contamination that gives rise to a lower ethanol yield.

Example 19

Improved Genetic Stability of the Plasmid Containing the Phosphite Utilization Genes It was also found that ethanologenic cyanobacterial cells having the phosphite utilization genes on the same plasmid as the ethanologenic genes had a greater genetic stability of the ethanologenic genes over the length of a culture run, in comparison to cells growing on phosphate.

A cyanobacterial culture containing a plasmid having both the ethanologenic genes and genes for the utilization of phosphite was induced for ethanol production and grown for 20 days on either phosphate or phosphite as the sole P source in the medium. At day 20, the cells were re-diluted in new medium, where the P source was either switched or remained the same. At day 40, samples were taken to test for the percentage of cells that had spontaneously lost at least a portion of the ethanol production gene cassette, presumably due to the stress that ethanol production exerts on the cell. A control cell culture (without the presence of phosphite-utilization genes), growing on phosphate for the 40 day period, had approximately 8.6-fold higher reversion rates than phosphite-utilizing cells grown on phosphite for the same amount of time, as measured by the presence of the ethanologenic enzyme Pdc in the culture cells (Table 9, below). Thus, it is possible that plasmid stability may increase in cells having the phosphite-utilizing genes, when these cells are grown on phosphite as the sole phosphorus source.

TABLE 9

| Plasmid Stability | |
|---|---|
| P Treatment (first batch - 14 days/second batch - 9 days) | Fold lower reversion of production gene at day 40 (in comparison to phosphate/phosphate) |
| Phosphate/Phosphate | Control |
| Phosphite/Phosphite | 8.6 × lower reversion |
| Phosphate/Phosphite | 2.2 × lower reversion |
| Phosphite/Phosphate | 2.6 × lower reversion |

The phosphite utilization genes on the plasmid may have created a selection pressure for the entire plasmid carrying the genes to remain in the cell, as long as phosphite was substantially the only P source. Cells that lost the plasmid (or the phosphite-utilization genes) would not be able to survive on phosphite. Thus, similar to the effect of antibiotic resistance genes on a plasmid, the system allowed the plasmids to be maintained in the cell, improving ethanol production and increasing the time that ethanol can be effectively produced in a culture.

Example 20

Co-localizing Product-production Genes with Phosphite Utilization Genes on the Same Operon to Increase Long Term Genetic Stability of Product Production The presence of the phosphite dehydrogenase gene on the same operon (of a plasmid or on the chromosomal DNA) as the production gene may also improve productivity, by forcing the cell to keep the production gene in order to keep the phosphite dehydrogenase gene when the culture is grown on phosphite. This is demonstrated by combining ethanologenic production genes with a phosphite dehydrogenase gene on an extrachromosomal plasmid.

The following two constructs are prepared and transformed into *Cyanobacterium* sp. PTA-13311:

1) pAB1_6.8:: PnirA*2-pdc(AB1opt1)-IScpcBA*1-ptx$D_{R4506}$-TdsrA-PcpcB-adh111(AB1opt2)-TB0011-PpstS-pst$ABC_{ABCC2104}$-TrbcS-FRT
2) pAB1_6.8:: Porf0316-pdc(AB1opt1)-IScpcBA*1-ptx$D_{R4506}$-TdsrA-PcpcB-adh111(AB1opt2)-TB0011-PpstS-pst$ABC_{ABCC2104}$-TrbcS-FRT Both of the above constructs are based on the endogenous parent plasmid pAB1_6.8, which is endogenous to *Cyanobacterium* sp. PTA-13311. Both constructs have a phosphite dehydrogenase gene, several other phosphite transport-related genes, and the ethanologenic genes pdc and adh.

The phosphite dehydrogenase gene is located on the same operon as the ethanologenic pdc gene, both controlled by an inducible promoter that is located upstream of the pdc gene. The first construct has a nitrate-inducible promoter PnirA*2. The second construct has a copper-inducible promoter Porf0316. The adh gene is constitutively expressed. The remaining phosphite utilization genes are located elsewhere on the plasmid.

The constructs are transformed to *Cyanobacterium* sp. PTA-13311. Once the transformation is confirmed, the cultures are scaled-up on culture medium with phosphate as the P source. Once the production phase is reached, expression of the pdc and ptxD genes is initiated by adding the specific inducing agent (nitrate or copper). As the culture progresses, the culture is fed with phosphite as the P source.

By use of this method, the single operon configuration allows for more ethanol to be produced over time, with a lower proportion of cells with an inactivated pdc gene, because the deletion/inactivation of the pdc gene would be likely to also inactivate the ptxD gene, and cells without the ptxD gene would not survive and thrive in phosphite medium. Further, the use of phosphite as the main P source decreases the amount of contamination with bacterial heterotrophs, resulting in less ethanol loss over time, and thus more final ethanol, in comparison to an ethanologenic culture growing on phosphate, or a culture having an ethanologenic construct where the phosphite dehydrogenase gene and pdc gene are not linked to the same promoter.

Example 21

Less Bacterial Contamination When Phosphite is the Phosphorus Source

Figure 21A:
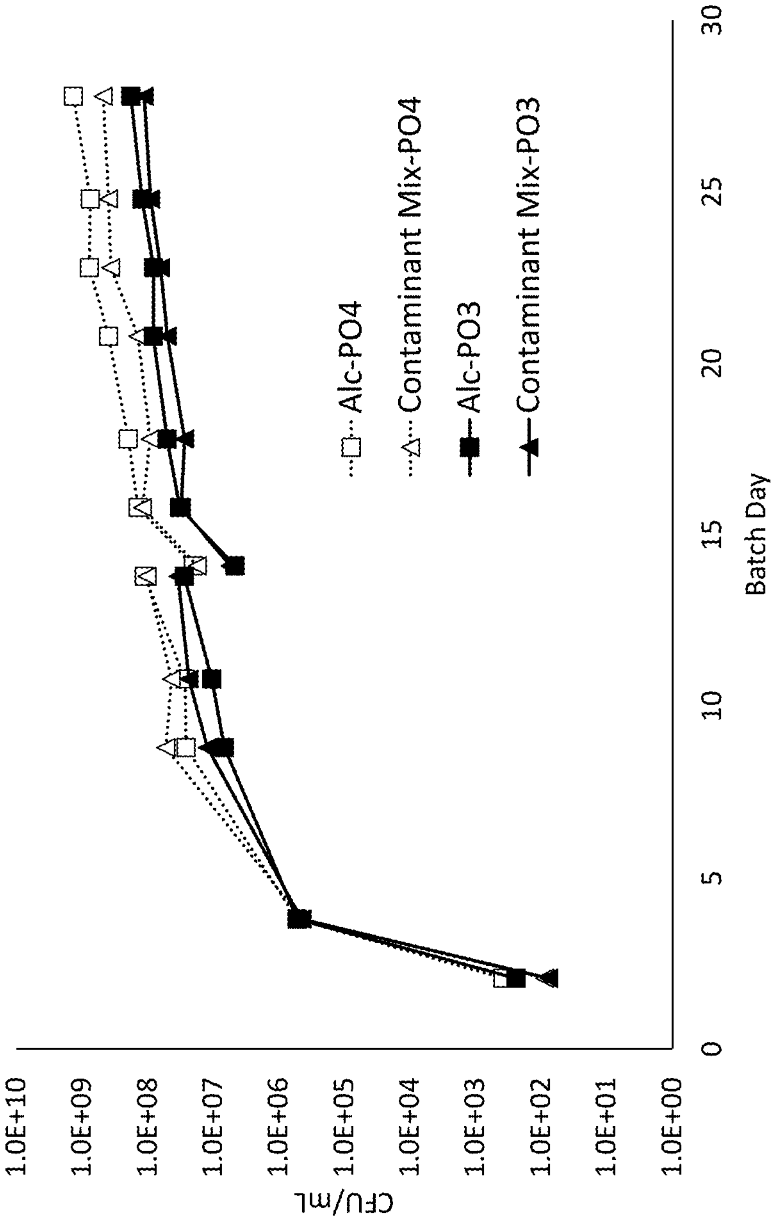
FIG. 21A is a line graph showing bacterial growth (in CFU/ml) in an intentionally contaminated cyanobacterial culture (either *Alcanivorax* or a mixed contaminant culture) over a 28 day batch, with a harvest/dilution to new medium with the same phosphorus source at day 14. The cultures were grown on either phosphite or phosphate as the sole phosphorus source. The bacterial count was much lower when the contaminated cultures were grown on $PO_3$ than when they were grown on $PO_4$.

To determine whether the use of phosphite instead of phosphate can lower bacterial contamination of the cultures, some of the above-described contaminated cultures were sampled for CFU of bacterial cells. In general, it was found that the phosphite-grown cultures had much lower contaminant cell counts than the phosphate-grown cultures (FIG. 21A). Thus, contamination can be lowered by using phosphite rather than phosphate as the phosphorus source in the medium.

Figure 21B:
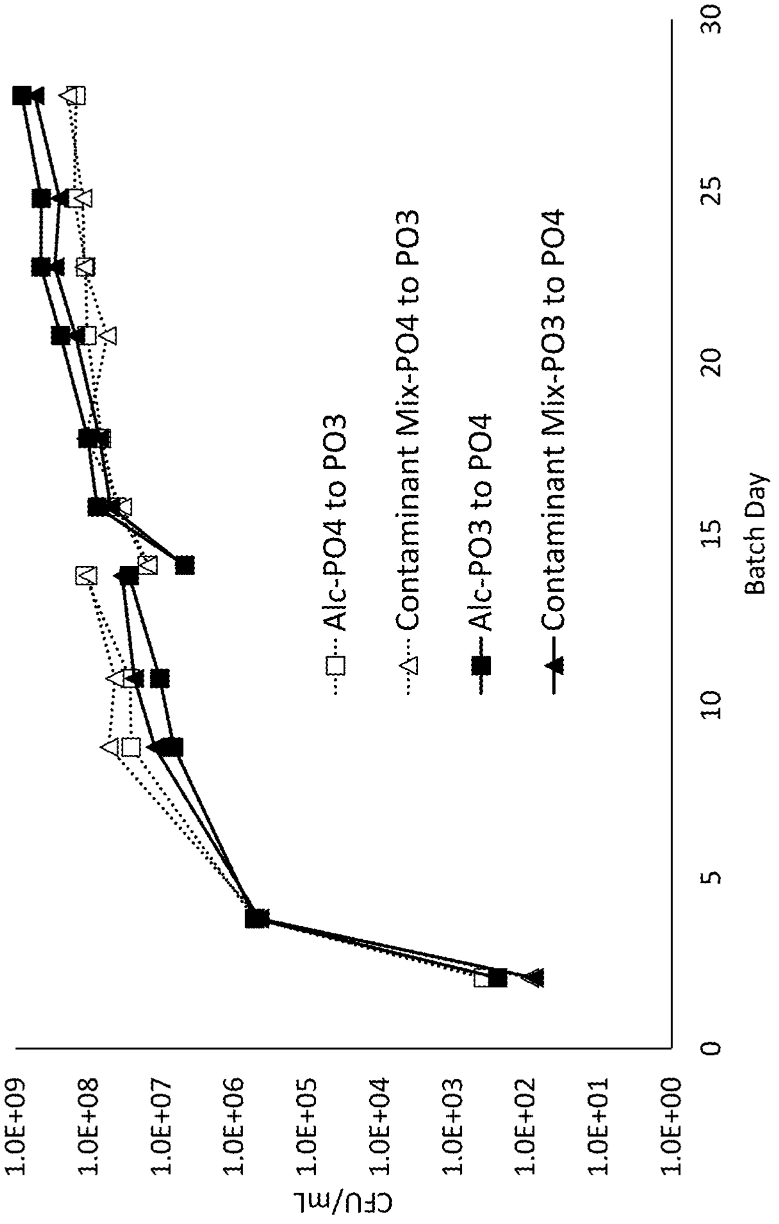
FIG. 21B is a line graph showing bacterial growth (in CFU/ml) in an intentionally contaminated cyanobacterial culture (either *Alcanivorax* or a mixed contaminant culture) over a 28 day batch, grown for the first 14 days on either phosphite or phosphate as the sole phosphorus source. The cells were then harvested/diluted to new medium with the opposite phosphorus source (phosphate or phosphite) at day 14. The bacterial count was much lower when the contaminated cultures were grown on $PO_3$ than when they were grown on $PO_4$.

Furthermore, P-source switching at culture dilution from phosphate to phosphite, results in lower bacterial abundance than continuing to deliver phosphate or when switching from phosphite to phosphate (FIG. 21B). This demonstrates the benefit of lower contaminant abundance when the phosphorous source is switched to phosphite between batches—the contaminants that thrive on phosphate may not, in many cases, be able to thrive on phosphite.

Example 22

Growth Cultures of Cyanobacterial Cells Having Both 1) the Phosphite Utilization Genes and 2) a Knockout of the P Regulatory Gene phoU Have Less Bacterial Contamination It was found that cultures of phosphite-utilizing strains, when growing on phosphite as the only added P source, still had a residual amount of phosphate in the medium. This situation could exist, for example, due to cell leakage or cell death, or carry-over from previous growth medium. This residual amount, even if small compared to the amount of phosphite in the culture medium, could still be enough for contaminating organisms to proliferate.

The following experiment was performed with ethanologenic cyanobacterial cells having a knockout of the phosphate metabolism regulatory gene phoU (orf0666) (see, for example, Burut-Archanai et al., (2013), Biochem. Engineering Jour. 74: 69-75; and Morohoshi et al., (2002), Appl. Envir. Microbiol. 68: 4107-4110), to see if there was a P uptake advantage over non-modified cells when a residual amount of phosphate was present in a culture medium in addition to phosphite. The strain also contained a gene cassette of the phosphite utilization genes, so the experiment was also performed to determine whether the modified host cells would produce comparable amounts of ethanol as when grown on phosphite alone as compared to phosphate. Further, the effect that the phosphite/phoU knock-out system has on contaminants was compared with cultures grown on phosphite and phosphate.

For this set of experiments, a different phosphite utilizing strain was used. The cyanobacterial strain AB0793 (ΔAB1_orf666; pAB1-6.8:: PnirA*2-pdc(AB1opt1)-TdsrA-PcpcB-ADH111(AB1opt)-TrbcS-Porf0316-ptxDR4506 (AB1opt)-His6-IScpcBA-ptxA2104(AB1opt)-IScpcBA*1-ptxB2104(AB1opt)-ISpsaAB-ptxC2104(AB1opt)-TB0011), containing the nitrate-inducible ethanologenic genes, and phosphite utilization genes, was grown in vertical photobioreactors in mBG-11 medium (with BG-11 nutrients, but free of P and N), with the addition of 17 mM nitrate, 25 μM $PO_3$ (as phosphorous acid) or $PO_4$ (as phosphoric acid). As the culture grew, the following nutrients were added intermittently: 35 μM $PO_4$ (as phosphoric acid) or $PO_3$ (as phosphorous acid) per $OD_{750}$. The cultures had a starting inoculation density of 0.2 $OD_{750}$. The cultures received light in a 12 hour on/12 hour off cycle, at 350 μmol photons $m^{-2}s^{-1}$, with a temperature of approximately 32° C. The treatments were run in duplicates, with the average of the treatments shown in FIG. 22A, 22B, and 22C.

Figure 22A:
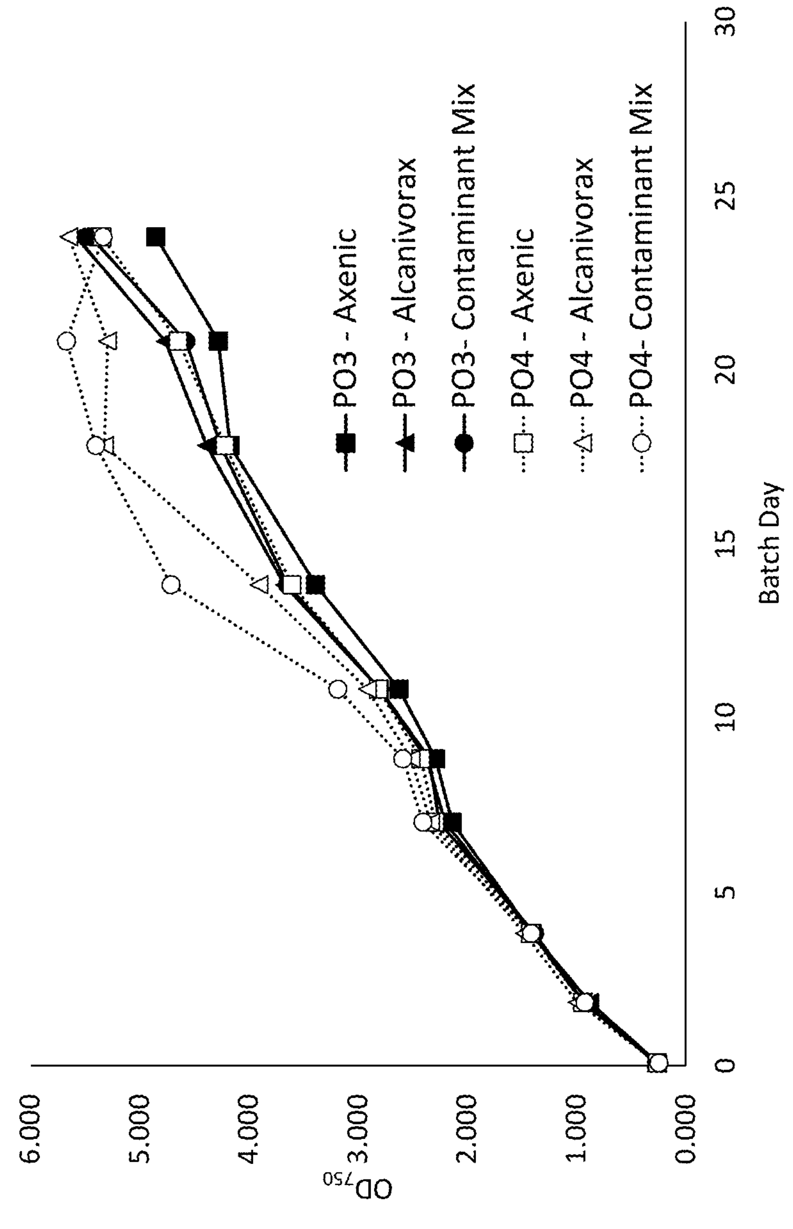
FIG. 22A is a line graph showing cyanobacterial cell growth (in $OD_{750}$) in medium intentionally contaminated with either *Alcanivorax* or a contaminant mix, with either $PO_4$ or $PO_3$ as the sole P source, when grown for a 24 day batch.
Figure 22B:
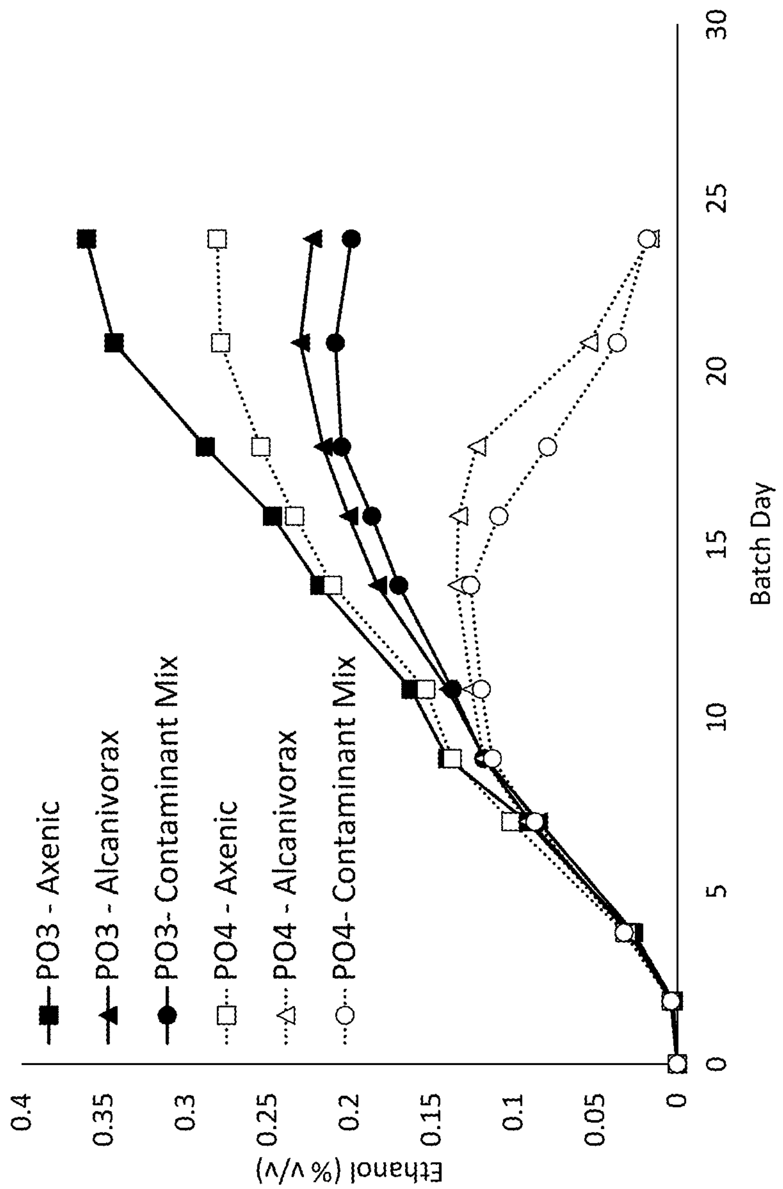
FIG. 22B is a line graph showing ethanol yield (% v/v) in the same culture as in FIG. 22A, with medium intentionally contaminated with either *Alcanivorax* or a contaminant mix, where the medium contained either $PO_4$ or $PO_3$ as the sole P source, when grown for a 24 day batch. The intentionally contaminated cultures growing on $PO_3$ had a higher yield of ethanol than the intentionally contaminated cultures growing on $PO_4$. By the end of the run at 24 days, very little ethanol remained in the intentionally contaminated cultures growing on $PO_4$.
Figure 22C:
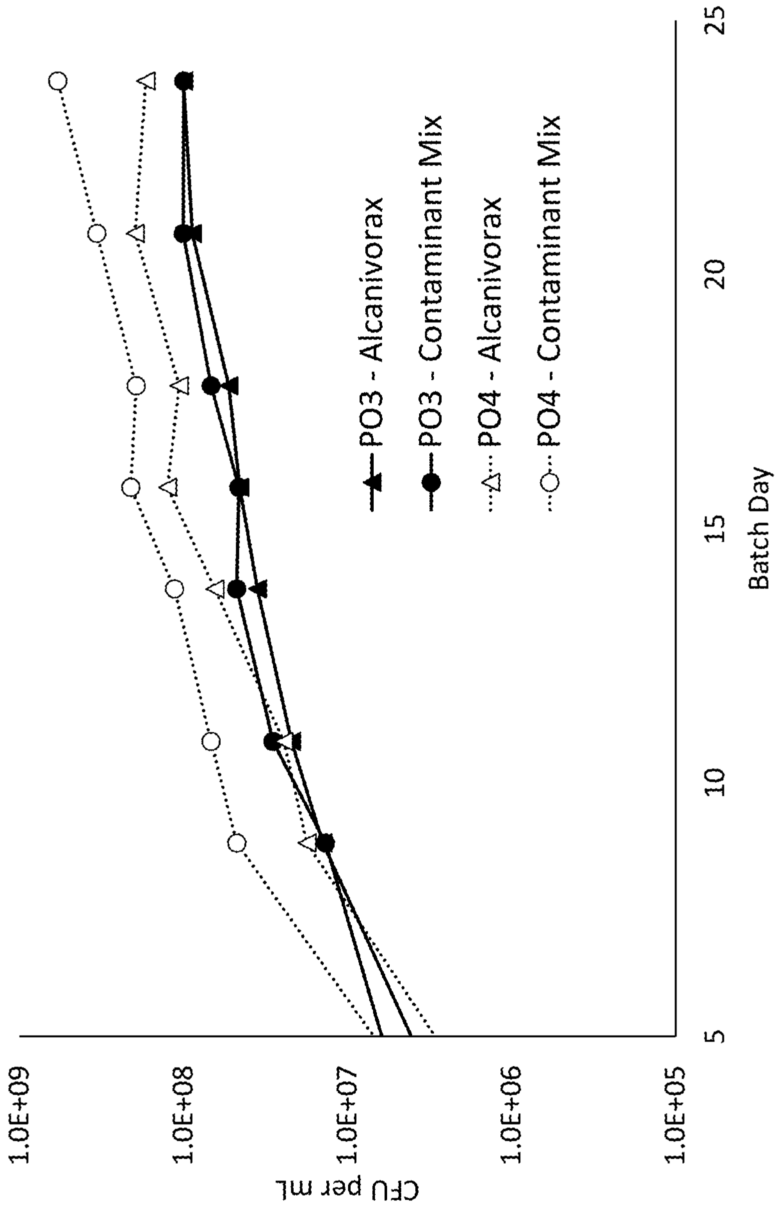
FIG. 22C is a line graph showing the level of contamination present (in CFU/ml) in the experiment described above in FIG. 22A and 22B. The $PO_4$—grown cells had a higher level of bacterial contamination than the $PO_3$—grown cells throughout the length of the run.

As shown in FIG. 22A, the cell density was slightly higher with the phosphate-grown cultures.

Axenic phosphite-grown cultures yield slightly more ethanol than the axenic phosphate-grown cultures. With the contaminated cultures, the results were more pronounced, however: when the phosphite-utilizing strain AB0793 was grown with phosphite as the only phosphorus source in the presence of contaminants, ethanol yields (FIG. 22B) were higher than with the phosphate-fed contaminated cultures.

Further, the cultures grown in phosphite had up to 15-fold lower abundance of contaminating bacteria (based on CFU counts). However, the presence of contaminants did result in some consumption of much of the ethanol present, even with phosphite as the sole phosphorus source.

As can be seen by the ethanol production graph (FIG. 22B), the use of phosphite instead of phosphate can increase the amount of ethanol that accumulates in the cultures, and can increase the amount of time that the culture is capable of yielding a high level of ethanol.

Example 23

Transformation of *Synechococcus* sp. with the Phosphite Utilization Genes

As a prophetic example, Synechococcus sp. PCC 7002 is transformed with the ptxD and ptxA,B,C genes from Ralstonia, harbored in a modified endogenous pAQ1 plasmid from *Synechococcus* sp. PCC 7002. The same plasmid also contains the pdc/adh ethanologenic cassette. The cells are screened for full segregation of the pAQ1 plasmid, and cultures are scaled up for outdoor testing. The cells are capable of utilizing phosphite, and are capable of outcompeting contaminating bacteria. Ethanol is produced and harvested from the cultures after two to six weeks of growth. A small amount of the culture is retained in the photobioreactor, and new phosphite-containing culture medium is added. The culture grows for another two to six weeks to produce ethanol. At the end of the run, the ethanol is harvested and processed for biofuel. The remaining biomass from both runs is collected and sold to be processed for biofuel production, animal feed, or other purposes.

Example 24

Transformation of *Synechocystis* sp. PCC 6803 with an Isoprene Production Gene and Phosphite Utilization Genes As another prophetic example, *Synechocystis* sp. PCC 6803 is transformed with the ptxD gene from *Ralstonia*, as well as the phosphite transporter genes from *Desulfotignum phosphitoxidans*. The genes are placed on the self replicating plasmid pVZ321. Another plasmid is used to carry an ispS gene for the production of isoprene, regulated by an inducible promoter. The cultures are then scaled up for outdoor testing. The cells are capable of utilizing phosphite, and are capable of out-competing contaminating bacteria and fungi. When the inducing agent is added, isoprene accumulates in the culture, and is harvested from the culture after about ten weeks of growth.

Example 25

*Anabaena* sp. Host Cells Having Phosphite Utilization Genes and Genes for the Production of 1,3-Propanediol As a prophetic example, a strain of *Anabaena* sp. is transformed with a gene encoding PtxD (WP_046983515.1) from *Delftia lacustris*, and phosphite transporter genes from *Nostoc* sp. PCC 7120, all harbored in a plasmid modified to additionally contain genes for 1,3-propanediol production, as described in PCT/US2013/065574, which is incorporated by reference herein in its entirety. The cells are screened for full segregation of the plasmid. The resulting cultures are scaled up for outdoor testing. The cells are capable of utilizing phosphite, and are capable of out-competing contaminating bacteria. 1,3-propanediol is produced and harvested from the cultures after two to six weeks of growth. Approximately 1% of the culture is retained in the photobioreactor, and new phosphite-containing medium is added. The culture grows for another two to six weeks to produce more 1,3-propanediol. This growth and harvest cycle is repeated as many times as desired. At the end of each run, the 1,3-propanediol is harvested and processed. The remaining biomass is collected and sold for biofuel production, animal feed, or other purposes.

Example 26

Synechocystis sp. Host Cells Having Phosphite Utilization Genes and and Genes for the Production of 1,2-Propanediol As a prophetic example, *Synechocystis* sp. PCC 6803_is transformed with a gene encoding PtxD (WP_044432324.1 from *Acinetobacter*), as well as phosphite transporter genes from *Trichodesmium erythraeum*. A separate plasmid is used to harbor genes for 1,2-propanediol production, as described in PCT/US2013/65568, which is incorporated by reference herein in its entirety. The cells are screened for full segregation of the plasmid, and cultures are scaled up for outdoor testing. The cells are capable of utilizing phosphite, and are capable of out-competing contaminating bacteria. 1,2-propanediol is produced and harvested from the cultures after two to six weeks of growth. A small amount of the culture is retained in the photobioreactor, and new phosphite-containing medium is added. The culture grows for another two to six weeks to produce more 1,2-propanediol. At the end of the run, the 1,2-propanediol is harvested and processed. The remaining biomass (from both runs) is collected and sold for biofuel production, animal feed, or other purposes.

Example 27

*Synechococcus* sp. Host Cells with Phosphite Utilization Genes and Ethanol Production Genes As a prophetic example, *Synechococcus* sp. PCC 7002 is transformed with a gene encoding PtxD (WP_046983515.1) from *Delftia lacustris*, as well as phosphite transporter genes from *Nostoc punctiforme*, all harbored in a plasmid modified to additionally contain an operon having a regulatable promoter, a gene encoding Pdc and a gene encoding Adh for the production of ethanol. The cells are screened for full segregation of the plasmid, and cultures are scaled up for outdoor testing. The cells are capable of utilizing phosphite, and are capable of out-competing contaminating bacteria. Ethanol is produced and harvested from the cultures after about 30 days of growth. A small amount of the culture is retained in the photobioreactor, and new phosphite-containing medium is added. The culture grows for another 30 days to produce more ethanol. By use of this method, less contamination occurs in comparison to similar *Synechococcus* sp. PCC 7002 host cells, but lacking the phosphite utilization genes, and growing on phosphate.

Example 28

*Spirulina* sp. Host Cells with Phosphite Utilization Genes

As a prophetic example, a *Spirulina* strain is transformed with a gene encoding PtxD (WP_011610233.1) from *Trichodesmium erythraeum*, as well as phosphite transporter genes from *Cyanothece* sp. CCY0110. The cells are screened for full segregation of the plasmid, and cultures are scaled up for outdoor testing. The cells are capable of utilizing phosphite, and are capable of out-competing contaminating bacteria. After 2 weeks of growth, the culture is harvested for biomass. About 10% of the culture is retained in the photobioreactor, and new phosphite-containing medium is added. The culture grows for another 2 weeks, and is again harvested for biomass. The process is repeated as needed. By use of this method, less contamination occurs in comparison to similar Spirulina host cells, but lacking the phosphite utilization genes, growing on phosphate. By use of this method, the culture can remain viable, with less contamination over time, than similar Spirulina cultures not having the phosphite utilization genes.

Example 29

*Synechococcus elongatus* PCC 7942 Host Cells with Phosphite Utilization Genes, and a PhoU Homolog Knock-out As a prophetic example, the genome of a *Synechococcus elongatus* PCC 7942 strain is examined to find a homolog to the phoU gene (phosphate regulation). The gene is removed from the strain, using knock-out methods known in the art. The strain is then transformed with a plasmid containing genes encoding PtxD (WP_011610233.1) from *Trichodes-*

*mium erythraeum*, and phosphite transporter genes from Cyanothece sp. ATCC 51142 (see Table 2). The cells are screened for full segregation of the plasmid, and cultures are scaled up for outdoor testing. The cells are capable of utilizing phosphite, and because of the additional knock-out of the phoU homolog gene, the cells can more readily take up any phosphate that occurs in the culture. Thus, the new strain is capable of out-competing contaminating bacteria. After two weeks of growth, the culture is harvested for biomass. About 10% of the culture is retained in the photobioreactor, and new phosphite-containing medium is added. The culture grows for another two weeks, and is again harvested for biomass. The process is repeated as needed. By use of this method, the culture can remain viable, with less contamination over time, than similar Synechococcus sp. PCC 7942 cultures not having the phosphite utilization genes and not having the knockout of the gene encoding the phoU homolog.

Example 30

Determination of Ethanol Production using Headspace Gas Chromatography with Flame Ionization Detection The concentration of ethanol was determined by gas chromatography using a 0.32 mm by 30 m DB-ALC1 GC capillary column having a film thickness of 1.80 μm, using flame ionization detection on an Agilent Gas Chromatograph (Agilent Technologies, model # 7890A) configured with a headspace sampler (Agilent Technologies, model #7697A). The method followed the manufacturer's instructions for blood alcohol quantitation (Agilent application note #5990-9021EN, entitled "Analysis of Ethanol in Blood with the Agilent 7820A GC and 7697A headspace sampler." The samples were heated to 85° C. for 15 minutes. The $N_2$ column flow was 12 ml/minute. The analyte concentration of each sample was determined by application of a $1/x^2$ weighted least squares linear calibration model to the measured response of each analyte.

Calibration method: The calibration model was generated by fitting the detector response of calibration standards to their known, or true, concentration. The calibration standards were prepared in volumetric glassware from ACS reagent grade (minimum 99.5% purity) ethanol and acetaldehyde at levels of 0.001, 0.01, 0.1, and 1.0% v/v. Since a sample matrix can affect analyte response, care was taken to ensure that calibration standards were prepared in an identical media/matrix as were the samples to be analyzed. Calibration was performed each time a sample set was analyzed, as was the confirmatory analysis of third-party certified reference materials. By use of this method, ethanol levels could be quantitated within the range of 0.001% - 1.0% v/v within about 15% accuracy, as confirmed by analysis of third-party certified standard reference materials.

Although the present invention has been described in considerable detail with reference to certain embodiments thereof, other embodiments are possible. Therefore, the spirit and scope of the appended claims should not be limited to the description of the embodiments contained therein.

What is claimed is:

1. A genetically modified cyanobacterial cell for the production of a product of interest, comprising:

a) at least one recombinant gene that encodes a heterologous phosphite dehydrogenase enzyme EC:1.20.1.1 that catalyzes the oxidation of phosphite to phosphate, wherein said enzyme has at least 85% identity to the protein sequence of the *Ralstonia* phosphite dehydrogenase enzyme (SEQ ID NO: 12);

b) an operon comprising at least one recombinant phosphite transporter gene encoding at least one phosphite transporter protein for transporting phosphite into the cell wherein the at least one phosphite transporter protein has at least 85% identity to a protein sequence selected from the group consisting of *Cyanothece* PtxA (SEQ ID NO: 19), *Cyanothece* PtxB (SEQ ID NO:22), *Cyanothece* PtxC (SEQ ID NO: 25), and *Desulfotignum phosphitoxidans* PtdC (SEQ ID NO: 28);

c) a knockout or knockdown of a gene encoding an endogenous protein having at least 85% identity to the repressor protein PhoU; and d) at least one recombinant production gene encoding a polypeptide for the production of said product of interest.

2. The genetically modified cyanobacterial cell of claim 1, wherein the recombinant phosphite dehydrogenase gene is operably linked to a constitutive promoter.

3. The genetically modified cyanobacterial cell of claim 1, wherein the recombinant phosphite dehydrogenase gene is operably linked to a regulatable promoter selected from the group consisting of: a metal-regulatable promoter, a nitrate-regulatable promoter, and a phosphorus-regulatable promoter.

4. A genetically modified cyanobacterial cell for the production of a product of interest, comprising:

a) a gene encoding a heterologous phosphite dehydrogenase enzyme EC:1.20.1.1;

b) a gene encoding a protein having at least 85% identity to the phosphite transporter from *Desulfotignum phosphitoxidans;* c) a knockout or knockdown of a gene encoding an endogenous repressor protein having at least 85% identity to the repressor protein PhoU; and d) at least one recombinant production gene encoding a polypeptide for the production of said product of interest.

5. The genetically modified cyanobacterial cell of claim 1, wherein the gene encoding the at least one phosphite transporter protein is operably linked to a constitutive promoter.

6. The genetically modified cyanobacterial cell of claim 1, wherein the recombinant phosphite transporter operon comprises a gene encoding a protein that has a nucleic acid sequence identity of at least 90% to at least one of the ptxABC operon sequences selected from the group consisting of SEQ ID NO: 17, SEQ ID NO: 20, and SEQ ID NO: 23.

7. The genetically modified cyanobacterial cell of claim 1, wherein the recombinant phosphite transporter operon comprises a gene encoding a protein that has a sequence identity of greater than 90% to the protein sequence of PtdC from *Desulfotignum phosphitoxidans* (SEQ ID NO: 28).

8. The genetically modified cyanobacterial cell of claim 1, wherein the at least one recombinant phosphite transporter gene is operably linked to a regulatable promoter selected from a group consisting of: a metal- regulatable promoter, a nitrate-regulatable promoter, and a phosphorus-regulatable promoter.

9. The genetically modified cyanobacterial cell of claim 1, wherein the knockout or knockdown of the gene encoding the endogenous repressor protein results in an increased level of phosphate transporter protein in the cyanobacterial cell.

10. The genetically modified cyanobacterial cell of claim 9, wherein the knockout or knockdown of the gene encoding the endogenous repressor protein results in cellular metabolism consistent with a constant phosphorus starvation mode, resulting in an enhanced capability to take up and incorporate phosphorus from the medium.

11. The genetically modified cyanobacterial cell of claim 1, wherein the at least one recombinant production gene comprises a gene encoding a pyruvate decarboxylase enzyme and a gene encoding an alcohol dehydrogenase enzyme.

12. The genetically modified cyanobacterial cell of claim 11, wherein the promoter operably linked to said gene encoding said pyruvate decarboxylase enzyme is a regulatable promoter, and wherein the promoter operably linked to said alcohol dehydrogenase enzyme is a constitutive promoter, further wherein the product of interest is ethanol.

13. A recombinant expression cassette comprising:

a) at least one recombinant phosphite transporter gene encoding a protein that is at least a part of a transporter system for phosphite; wherein the protein has at least 85% identity to a protein sequence selected from the group consisting of SEQ ID NO: 19, 22, 25, and 28;

b) at least one recombinant phosphite dehydrogenase gene encoding an enzyme that catalyzes the oxidation of phosphite to phosphate;

wherein at least one of said genes is operably linked to a regulatable promoter, wherein said expression cassette provides sufficient expression of said proteins and enzymes in a genetically modified cyanobacterial cell comprising said expression cassette to confer an ability of said genetically modified cyanobacterial cell to metabolize phosphite as a phosphorus source for supporting growth of said cyanobacterial cell, further comprising at least one recombinant production gene encoding a polypeptide for the production of a product of interest, wherein said recombinant expression cassette is present on a plasmid derived from an endogenous cyanobacterial plasmid.

14. A method of producing a product of interest comprising the following method steps:

a) providing a genetically modified cyanobacterial cell of claim 1; and b) growing said genetically modified cyanobacterial cell in a liquid medium exposed to photosynthetically active radiation, wherein the medium comprises phosphite as a source of phosphorus, the cell thereby producing the product of interest;

wherein step b) comprises a non-axenic culturing condition wherein contaminating heterotrophic organisms are present in the medium, further wherein the ratio of contaminating heterotrophic organisms to cyanobacterial cells is less than when phosphate is the main source of phosphorus in the medium.

15. The method of claim 14, wherein during step b) the presence of contaminant cells is maintained below $1\times10^6$ colony forming units per milliliter (CFU/mL) after about 30 days of cultivation.

16. The method of claim 14, wherein during step b) the growth of contaminant cells is reduced or inhibited by limiting availability of phosphate in the medium to less than 5 μM.

17. The method of claim 14, wherein the contaminating heterotrophic organisms are present in at least a 5-fold lower concentration than when a normal amount of phosphate is provided to the medium.

18. The method of claim 14, wherein the product of interest is selected from the group consisting of: an alcohol, a biofuel, an alkane, a nutraceutical, a pharmaceutical, a lipid, a carbohydrate, biomass, a protein, an amino acid, an amino acid derivative, a cell extract, and a pigment.

19. A method of producing a product of interest from cyanobacteria, comprising:

a) providing a genetically modified cyanobacterial cell of claim 1, wherein the phosphite dehydrogenase gene and at least one of the recombinant production genes are present on the same extrachromosomal plasmid; and b) growing the genetically modified cyanobacterial cell in a medium comprising phosphite as the main source of phosphorus, under conditions to produce the product of interest, wherein the proportion of cells in which the at least one recombinant production gene remains functional is higher at the end of the cultivation period than in an otherwise identical cyanobacterium that does not have the phosphite dehydrogenase gene, cultured under identical conditions but growing on phosphate instead of phosphite.

20. The method of claim 19, wherein the phosphite dehydrogenase gene and at least one of the recombinant production genes are included in the same operon and operably linked to one regulatable promoter, further wherein the at least one recombinant production gene is located upstream of the phosphite dehydrogenase gene.

21. The genetically modified cyanobacterial cell of claim 2, wherein the constitutive promoter is Porf0615.

22. The genetically modified cyanobacterial cell of claim 5, wherein the constitutive promoter is Porf0615.

* * * * *